(12) United States Patent
West et al.

(10) Patent No.: US 10,865,383 B2
(45) Date of Patent: Dec. 15, 2020

(54) METHODS AND FORMULATIONS FOR ORTHOPEDIC CELL THERAPY

(75) Inventors: Michael West, Mill Valley, CA (US); Hal Sternberg, Berkeley, CA (US)

(73) Assignee: LINEAGE CELL THERAPEUTICS, INC., Carlsbad, CA (US)

( * ) Notice: Subject to any disclaimer, the term of this patent is extended or adjusted under 35 U.S.C. 154(b) by 0 days.

(21) Appl. No.: 14/131,429

(22) PCT Filed: Jul. 12, 2012

(86) PCT No.: PCT/US2012/046564
§ 371 (c)(1),
(2), (4) Date: Apr. 29, 2014

(87) PCT Pub. No.: WO2013/010045
PCT Pub. Date: Jan. 17, 2013

(65) Prior Publication Data
US 2014/0234964 A1    Aug. 21, 2014

Related U.S. Application Data

(60) Provisional application No. 61/507,041, filed on Jul. 12, 2011, provisional application No. 61/601,499, filed on Feb. 21, 2012.

(51) Int. Cl.
*C12N 5/077* (2010.01)

(52) U.S. Cl.
CPC ........ *C12N 5/0655* (2013.01); *C12N 2501/15* (2013.01); *C12N 2501/155* (2013.01); *C12N 2501/19* (2013.01); *C12N 2533/54* (2013.01); *C12N 2533/80* (2013.01); *C12N 2537/10* (2013.01)

(58) Field of Classification Search
CPC .................................................. C12N 5/0655
See application file for complete search history.

(56) References Cited

U.S. PATENT DOCUMENTS

| | | |
|---|---|---|
| 4,501,860 A | 2/1985 | Campbell et al. |
| 4,507,413 A | 3/1985 | Thoma et al. |
| 4,582,865 A | 4/1986 | Balazs et al. |
| 4,644,059 A | 2/1987 | Gordon |
| 4,713,448 A | 12/1987 | Balazs et al. |
| 4,767,745 A | 8/1988 | Young et al. |
| 4,851,121 A | 7/1989 | Yakota et al. |
| 4,925,945 A | 5/1990 | Klein et al. |
| 4,970,303 A | 11/1990 | Reardan et al. |
| 5,135,919 A | 8/1992 | Folkman et al. |
| 5,166,317 A | 11/1992 | Wallace |
| 5,290,807 A | 3/1994 | Folkman et al. |
| 5,443,950 A | 8/1995 | Naughton et al. |
| 5,443,953 A | 8/1995 | Hansen et al. |
| 5,463,022 A | 10/1995 | Inoue et al. |
| 5,480,772 A | 1/1996 | Wangh |
| 5,504,074 A | 4/1996 | D'Amato et al. |
| 5,554,754 A | 9/1996 | Ravichandran et al. |
| 5,589,376 A | 12/1996 | Anderson et al. |
| 5,616,568 A | 4/1997 | Pouyani et al. |
| 5,635,603 A | 6/1997 | Hansen et al. |
| 5,639,725 A | 6/1997 | O'Reilly et al. |
| 5,651,992 A | 7/1997 | Wangh |
| 5,652,347 A | 7/1997 | Pouyani et al. |
| 5,661,143 A | 8/1997 | D'Amato et al. |
| 5,698,586 A | 12/1997 | Kishimoto et al. |
| 5,733,876 A | 3/1998 | O'Reilly et al. |
| 5,762,918 A | 6/1998 | Thorpe |
| 5,792,845 A | 8/1998 | O'Reilly et al. |
| 5,827,740 A | 10/1998 | Pittenger |
| 5,830,651 A | 11/1998 | Cauley |
| 5,837,682 A | 11/1998 | Folkman et al. |
| 5,843,780 A | 12/1998 | Thomson |
| 5,854,205 A | 12/1998 | O'Reilly et al. |
| 5,854,221 A | 12/1998 | Cao et al. |
| 5,861,372 A | 1/1999 | Folkman et al. |
| 5,874,417 A | 2/1999 | Prestwich et al. |
| 5,880,270 A | 3/1999 | Berninger et al. |
| 5,885,795 A | 3/1999 | O'Reilly et al. |
| 5,888,705 A | 3/1999 | Rubin et al. |
| 5,892,069 A | 4/1999 | D'Amato et al. |
| 5,942,435 A | 8/1999 | Wheeler |
| 5,945,403 A | 8/1999 | Folkman et al. |

(Continued)

FOREIGN PATENT DOCUMENTS

| | | |
|---|---|---|
| EP | 0045665 A1 | 2/1982 |
| EP | 0339264 A1 | 11/1989 |

(Continued)

OTHER PUBLICATIONS

Xu et al. Growth Factors 2006;24:268-78.*
Bai et al. Biochem Biophys Res Comm 2004;325:453-60.*
Girkontaite et al. Matrix Biol 1996;15:231-8.*
PureStem®. 4D20.8, Company datasheet, 2008.*
PureStem®. SM30, Company datasheet, 2008.*
Coleman et al. Develop Dynamics 2003;228-216.*
Clayton et al. Sci 2007;427:132-7.*
Nakagawa et al. Arthritis & Rheumatism 2009;60:3686-92.*
Chimal-Monroy et al. Int J Dev Biol 1997;41:91-102.*
West et al. Regen Med 2008;3:287-308.*
Sternberg et al. Regen Med 2013;8:125-44.*
Kawaguchi et al. Bone 2005;36: 758-69.*

(Continued)

*Primary Examiner* — Scott Long
(74) *Attorney, Agent, or Firm* — Mintz, Levin, Cohn, Ferris, Glovsky and Popeo, P.C.

(57) ABSTRACT

Aspects of the present invention include methods and compositions related to the production and use of clonal lineages of embryonic progenitor cell lines derived from differentiating cultures of primordial stem cells, in particular, said methods and compositions relate to methods of differentiating cells in the presence of members of the BMP family of growth factors and the applications of said cell lines in the treatment of degenerative orthopedic diseases such as osteoarthritis.

20 Claims, 25 Drawing Sheets

Specification includes a Sequence Listing.

(56) References Cited

U.S. PATENT DOCUMENTS

| | | |
|---|---|---|
| 5,945,577 A | 8/1999 | Stice et al. |
| 6,001,647 A | 12/1999 | Peck et al. |
| 6,011,197 A | 1/2000 | Strelchenko |
| 6,017,954 A | 1/2000 | Folkman et al. |
| 6,024,688 A | 2/2000 | Folkman et al. |
| 6,086,865 A | 7/2000 | Folkman et al. |
| 6,174,861 B1 | 1/2001 | O'Reilly et al. |
| 6,235,970 B1 | 5/2001 | Stice et al. |
| 6,241,984 B1 | 6/2001 | Hoffman et al. |
| 6,280,718 B1 | 8/2001 | Kaufman et al. |
| 6,303,576 B1 | 10/2001 | Blaschuk et al. |
| 6,310,039 B1 | 10/2001 | Kratz |
| 6,326,201 B1 | 12/2001 | Fung et al. |
| 6,387,978 B2 | 5/2002 | Ronan et al. |
| 6,436,704 B1 | 8/2002 | Roberts et al. |
| 6,521,223 B1 | 2/2003 | Calias et al. |
| 6,534,591 B2 | 3/2003 | Rhee et al. |
| 6,548,081 B2 | 4/2003 | Sadozai et al. |
| 6,551,610 B2 | 4/2003 | Shalaby et al. |
| 6,562,363 B1 | 5/2003 | Mantelle et al. |
| 6,602,711 B1 | 8/2003 | Thomson et al. |
| 6,610,535 B1 | 8/2003 | Lu et al. |
| 6,617,450 B1 | 9/2003 | Stocker et al. |
| 6,630,457 B1 | 10/2003 | Aeschlimann et al. |
| 6,635,622 B2 | 10/2003 | Tomiyama et al. |
| 6,649,742 B1 | 11/2003 | Better et al. |
| 6,656,714 B2 | 12/2003 | Holmes et al. |
| 6,664,372 B1 | 12/2003 | Janda et al. |
| 6,825,269 B1 | 11/2004 | Gottschall |
| 6,887,706 B2 | 5/2005 | Zhang et al. |
| 6,913,764 B2 | 7/2005 | Vogt et al. |
| 6,927,285 B2 | 8/2005 | Cech et al. |
| 6,946,293 B1 | 9/2005 | Lu et al. |
| 7,008,635 B1 | 3/2006 | Coury et al. |
| 7,033,831 B2 | 4/2006 | Fisk et al. |
| 7,217,569 B2 | 5/2007 | Thomson |
| 7,510,870 B2 | 3/2009 | Oh |
| 7,582,479 B2 | 9/2009 | Thomson |
| 7,928,069 B2 | 4/2011 | Prestwich et al. |
| 7,951,591 B2 | 5/2011 | Robl et al. |
| 7,981,871 B2 | 7/2011 | Prestwich et al. |
| 8,048,999 B2 | 11/2011 | Yamanaka et al. |
| 8,058,065 B2 | 11/2011 | Yamanaka et al. |
| 8,090,542 B2 | 1/2012 | Khvorova et al. |
| 8,129,187 B2 | 3/2012 | Yamanaka et al. |
| 8,202,701 B2 | 6/2012 | Boyan et al. |
| 8,247,384 B2 | 8/2012 | Green et al. |
| 8,278,104 B2 | 10/2012 | Yamanaka et al. |
| 8,324,184 B2 | 12/2012 | Prestwich et al. |
| 8,685,386 B2 | 4/2014 | West et al. |
| 8,753,884 B2 | 6/2014 | Cibelli et al. |
| 8,859,523 B2 | 10/2014 | Prestwich et al. |
| 8,927,279 B2 | 1/2015 | Jaenisch et al. |
| 9,732,128 B2 | 8/2017 | West et al. |
| 10,137,199 B2 | 11/2018 | Zarembinski et al. |
| 10,501,723 B2 | 12/2019 | West et al. |
| 2001/0012513 A1 | 8/2001 | Robl |
| 2002/0001842 A1 | 1/2002 | Chapman |
| 2002/0090722 A1 | 7/2002 | Dominko et al. |
| 2002/0142397 A1 | 10/2002 | Collas et al. |
| 2002/0183265 A1 | 12/2002 | Vogt et al. |
| 2003/0044976 A1 | 3/2003 | Dominko |
| 2003/0046722 A1 | 3/2003 | Collas et al. |
| 2003/0087877 A1 | 5/2003 | Calias et al. |
| 2003/0125782 A1 | 7/2003 | Streeter |
| 2003/0129745 A1 | 7/2003 | Robl et al. |
| 2003/0224345 A1 | 12/2003 | West et al. |
| 2003/0229908 A1 | 12/2003 | Cibelli et al. |
| 2003/0232430 A1 | 12/2003 | Cibelli et al. |
| 2004/0014206 A1 | 1/2004 | Robl et al. |
| 2004/0014210 A1 | 1/2004 | Jessell et al. |
| 2004/0072338 A1 | 4/2004 | Tsuzuki et al. |
| 2004/0091936 A1 | 5/2004 | West |
| 2004/0157328 A1 | 8/2004 | Tsuzuki et al. |
| 2004/0199935 A1 | 10/2004 | Chapman |
| 2004/0219563 A1 | 11/2004 | West et al. |
| 2005/0014258 A1 | 1/2005 | Collas et al. |
| 2005/0019865 A1 | 1/2005 | Kihm et al. |
| 2005/0054100 A1 | 3/2005 | Rennard et al. |
| 2005/0058629 A1 | 3/2005 | Harmon et al. |
| 2005/0074880 A1 | 4/2005 | Sang et al. |
| 2005/0153442 A1 | 7/2005 | Katz et al. |
| 2005/0175595 A1 | 8/2005 | Kukharchuk et al. |
| 2005/0176620 A1 | 8/2005 | Prestwich et al. |
| 2005/0181018 A1 | 8/2005 | Peyman |
| 2005/0273870 A1 | 12/2005 | Robl et al. |
| 2006/0008858 A1 | 1/2006 | Hall et al. |
| 2006/0051332 A1 | 3/2006 | Lanza |
| 2006/0073588 A1 | 4/2006 | Adkisson et al. |
| 2006/0147426 A1 | 7/2006 | Schiller et al. |
| 2006/0148078 A1 | 7/2006 | Gerecht-Nir et al. |
| 2006/0205674 A2 | 9/2006 | Satyam |
| 2006/0212952 A1 | 9/2006 | Collas et al. |
| 2006/0246446 A1 | 11/2006 | Evans et al. |
| 2006/0251642 A1 | 11/2006 | Wolfe et al. |
| 2007/0041955 A1 | 2/2007 | Warzecha |
| 2007/0042491 A1 | 2/2007 | Karp et al. |
| 2007/0128727 A1 | 6/2007 | Kraemer et al. |
| 2007/0190646 A1 | 8/2007 | Engler et al. |
| 2007/0248574 A1 | 10/2007 | Miller et al. |
| 2007/0259423 A1 | 11/2007 | Odorico et al. |
| 2008/0031962 A1 | 2/2008 | Boyan et al. |
| 2008/0070303 A1 | 3/2008 | West et al. |
| 2008/0076176 A1 | 3/2008 | Dominko |
| 2009/0029912 A1 | 1/2009 | Gronthos et al. |
| 2009/0047263 A1 | 2/2009 | Yamanaka |
| 2009/0081784 A1 | 3/2009 | Vodyanyk et al. |
| 2009/0117078 A1 | 5/2009 | Prestwich et al. |
| 2009/0117656 A1 | 5/2009 | Akashi et al. |
| 2009/0227032 A1 | 9/2009 | Yamanaka et al. |
| 2009/0246875 A1 | 10/2009 | Yamanaka et al. |
| 2009/0263896 A1 | 10/2009 | Kelly et al. |
| 2009/0271335 A1 | 10/2009 | West et al. |
| 2009/0280096 A1 | 11/2009 | Kubo et al. |
| 2009/0304654 A1 | 12/2009 | Lue et al. |
| 2010/0062533 A1 | 3/2010 | Yamanaka |
| 2010/0119490 A1 | 5/2010 | Yoon et al. |
| 2010/0150876 A1 | 6/2010 | Verfaillie et al. |
| 2010/0167404 A1 | 7/2010 | West et al. |
| 2010/0183620 A1 | 7/2010 | Bhawe et al. |
| 2010/0184033 A1* | 7/2010 | West .................. C12N 5/0606 435/6.16 |
| 2010/0203021 A1 | 8/2010 | Goumans et al. |
| 2010/0210014 A1 | 8/2010 | Yamanaka |
| 2010/0216236 A1 | 8/2010 | Yamanaka |
| 2010/0261274 A1 | 10/2010 | Vodyanyk et al. |
| 2010/0279404 A1 | 11/2010 | Yamanaka et al. |
| 2011/0110899 A1 | 5/2011 | Shi et al. |
| 2011/0143441 A1 | 6/2011 | West et al. |
| 2011/0190730 A1 | 8/2011 | Kirkland et al. |
| 2011/0223669 A1 | 9/2011 | Yamanaka et al. |
| 2011/0250692 A1 | 10/2011 | Yamanaka et al. |
| 2011/0274666 A1 | 11/2011 | Turner et al. |
| 2012/0171171 A1 | 7/2012 | West et al. |
| 2012/0278911 A1 | 11/2012 | Choi et al. |
| 2013/0011918 A1 | 1/2013 | West et al. |
| 2013/0115673 A1 | 5/2013 | West et al. |
| 2014/0178988 A1 | 6/2014 | West et al. |
| 2014/0178994 A1 | 6/2014 | West et al. |
| 2014/0248700 A1 | 9/2014 | Cibelli et al. |
| 2014/0349396 A1 | 11/2014 | West et al. |
| 2015/0005234 A1 | 1/2015 | Govil |
| 2015/0275177 A1 | 10/2015 | West et al. |
| 2016/0369237 A1 | 12/2016 | West et al. |
| 2017/0335392 A1 | 11/2017 | West et al. |
| 2018/0135018 A1 | 5/2018 | West et al. |
| 2018/0170982 A1 | 6/2018 | West et al. |
| 2018/0325958 A1 | 11/2018 | Binette et al. |
| 2018/0369391 A1 | 12/2018 | Onorato |

(56) References Cited

U.S. PATENT DOCUMENTS

| | | |
|---|---|---|
| 2019/0241867 A1 | 8/2019 | West et al. |
| 2019/0282699 A1 | 9/2019 | Zarembinski et al. |

FOREIGN PATENT DOCUMENTS

| | | |
|---|---|---|
| EP | 1391503 A1 | 2/2004 |
| EP | 1970446 A1 | 9/2008 |
| EP | 2202309 A1 | 6/2010 |
| EP | 2419511 A1 | 2/2012 |
| EP | 2734617 A1 | 5/2014 |
| EP | 2888286 A1 | 7/2015 |
| EP | 2917350 A1 | 9/2015 |
| JP | 63-44526 | 2/1988 |
| JP | 2004-033135 A | 2/2004 |
| JP | 2004-513071 A | 4/2004 |
| JP | 2004-141053 A | 5/2004 |
| WO | WO-94/10292 A1 | 5/1994 |
| WO | WO-96/33750 A1 | 10/1996 |
| WO | WO-97/35967 A2 | 10/1997 |
| WO | WO-98/07841 A1 | 2/1998 |
| WO | WO-98/22114 A1 | 5/1998 |
| WO | WO-98/30683 A2 | 7/1998 |
| WO | WO-99/01163 A1 | 1/1999 |
| WO | WO-99/05266 A2 | 2/1999 |
| WO | WO-99/16864 A1 | 4/1999 |
| WO | WO-99/20741 A1 | 4/1999 |
| WO | WO-99/45100 A1 | 9/1999 |
| WO | WO-99/53022 A2 | 10/1999 |
| WO | WO-00/16818 A1 | 3/2000 |
| WO | WO-00/47720 A2 | 8/2000 |
| WO | WO-00/65137 A1 | 11/2000 |
| WO | WO-00/78929 A1 | 12/2000 |
| WO | WO-01/00650 A1 | 1/2001 |
| WO | WO-01/19977 A1 | 3/2001 |
| WO | WO-01/26454 A1 | 4/2001 |
| WO | WO-01/30978 A1 | 5/2001 |
| WO | WO-01/39784 A1 | 6/2001 |
| WO | WO-01/46401 A1 | 6/2001 |
| WO | WO-01/82991 A2 | 11/2001 |
| WO | WO-01/93846 A2 | 12/2001 |
| WO | WO-02/06373 A1 | 1/2002 |
| WO | WO-02/41877 A1 | 5/2002 |
| WO | WO-02/090390 A1 | 11/2002 |
| WO | WO-02/097065 A2 | 12/2002 |
| WO | WO-03/018767 A2 | 3/2003 |
| WO | WO-03/018780 A1 | 3/2003 |
| WO | WO-03/046141 A2 | 6/2003 |
| WO | WO-03/053489 A2 | 7/2003 |
| WO | WO-03/057836 A2 | 7/2003 |
| WO | WO-03/074654 A2 | 9/2003 |
| WO | WO-03/100011 A2 | 12/2003 |
| WO | WO-2004/037164 A2 | 5/2004 |
| WO | WO-2005/049788 A2 | 6/2005 |
| WO | WO-2005/068610 A1 | 7/2005 |
| WO | WO-2006/052646 A2 | 5/2006 |
| WO | WO-2006/071773 A2 | 7/2006 |
| WO | WO-2006/112684 A1 | 10/2006 |
| WO | WO-2006/113407 A2 | 10/2006 |
| WO | WO-2006/130504 A2 | 12/2006 |
| WO | WO-2006/138552 A2 | 12/2006 |
| WO | WO-2007/019398 A1 | 2/2007 |
| WO | WO-2007/026255 A2 | 3/2007 |
| WO | WO-2007/047894 A2 | 4/2007 |
| WO | WO-2007/058671 A1 | 5/2007 |
| WO | WO-2007/062198 A1 | 5/2007 |
| WO | WO-2007/115337 A2 | 10/2007 |
| WO | WO-2008/023026 A2 | 2/2008 |
| WO | WO-2008/103462 A2 | 8/2008 |
| WO | WO-2008/156685 A2 | 12/2008 |
| WO | WO-2009/101407 A2 | 8/2009 |
| WO | WO-2009/102452 A2 | 8/2009 |
| WO | WO-2009/133971 A1 | 11/2009 |
| WO | WO-2009/157593 A1 | 12/2009 |
| WO | WO-2010/033906 A2 | 3/2010 |
| WO | WO-2010/050626 A1 | 5/2010 |
| WO | WO-2010/137746 A1 | 12/2010 |
| WO | WO-2011/009106 A2 | 1/2011 |
| WO | WO-2011/016588 A1 | 2/2011 |
| WO | WO-2011/103343 A2 | 8/2011 |
| WO | WO-2013/10045 A1 | 1/2013 |
| WO | WO-2013/169202 A1 | 11/2013 |

OTHER PUBLICATIONS

Toh Wei Seong (PhD Thesis. Feb. 26, 2010. National University of Singapore. "Differentiation and Derivation of Lineage-Committed Chondroprogenitors and Chondrogenic cells from Human Embryonic Stem Cells for Cartilage Tissue Engineering and Regeneration"). (Year: 2010).*
Tang et al. (Expert Opin. Biol. Ther. 2009; 9(6): 689-701). (Year: 2009).*
West et al. (Regen. Med. (2008) 3(3), 287-308). (Year: 2008).*
Estes et al. (Arthritis & Rheumatism vol. 54, No. 4, Apr. 2006, pp. 1222-1232). (Year: 2006).*
Gilbert, S.F., *Developmental Biology*, $10^{th}$ edition, Sinauer Associates, Inc., Sunderland, MA, 2014, pp. 490-491.
Merriam-Webster online dictionary, full definition of "minimize," available online at www.merriam-webster.com/dictionary/minimize.
U.S. Appl. No. 12/234,445, filed Sep. 19, 2008, U.S. Pat. No. 8,859,523, Issued.
U.S. Appl. No. 12/244,135, filed Oct. 2, 2008, U.S. Pat. No. 7,928,069, Issued.
U.S. Appl. No. 10/581,571, filed Jul. 13, 2007, U.S. Pat. No. 7,981,871, Issued.
U.S. Appl. No. 13/184,401, filed Jul. 15, 2011, U.S. Pat. No. 8,691,793, Issued.
U.S. Appl. No. 14/525,378, filed Oct. 28, 2014, U.S. Pat. No. 10,501,723, Issued.
U.S. Appl. No. 12/152,779, filed May 16, 2008, U.S. Pat. No. 8,753,884, Issued.
U.S. Appl. No. 14/272,365, filed May 7, 2014, 2014-0248700, Abandoned.
U.S. Appl. No. 11/604,047, filed Nov. 21, 2006, 2008-0070303, Abandoned.
U.S. Appl. No. 15/247,786, filed Aug. 25, 2016, 2016-0369237, Published.
U.S. Appl. No. 12/501,630, filed Jul. 16, 2009, 2010-0184033, Published.
U.S. Appl. No. 13/384,289, filed Mar. 16, 2012, U.S. Pat. No. 8,685,386, Issued.
U.S. Appl. No. 14/172,765, filed Feb. 4, 2014, 2014-0178994, Published.
U.S. Appl. No. 13/683,241, filed Nov. 21, 2012, 2013-0115673, Abandoned.
U.S. Appl. No. 15/846,181, filed Dec. 18, 2017, 2019-0241867, Published.
U.S. Appl. No. 09/635,370, filed Aug. 9, 2000, U.S. Pat. No. 6,946,293, Issued.
U.S. Appl. No. 09/724,632, filed Nov. 28, 2000, U.S. Pat. No. 6,610,535, Issued.
U.S. Appl. No. 14/238,160, filed Apr. 29, 2014, 2014-0349396, Published.
U.S. Appl. No. 14/048,910, filed Oct. 8, 2013, 2014-0178988, Abandoned.
U.S. Appl. No. 15/620,287, filed Jun. 12, 2017, 2018-0135018, Published.
U.S. Appl. No. 14/275,795, filed May 12, 2014, U.S. Pat. No. 10,137,199, Issued.
U.S. Appl. No. 16/164,413, filed Oct. 18, 2018, 2019-0282699, Published.
U.S. Appl. No. 14/820,497, filed Aug. 6, 2015, 2018-036391, Published.
U.S. Appl. No. 15/834,242, filed Dec. 7, 2017, 2018-0325958, Published.
U.S. Appl. No. 13/579,875, filed Feb. 17, 2011, 2013-0011918, Abandoned.

(56) References Cited

OTHER PUBLICATIONS

U.S. Appl. No. 14/876,779, filed Oct. 6, 2015, Abandoned.
U.S. Appl. No. 15/162,543, filed May 23, 2016, 2017-0335392, Published.
U.S. Appl. No. 13/279,123, filed Oct. 21, 2011, U.S. Pat. No. 9,732,128, Issued.
U.S. Appl. No. 15/647,687, filed Jul. 12, 2017, 2018-0170982, Published.
U.S. Appl. No. 16/708,725, filed Dec. 10, 2019, Pending.
Agren et al., Developmentally programmed expression of hyaluronan in human skin and its appendages. J Invest Dermatol. Aug. 1997;109(2):21924.
Ahlgren et al., The morphogenesis of the pancreatic mesenchyme is uncoupled from that of the pancreatic epithelium in IPF1/PDX1deficient mice. Development. May 1996;122(5):140916.
Akita et al., Leukemia inhibitory factor-transfected embryonic fibroblasts and vascular endothelial growth factor successfully improve the skin substitute wound healing by increasing angiogenesis and matrix production. J Dermatol Sci. Oct. 2004;36(1):11-23.
Amabile et al., Induced pluripotent stem cells: current progress and potential for regenerative medicine. Trends Mol Med. Feb. 2009;15(2):59-68.
Ancey et al., Secretion of IL-6, IL-11 and LIF by human cardiomyocytes in primary culture. Cytokine. May 21, 2002;18(4):199-205.
Anzai et al., Self-renewal and differentiation of a basic fibroblast growth factor-dependent multipotent hematopoietic cell line derived from embryonic stem cells. Dev Growth Differ. Feb. 1999;41(1):51-8.
Apelqvist et al., Sonic hedgehog directs specialised mesoderm differentiation in the intestine and pancreas. Curr Biol. Oct. 1, 1997;7(10):801-4.
Arnold et al., Evaluation of resorbable barriers for preventing surgical adhesions. Fertil Steril. Jan. 2000;73(1):157-61.
Asada et al., Identification of alpha- and beta-cells in intact isolated islets of Langerhans by their characteristic cytoplasmic Ca2+ concentration dynamics and immunocytochemical staining. Diabetes. May 1998;47(5):751-7.
Assady et al., Insulin production by human embryonic stem cells. Diabetes. Aug. 2001;50(8):1691-7.
Assou et al., A gene expression signature shared by human mature oocytes and embryonic stem cells. BMC Genomics. Jan. 8, 2009;10:10. 15 pages.
ATCC Receipt for Budapest Restricted Certificate of Deposit. 1 page, Mar. 16, 2012.
ATCC Receipt for Budapest Restricted Certificate of Deposit. 2 page, Jan. 28, 2013.
Bahney et al., A bioresponsive hydrogel tuned to chondrogenesis of human mesenchymal stem cells. FASEB J. May 2011;25(5):1486-96.
Ballatori et al., Glutathione dysregulation and the etiology and progression of human diseases. Biol Chem. Mar. 2009;390(3):191-214.
Ballios et al., A hydrogel-based stem cell delivery system to treat retinal degenerative diseases. Biomaterials. Mar. 2010;31(9):2555-64.
Bara et al., Concise review: Bone marrow-derived mesenchymal stem cells change phenotype following in vitro culture: implications for basic research and the clinic. Stem Cells. Jul. 2014;32(7):1713-23.
Bellis, Advantages of RGD peptides for directing cell association with biomaterials. Biomaterials. Jun. 2011;32(18):4205-10.
Benesch et al., Thiolation of Proteins. Proc Natl Acad Sci U S A. Sep. 15, 1958;44(9):848-53.
Bensley, Studies on the pancreas of the guinea pig. Amer J Anat. Nov. 1911;12(3):297-388.
Bhang et al., Efficacious and clinically relevant conditioned medium of human adipose-derived stem cells for therapeutic angiogenesis. Mol Ther. Apr. 2014;22(4):862-72.
Bhattacharya et al., Comparison of the gene expression profile of undifferentiated human embryonic stem cell lines and differentiating embryoid bodies. BMC Dev Biol. Oct. 5, 2005;5:22, 16 pages.
Bibikova et al., Human embryonic stem cells have a unique epigenetic signature. Genome Res. Sep. 2006;16(9):1075-83.
Binello et al., Stem cells as therapeutic vehicles for the treatment of high-grade gliomas. Neuro Oncol. Mar. 2012;14(3):256-65.
Boheler et al., Differentiation of pluripotent embryonic stem cells into cardiomyocytes. Circ Res. Aug. 9, 2002;91(3):189-201.
Bongso et al., Isolation and culture of inner cell mass cells from human blastocysts. Hum Reprod. Nov. 1994;9(11):2110-7.
Bonner-Weir et al., A second pathway for regeneration of adult exocrine and endocrine pancreas. A possible recapitulation of embryonic development. Diabetes. Dec. 1993;42(12):1715-20.
Bonner-Weir et al., in vitro cultivation of human islets from expanded ductal tissue. Proc Natl Acad Sci U S A. Jul. 5, 2000;97(14):7999-8004.
Borsani et al., EYA4, a novel vertebrate gene related to Drosophila eyes absent. Hum Mol Genet. Jan. 1999;8(1):11-23.
Bosco et al., Homologous but not heterologous contact increases the insulin secretion of individual pancreatic B-cells. Exp Cell Res. Sep. 1989;184(1):72-80.
Boxall et al., Markers for characterization of bone marrow multipotential stromal cells. Stem Cells Int. 2012;2012:975871.
Boyce et al., Comparative assessment of cultured skin substitutes and native skin autograft for treatment of full-thickness burns. Ann Surg. Dec. 1995;222(6):743-52.
Boyce et al., Hyaluronic acid induces tumour necrosis factor-alpha production by human macrophages in vitro. Br J Plast Surg. Jul. 1997;50(5):362-8.
Boyce et al., Reduced wound contraction after grafting of full-thickness burns with a collagen and chondroitin-6-sulfate (Gag) dermal skin substitute and coverage with biobrane. J Burn Care Rehabil. Jul.-Aug. 1988;9(4):364-70.
Boyce et al., Skin anatomy and antigen expression after burn wound closure with composite grafts of cultured skin cells and biopolymers. Plast Reconstr Surg. Apr. 1993;91(4):632-41.
Boyer et al., Isolation of endothelial cells and their progenitor cells from human peripheral blood. J Vasc Surg. Jan. 2000;31(1 Pt 1):181-9.
Brady et al., Analysis of gene expression in a complex differentiation hierarchy by global amplification of cDNA from single cells. Curr Biol. Aug. 1, 1995;5(8):909-22.
Brons et al., Glucocorticoids stimulate the division of rat pancreatic islet tumour cells in tissue culture. Diabetologia. Nov. 1984;27(5):540-4.
Brown et al., Absorption of hyaluronan applied to the surface of intact skin. J Invest Dermatol. Nov. 1999;113(5):740-6.
Aigner et al., Cartilage tissue engineering with novel nonwoven structured biomaterial based on hyaluronic acid benzyl ester. J Biomed Mater Res. Nov. 1998;42(2):172-81.
Alberio et al., Differential nuclear remodeling of mammalian somatic cells by Xenopus laevis oocyte and egg cytoplasm. Exp Cell Res. Jul. 1, 2005;307(1):131-41.
Almquist et al., Synthesis and biological activity of a ketomethylene analogue of a tripeptide inhibitor of angiotensin converting enzyme. J Med Chem. Dec. 1980;23(12):1392-8.
Ambrosi et al., Genome-wide reprogramming in hybrids of somatic cells and embryonic stem cells. Stem Cells. May 2007;25(5):1104-13.
Ambrosi et al., Reprogramming mediated by stem cell fusion. J Cell Mol Med. Apr.-Jun. 2005;9(2):320-30.
Amit et al., Clonally derived human embryonic stem cell lines maintain pluripotency and proliferative potential for prolonged periods of culture. Dev Biol. Nov. 15, 2000;227(2):271-8.
Anokye-Danso et al., Highly efficient mIRNA-mediated reprogramming of mouse and human somatic cells to pluripotency. Cell Stem Cell. Apr. 8, 2011;8(4):376-88.
Anseth et al., In situ forming degradable networks and their application in tissue engineering and drug delivery. J Control Release. Jan. 17, 2002;78(1-3):199-209.
Anthony-Cahill et al., Site-specific mutagenesis with unnatural amino acids. Trends Biochem Sci. Oct. 1989;14(10):400-3.

(56) References Cited

OTHER PUBLICATIONS

Bain et al., Embryonic stem cells express neuronal properties in vitro. Dev Biol. Apr. 1995;168(2):342-57.
Barbucci et al., Synthesis, chemical and rheological characterization of new hyaluronic acid-based hydrogels. J Biomater Sci Polym Ed. 2000;11(4):383-99.
Belluco et al., Prevention of postsurgical adhesions with an autocrosslinked hyaluronan derivative gel. J Surg Res. Oct. 2001;100(2):217-21.
Benedetti et al., Biocompatibility and biodegradation of different hyaluronan derivatives (Hyaff) implanted in rats. Biomaterials. Dec. 1993;14(15):1154-60.
Benedetti et al., Microspheres of hyaluronic acid esters—Fabrication methods and in vitro hydrocortisone release. Journal of Controlled Release. Jul. 1990;13(1):33-41.
Benner, Expanding the genetic lexicon: incorporating non-standard amino acids into proteins by ribosome-based synthesis. Trends Biotechnol. May 1994;12(5):158-63.
Betts et al., Reprogramming of telomerase activity and rebuilding of telomere length in cloned cattle. Proc Natl Acad Sci U S A. Jan. 30, 2001;98(3):1077-82.
Binet et al., WNT16B is a new marker of cellular senescence that regulates p53 activity and the phosphoinositide 3-kinase/AKT pathway. Cancer Res. Dec. 15, 2009;69(24):9183-91.
Bitter et al., A modified uronic acid carbazole reaction. Anal Biochem. Oct. 1962;4:330-4.
Bocchetta et al., The SV40 large T antigen-p53 complexes bind and activate the insulin-like growth factor-I promoter stimulating cell growth. Cancer Res. Feb. 15, 2008;68(4):1022-9.
Bodnar et al., Extension of life-span by introduction of telomerase into normal human cells. Science. Jan. 16, 1998;279(5349):349-52.
Bonilla-Claudio et al., Bmp signaling regulates a dose-dependent transcriptional program to control facial skeletal development. Development. Feb. 2012;139(4):709-19.
Brown et al., Alterations in chondrocyte cytoskeletal architecture during phenotypic modulation by retinoic acid and dihydrocytochalasin B-induced reexpression. J Cell Biol. Jan. 1988;106(1):171-9.
Brown et al., Enhancement of wound healing by topical treatment with epidermal growth factor. N Engl J Med. Jul. 13, 1989;321(2):76-9.
Brun et al., In vitro reconstructed tissues on hyaluronan-based temporary scaffolding. J Mater Sci Mater Med. Oct.-Nov. 1999;10(10/11):683-8.
Bryant et al., The effects of scaffold thickness on tissue engineered cartilage in photocrosslinked poly(ethylene oxide) hydrogels. Biomaterials. Mar. 2001;22(6):619-26.
Bulpitt et al., New strategy for chemical modification of hyaluronic acid: preparation of functionalized derivatives and their use in the formation of novel biocompatible hydrogels. J Biomed Mater Res. Nov. 1999;47(2):152-69.
Burdick et al., Photoencapsulation of osteoblasts in injectable RGD-modified PEG hydrogels for bone tissue engineering. Biomaterials. Nov. 2002;23(22):4315-23.
Burns et al., Prevention of tissue injury and postsurgical adhesions by precoating tissues with hyaluronic acid solutions. J Surg Res. Dec. 1995;59(6):644-52.
Butterworth et al., A modification of the Ellman procedure for the estimation of protein sulfhydryl groups. Arch Biochem Biophys. Mar. 20, 1967;118(3):716-23.
Byrne et al., Nuclei of adult mammalian somatic cells are directly reprogrammed to oct-4 stem cell gene expression by amphibian oocytes. Curr Biol. Jul. 15, 2003;13(14):1206-13.
Campbell et al., Nuclear equivalence, nuclear transfer, and the cell cycle. Cloning. 1999;1(1):3-15.
Campbell et al., Nuclear transfer in practice. Cloning Stem Cells. 2001;3(4):201-8.
Campoccia et al., Quantitative assessment of the tissue response to films of hyaluronan derivatives. Biomaterials. May 1996;17(10):963-75.
Cao et al., Comparative study of the use of poly(glycolic acid), calcium alginate and pluronics in the engineering of autologous porcine cartilage. J Biomater Sci Polym Ed. 1998;9(5):475-87.
Casabona et al., Prefabricated engineered bone flaps: an experimental model of tissue reconstruction in plastic surgery. Plast Reconstr Surg. Mar. 1998;101(3):577-81.
Cauffman et al., Oct-4 mRNA and protein expression during human preimplantation development. Mol Hum Reprod. Mar. 2005;11(3):173-81.
Cawthon et al., Association between telomere length in blood and mortality in people aged 60 years or older. Lancet. Feb. 1, 2003;361(9355):393-5.
Chen et al., Embryonic stem cells generated by nuclear transfer of human somatic nuclei into rabbit oocytes. Cell Res. Aug. 2003;13(4):251-63.
Chen et al., Multilineage differentiation of rhesus monkey embryonic stem cells in three-dimensional culture systems. Stem Cells. 2003;21(3):281-95.
Chen et al., Photoimmobilization of sulfated hyaluronic acid for antithrombogenicity. Bioconjug Chem. Sep.-Oct. 1997;8(5):730-4.
Chiu et al., Differential expression of telomerase activity in hematopoietic progenitors from adult human bone marrow. Stem Cells. Mar. 1996;14(2):239-48.
Choi et al., Studies on gelatin-containing artificial skin: II. Preparation and characterization of cross-linked gelatin-hyaluronate sponge. J Biomed Mater Res. 1999;48(5):631-9.
Clark et al., Gene targeting in livestock: a preview. Transgenic Res. 2000;9(4-5):263-75.
Cohen et al., Induced differentiation in HT29, a human colon adenocarcinoma cell line. J Cell Sci. Aug. 1999;112 (Pt 16):2657-66.
Collas et al., On the way to reprogramming cells to pluripotency using cell-free extracts. Reprod Biomed Online. Jun. 2006;12(6):762-70.
Collas, Nuclear reprogramming in cell-free extracts. Philos Trans R Soc Lond B Biol Sci. Aug. 29, 2003;358(1436):1389-95.
Cooper et al., The effect of an arginine-glycine-aspartic acid peptide and hyaluronate synthetic matrix on epithelialization of meshed skin graft interstices. J Burn Care Rehabil. Mar.-Apr. 1996;17(2):108-16.
Cowan et al., Nuclear reprogramming of somatic cells after fusion with human embryonic stem cells. Science. Aug. 26, 2005;309(5739):1369-73.
Cram et al., Human skin storage techniques: a study utilizing a nude mouse recipient. J Trauma. Oct. 1983;23(10):924-6.
Cruise et al., A sensitivity study of the key parameters in the interfacial photopolymerization of poly(ethylene glycol) diacrylate upon porcine islets. Biotechnol Bioeng. Mar. 20, 1998;57(6):655-65.
Day et al., (Feb. 15, 2002, e-published Nov. 20, 2001). Hyaluronan-binding proteins: tying up the giant. J Biol Chem. 277(7):4585-8.
Day et al., Hyaluronan: polysaccharide chaos to protein organisation. Curr Opin Struct Biol. Oct. 2001;11(5):617-22.
Deng et al., Fibroblast growth factor receptor-1 (FGFR-1) is essential for normal neural tube and limb development. Dev Biol. May 1, 1997;185(1):42-54.
Denning et al., Gene targeting in primary fetal fibroblasts from sheep and pig. Cloning Stem Cells. 2001;3(4):221-31.
Dimitrov et al., Remodeling somatic nuclei in Xenopus laevis egg extracts: molecular mechanisms for the selective release of histones H1 and H1(0) from chromatin and the acquisition of transcriptional competence. EMBO J. Nov. 1, 1996;15(21):5897-906.
Dizerega et al., Peritoneal repair and post-surgical adhesion formation. Hum Reprod Update. Nov.-Dec. 2001;7(6):547-55.
Djuric et al., Epigenetics of induced pluripotency, the seven-headed dragon. Stem Cell Res Ther. Mar. 15, 2010;1(1):3.
Do et al., Nuclei of embryonic stem cells reprogram somatic cells. Stem Cells. 2004;22(6):941-9.
Dominko et al., Bovine oocyte cytoplasm supports development of embryos produced by nuclear transfer of somatic cell nuclei from various mammalian species. Biol Reprod. Jun. 1999;60(6):1496-502.
Duray et al., Tissue culture in microgravity. Sci Med (Phila). May-Jun. 1997;4(3):46-55.

(56) References Cited

OTHER PUBLICATIONS

Dyson et al., Effects of buried charged groups on cysteine thiol ionization and reactivity in *Escherichia coli* thioredoxin: structural and functional characterization of mutants of Asp 26 and Lys 57. Biochemistry. Mar. 4, 1997;36(9):2622-36.

Elbert et al., Conjugate addition reactions combined with free-radical cross-linking for the design of materials for tissue engineering. Biomacromolecules. 2001 Summer;2(2):430-41.

Elisseeff et al., Photoencapsulation of chondrocytes in poly(ethylene oxide)-based semi-interpenetrating networks. J Biomed Mater Res. Aug. 2000;51(2):164-71.

Ellman, A colorimetric method for determining low concentrations of mercaptans. Arch Biochem Biophys. Apr. 1958;74(2):443-50.

Entwistle et al., HA receptors: regulators of signalling to the cytoskeleton. J Cell Biochem. Jun. 15, 1996;61(4):569-77.

Feinberg et al., Hyaluronate in vasculogenesis. Science. Jun. 10, 1983;220(4602):1177-9.

Foschi et al., Hyaluronic acid prevents oxygen free-radical damage to granulation tissue: a study in rats. Int J Tissue React. 1990;12(6):333-9.

Frampton, Hylan G-F 20 single-injection formulation. Drugs Aging. Jan. 1, 2010;27(1):77-85.

Fraser et al., Hyaluronan: its nature, distribution, functions and turnover. J Intern Med. Jul. 1997;242(1):27-33.

Fratianne et al., Keratinocyte allografts accelerate healing of split-thickness donor sites: applications for improved treatment of burns. J Burn Care Rehabil. Mar.-Apr. 1993;14(2 Pt 1):148-54.

Friedman et al., Relative Nucleophilic Reactivities of Amino Groups and Mercaptide Ions in Addition Reactions with a,beta-Unsaturated Compounds. J Am Chem Soc. 1965;87(16):3672-82.

Fulka et al., Nucleus transfer in mammals: how the oocyte cytoplasm modifies the transferred nucleus. Theriogenology. Apr. 1, 2001;55(6):1373-80.

Gallicchio et al., Suppression of Hematopoietic Support Function is Associate with Over-Expression of IL-4 and TGFbeta1 in LP-BM5 MuLV Infected Stromal Cell Lines. Antiviral Research. 1995;26(3):A273.

Ghofrani et al., The influence of systemic growth hormone administration on the healing time of skin graft donor sites in a pig model. Plast Reconstr Surg. Aug. 1999;104(2):470-5.

Gibbs et al., Evolutionary and biomedical insights from the rhesus macaque genome. Science. Apr. 13, 2007;316(5822):222-34.

Gibran et al., Basic fibroblast growth factor in the early human burn wound. J Surg Res. Mar. 1994;56(3):226-34.

Glass et al., Characterization of a hyaluronic acid-Arg-Gly-Asp peptide cell attachment matrix. Biomaterials. Jun. 1996;17(11):1101-8.

Gospodarowicz et al., Fibroblast growth factor: structural and biological properties. J Cell Physiol Suppl. 1987;Suppl 5:15-26.

Gowland et al., Marked Enhanced Efficacy of Cyclosporin When Combined with Hyaluronic Acid. Clinical Drug Investigation. 1996;11:245-50.

Hakelien et al., Novel approaches to transdifferentiation. Cloning Stem Cells. 2002;4(4):379-87.

Hamano et al., Functional studies on B cell hybridomas with B cell surface antigens. IV. Direct effects of cytochalasin B on differentiation. J Immunol. Jan. 1984;132(1):122-8.

Hann et al., On the double bond isostere of the peptide bond: preparation of an enkephalin analogue. Journal of the Chemical Society, Perkin Transactions 1. 1982;1:307-14.

Hanthamrongwit et al., Chondroitin-6-sulphate incorporated into collagen gels for the growth of human keratinocytes: the effect of cross-linking agents and diamines. Biomaterials. Apr. 1996;17(8):775-80.

Harris et al., Use of hyaluronic acid and cultured autologous keratinocytes and fibroblasts in extensive burns. Lancet. Jan. 2, 1999;353(9146):35-6.

Haynes et al., The effects of cytochalasin B and colchicine on cell motility and ultrastructure in primary cultures of malignant gliomas. Acta Neuropathol. Oct. 13, 1978;44(1):21-30.

Hebda et al., Basic fibroblast growth factor stimulation of epidermal wound healing in pigs. J Invest Dermatol. Dec. 1990;95(6):626-31.

Hemmrich et al., Implantation of preadipocyte-loaded hyaluronic acid-based scaffolds into nude mice to evaluate potential for soft tissue engineering. Biomaterials. Dec. 2005;26(34):7025-37.

Heo et al., Spontaneous differentiation of mouse embryonic stem cells in vitro: characterization by global gene expression profiles. Biochem Biophys Res Commun. Jul. 15, 2005;332(4):1061-9.

Holladay et al., Synthesis of hydroxyethylene and ketomethylene dipeptide isosteres. Tetrahedron Letters. 1983;24(41):4401-4.

Hong et al., Study on gelatin-containing artificial skin IV: A comparative study on the effect of antibiotic and EGF on cell proliferation during epidermal healing. Biomaterials. Oct. 2001;22(20):2777-83.

Hooker et al., Prevention of adhesion formation with use of sodium hyaluronate-based bioresorbable membrane in a rat model of ventral hernia repair with polypropylene mesh—a randomized, controlled study. Surgery. Feb. 1999;125(2):211-6.

Houlihan et al., The relative solution and interfacial hydrophobicity of ethylene oxide-propylene oxide-ethylene oxide block copolymers. Colloids and Surfaces. Dec. 11, 1992;69(2-3):147-53.

Hruby, Conformational restrictions of biologically active peptides via amino acid side chain groups. Life Sci. Jul. 19, 1982;31(3):189-99.

Hu et al., Improvement of Schwann cell attachment and proliferation on modified hyaluronic acid strands by polylysine. Tissue Eng. Dec. 2000;6(6):585-93.

Hu et al., Polypeptide resurfacing method improves fibroblasts adhesion to hyaluronan strands. J Biomed Mater Res. Oct. 1999;47(1):79-84.

Huang-Lee et al., Effects of hyaluronan on collagen fibrillar matrix contraction by fibroblasts. J Biomed Mater Res. Jan. 1994;28(1):123-32.

Hubbell et al., Biomaterials in tissue engineering. Biotechnology (N Y). Jun. 1995;13(6):565-76.

Hudson et al., Methionine enkephalin and isosteric analogues. I. Synthesis on a phenolic resin support. Int J Pept Protein Res. 1979;14(3):177-85.

Human Protein Atlas, EYA4 expression across different tissues. Retrieved online at: http://www.proteinatlas.org/ENSG00000112319-EYA4/tissue. Web. Jul. 24, 2020. 4 pages.

Ibba et al., Towards engineering proteins by site-directed incorporation in vivo of non-natural amino acids. Biotechnology (N Y). Jul. 1994;12(7):678-82.

Iio et al., Cell growth on poly(vinyl alcohol) hydrogel membranes containing biguanido groups. J Biomed Mater Res. Apr. 1994;28(4):459-62.

Ikada et al., Protein release from gelatin matrices. Adv Drug Deliv Rev. May 4, 1998;31(3):287-301.

Illum et al., Hyaluronic acid ester microspheres as a nasal delivery system for insulin. Journal of Controlled Release. Feb. 1994;29(1-2);133-41.

Ishikawa et al., Novel [2,3]-sigmatropic rearrangement for carbon-nitrogen bond formation. J Am Chem Soc. Aug. 8, 2001;123(31):7734-5.

Jackson et al., Paclitaxel-loaded crosslinked hyaluronic acid films for the prevention of postsurgical adhesions. Pharm Res. Apr. 2002;19(4):411-7.

Jaeger et al., Predicting optimal and suboptimal secondary structure for RNA. Methods Enzymol. 1990;183:281-306.

Jennings-White et al., Synthesis of ketomethylene analogs of dipeptides. Tetrahedron Letters. 1982;23(25):2533-4.

Jeong et al., Thermoreversible Gelation of PEG-PLGA-PEG Triblock Copolymer Aqueous Solutions. Macromolecules. 1999;32(21):7064-9.

Jiang et al., Polyanion/gelatin complexes as pH-sensitive gels for controlled protein release. J Appl Polym Sci. 2001;80:1416-25.

Jones et al., Multivalent poly(ethylene glycol)-containing conjugates for in vivo antibody suppression. Bioconjug Chem. Nov.-Dec. 2003;14(6):1067-76.

Keller et al., Preparation and some properties of maleimido acids and maleoyl derivatives of peptides. Helv Chim Acta. Mar. 12, 1975;58(2):531-41.

(56) References Cited

OTHER PUBLICATIONS

King et al., Development and in vitro characterization of vascular endothelial growth factor (VEGF)-loaded poly(DL-lactic-co-glycolic acid)/poly(ethylene glycol) microspheres using a solid encapsulation/single emulsion/solvent extraction technique. J Biomed Mater Res. Sep. 5, 2000;51(3):383-90.

Kirazov et al., Ontogenetic changes in protein level of amyloid precursor protein (APP) in growth cones and synaptosomes from rat brain and prenatal expression pattern of APP mRNA isoforms in developing rat embryo. Int J Dev Neurosci. Jun. 2001;19(3):287-96.

Kirker et al., Glycosaminoglycan hydrogel films as bio-interactive dressings for wound healing. Biomaterials. Sep. 2002;23(17):3661-71.

Kirker et al., Glycosaminoglycan hydrogels as supplemental wound dressings for donor sites. J Burn Care Rehabil. May-Jun. 2004;25(3):276-86.

Knudson et al., Cartilage proteoglycans. Semin Cell Dev Biol. Apr. 2001;12(2):69-78.

Kortemme et al., Ionisation of cysteine residues at the termini of model alpha-helical peptides. Relevance to unusual thiol pKa values in proteins of the thioredoxin family. J Mol Biol. Nov. 10, 1995;253(5):799-812.

Koyano et al., Attachment and growth of cultured fibroblast cells on PVA/chitosan-blended hydrogels. J Biomed Mater Res. Mar. 5, 1998;39(3):486-90.

Krejci et al., In vitro reconstitution of skin: fibroblasts facilitate keratinocyte growth and differentiation on acellular reticular dermis. J Invest Dermatol. Nov. 1991;97(5):843-8.

Kuhl et al., Tethered epidermal growth factor as a paradigm for growth factor-induced stimulation from the solid phase. Nat Med. Sep. 1996;2(9):1022-7.

Kuo et al., Chemical modification of hyaluronic acid by carbodiimides. Bioconjug Chem. Jul.-Aug. 1991;2(4):232-41.

Kure-Bayashi et al., Successful implantation of in vitro-matured, electro-activated oocytes in the pig. Theriogenology. Mar. 15, 2000;53(5):1105-19.

Kwon et al., Production of Live Young by Serial Nuclear Tranfer with Mitotic Stages of Donor Nuclei in Mice. J Reproduct Dev. 1997;43(1):25-31.

Langer, Biomaterials in drug delivery and tissue engineering: one laboratorys experience. Acc Chem Res. Feb. 2000;33(2):94-101.

Larsen et al., Drug delivery systems using hyaluronan and its derivatives. Advanced Drug Delivery Reviews. 1991;7(2):279-93.

Larsen et al., Hylan gel biomaterial: dermal and immunologic compatibility. J Biomed Mater Res. Sep. 1993;27(9):1129-34.

Lee et al., Biomedical applications of collagen. Int J Pharm. Jun. 19, 2001;221(1-2):1-22.

Lesley et al., CD44 in inflammation and metastasis. Glycoconj J. Aug. 1997;14(5):611-22.

Lewitzky et al., Reprogramming somatic cells towards pluripotency by defined factors. Curr Opin Biotechnol. Oct. 2007;18(5):467-73.

Li et al., Chemical modification of surface active poly(ethylene oxide)-poly (propylene oxide) triblock copolymers. Bioconjug Chem. Sep.-Oct. 1996;7(5):592-9.

Lund et al., Human embryonic stem cell-derived cells rescue visual function in dystrophic RCS rats. Cloning Stem Cells. 2006 Fall;8(3):189-99.

Lundorff et al., Reduction of post-surgical adhesions with ferric hyaluronate gel: a European study. Hum Reprod. Sep. 2001;16(9):1982-8.

Mantell et al., Telomerase activity in germline and embryonic cells of Xenopus. EMBO J. Jul. 1, 1994;13(13):3211-7.

Matsue et al., Age-related alterations of gene expression profiles in the rat incisor germ. JJSEDP. 2011;3(1):21-35.

Mclaren, Mammalian germ cells: birth, sex, and immortality. Cell Struct Funct. Jun. 2001;26(3):119-22.

Merriam-Webster, Comparable. Retrieved online at: http://www.merriam-webster.com/dictionary/comparable. Retreived Jul. 24, 2020. 11 pages.

Monk et al., Human embryonic genes re-expressed in cancer cells. Oncogene. Dec. 6, 2001;20(56):8085-91.

Munsie et al., Isolation of pluripotent embryonic stem cells from reprogrammed adult mouse somatic cell nuclei. Curr Biol. Aug. 24, 2000;10(16):989-92.

Mustoe et al., Growth factor-induced acceleration of tissue repair through direct and inductive activities in a rabbit dermal ulcer model. J Clin Invest. Feb. 1991;87(2):694-703.

NCBI, ADH1A alcohol dehydrogenase 1A (class I), alpha polypeptide [*Homo sapiens* (human)]. Retrieved online at: www.ncbi.nlm.nih.gov/gene/124. 8 pages, Jul. 24, 2020.

NCBI, ADH1B alcohol dehydrogenase 1B (class I), beta polypeptide [*Homo sapiens* (human)]. Retrieved online at: www.ncbi.nlm.nih.gov/gene/125. 11 pages, Jul. 24, 2020.

NCBI, GEO Profiles, Eya4—Brown and white adipose tissues. Mus musculus. 41285267. Retrieved online at: http://www.ncbi.nlm.nih.gov/geo/tools/profileGraph.cgi?ID=GDS2813:1432461_at. Jul. 24, 2020, 2 pages.

NCBI, GEO Profiles, Eya4—Morbidly obese and non-obese individuals: adipose stem cells. *Homo sapiens*. 111038010. Retrieved online at: http://www.ncbi.nlm.nih.gov/geoprofiles/111038010. Jul. 24, 2020, 1 page.

Neely et al., Gelatinase activities in wounds of healing-impaired mice versus wounds of nonhealing-impaired mice. J Burn Care Rehabil. Sep.-Oct. 2000;21(5):395-402.

NIH. Stem Cells: Scientific Progress and Future Research Directions, Department of Health and Human Services, Chapter 1, pp. 1-4, Jun. 2001.

Reynolds et al., Clonal and population analyses demonstrate that an EGF-responsive mammalian embryonic CNS precursor is a stem cell. Dev Biol. Apr. 10, 1996;175(1):1-13.

Rufer et al., Telomere fluorescence measurements in granulocytes and T lymphocyte subsets point to a high turnover of hematopoietic stem cells and memory T cells in early childhood. J Exp Med. Jul. 19, 1999;190(2):157-67.

Sakata et al., Expression of osteoprotegerin (osteoclastogenesis inhibitory factor) in cultures of human dental mesenchymal cells and epithelial cells. J Bone Miner Res. Sep. 1999;14(9):1486-92.

Sansom et al., The level of the transcription factor Pax6 is essential for controlling the balance between neural stem cell self-renewal and neurogenesis. PLoS Genet. Jun. 2009;5(6):e1000511, 16 pages.

Sarugaser et al., Human umbilical cord perivascular (HUCPV) cells: a source of mesenchymal progenitors. Stem Cells. Feb. 2005;23(2):220-9.

Sawada et al., Adhesion preventive effect of hyaluronic acid after intraperitoneal surgery in mice. Hum Reprod. Jun. 1999;14(6):1470-2.

Schatteman et al., Old bone marrow cells inhibit skin wound vascularization. Stem Cells. Mar. 2006;24(3):717-21.

Scott et al., Compositional Effects on Network Structure of Highly Cross-Linked Copolymers of PEG-Containing Multiacrylates with Acrylic Acid. Macromolecules. 1999;32(19);6139-48.

Seale et al., Transcriptional control of brown adipocyte development and physiological function—of mice and men. Genes Dev. Apr. 1, 2009;23(7):788-97.

Shi et al., The efficacy of mesenchymal stem cells to regenerate and repair dental structures. Orthod Craniofac Res. Aug. 2005;8(3):191-9.

Short et al., Percutaneous absorption of biologically-active interferon-gamma in a human skin graft-nude mouse model. Pharm Res. Jul. 1996;13(7):1020-7.

Shumakov et al., Mesenchymal bone marrow stem cells more effectively stimulate regeneration of deep burn wounds than embryonic fibroblasts. Bull Exp Biol Med. Aug. 2003;136(2):192-5.

Sinha et al., Transforming growth factor-beta1 signaling contributes to development of smooth muscle cells from embryonic stem cells. Am J Physiol Cell Physiol. Dec. 2004;287(6):C1560-8.

Slagboom et al., Genetic determination of telomere size in humans: a twin study of three age groups. Am J Hum Genet. Nov. 1994;55(5):876-82.

Smith et al., Efficacy of growth factors in the accelerated closure of interstices in explanted meshed human skin grafts. J Burn Care Rehabil. Jan.-Feb. 2000;21(1 Pt 1):5-9.

(56) References Cited

OTHER PUBLICATIONS

Stockholm et al., The origin of phenotypic heterogeneity in a clonal cell population in vitro. PLoS One. Apr. 25, 2007;2(4):e394.
Stojkovic et al., Derivation of a human blastocyst after heterologous nuclear transfer to donated oocytes. Reprod Biomed Online. Aug. 2005;11(2):226-31.
Surani et al., Development of gynogenetic eggs in the mouse: implications for parthenogenetic embryos. Science. Dec. 2, 1983;222(4627):1034-6.
Sutherland, Novel and established applications of microbial polysaccharides. Trends Biotechnol. Jan. 1998;16(1):41-6.
Tada et al., Pluripotency of reprogrammed somatic genomes in embryonic stem hybrid cells. Dev Dyn. Aug. 2003;227(4):504-10.
Takeda et al., Characterization of dental pulp stem cells of human tooth germs. J Dent Res. Jul. 2008;87(7):676-81.
Tan et al., Lunatic and manic fringe cooperatively enhance marginal zone B cell precursor competition for delta-like 1 in splenic endothelial niches. Immunity. Feb. 20, 2009;30(2):254-63.
The Free Dictionary, Viscosupplementation, Retrieved online at: http://medical-dictionary.thefreedictionary.com/viscosupplementation. 2 pages, Web, Jul. 24, 2020.
The Gordon Research Conference in Signal Transduction by Engineered Extracellular Matrices. pp. 1-6, Jun. 23-27, 2002.
Unemori et al., Reorganization of polymerized actin: a possible trigger for induction of procollagenase in fibroblasts cultured in and on collagen gels. J Cell Biol. Sep. 1986;103(3):1021-31.
Van Ooij et al., Temporal expression of the human alcohol dehydrogenase gene family during liver development correlates with differential promoter activation by hepatocyte nuclear factor 1, CCAAT/enhancer-binding protein alpha, liver activator protein, and D-element-binding protein. Mol Cell Biol. Jul. 1992;12(7):3023-31.
Verco et al., Development of a novel glucose polymer solution (icodextrin) for adhesion prevention: pre-clinical studies. Hum Reprod. Aug. 2000;15(8):1764-72.
Vogel, Misguided chromosomes foil primate cloning. Science. Apr. 11, 2003;300(5617):225-7.
Wang et al., Myc activates telomerase. Genes Dev. Jun. 15, 1998;12(12):1769-74.
Wang et al., Transcriptional silencing of a novel hTERT reporter locus during in vitro differentiation of mouse embryonic stem cells. Mol Biol Cell. Feb. 2007;18(2):669-77.
Watson et al., Cell lineage determination in the mouse. Cell Struct Funct. Jun. 2001;26(3):123-9.
Willen et al., Patterns of glycosaminoglycan/proteoglycan immunostaining in human skin during aging. J Invest Dermatol. Jun. 1991;96(6):968-74.
Winter et al., Cartilage-like gene expression in differentiated human stem cell spheroids: a comparison of bone marrow-derived and adipose tissue-derived stromal cells. Arthritis Rheum. Feb. 2003;48(2):418-29.
Woll et al., Wnt signaling promotes hematoendothelial cell development from human embryonic stem cells. Blood. Jan. 1, 2008;111(1):122-31.
Xu et al., Chondrogenic differentiation of human mesenchymal stem cells in three-dimensional alginate gels. Tissue Eng Part A. May 2008;14(5):667-80.
Xu, Endothelial progenitor cells in angiogenesis. Sheng Li Xue Bao. Feb. 25, 2005;57(1):1-6.
Yang et al., Clones of ectopic stem cells in the regeneration of muscle defects in vivo. PLoS One. Oct. 20, 2010;5(10):e13547, 8 pages.
Yates et al., Epidermal growth factor and related growth factors. Int J Dermatol. Oct. 1991;30(10):687-94.
Yoldemir et al., Comparison of the reduction of postoperative adhesions by two barriers, one solution, and two pharmacologic agents in the rat uterine model. Fertil Steril. Aug. 2002;78(2):335-9.
Yu et al., Amphiphilic Thermosensitive N-Isopropylacrylamide Terpolymer Hydrogels Prepared by Micellar Polymerization in Aqueous Media. Macromolecules. 1994;27(16):4554-60.

Yuen et al., Generation of a primitive erythroid cell line and promotion of its growth by basic fibroblast growth factor. Blood. May 1, 1998;91(9):3202-9.
Zambidis et al., Hematopoietic differentiation of human embryonic stem cells progresses through sequential hematoendothelial, primitive, and definitive stages resembling human yolk sac development. Blood. Aug. 1, 2005;106(3):860-70.
Zara et al., A carbohydrate-directed heterobifunctional cross-linking reagent for the synthesis of immunoconjugates. Anal Biochem. Apr. 1991;194(1):156-62.
Zhang et al., Multilineage differentiation potential of stem cells derived from human dental pulp after cryopreservation. Tissue Eng. Oct. 2006;12(10):2813-23.
Zhao et al., Consequences of knocking out BMP signaling in the mouse. Genesis. Jan. 2003;35(1):43-56.
Zhao et al., Hydrazide-containing inhibitors of HIV-1 integrase. J Med Chem. Mar. 14, 1997;40(6):937-41.
Zhong et al., Biodegradation of hyaluronic acid derivatives by hyaluronidase. Biomaterials. Apr. 1994;15(5):359-65.
Ziegler et al., Phenotypic expression of malignancy in hybrid and cybrid mouse cells. Somatic Cell Genet. Jul. 1978;4(4):477-89.
Zimmermann et al., Novel hydrogels as supports for in vitro cell growth: poly(ethylene glycol)- and gelatine-based (meth)acrylamidopeptide macromonomers. Biomaterials. May 2002;23(10):2127-34.
Zinzar et al., Azacytidine plus verapamil induces the differentiation of a newly characterized biphenotypic human myeloid-B lymphoid leukemic cell line BW-90. Leuk Res. Aug. 1988;22(8):677-85.
Zoller et al., New recombinant DNA methodology for protein engineering. Curr Opin Biotechnol. Aug. 1992;3(4):348-54.
Brugmann et al., Induction and specification of the vertebrate ectodermal placodes: precursors of the cranial sensory organs. Biol Cell. May 2005;97(5):303-19.
Brustle et al., Embryonic stem cell-derived glial precursors: a source of myelinating transplants. Science. Jul. 30, 1999;285(5428):754-6.
Burdick et al., Controlled degradation and mechanical behavior of photopolymerized hyaluronic acid networks. Biomacromolecules. Jan.-Feb. 2005;6(1):386-91.
Burdick et al., Hyaluronic acid hydrogels for biomedical applications. Adv Mater. Mar. 25, 2011;23(12):H41-56.
Burns et al., A hyaluronate based gel for the prevention of postsurgical adhesions: evaluation in two animal species. Fertil Steril. Nov. 1996;66(5):814-21.
Cai et al., Injectable glycosaminoglycan hydrogels for controlled release of human basic fibroblast growth factor. Biomaterials. Oct. 2005;26(30):6054-67.
Caicco et al., Characterization of hyaluronan-methylcellulose hydrogels for cell delivery to the injured spinal cord. J Biomed Mater Res A. May 2013;101(5):1472-7.
Camara-Clayette et al., Quantitative Oct4 overproduction in mouse embryonic stem cells results in prolonged mesoderm commitment during hematopoietic differentiation in vitro. Stem Cells. Aug. 2006;24(8):1937-45.
Campoccia et al., Semisynthetic resorbable materials from hyaluronan esterification. Biomaterials. Dec. 1998;19(23):2101-27.
Carlsson et al., Protein thiolation and reversible protein-protein conjugation. N-Succinimidyl 3-(2-pyridyldithio)propionate, a new heterobifunctional reagent. Biochem J. Sep. 1, 1978;173(3):723-37.
Carpenter et al., Characterization and differentiation of human embryonic stem cells. Cloning Stem Cells. 2003;5(1):79-88.
Chamow et al., Conjugation of soluble CD4 without loss of biological activity via a novel carbohydrate-directed cross-linking reagent. J Biol Chem. Aug. 5, 1992;267(22):15916-22.
Chang et al., Tissue engineering-based cartilage repair with mesenchymal stem cells in a porcine model. J Orthop Res. Dec. 2011;29(12):1874-80.
Chen et al., Effect of periostin on the function of human umbilical vein endothelial cells in acidic environment. Beijing Da Xue Xue Bao Yi Xue Ban. Dec. 18, 2011;43(6):855-60.
Chen et al., Functions of hyaluronan in wound repair. Wound Repair Regen. Mar.-Apr. 1999;7(2):79-89.

(56) References Cited

OTHER PUBLICATIONS

Chen et al., Towards an optimized culture medium for the generation of mouse induced pluripotent stem cells. J Biol Chem. Oct. 1, 2010;285(40):31066-72.
Cheung et al., Receptor for hyaluronan-mediated motility (RHAMM), a hyaladherin that regulates cell responses to growth factors. Biochem Soc Trans. Feb. 1999;27(2):135-42.
Chin et al., Induced pluripotent stem cells and embryonic stem cells are distinguished by gene expression signatures. Cell Stem Cell. Jul. 2, 2009;5(1):111-23.
Cibelli et al., Somatic Cell Nuclear Transfer in Humans: Pronuclear and Early Embryonic Development. e-biomed: The Journal of Regenerative Medicine. Nov. 26, 2001;2:25-31.
Cibelli et al., Transgenic bovine chimeric offspring produced from somatic cell-derived stem-like cells. Nat Biotechnol. Jul. 1998;16(7):642-6.
Collis et al., Rapid hyaluronan uptake is associated with enhanced motility: implications for an intracellular mode of action. FEBS Lett. Dec. 4, 1998;440(3):444-9.
Compte et al., Tumor immunotherapy using gene-modified human mesenchymal stem cells loaded into synthetic extracellular matrix scaffolds. Stem Cells. Mar. 2009;27(3):753-60.
Contreras-Ruiz et al., Intracellular trafficking of hyaluronic acid-chitosan oligomer-based nanoparticles in cultured human ocular surface cells. Mol Vis. Jan. 27, 2011;17:279-90.
Cooper et al., Reversible and irreversible protein glutathionylation: biological and clinical aspects. Expert Opin Drug Metab Toxicol. Jul. 2011;7(7):891-910.
Cossel et al., Intermediate cells in the adult human pancreas. Contribution to the transformation of differentiated cells in vertebrates. Virchows Arch B Cell Pathol Incl Mol Pathol. 1984;47(4):313-88.
Darlington et al., Expression of RESP18 in peptidergic and catecholaminergic neurons. J Histochem Cytochem. Sep. 1997;45(9):1265-77.
David et al., Forward programming of pluripotent stem cells towards distinct cardiovascular cell types. Cardiovasc Res. Nov. 1, 2009;84(2):263-72.
David et al., MesP1 drives vertebrate cardiovascular differentiation through Dkk-1-mediated blockade of Wnt-signalling. Nat Cell Biol. Mar. 2008;10(3):338-45.
Davidson et al., Hyaluronate derivatives and their application to wound healing: preliminary observations. Clin Mater. 1991;8(1-2):171-7.
De Iaco et al., A novel hyaluronan-based gel in laparoscopic adhesion prevention: preclinical evaluation in an animal model. Fertil Steril. Feb. 1998;69(2):318-23.
De Peppo et al., State of the Art in Stem Cell Research: Human Embryonic Stem Cells, Induced Pluripotent Stem Cells, and Transdifferentiation. Journal of Blood Transfusion. 2012;10 pages. Article ID 317632, 10 pages.
De Vargas et al., Individual beta cells within the intact islet differentially respond to glucose. J Biol Chem. Oct. 17, 1997;272(42):26573-7.
Demeure et al., CD31 (PECAM-1) is a differentiation antigen lost during human CD4 T-cell maturation into Th1 or Th2 effector cells. Immunology. May 1996;88(1):110-5.
Denning et al., Common culture conditions for maintenance and cardiomyocyte differentiation of the human embryonic stem cell lines, BG01 and HUES-7. Int J Dev Biol. 2006;50(1):27-37.
Desai et al., CD44 expression is developmentally regulated in the mouse lens and increases in the lens epithelium after injury. Differentiation. Feb. 2010;79(2):111-119.
Diekman et al., Chondrogenesis of adult stem cells from adipose tissue and bone marrow: induction by growth factors and cartilage-derived matrix. Tissue Eng Part A. Feb. 2010;16(2):523-33.
Domen et al., Self-renewal, differentiation or death: regulation and manipulation of hematopoietic stem cell fate. Mol Med Today. May 1999;5(5):201-8.
Donthwaite et al., An essential role for the interaction between hyaluronan and hyaluronan binding proteins during joint development. J Histochem Cytochem. May 1998;46(5):641-51.
Doty, Optimizing 3D Cell Culture with Customizable Hydrogels. ESI-BIO, retrieved online at: https://www.biocompare.com/Bench-Tips/161916-Optimizing-3D-Cell-Culture-with-Customizable-Hydrogels/. 7 pages. May 23, 2014.
Du et al., Adipose-derived stem cells differentiate to keratocytes in vitro. Molecular Vision. Dec. 10, 2010;16:2680-2689.
Dulac et al., A novel family of genes encoding putative pheromone receptors in mammals. Cell. Oct. 20, 1995;83(2):195-206.
Edlund, Transcribin. pancreas. Diabetes. Dec. 1998;47(12):1817-23.
Eggermann et al., Endothelial progenitor cell culture and differentiation in vitro: a methodological comparison using human umbilical cord blood. Cardiovasc Res. May 1, 2003;58(2):478-86.
Elisseeff et al., Transdermal photopolymerization for minimally invasive implantation. Proc Natl Acad Sci U S A. Mar. 16, 1999;96(6):3104-7.
Engler et al., Matrix elasticity directs stem cell lineage specification. Cell. Aug. 25, 2006;126(4):677-89.
Espandar et al., Adipose-derived stem cells on hyaluronic acid-derived scaffold: a new horizon in bioengineered cornea. Arch Ophthalmol. Feb. 2012;130(2):202-8.
Eyckmans et al., A clinically relevant model of osteoinduction: a process requiring calcium phosphate and BMP/Wnt signalling. J Cell Mol Med. Jun. 2010;14(6B):1845-56.
Fairbanks et al., A Versatile Synthetic Extracellular Matrix Mimic via Thiol-Norbornene Photopolymerization. Adv Mater. Dec. 28, 2009;21(48):5005-5010.
Fehling et al., Tracking mesoderm induction and its specification to the hemangioblast during embryonic stem cell differentiation. Development. Sep. 2003;130(17):4217-27.
Feng et al., Hemangioblastic derivatives from human induced pluripotent stem cells exhibit limited expansion and early senescence. Stem Cells. Apr. 2010;28(4):704-12.
Feng et al., The RNA component of human telomerase. Science. Sep. 1, 1995;269(5228):1236-41.
Fernandes et al., Differentiation of new insulin-producing cells is induced by injury in adult pancreatic islets. Endocrinology. Apr. 1997;138(4):1750-62.
Fernandez-Valle et al., Actin plays a role in both changes in cell shape and gene-expression associated with Schwann cell myelination. J Neurosci. Jan. 1, 1997;17(1):241-50.
Ferreira et al., Calcineurin is associated with the cytoskeleton of cultured neurons and has a role in the acquisition of polarity. Mol Biol Cell. Dec. 1993;4(12):1225-38.
Flemr et al., Lin28a Is Dormant, Functional, and Dispensable During Mouse Oocyte-to-Embryo Transition. Biology of Reproduction. Jun. 2014;90(6):1-9.
Forman et al., Glutathione: overview of its protective roles, measurement, and biosynthesis. Mol Aspects Med. Feb.-Apr. 2009;30(1-2):1-12.
Forsyth et al., Human embryonic stem cell telomere length impacts directly on clonal progenitor isolation frequency. Rejuvenation Res. Feb. 2008;11(1):5-17.
Freberg et al., Epigenetic reprogramming of OCT4 and NANOG regulatory regions by embryonal carcinoma cell extract. Mol Biol Cell. May 2007;18(5):1543-53.
Fricker et al., Site-specific migration and neuronal differentiation of human neural progenitor cells after transplantation in the adult rat brain. J Neurosci. Jul. 15, 1999;19(14):5990-6005.
Friedrich et al., CD34–/CD133+/VEGFR-2+ endothelial progenitor cell subpopulation with potent vasoregenerative capacities. Circ Res. Feb. 17, 2006;98(3):e20-5.
Frost et al., The importance of imprinting in the human placenta. PLoS Genet. Jul. 1, 2010;6(7):e1001015, 9 pages.
Gallogly et al., Mechanistic and kinetic details of catalysis of thiol-disulfide exchange by glutaredoxins and potential mechanisms of regulation. Antioxid Redox Signal. May 2009; 11(5):1059-81.
Gamini et al., Structural investigations of cross-linked hyaluronan. Biomaterials. Feb. 2002;23(4):1161-7.

(56) References Cited

OTHER PUBLICATIONS

Garbern et al., Delivery of basic fibroblast growth factor with a pH-responsive, injectable hydrogel to improve angiogenesis in infarcted myocardium. Biomaterials. Mar. 2011;32(9):2407-16.
Gaudana et al., Recent perspectives in ocular drug delivery. Pharm Res. May 2009;26(5):1197-216.
Gerdin et al., Dynamic role of hyaluronan (HYA) in connective tissue activation and inflammation. J Intern Med. Jul. 1997;242(1):49-55.
Gerecht et al., Hyaluronic acid hydrogel for controlled self-renewal and differentiation of human embryonic stem cells. Proc Natl Acad Sci U S A. Jul. 3, 2007;104(27):11298-303.
Gilpin et al., Recombinant human growth hormone accelerates wound healing in children with large cutaneous burns. Ann Surg. Jul. 1994;220(1):19-24.
Githens et al., Biochemical and histochemical characterization of cultured rat and hamster pancreatic ducts. Pancreas. 1987;2(4):427-38.
Githens et al., Isolation and culture of hamster pancreatic ducts. J Tissue Cult Methods. Sep. 1983;8(3):97-102.
Githens et al., Rat pancreatic interlobular duct epithelium: isolation and culture in collagen gel. In Vitro Cell Dev Biol. Aug. 1989;25(8):679-88.
Githens, The pancreatic duct cell: proliferative capabilities, specific characteristics, metaplasia, isolation, and culture. J Pediatr Gastroenterol Nutr. Jul.-Aug. 1988;7(4):486-506.
Gladhaug et al., Regulation of surface expression of high-affinity receptors for epidermal growth factor (EGF) in hepatocytes by hormones, differentiating agents, and phorbol ester. Dig Dis Sci. Feb. 1992;37(2):233-9.
Goldman et al., A boost of BMP4 accelerates the commitment of human embryonic stem cells to the endothelial lineage. Stem Cells. Aug. 2009;27(8):1750-9.
Golosow et al., Epitheliomesenchymal interactions in pancreatic morphogenesis. Dev Biol. Apr. 1962;4(2):242-255.
Gonzalez et al., Distribution patterns of estrogen receptor alpha and beta in the human cortex and hippocampus during development and adulthood. J Comp Neurol. Aug. 20, 2007;503(6):790-802.
Graham et al., SOX2 functions to maintain neural progenitor identity. Neuron. Aug. 28, 2003;39(5):749-65.
Greenhalgh et al., PDGF and FGF stimulate wound healing in the genetically diabetic mouse. Am J Pathol. Jun. 1990;136(6):1235-46.
Grogan et al., Identification of markers to characterize and sort human articular chondrocytes with enhanced in vitro chondrogenic capacity. Arthritis Rheum. Feb. 2007;56(2):586-95.
Grohmann et al., Characterization of differentiated subcutaneous and visceral adipose tissue from children: the influences of TNF-alpha and IGF-I. J Lipid Res. Jan. 2005;46(1):93-103.
Gronthos et al., Postnatal human dental pulp stem cells (DPSCs) in vitro and in vivo. Proc Natl Acad Sci U S A. Dec. 5, 2000;97(25):13625-30.
Gu et al., Epithelial cell proliferation and islet neogenesis in IFN-g transgenic mice. Development. May 1993;118(1):33-46.
Gu et al., Transitional cells in the regenerating pancreas. Development. Jul. 1994;120(7):1873-81.
Guan et al., Embryonic stem cell differentiation models: cardiogenesis, myogenesis, neurogenesis, epithelial and vascular smooth muscle cell differentiation in vitro. Cytotechnology. Jul. 1999;30(1-3):211-26.
Guoxun et al., The expression of PP1 in the development and regeneration of pancreas. Annual Meeting of the Federation of American Societies for Experimental Biology on Experimental Biology 2001. FASEB Journal. Mar. 31-Apr. 4, 2001;15(5):Abstract A1184. 1 page.
Gurdon et al., The future of cloning. Nature. Dec. 16, 1999;402(6763):743-6.
Gutowska et al., Injectable gels for tissue engineering. Anat Rec. Aug. 1, 2001;263(4):342-9.
Halban et al., The possible importance of contact between pancreatic islet cells for the control of insulin release. Endocrinology. Jul. 1982;111(1):86-94.
Hammachi et al., Transcriptional activation by Oct4 is sufficient for the maintenance and induction of pluripotency. Cell Rep. Feb. 23, 2012;1(2):99-109.
Hanjaya-Putra et al., Vascular endothelial growth factor and substrate mechanics regulate in vitro tubulogenesis of endothelial progenitor cells. J Cell Mol Med. Oct. 2010;14(10):2436-47.
Hansis et al., Nuclear reprogramming of human somatic cells by xenopus egg extract requires BRG1. Curr Biol. Aug. 24, 2004;14(16):1475-80.
Hanson et al., Clinical applications of mesenchymal stem cells in soft tissue augmentation. Aesthet Surg J. Nov.-Dec. 2010;30(6):838-42.
Hardwick et al., Molecular cloning of a novel hyaluronan receptor that mediates tumor cell motility. J Cell Biol. Jun. 1992;117(6):1343-50.
Hashemibeni et al., Effect of Transforming Growth Factor—beta3 and Bone Morphogenetic Protein-6 Growth Factors on Chondrogenic Differentiation of Adipose-derived Stem Cells in Alginate Scaffold. Journal of Isfahan Medical School. 2010;28(112):607-620.
Hayflick et al., The serial cultivation of human diploid cell strains. Exp Cell Res. Dec. 1961;25:585-621.
Hegert et al., Differentiation plasticity of chondrocytes derived from mouse embryonic stem cells. J Cell Sci. Dec. 1, 2002;115(Pt 23):4617-28.
Heimann et al., Rat pancreatic duct epithelium cultured on a porous support coated with extracellular matrix. Pancreas. Sep. 1991;6(5):514-21.
Hennink et al., Novel crosslinking methods to design hydrogels. Adv Drug Deliv Rev. Jan. 17, 2002;54(1):13-36.
Henquin et al., Opposite effects of tolbutamide and diazoxide on 86Rb+ fluxes and membrane potential in pancreatic B cells. Biochem Pharmacol. Apr. 1, 1982;31(7):1407-15.
Hiyama et al., Transplantation of mesenchymal stem cells in a canine disc degeneration model. J Orthop Res. May 2008;26(5):589-600.
Hochedlinger et al., Ectopic expression of Oct-4 blocks progenitor-cell differentiation and causes dysplasia in epithelial tissues. Cell. May 6, 2005;121(3):465-77.
Holtzer et al., Effects of cytochaslasin B and colcemide on myogenic cultures. Proc Natl Acad Sci U S A. Feb. 1975;72(2):513-7.
Hornsby et al., Redifferentiation, cellular elongation and the cell surface during lens regeneration. J Embryol Exp Morphol. Jun. 1977;39:23-43.
Huang et al., Improving cell therapy—experiments using transplanted telomerase-immortalized cells in immunodeficient mice. Mech Ageing Dev. Jan. 2007;128(1):25-30.
Huang et al., The effects of microenvironment in mesenchymal stem cell-based regeneration of intervertebral disc. Spine J. Mar. 2013;13(3):352-62.
Huangfu et al., Induction of pluripotent stem cells by defined factors is greatly improved by small-molecule compounds. Nat Biotechnol. Jul. 2008;26(7):795-7.
Huangfu et al., Induction of pluripotent stem cells from primary human fibroblasts with only Oct4 and Sox2. Nat Biotechnol. Nov. 2008;26(11):1269-75.
Hubbell et al., Bioactive biomaterials. Curr Opin Biotechnol. Apr. 1999;10(2):123-9.
Huotari et al., Growth factor-mediated proliferation and differentiation of insulin-producing INS-1 and RINm5F cells: identification of betacellulin as a novel beta-cell mitogen. Endocrinology. Apr. 1998;139(4):1494-9.
Hwang et al., Derivation of chondrogenically-committed cells from human embryonic cells for cartilage tissue regeneration. PLoS One. Jun. 25, 2008;3(6):e2498. 10 pages.
Hwang et al., In vivo commitment and functional tissue regeneration using human embryonic stem cell-derived mesenchymal cells. Proc Natl Acad Sci U S A. Dec. 30, 2008;105(52):20641-6.
Ibba, Strategies for in vitro and in vivo translation with non-natural amino acids. Biotechnol Genet Eng Rev. 1996;13:197-216.

(56) References Cited

OTHER PUBLICATIONS

Itskovitz-Eldor et al., Differentiation of human embryonic stem cells into embryoid bodies compromising the three embryonic germ layers. Mol Med. Feb. 2000;6(2):88-95.

Jaeger et al., Improved predictions of secondary structures for RNA. Proc Natl Acad Sci U S A. Oct. 1989;86(20):7706-10.

James et al., Expansion and maintenance of human embryonic stem cell-derived endothelial cells by TGFbeta inhibition is ld1 dependent. Nat Biotechnol. Feb. 2010;28(2):161-6.

James et al., Lentiviral Transduction and Clonal Selection of hESCs with Endothelial-Specific Transgenic Reporters. Curr Protoc Stem Cell Biol. 2011;17:1F.12.1-1F.12.14. 14 pages.

Johns et al., An improved method to determine cell viability by simultaneous staining with fluorescein diacetate-propidium iodide. J Histochem Cytochem. Jan. 1985;33(1):77-9.

Johns et al., Reduction of adhesion formation by postoperative administration of ionically cross-linked hyaluronic acid. Fertil Steril. Jul. 1997;68(1):37-42.

Johns et al., Reduction of postsurgical adhesions with Intergel adhesion prevention solution: a multicenter study of safety and efficacy after conservative gynecologic surgery. Fertil Steril. Sep. 2001;76(3):595-604.

Johnstone et al., In vitro chondrogenesis of bone marrow-derived mesenchymal progenitor cells. Exp Cell Res. Jan. 10, 1998;238(1):265-72.

Juhlin, Hyaluronan in skin. J Intern Med. Jul. 1997;242(1):61-6.

Kalkhoff et al., Fluctuations of calcium, phosphorus, sodium, potassium, and chlorine in single alpha and beta cells during glucose perifusion of rat islets. J Clin Invest. Aug. 1981;68(2):517-24.

Katagiri et al., Remodeling of sperm chromatin induced in egg extracts of amphibians. Int J Dev Biol. Jun. 1994;38(2):209-16.

Kato et al., Developmental potential of mouse follicular epithelial cells and cumulus cells after nuclear transfer. Biol Reprod. Oct. 1999;61(4):1110-4.

Keller et al., Inhibition of hyaluronan synthesis reduces versican and fibronectin levels in trabecular meshwork cells. PLoS One. 2012;7(11):e48523.

Kenchington, Chemical modification of the side chains of gelatin. Biochem J. Mar. 1958;68(3):458-68.

Kern et al., Comparative analysis of mesenchymal stem cells from bone marrow, umbilical cord blood, or adipose tissue. Stem Cells. May 2006;24(5):1294-301.

Kikyo et al., Reprogramming nuclei: insights from cloning, nuclear transfer and heterokaryons. J Cell Sci. Jan. 2000;113 ( Pt 1):11-20.

Kim et al., Comparative study of LHX8 expression between odontoma and dental tissue-derived stem cells. J Oral Pathol Med. Mar. 2011;40(3):250-6.

Kim et al., Generation of human induced pluripotent stem cells by direct delivery of reprogramming proteins. Cell Stem Cell. Jun. 5, 2009;4(6):472-6.

Kim et al., Oct4-induced pluripotency in adult neural stem cells. Cell. Feb. 6, 2009;136(3):411-9.

King et al., Global burden of diabetes, 1995-2025: prevalence, numerical estimates, and projections. Diabetes Care. Sep. 1998;21(9):1414-31.

Klein et al., Cell-cycle control by physiological matrix elasticity and in vivo tissue stiffening. Curr Biol. Sep. 29, 2009;19(18):1511-8.

Klimanskaya et al., Derivation and comparative assessment of retinal pigment epithelium from human embryonic stem cells using transcriptomics. Cloning Stem Cells. 2004;6(3):217-45.

Kompella et al., Recent advances in ophthalmic drug delivery. Ther Deliv. Sep. 2010;1(3):435-56.

Korbutt et al., Islet transplantation. Adv Exp Med Biol. 1997;426:397-410.

Korsgren et al., In vitro screening of putative compounds inducing fetal porcine pancreatic beta-cell differentiation: implications for cell transplantation in insulin-dependent diabetes mellitus. Ups J Med Sci. 1993;98(1):39-52.

Kouskoff et al., Sequential development of hematopoietic and cardiac mesoderm during embryonic stem cell differentiation. Proc Natl Acad Sci U S A. Sep. 13, 2005;102(37):13170-5.

Koutsopoulos et al., Controlled release of functional proteins through designer self-assembling peptide nanofiber hydrogel scaffold. Proc Natl Acad Sci U S A Mar. 24, 2009;106(12):4623-8.

Krivokharchenko et al., Development of parthenogenetic rat embryos. Biol Reprod. Mar. 2003;68(3):829-36.

Krueger et al., Biology of human skin transplanted to the nude mouse: I. Response to agents which modify epidermal proliferation. J Invest Dermatol. Jun. 1981;76(6):506-10.

Krueger et al., Involved and uninvolved skin from psoriatic subjects: are they equally diseased? Assessment by skin transplanted to congenitally athymic (nude) mice. J Clin Invest. Dec. 1981;68(6):1548-57.

Kuniba et al., Molecular karyotyping in 17 patients and mutation screening in 41 patients with Kabuki syndrome. J Hum Gen. 2009;54:304-309.

Laflamme et al., Cardiomyocytes derived from human embryonic stem cells in pro-survival factors enhance function of infarcted rat hearts. Nat Biotechnol. Sep. 2007;25(9):1015-24.

Lambillotte et al., Direct glucocorticoid inhibition of insulin secretion. An in vitro study of dexamethasone effects in mouse islets. J Clin Invest. Feb. 1, 1997;99(3):414-23.

Lampeter et al., Regeneration of beta-cells in response to islet inflammation. Exp Clin Endocrinol Diabetes. 1995;103 Suppl 2:74-8.

Lanza et al., Extension of cell life-span and telomere length in animals cloned from senescent somatic cells. Science. Apr. 28, 2000;288(5466):665-9.

Lanza et al., Human therapeutic cloning. Nat Med. Sep. 1999;5(9):975-7.

Lanza et al., Regeneration of the infarcted heart with stem cells derived by nuclear transplantation. Circ Res. Apr. 2, 2004;94(6):820-7.

Lanzendorf et al., Pregnancy following transfer of ooplasm from cryopreserved-thawed donor oocytes into recipient oocytes. Fertil Steril. Mar. 1999;71(3):575-7.

Larson et al., Sox11 is expressed in early progenitor human multipotent stromal cells and decreases with extensive expansion of the cells. Tissue Eng Part A. Nov. 2010;16(11):3385-94.

Laudes et al., Role of the POZ zinc finger transcription factor FBI-1 in human and murine adipogenesis. J Biol Chem. Mar. 19, 2004;279(12):11711-8.

Laurent et al., Functions of hyaluronan. Ann Rheum Dis. May 1995;54(5):429-32.

Laurent et al., Hyaluronan. FASEB J. Apr. 1992;6(7):2397-404.

Leach et al., Reduction of postsurgical adhesion formation in the rabbit uterine horn model with use of hyaluronate/carboxymethylcellulose gel. Fertil Steril. Mar. 1998;69(3):415-8.

Lee et al., Chondrogenic differentiation of mesenchymal stem cells and its clinical applications. Yonsei Med J. Jun. 30, 2004;45 Suppl:41-7.

Lee et al., Controlled growth factor release from synthetic extracellular matrices. Nature. Dec. 21-28, 2000;408(6815):998-1000.

Lee et al., Human homologs of the Xenopus oocyte cortical granule lectin XL35. Glycobiology. Jan. 2001;11(1):65-73.

Lee et al., Hydrogels for tissue engineering. Chem Rev. Jul. 2001;101(7):1869-79.

Lee et al., Magnetic cryopreservation for dental pulp stem cells. Cells Tissues Organs. 2012;196(1):23-33.

Leonard et al., Role of transforming growth factor-beta in chondrogenic pattern formation in the embryonic limb: stimulation of mesenchymal condensation and fibronectin gene expression by exogenenous TGF-beta and evidence for endogenous TGF-beta-like activity. Dev Biol. May 1991;145(1):99-109.

Letsinger et al., Cholesteryl-conjugated oligonucleotides: synthesis, properties, and activity as inhibitors of replication of human immunodeficiency virus in cell culture. Proc Natl Acad Sci USA. Sep. 1989;86(17):6553-6.

Levenberg et al., Differentiation of human embryonic stem cells on three-dimensional polymer scaffolds. Proc Natl Acad Sci U S A. Oct. 28, 2003;100(22):12741-6.

(56) References Cited

OTHER PUBLICATIONS

Li et al., Bone morphogenetic protein 4 induces efficient hematopoietic differentiation of rhesus monkey embryonic stem cells in vitro. Blood. Jul. 15, 2001;98(2):335-42.

Li et al., Multilineage differentiation of human mesenchymal stem cells in a three-dimensional nanofibrous scaffold. Biomaterials. Sep. 2005;26(25):5158-66.

Li et al., Nuclear transfer: progress and quandaries. Reprod Biol Endocrinol. Nov. 7, 2003;1:84, 6 pages.

Lian et al., Efficient differentiation of human pluripotent stem cells to endothelial progenitors via small-molecule activation of WNT signaling, Stem Cell Reports. Nov. 11, 2014;3(5):804-16.

Liang et al., The roles of Mesp family proteins: functional diversity and redundancy in differentiation of pluripotent stem cells and mammalian mesodermal development. Protein Cell. Aug. 2015;6(8):553-561.

Liang et al., Tuning the non-equilibrium state of a drug-encapsulated polyethylene glycol) hydrogel for stem and progenitor cell mobilization. Biomaterials. Mar. 2011;32(7):2004-12.

Lillard-Wetherell et al., Association and regulation of the BLM helicase by the telomere proteins TRF1 and TRF2. Hum Mol Genet. Sep. 1, 2004;13(17):1919-32.

Lin et al., The role of the fetal fibroblast and transforming growth factor-beta in a model of human fetal wound repair. Semin Pediatr Surg. Aug. 1996;5(3):165-74.

Liu et al., Crosslinked hyaluronan hydrogels containing mitomycin C reduce postoperative abdominal adhesions. Fertil Steril. Apr. 2005;83 Suppl 1:1275-83.

Liu et al., Disulfide-crosslinked hyaluronan-gelatin sponge: growth of fibrous tissue in vivo. J Biomed Mater Res A. Jan. 1, 2004;68(1);142-9.

Loebel et al., Lineage choice and differentiation in mouse embryos and embryonic stem cells. Dev Biol. Dec. 1, 2003;264(1):1-14.

Loi et al., Development of parthenogenetic and cloned ovine embryos: effect of activation protocols. Biol Reprod. May 1998;58(5):1177-87.

Lowe, Thiol-ene "clicl" reactions and recent applications in polymer and materials synthesis. Polym Chem. 2010;1:17-36.

Madsen et al., Pancreatic development and maturation of the islet B cell. Studies of pluripotent islet cultures. Eur J Biochem. Dec. 15, 1996;242(3):435-45.

Malaisse et al., Insulin release: the fuel hypothesis. Metabolism. Apr. 1979;28(4):373-86.

Mao et al., Craniofacial tissue engineering by stem cells. J Dent Res. Nov. 2006;85(11):966-79.

Marion et al., Telomeres acquire embryonic stem cell characteristics in induced pluripotent stem cells. Cell Stem Cell. Feb. 6, 2009;4(2):141-54.

Marshall et al., Parthenogenetic activation of marmoset (*Callithrix jacchus*) oocytes and the development of marmoset parthenogenones in vitro and in vivo. Biol Reprod. Dec. 1998;59(6):1491-7.

Martin, Wound healing—aiming for perfect skin regeneration. Science. Apr. 4, 1997;276(5309):75-81.

Martinez-Conesa et al., Characterization of ocular surface epithelial and progenitor cell markers in human adipose stromal cells derived from lipoaspirates. Invest Ophthalmol Vis Sci. Jan. 31, 2012;53(1):513-20.

Mauck et al., Chondrogenic differentiation and functional maturation of bovine mesenchymal stem cells in long-term agarose culture. Osteoarthritis Cartilage. Feb. 2006;14(2):179-89.

Maxson et al., Differential stimulation of sea urchin early and late H2B histone gene expression by a gastrula nuclear extract after injection into Xenopus laevis oocytes. Mol Cell Biol. Mar. 1988;8(3):1236-46.

Mazumder et al., Cell-adhesive thermogelling PNIPAAm/hyaluronic acid cell delivery hydrogels for potential application as minimally invasive retinal therapeutics. J Biomed Mater Res A. Jul. 2012;100(7):1877-87.

Meirelles et al., Complete replacement of the mitochondrial genotype in a Bos indicus calf reconstructed by nuclear transfer to a Bos taurus oocyte. Genetics. May 2001;158(1):351-6.

Meister, Glutathione metabolism and its selective modification. J Biol Chem. Nov. 25, 1988;263(33):17205-8.

Melander, Pharmacological intervention: the antidiabetic approach. Eur J Clin Invest. Sep. 1998;28 Suppl 2:23-5; discussion 25-6.

Melmed, Intermediate cells of the pancreas. An appraisal. Gastroenterology. Jan. 1979;76(1):196-201.

Miettinen, Epidermal growth factor receptor in mice and men—any applications to clinical practice? Ann Med. Dec. 1997;29(6):531-4.

Mironov et al., Bioprinting living structures. Journal of Materials Chemistry. 2007;17(20):2054-60.

Mitalipov et al., Rhesus monkey embryos produced by nuclear transfer from embryonic blastomeres or somatic cells. Biol Reprod. May 2002;66(5):1367-73.

Mohand-Kaci et al., Optimized hyaluronic acid-hydrogel design and culture conditions for preservation of mesenchymal stem cell properties. Tissue Eng Part C Methods. Apr. 2013;19(4):288-98.

Mooney et al., Cell delivery mechanisms for tissue repair. Cell Stem Cell. Mar. 6, 2008;2(3):205-13.

Mukouyama et al., In vitro expansion of murine multipotential hematopoietic progenitors from the embryonic aorta-gonad-mesonephros region. Immunity. Jan. 1998;8(1):105-14.

Mummery et al., Differentiation of human embryonic stem cells to cardiomyocytes: role of coculture with visceral endoderm-like cells. Circulation. Jun. 3, 2003;107(21):2733-40.

Murashita et al., Acceleration of granulation tissue ingrowth by hyaluronic acid in artificial skin. Br J Plast Surg. Jan. 1996;49(1):58-63.

Murohara et al., Transplanted cord blood-derived endothelial precursor cells augment postnatal neovascularization. J Clin Invest. Jun. 2000;105(11):1527-36.

Nakagawa et al., Generation of induced pluripotent stem cells without Myc from mouse and human fibroblasts. Nat Biotechnol. Jan. 2008;26(1):101-6.

Nakahara et al., High-efficiency production of subculturable vascular endothelial cells from feeder-free human embryonic stem cells without cell-sorting technique. Cloning Stem Cells. Dec. 2009:11(4):509-22.

Nakamura et al., Telomerase catalytic subunit homologs from fission yeast and human. Science. Aug. 15, 1997;277(5328):955-9.

Nanney, Epidermal and dermal effects of epidermal growth factor during wound repair. J Invest Dermatol. May 1990;94(5):624-9.

Neri et al., Mouse fibroblasts are reprogrammed to Oct-4 and Rex-1 gene expression and alkaline phosphatase activity by embryonic stem cell extracts. Cloning Stem Cells. 2007 Fall;9(3):394-406.

Nielsen et al., Beta cell proliferation and growth factors. J Mol Med (Berl). Jan. 1999;77(1):62-6.

Niki et al., Effects of specific inhibitors of sweet taste response on glucose-insulin release. Biomed Res. 1993;14:13-18.

Niki et al., Insulin secretion by anomers of d-glucose. Science. Oct. 11, 1974;186(4159):150-1.

Niwa et al., Quantitative expression of Oct-3/4 defines differentiation, dedifferentiation or self-renewal of ES cells. Nat Genet. Apr. 2000;24(4):372-6.

Ofek et al., Mechanical characterization of differentiated human embryonic stem cells. J Biomech Eng. Jun. 2009;131(6):061011-1-061011-8.

Offield et al., PDX-1 is required for pancreatic outgrowth and differentiation of the rostral duodenum. Development. Mar. 1996;122(3):983-95.

Ohlsson et al., IPF1, a homeodomain-containing transactivator of the insulin gene. EMBO J. Nov. 1993;12(11):4251-9.

Ohneda et al., Hematopoietic stem cell maintenance and differentiation are supported by embryonic aorta-gonad-mesonephros region-derived endothelium. Blood. Aug. 1, 1998;92(3):908-19.

Okabe et al., Development of neuronal precursor cells and functional postmitotic neurons from embryonic stem cells in vitro. Mech Dev. Sep. 1996:59(1):89-102.

Omim, 300297, APELIN; APLN, APJ Receptor Ligand. 3 pages, created Feb. 7, 2001.

(56) References Cited

OTHER PUBLICATIONS

Omim, 600052, Apelin Receptor; APLNR, APJ Putative Receptor Protein Related to Angiotensin Receptor; APJR Angiotensin Receptor-Like 1; AGTRL1. 3 pages, created Jul. 26, 1994.
Omim, 600750, Pentraxin II, Neuronal; NPTX2, NP2, Neuronal Activity-Regulated Pentraxin; NARP. 2 pages, created Aug. 28, 1995.
Omim, 609873, Intelectin 1; ITLN1, INTL Lactoferrin Receptor; LFR, HL1. 2 pages, created Feb. 1, 2006.
Omim, 612879, Mam Domain-Containing Protein2; MAMDC2. 2 pages, created Jun. 26, 2009.
Osada et al., The effect of cross-linked hyaluronate hydrogel on the reduction of post-surgical adhesion reformation in rabbits. J Int Med Res. Sep.-Oct. 1999;27(5):233-41.
Osada et al., The effect of hyaluronic acid-carboxymethylcellulose in reducing adhesion reformation in rabbits. J Int Med Res. 1999;27(6):292-6.
Otonkoski et al., Hepatocyte growth factor/scatter factor has insulinotropic activity in human fetal pancreatic cells. Diabetes. Jul. 1994;43(7):947-53.
Otonkoski et al., Nicotinamide is a potent inducer of endocrine differentiation in cultured human fetal pancreatic cells. J Clin Invest. Sep. 1993;92(3):1459-66.
Otulakowski et al., Use of a human skin-grafted nude mouse model for the evaluation of topical retinoic acid treatment. J Invest Dermatol. Apr. 1994;102(4):515-8.
Overman et al., A role for ephrin-A5 in axonal sprouting, recovery, and activity-dependent plasticity after stroke. Proc Natl Acad Sci U S A. Aug. 14, 2012;109(33):E2230-9.
Ozil et al., Activation of rabbit oocytes: the impact of the Ca2+ signal regime on development. Development. Mar. 2001;128(6):917-28.
Pacini et al., Constitutive expression of pluripotency-associated genes in mesodermal progenitor cells (MPCs). PLoS One. Mar. 25, 2010;5(3):e9861, 7 pages.
Pan et al., Sox2 modulates reprogramming of gene expression in two-cell mouse embryos. Biol Reprod. Aug. 2011;85(2):409-16.
Papapetrou et al., Stoichiometric and temporal requirements of Oct4, Sox2, Klf4, and c-Myc expression for efficient human iPSC induction and differentiation. Proc Natl Acad Sci U S A. Aug. 4, 2009;106(31):12759-64.
Park et al., Reprogramming of human somatic cells to pluripotency with defined factors. Nature. Jan. 10, 2008;451(7175):141-6.
Patel et al., Mitotic clonal expansion during preadipocyte differentiation: calpain-mediated turnover of p27. J Biol Chem. Jun. 9, 2000;275(23):17653-60.
Patel et al., Poly(ethylene glycol) hydrogel system supports preadipocyte viability, adhesion, and proliferation. Tissue Eng. Sep.-Oct. 2005;11(9-10):1498-505.
Patrick et al., Preadipocyte seeded PLGA scaffolds for adipose tissue engineering. Tissue Eng. Apr. 1999;5(2):139-51.
Patterson et al., In Vivo Imaging of Bone Regeneration Induced by Angiogenic and Osteoinductive Hydrogel Scaffolds. Biomedical Optics. 3 pages, Jan. 1, 2006.
Pearson et al., Improved tools for biological sequence comparison. Proc Natl Acad Sci U S A. Apr. 1988;85(8):2444-8.
Pelttari et al., Premature induction of hypertrophy during in vitro chondrogenesis of human mesenchymal stem cells correlates with calcification and vascular invasion after ectopic transplantation in SCID mice. Arthritis Rheum. Oct. 2006;54(10):3254-66.
Peppas et al., Hydrogels in Biology and Medicine: From Molecular Principles to Bionanotechnology. Advanced Materials. Jun. 2006;18(11):1345-60.
Peppas et al., Hydrogels in pharmaceutical formulations. Eur J Pharm Biopharm. Jul. 2000;50(1):27-46.
Pignolo et al., Circulating osteogenic precursor cells. Crit Rev Eukaryot Gene Expr. 2010;20(2):171-80.
Pittenger et al., Multilineage potential of adult human mesenchymal stem cells. Science. Apr. 2, 1999;284(5411):143-7.

Plath et al., Progress in understanding reprogramming to the induced pluripotent state. Nat Rev Genet. Apr. 2011;12(4):253-65.
Prather et al., Nuclear transplantation in early pig embryos. Biol Reprod. Sep. 1989;41(3):414-8.
Pratsinis et al., Differential proliferative response of fetal and adult human skin fibroblasts to transforming growth factor-beta. Wound Repair Regen. May-Jun. 2004:12(3):374-83.
Prestwich et al., Controlled chemical modification of hyaluronic acid: synthesis, applications, and biodegradation of hydrazide derivatives. J Control Release. Apr. 30, 1998;53(1-3):93-103.
Prestwich et al., The translational imperative: making cell therapy simple and effective. Acta Biomater. Dec. 2012;8(12):4200-7.
Prestwich et al., Therapeutic applications of hyaluronic acid and hyaluronan derivatives. PSTT. Apr. 1998;1:42-3.
Prestwich, Biomaterials from Chemically-Modified Hyaluronan. Glycoforum. 2001;5(A4). Retrieved online at: https://www.glycoforum.gr.jp/article/05A4.html. Mar. 29, 2001.
Prestwich, Hyaluronic acid-based clinical biomaterials derived for cell and molecule delivery in regenerative medicine. J Control Release. Oct. 30, 2011;155(2):193-9.
Prevo et al., Mouse LYVE-1 is an endocytic receptor for hyaluronan in lymphatic endothelium. J Biol Chem. Jun. 1, 2001;276(22):19420-30.
Priam et al., New cellular models for tracking the odontoblast phenotype. Arch Oral Biol. Feb. 2005;50(2):271-7.
Puchelle et al., Human airway xenograft models of epithelial cell regeneration. Respir Res. 2000;1(3):125-8.
Rall et al., Glucocorticoids modulate the in vitro development of the embryonic rat pancreas. J Cell Biol. Nov. 1977;75(2 Pt 1):398-409.
Reynolds et al., Generation of neurons and astrocytes from isolated cells of the adult mammalian central nervous system. Science. Mar. 27, 1992;255(5052):1707-10.
Rieke et al., Sustained subconjunctival protein delivery using a thermosetting gel delivery system. J Ocul Pharmacol Ther. Feb. 2010;26(1):55-64.
Rindler et al., Retention of differentiated properties in an established dog kidney epithelial cell line (MDCK). J Cell Biol. Jun. 1979;81(3):635-48.
Rizo et al., Constrained peptides: models of bioactive peptides and protein substructures. Annu Rev Biochem. 1992;61:387-418.
Robson et al., The safety and effect of topically applied recombinant basic fibroblast growth factor on the healing of chronic pressure sores. Ann Surg. Oct. 1992;216(4):401-6; discussion 406-8.
Rodgers et al., Effect of oxiplex* films (PEO/CMC) on adhesion formation and reformation in rabbit models and on peritoneal infection in a rat model. Fertil Steril. Apr. 2000;73(4):831-8.
Rodgers et al., Reduction of adhesion formation with hyaluronic acid after peritoneal surgery in rabbits. Fertil Steril. Mar. 1997;67(3):553-8.
Rosenberg, In vivo cell transformation: neogenesis of beta cells from pancreatic ductal cells. Cell Transplant. Jul.-Aug. 1995;4(4):371-83.
Rosler et al., Long-term culture of human embryonic stem cells in feeder-free conditions. Dev Dyn. Feb. 2004;229(2):259-74.
Roy et al., Functional engraftment of human ES cell-derived dopaminergic neurons enriched by coculture with telomerase-immortalized midbrain astrocytes. Nat Med. Nov. 2006;12(11):1259-68.
Ruiz-Cardona et al., Application of benzyl hyaluronate membranes as potential wound dressings: evaluation of water vapour and gas permeabilities. Biomaterials. Aug. 1996;17(16):1639-43.
Saif et al., The synergistic effect of SaOS-2 cell extract and other bone-inducing agents on human bone cell cultivation. Drug Discov Ther. Dec. 2012;6(6):315-20.
Sakai et al., Differentiation of mesenchymal stem cells transplanted to a rabbit degenerative disc model: potential and limitations for stem cell therapy in disc regeneration. Spine (Phila Pa 1976). Nov. 1, 2005;30(21):2379-87.
Sanvito et al., TGF-beta 1 influences the relative development of the exocrine and endocrine pancreas in vitro. Development. Dec. 1994;120(12):3451-62.

(56) References Cited

OTHER PUBLICATIONS

Saretzki et al., Downregulation of multiple stress defense mechanisms during differentiation of human embryonic stem cells. Stem Cells. Feb. 2008;26(2):455-64.
Sato et al., Glucose regulation of insulin secretion independent of the opening or closure of adenosine triphosphate-sensitive K+ channels in beta cells. Endocrinology. May 1999;140(5):2252-7.
Sauman et al., Cytochalasin-D treatment triggers premature apoptosis of insect ovarian follicle and nurse cells. Int J Dev Biol. Sep. 1993;37(3):441-50.
Schaetzlein et al., Telomere length is reset during early mammalian embryogenesis. Proc Natl Acad Sci U S A. May 25, 2004;101(21):8034-8.
Schmied et al., Differentiation of islet cells in long-term culture. Pancreas. May 2000;20(4):337-47.
Schuit, Factors determining the glucose sensitivity and glucose responsiveness of pancreatic beta cells. Horm Res. 1996;46(3):99-106.
Schuldiner et al., Effects of eight growth factors on the differentiation of cells derived from human embryonic stem cells. Proc Natl Acad Sci U S A. Oct. 10, 2000;97(21):11307-12.
Secchi et al., Pancreas and islet transplantation: current progresses, problems and perspectives. Horm Metab Res. Jan. 1997;29(1):1-8.
Seong, Differentiation and Derivation of Lineage committed Chondroprogenitors and Chondrogenic Cells From Human Embryonic Stem Cells for Cartilage Tissue Engineering and Regeneration. A Thesis submitted for the degree of Doctor of Philosophy Department of Oral and Maxillofacial Surgery. National University of Singapore. 190 pages, (2010).
Shaikh et al., High-resolution mapping and analysis of copy number variations in the human genome: a data resource for clinical and research applications. Genome Res. Sep. 2009;19(9):1682-90.
Shamblott et al., Derivation of pluripotent stem cells from cultured human primordial germ cells. Proc Natl Acad Sci U S A. Nov. 10, 1998;95(23):13726-31.
Shaw et al., Regeneration of pancreatic tissue from the transplanted pancreatic duct in the dog. Am J Physiol. Mar. 1926;76(1):49-53.
Shawi et al., Telomerase, senescence and ageing. Mech Ageing Dev. Jan.-Feb. 2008;129(1-2):3-10.
Shen et al., BMP-2 enhances TGF-beta3-mediated chondrogenic differentiation of human bone marrow multipotent mesenchymal stromal cells in alginate bead culture. Tissue Eng Part A. Jun. 2009;15(6):1311-20.
Shen et al., The role of BMP-7 in chondrogenic and osteogenic differentiation of human bone marrow multipotent mesenchymal stromal cells in vitro. J Cell Biochem. Feb. 1, 2010;109(2):406-16.
Shu et al., Attachment and spreading of fibroblasts on an RGD peptide-modified injectable hyaluronan hydrogel. J Biomed Mater Res A. Feb. 1, 2004;68(2):365-75.
Shu et al., Disulfide cross-linked hyaluronan hydrogels. Biomacromolecules. Nov.-Dec. 2002;3(6):1304-11.
Sigma-Aldrich, HyStem-C Cell Culture Scaffold Kit for 7.5 mL of hydrogel scaffold solution. Catalog No. HYSC020-1KT. Retrieved online at: https://www.sigmaaldrich.com/catalog/product/sigma/hysc020?lang=en&region=US. 3 pages, (2020).
Simerly et al., Embryogenesis and blastocyst development after somatic cell nuclear transfer in nonhuman primates: overcoming defects caused by meiotic sp ndle extraction. Dev Biol. Dec. 15, 2004;276(2):237-52.
Simerly et al., Molecular correlates of primate nuclear transfer failures. Science. Apr. 11, 2003;300(5617):297.
Sjoholm, Diabetes mellitus and impaired pancreatic beta-cell proliferation. J Intern Med. Mar. 1996;239(3):211-20.
Smith et al., Comparison of Biosequences. Advances in Applied Mathematics. 1981:2:482-9.
Smith et al., Cytoplasmic transfer of the mitogenic response to platelet-derived growth factor. Proc Natl Acad Sci U S A. Jul. 1981;78(7):4363-7.
Solter et al., Differential imprinting and expression of maternal and paternal genomes. Annu Rev Genet. 1988;22:127-46.
Song et al., Expansion of Pdx1-expressing pancreatic epithelium and islet neogenesis in transgenic mice overexpressing transforming growth factor alpha. Gastroenterology. Dec. 1999;117(6):1416-26.
Sorenson et al., Adaptation of islets of Langerhans to pregnancy: beta-cell growth, enhanced insulin secretion and the role of lactogenic hormones. Horm Metab Res. Jun. 1997;29(6):301-7.
Sreekumar et al., Mechanism of RPE cell death in a-crystallin deficient mice: a novel and critical role for MRP1-mediated GSH efflux. PLoS One. 2012;7(3):e33420. 13 pages.
Sternberg et al., A human embryonic stem cell-derived clonal progenitor cell line with chondrogenic potential and markers of craniofacial mesenchyme. Regen Med. Jul. 2012;7(4):481-501.
Sternberg et al., Defining cell-matrix combination products in the era of pluripotency. Biomatter. Jan.-Mar. 2013;3(1). pii: e24496. 7 pages.
Sturm et al., Abnormal development of embryonic and extraembryonic cell lineages in parthenogenetic mouse embryos. Dev Dyn. Sep. 1994;201(1):11-28.
Suda et al., Circulating osteogenic precursor cells in heterotopic bone formation. Stem Cells. Sep. 2009;27(9):2209-19.
Suh et al., Human embryonic stem cells express a unique set of microRNAs. Dev Biol. Jun. 15, 2004;270(2):488-98.
Suhr et al., Telomere dynamics in human cells reprogrammed to pluripotency. PLoS One. Dec. 2, 2009;4(12):e8124. 9 pages.
Sullivan et al., Elucidating nuclear reprogramming mechanisms: taking a synergistic approach. Reprod Biomed Online. Jan. 2008;16(1):41-50.
Sutherland, Pancreas and islet cell transplantation: now and then. Transplant Proc. Aug. 1996;28(4):2131-3.
Swift et al., Age-related alterations in the inflammatory response to dermal injury. J Invest Dermatol. Nov. 2001;117(5):1027-35.
Tada et al., Embryonic germ cells induce epigenetic reprogramming of somatic nucleus in hybrid cells. EMBO J. Nov. 3, 1997;16(21):6510-20.
Takahashi et al., Induction of pluripotent stem cells from adult human fibroblasts by defined factors. Cell. Nov. 30, 2007;131(5):861-72.
Takahashi et al., Induction of pluripotent stem cells from mouse embryonic and adult fibroblast cultures by defined factors. Cell. Aug. 25, 2006;126(4):663-76.
Tamai et al., Cytochalasin B inhibits morphogenetic movement and muscle differentiation of activin-treated ectoderm in Xenopus. Dev Growth Differ. Feb. 1999;41(1):41-9.
Tammi et al., Hyaluronan enters keratinocytes by a novel endocytic route for catabolism. J Biol Chem. Sep. 14, 2001;276(37):35111-22.
Taranger et al., Induction of dedifferentiation, genomewide transcriptional programming, and epigenetic reprogramming by extracts of carcinoma and embryonic stem cells. Mol Biol Cell. Dec. 2005;16(12):5719-35.
Tatsumi et al., Simple and highly efficient method for production of endothelial cells from human embryonic stem cells. Cell Transplant. 2011;20(9):1423-30.
Thomas et al., Mutation of the pancreatic islet inward rectifier Kir6.2 also leads to familial persistent hyperinsulinemic hypoglycemia of infancy. Hum Mol Genet. Nov. 1996;5(11):1809-12.
Thomson et al., Embryonic stem cell lines derived from human blastocysts. Science. Nov. 6, 1998;282(5391):1145-7.
Thomson et al., Neural differentiation of rhesus embryonic stem cells. APMIS. Jan. 1998;106(1):149-56.
Tokura et al., Studies on Chitin VIII. Some Properties of Water Soluble Chitin Derivatives. Polymer Journal. 1983;15:485-9.
Tompkins et al., Prompt eschar excision: a treatment system contributing to reduced burn mortality. A statistical evaluation of burn care at the Massachusetts General Hospital (1974-1984). Ann Surg. Sep. 1986;204(3):272-81.
Tompkins et al., Significant reductions in mortality for children with burn injuries through the use of prompt eschar excision. Ann Surg. Nov. 1988;208(5):577-85.
Toole, Hyaluronan in morphogenesis. J Intern Med. Jul. 1997;242(1):35-40.
Trube et al., Opposite effects of tolbutamide and diazoxide on the ATP-dependent K+ channel in mouse pancreatic beta-cells. Pflugers Arch. Nov. 1986;407(5):493-9.

(56) References Cited

OTHER PUBLICATIONS

Tung et al., Characterization of rat testicular peritubular myoid cells in culture: alpha-smooth muscle isoactin is a specific differentiation marker. Biol Reprod. Feb. 1990;42(2):351-65.
Upchurch et al., Expression of peptide YY in all four islet cell types in the developing mouse pancreas suggests a common peptide YY-producing progenitor. Development. Feb. 1994;120(2):245-52.
Van Hoof et al., Phosphorylation dynamics during early differentiation of human embryonic stem cells. Cell Stem Cell. Aug. 7, 2009;5(2):214-26.
Van Nest et al., Effects of dexamethasone and 5-bromodeoxyuridine on protein synthesis and secretion during in vitro pancreatic development. Dev Biol. Aug. 1983;98(2):295-303.
Vanderhooft et al., Rheological properties of cross-linked hyaluronan-gelatin hydrogels for tissue engineering. Macromol Biosci. Jan. 9, 2009;9(1):20-8.
Vaziri et al., Loss of telomeric DNA during aging of normal and trisomy 21 human lymphocytes. Am J Hum Genet. Apr. 1993;52(4):661-7.
Vercruysse et al., Synthesis and in vitro degradation of new polyvalent hydrazide cross-linked hydrogels of hyaluronic acid. Bioconjug Chem. Sep.-Oct. 1997;8(5):686-94.
Vishnubhatla et al., The Development of Stem Cell-derived Exosomes as a Cell-free Regenerative Medicine. J Circ Biomark. 2014;3(2):1-14.
Vogel, Cell biology. Stem cells: new excitement, persistent questions. Science. Dec. 1, 2000;290(5497):1672-4.
Wade et al., Chromatin remodeling in nuclear cloning. Eur J Biochem. May 2002;269(9):2284-7.
Wakayama et al., Full-term development of mice from enucleated oocytes injected with cumulus cell nuclei. Nature. Jul. 23, 1998;394(6691):369-74.
Wang et al., Duct- to islet-cell differentiation and islet growth in the pancreas of duct-ligated adult rats. Diabetologia. Dec. 1995;38(12):1405-11.
Wang et al., Secretagogue-induced oscillations of cytoplasmic Ca2+ in single beta and alpha-cells obtained from pancreatic islets by fluorescence-activated cell sorting. Biochem Biophys Res Commun. Jan. 30, 1990;166(2):813-8.
Wangh et al., Efficient reactivation of Xenopus erythrocyte nuclei in Xenopus egg extracts. J Cell Sci. Jun. 1995;108 ( Pt 6):2187-96.
Ware et al., Derivation of naive human embryonic stem cells. Proc Natl Acad Sci U S A. Mar. 25, 2014;111(12):4484-9.
Warren et al., The Pathology of Diabetes, with Special Reference to Pancreatic Regeneration. Am J Pathol. Jul. 1925;1(4):415-430.
Weir et al., Scientific and political impediments to successful islet transplantation. Diabetes. Aug. 1997;46(8):1247-56.
Wen et al., Intra-articular Hyaluronic Acid Injections for Knee Osteoarthritis. Am Fam Physician. Aug. 1, 2000;62(3):565-70.
Werner et al., Induction of keratinocyte growth factor expression is reduced and delayed during wound healing in the genetically diabetic mouse. J Invest Dermatol. Oct. 1994;103(4):469-73.
Wernig et al., In vitro reprogramming of fibroblasts into a pluripotent ES-cell-like state. Nature. Jul. 19, 2007;448(7151):318-24.
Wessels et al., Early Pancreas Organogenesis: Morphogenesis, Tissue Interactions, and Mass Effects. Dev Biol. Mar. 1967;15(3):237-70.
White et al., Live confocal microscopy of oligonucleotide uptake by keratinocytes in human skin grafts on nude mice. J Invest Dermatol. Jun. 1999;112(6):887-92.
Wianny et al., Proliferation and differentiation of porcine inner cell mass and epiblast in vitro. Biol Reprod. Oct. 1997;57(4):756-64.
Wilmut et al., Viable offspring derived from fetal and adult mammalian cells. Nature. Feb. 27, 1997;385(6619):810-3.
Wollheim et al., Regulation of insulin release by calcium. Physiol Rev. Oct. 1981;61(4):914-73.
Wright et al., Telomerase activity in human germline and embryonic tissues and cells. Dev Genet. 1996;18(2):173-9.
Wu et al., Wdnm1-like, a new adipokine with a role in MMP-2 activation. Am J Physiol Endocrinol Metab. Jul. 2008;295(1):E205-15.
Xu et al., Altered microRNA expression profile in exosomes during osteogenic differentiation of human bone marrow-derived mesenchymal stem cells. PLoS One. Dec. 11, 2014;9(12):e114627. 19 pages.
Xu et al., Characterization and enrichment of cardiomyocytes derived from human embryonic stem cells. Circ Res. Sep. 20, 2002;91(6):501-8. Including Supplementary Materials and Methods.
Yamada-Fukunaga et al., Age-associated telomere shortening in mouse oocytes. Reprod Biol Endocrinol. Nov. 21, 2013;11:108. 11 pages.
Yang et al., A cross-linked hyaluronan gel accelerates healing of corneal epithelial abrasion and alkali burn injuries in rabbits. Vet Ophthalmol. May 2010;13(3):144-50.
Yang et al., Poly(glutamic acid) poly(ethylene glycol) hydrogels prepared by photoinduced polymerization: Synthesis, characterization, and preliminary release studies of protein drugs. J Biomed Mater Res. Oct. 2002;62(1):14-21.
Yoder, Human endothelial progenitor cells. Cold Spring Harb Perspect Med. Jul. 2012;2(7):a006692. 14 pages.
Yoon et al., Differentiation and expansion of beta cell mass in porcine neonatal pancreatic cell clusters transplanted into nude mice. Cell Transplant. Nov.-Dec. 1999;8(6):673-89.
Yoshimura et al., Cell-assisted lipotransfer for facial lipoatrophy: efficacy of clinical use of adipose-derived stem cells. Dermatol Surg. Sep. 2008;34(9):1178-85.
Yu et al., Induced pluripotent stem cell lines derived from human somatic cells. Science. Dec. 21, 2007;318(5858):1917-20.
Yu et al., Initial Characterization of Osteoblast Differentiation and Loss of RUNX2 Stability in the Newly Established SK11 Human Embryonic Stem Cell-Derived Cell Line. J Cell Physiol. Feb. 2015;230(2):237-41.
Yuan et al., Transdifferentiation of human islets to pancreatic ductal cells in collagen matrix culture. Differentiation. Oct. 1996;61(1):67-75.
Yujiri et al., MEK kinase 1 (MEKK1) transduces c-Jun NH2-terminal kinase activation in response to changes in the microtubule cytoskeleton. J Biol Chem. Apr. 30, 1999;274(18):12605-10.
Zaidi et al., Disulfide linkage of biotin identifies a 106-kDa Ca2+ release channel in sarcoplasmic reticulum. J Biol Chem. Dec. 25, 1989;264(36):21737-47.
Zanetti et al., Induction of chondrogenesis in limb mesenchymal cultures by disruption of the actin cytoskeleton. J Cell Biol. Jul. 1984;99(1 Pt 1):115-23.
Zhang et al., The use of injectable sonication-induced silk hydrogel for VEGF(165) and BMP-2 delivery for elevation of the maxillary sinus floor. Biomaterials. Dec. 2011;32(35):9415-24.
Zhang et al., Wnt/beta-catenin signaling activates bone morphogenetic protein 2 expression in osteoblasts. Bone. Jan. 2013;52(1):145-56.
Zheng Shu et al., In situ crosslinkable hyaluronan hydrogels for tissue engineering. Biomaterials. Mar.-Apr. 2004;25(7-8):1339-48.
Zhong et al., Hydrogel matrix to support stem cell survival after brain transplantation in stroke. Neurorehabil Neural Repair. Sep. 2010;24(7):636-44.
Zhou et al., Purification and subunit characterization of the rat liver endocytic hyaluronan receptor. J Biol Chem. Nov. 26, 1999;274(48):33831-4.
Zhou et al., Telomerase reverse transcriptase activates the expression of vascular endothelial growth factor independent of telomerase activity. Biochem Biophys Res Commun. Sep. 4, 2009;386(4):739-43.
Zhu et al., Reprogramming of human primary somatic cells by OCT4 and chemical compounds. Cell Stem Cell. Dec. 3, 2010;7(6):651-5.
Zuker et al., On finding all suboptimal foldings of an Rna molecule. Science. Apr. 7, 1989;244(4900):48-52.
Zustiak et al., Characterization of protein release from hydrolytically degradable poly(ethylene glycol) hydrogels. Biotechnol Bioeng. Jan. 2011;108(1):197-206.

(56) References Cited

OTHER PUBLICATIONS

Zwaka et al., A germ cell origin of embryonic stem cells? Development. Jan. 2005;132(2):227-33.

* cited by examiner

MEL2 P21 D14 pellet TGFb3 10ng/ml

MEL2 P21 D14 pellet TGFb3 10ng/ml

MEL2 P21 D14 pellet BMP7 100ng/ml + TGFb3 10ng/ml

MEL2 P21 D14 pellet BMP7 100ng/ml + TGFb3 10ng/ml

CF822 MEL2 P21 D14 pellet GDF5 100ng/ml + TGFb3 10ng/ml

CF823 MEL2 P21 D14 pellet GDF5 100ng/ml + TGFb3 10ng/ml

CF824 7SMOO32 P21 D14 pellet TGFb3 10ng/ml

CF825 7SMOO32 P21 D14 pellet TGFb3 10ng/ml

CF826 7SMOO32 P21 D14 pellet GDF5 100ng per ml + TGFb3 10ng/ml

CF827 7SMOO32 P21 D14 pellet GDF5 100ng per ml + TGFb3 10ng/ml

CF828 7SMOO32 P21 D14 pellet BMP7 100ng/ml + TGFb3 10ng/ml

CF829 7SMOO32 P21 D14 pellet BMP7 100ng/ml + TGFb3 10ng/ml

CF854 MEL2 P21 D21 pellet TGFb3 10ng/ml

CF855 MEL2 P21 D21 pellet TGFb3 10ng/ml

CF856 MEL2 P21 D21 pellet BMP7 100ng/ml + TGFb3 10ng/ml

20X saf O and Col2

CF857 MEL2 P21 D21 pellet BMP7 100ng/ml + TGFb3 10ng/ml

CF858 MEL2 P21 D21 pellet GDF5 100ng/ml + TGFb3 10ng/ml

CF859 MEL2 P21 D21 pellet GDF5 100ng/ml + TGFb3 10ng/ml

CF860 E15 P16 D14 pellet TGFb3 10ng/ml

CF861 E15 P16 D14 pellet TGFb3 10ng/ml

CF862 E15 P16 D14 pellet GDF5 100 ng/ml +TGFb3 10ng/ml

CF863 E15 P16 D14 pellet GDF5 100 ng/ml +TGFb3 10ng/ml

CF864 E15 P16 D14 pellet BMP7 100 ng/ml +TGFb3 10ng/ml

CF865 E15 P16 D14 pellet BMP7 100 ng/ml +TGFb3 10ng/ml

CF866 E15 P16 D14 pellet TGFb3 10ng/ml

CF867 E15 P16 D21 pellet TGFb3 10ng/ml

CF868 E15 P16 D21 pellet GDF5 100 ng/ml +TGFb3 10ng/ml

CF869 E15 P16 D21 pellet GDF5 100 ng/ml +TGFb3 10ng/ml

CF870 E15 P16 D21 pellet BMP7 100 ng/ml +TGFb3 10ng/ml

20X Saf ) and Col2

CF871 E15 P16 D21 pellet BMP7 100 ng/ml +TGFb3 10ng/ml

20x scale Col 2

CF872 E15 P19 D14 pellet TGFb3 10ng/ml

CF873 E15 P19 D14 pellet TGFb3 10ng/ml

CF874 E15 P19 D14 pellet GDF5 100 ng/ml + TGFb3 10ng/ml

CF875 E15 P19 D14 pellet GDF5 100 ng/ml + TGFb3 10ng/ml

CF876 E15 P19 D14 pellet BMP7 100 ng/ml + TGFb3 10ng/ml

CF877 E15 P19 D14 pellet GDF5 100 ng/ml + TGFb3 10ng/ml

Scale Saf O

Positive ctrl COL2 (goat femur)

Positive ctrl Saf O (goat femur)

Istotype ctrl (CF868 E15 P16 D21 pellet GDF5 100 ng per ml +TGFb3 10 ng/ml)

SEQUENCE LISTING

```
<160> NUMBER OF SEQ ID NOS: 106

<210> SEQ ID NO 1
<211> LENGTH: 19
<212> TYPE: DNA
<213> ORGANISM: Homo sapiens

<400> SEQUENCE: 1
ccgacagcaa cgtggtctt                                                   19

<210> SEQ ID NO 2
<211> LENGTH: 19
<212> TYPE: DNA
<213> ORGANISM: Homo sapiens

<400> SEQUENCE: 2
caggttggcc cagatgatg                                                   19

<210> SEQ ID NO 3
<211> LENGTH: 20
<212> TYPE: DNA
<213> ORGANISM: Homo sapiens

<400> SEQUENCE: 3
tgctcagatt gcaaaagtgg                                                  20

<210> SEQ ID NO 4
<211> LENGTH: 20
<212> TYPE: DNA
<213> ORGANISM: Homo sapiens

<400> SEQUENCE: 4
tatctgggaa acccacgaag                                                  20

<210> SEQ ID NO 5
<211> LENGTH: 20
<212> TYPE: DNA
<213> ORGANISM: Homo sapiens

<400> SEQUENCE: 5
cctggtcctg gaagtcacat                                                  20

<210> SEQ ID NO 6
<211> LENGTH: 20
<212> TYPE: DNA
<213> ORGANISM: Homo sapiens

<400> SEQUENCE: 6
```

| ccatgttgtc cactcaccag | 20 |

<210> SEQ ID NO 7
<211> LENGTH: 20
<212> TYPE: DNA
<213> ORGANISM: Homo sapiens

<400> SEQUENCE: 7

| atccgtagag agcacggaga | 20 |

<210> SEQ ID NO 8
<211> LENGTH: 20
<212> TYPE: DNA
<213> ORGANISM: Homo sapiens

<400> SEQUENCE: 8

| ggactctcca tgggacaaga | 20 |

<210> SEQ ID NO 9
<211> LENGTH: 22
<212> TYPE: DNA
<213> ORGANISM: Homo sapiens

<400> SEQUENCE: 9

| ggcaatagca ggttcacgta ca | 22 |

<210> SEQ ID NO 10
<211> LENGTH: 22
<212> TYPE: DNA
<213> ORGANISM: Homo sapiens

<400> SEQUENCE: 10

| cgataacagt cttgccccac tt | 22 |

<210> SEQ ID NO 11
<211> LENGTH: 18
<212> TYPE: DNA
<213> ORGANISM: Homo sapiens

<400> SEQUENCE: 11

| tggcctgaga cagcatga | 18 |

<210> SEQ ID NO 12
<211> LENGTH: 19
<212> TYPE: DNA
<213> ORGANISM: Homo sapiens

<400> SEQUENCE: 12

| agtgttggga gccagattg | 19 |

<210> SEQ ID NO 13
<211> LENGTH: 20
<212> TYPE: DNA
<213> ORGANISM: Homo sapiens

<400> SEQUENCE: 13

| atccgtagag agcacggaga | 20 |

<210> SEQ ID NO 14
<211> LENGTH: 20
<212> TYPE: DNA
<213> ORGANISM: Homo sapiens

```
<400> SEQUENCE: 14
ggactctcca tgggacaaga                                               20

<210> SEQ ID NO 15
<211> LENGTH: 20
<212> TYPE: DNA
<213> ORGANISM: Homo sapiens

<400> SEQUENCE: 15
tacgactaca ccgaccacca                                               20

<210> SEQ ID NO 16
<211> LENGTH: 20
<212> TYPE: DNA
<213> ORGANISM: Homo sapiens

<400> SEQUENCE: 16
tcaaggtcga gtgagctgtg                                               20

<210> SEQ ID NO 17
<211> LENGTH: 20
<212> TYPE: DNA
<213> ORGANISM: Homo sapiens

<400> SEQUENCE: 17
tccagctaca tctcgcacct                                               20

<210> SEQ ID NO 18
<211> LENGTH: 20
<212> TYPE: DNA
<213> ORGANISM: Homo sapiens

<400> SEQUENCE: 18
cggtccttgc tcaactttct                                               20

<210> SEQ ID NO 19
<211> LENGTH: 20
<212> TYPE: DNA
<213> ORGANISM: Homo sapiens

<400> SEQUENCE: 19
ggacttggct cagtctctgg                                               20

<210> SEQ ID NO 20
<211> LENGTH: 20
<212> TYPE: DNA
<213> ORGANISM: Homo sapiens

<400> SEQUENCE: 20
tggggatgga gttcttcttg                                               20

<210> SEQ ID NO 21
<211> LENGTH: 20
<212> TYPE: DNA
<213> ORGANISM: Homo sapiens

<400> SEQUENCE: 21
ggcctccaag gagtaagacc                                               20

<210> SEQ ID NO 22
<211> LENGTH: 20
<212> TYPE: DNA
<213> ORGANISM: Homo sapiens
```

```
<400> SEQUENCE: 22 agggtctac atggcaactg                                              20

<210> SEQ ID NO 23
<211> LENGTH: 19
<212> TYPE: DNA
<213> ORGANISM: Homo sapiens

<400> SEQUENCE: 23
atttggtcgt ggacgtggt                                              19

<210> SEQ ID NO 24
<211> LENGTH: 24
<212> TYPE: DNA
<213> ORGANISM: Homo sapiens

<400> SEQUENCE: 24
tttggctgta agtttattca atgc                                        24

<210> SEQ ID NO 25
<211> LENGTH: 20
<212> TYPE: DNA
<213> ORGANISM: Homo sapiens

<400> SEQUENCE: 25
aaacgattgc agggtttcac                                             20

<210> SEQ ID NO 26
<211> LENGTH: 20
<212> TYPE: DNA
<213> ORGANISM: Homo sapiens

<400> SEQUENCE: 26
ctctcgtcgg tgactgttca                                             20

<210> SEQ ID NO 27
<211> LENGTH: 20
<212> TYPE: DNA
<213> ORGANISM: Homo sapiens

<400> SEQUENCE: 27
tctaccccaa tccagcaaac                                             20

<210> SEQ ID NO 28
<211> LENGTH: 20
<212> TYPE: DNA
<213> ORGANISM: Homo sapiens

<400> SEQUENCE: 28
gttgggagcc agattgtcat                                             20

<210> SEQ ID NO 29
<211> LENGTH: 25
<212> TYPE: DNA
<213> ORGANISM: Homo sapiens

<400> SEQUENCE: 29
cacactggta agtggggcaa gaccg                                       25

<210> SEQ ID NO 30
<211> LENGTH: 20
<212> TYPE: DNA
```

<213> ORGANISM: Homo sapiens

<400> SEQUENCE: 30
acgaggtcct cactggtgaa					20

<210> SEQ ID NO 31
<211> LENGTH: 20
<212> TYPE: DNA
<213> ORGANISM: Homo sapiens

<400> SEQUENCE: 31
tgagtcctca agcctcctgt					20

<210> SEQ ID NO 32
<211> LENGTH: 20
<212> TYPE: DNA
<213> ORGANISM: Homo sapiens

<400> SEQUENCE: 32
tggtctgcag cagttgattc					20

<210> SEQ ID NO 33
<211> LENGTH: 20
<212> TYPE: DNA
<213> ORGANISM: Homo sapiens

<400> SEQUENCE: 33
acagctgggg acattagtgg					20

<210> SEQ ID NO 34
<211> LENGTH: 20
<212> TYPE: DNA
<213> ORGANISM: Homo sapiens

<400> SEQUENCE: 34
gtggaatgca gaggtggttt					20

<210> SEQ ID NO 35
<211> LENGTH: 20
<212> TYPE: DNA
<213> ORGANISM: Homo sapiens

<400> SEQUENCE: 35
gctaagggtg aaagggttc					20

<210> SEQ ID NO 36
<211> LENGTH: 20
<212> TYPE: DNA
<213> ORGANISM: Homo sapiens

<400> SEQUENCE: 36
ctccaggatc accttttgga					20

<210> SEQ ID NO 37
<211> LENGTH: 20
<212> TYPE: DNA
<213> ORGANISM: Homo sapiens

<400> SEQUENCE: 37
ggactctgtc acacccacct					20

<210> SEQ ID NO 38
<211> LENGTH: 20

```
<212> TYPE: DNA
<213> ORGANISM: Homo sapiens

<400> SEQUENCE: 38
agctcggaga tgtcgttgtt                                              20

<210> SEQ ID NO 39
<211> LENGTH: 20
<212> TYPE: DNA
<213> ORGANISM: Homo sapiens

<400> SEQUENCE: 39
agcatcattc ggctgttacc                                              20

<210> SEQ ID NO 40
<211> LENGTH: 20
<212> TYPE: DNA
<213> ORGANISM: Homo sapiens

<400> SEQUENCE: 40
ctgaggggtg gaactgtagc                                              20

<210> SEQ ID NO 41
<211> LENGTH: 20
<212> TYPE: DNA
<213> ORGANISM: Homo sapiens

<400> SEQUENCE: 41
cccatcagca tcctcttcat                                              20

<210> SEQ ID NO 42
<211> LENGTH: 20
<212> TYPE: DNA
<213> ORGANISM: Homo sapiens

<400> SEQUENCE: 42
tgtagatgct cctgccacag                                              20

<210> SEQ ID NO 43
<211> LENGTH: 20
<212> TYPE: DNA
<213> ORGANISM: Homo sapiens

<400> SEQUENCE: 43
accacgcttc ctatgtgacc                                              20

<210> SEQ ID NO 44
<211> LENGTH: 20
<212> TYPE: DNA
<213> ORGANISM: Homo sapiens

<400> SEQUENCE: 44
tgttgtaact gggtggcaaa                                              20

<210> SEQ ID NO 45
<211> LENGTH: 20
<212> TYPE: DNA
<213> ORGANISM: Homo sapiens

<400> SEQUENCE: 45
tcgagggttt gatggacttc                                              20

<210> SEQ ID NO 46
```

```
<211> LENGTH: 20
<212> TYPE: DNA
<213> ORGANISM: Homo sapiens

<400> SEQUENCE: 46
catcttctcc cctcattcca                                              20

<210> SEQ ID NO 47
<211> LENGTH: 20
<212> TYPE: DNA
<213> ORGANISM: Homo sapiens

<400> SEQUENCE: 47
tggcaacaaa atcagcagag                                              20

<210> SEQ ID NO 48
<211> LENGTH: 20
<212> TYPE: DNA
<213> ORGANISM: Homo sapiens

<400> SEQUENCE: 48
gccattgtca acagcagaga                                              20

<210> SEQ ID NO 49
<211> LENGTH: 20
<212> TYPE: DNA
<213> ORGANISM: Homo sapiens

<400> SEQUENCE: 49
cctccaaggc aataggatca                                              20

<210> SEQ ID NO 50
<211> LENGTH: 19
<212> TYPE: DNA
<213> ORGANISM: Homo sapiens

<400> SEQUENCE: 50
gctgcgcttg atctcgttc                                               19

<210> SEQ ID NO 51
<211> LENGTH: 20
<212> TYPE: DNA
<213> ORGANISM: Homo sapiens

<400> SEQUENCE: 51
tgatctgcag tggctcattc                                              20

<210> SEQ ID NO 52
<211> LENGTH: 20
<212> TYPE: DNA
<213> ORGANISM: Homo sapiens

<400> SEQUENCE: 52
aaaagagccc agctttgtga                                              20

<210> SEQ ID NO 53
<211> LENGTH: 20
<212> TYPE: DNA
<213> ORGANISM: Homo sapiens

<400> SEQUENCE: 53
gtgctaaagg tgccaatggt                                              20
```

```
<210> SEQ ID NO 54
<211> LENGTH: 20
<212> TYPE: DNA
<213> ORGANISM: Homo sapiens

<400> SEQUENCE: 54
accaggttca ccgctgttac                                               20

<210> SEQ ID NO 55
<211> LENGTH: 20
<212> TYPE: DNA
<213> ORGANISM: Homo sapiens

<400> SEQUENCE: 55
gtgctaaagg tgccaatggt                                               20

<210> SEQ ID NO 56
<211> LENGTH: 20
<212> TYPE: DNA
<213> ORGANISM: Homo sapiens

<400> SEQUENCE: 56
ctcctcgctt tccttcctct                                               20

<210> SEQ ID NO 57
<211> LENGTH: 20
<212> TYPE: DNA
<213> ORGANISM: Homo sapiens

<400> SEQUENCE: 57
tcccaatctt gccttcattc                                               20

<210> SEQ ID NO 58
<211> LENGTH: 20
<212> TYPE: DNA
<213> ORGANISM: Homo sapiens

<400> SEQUENCE: 58
gtcatggaac gccactaggt                                               20

<210> SEQ ID NO 59
<211> LENGTH: 17
<212> TYPE: DNA
<213> ORGANISM: Homo sapiens

<400> SEQUENCE: 59
tcgaggacag cgaggcc                                                  17

<210> SEQ ID NO 60
<211> LENGTH: 22
<212> TYPE: DNA
<213> ORGANISM: Homo sapiens

<400> SEQUENCE: 60
tcgagggtgt agcgtgtaga ga                                            22

<210> SEQ ID NO 61
<211> LENGTH: 20
<212> TYPE: DNA
<213> ORGANISM: Homo sapiens

<400> SEQUENCE: 61
caaggcacca tctccaggaa                                               20
```

<210> SEQ ID NO 62
<211> LENGTH: 24
<212> TYPE: DNA
<213> ORGANISM: Homo sapiens

<400> SEQUENCE: 62
aaagggtatt tgtggcagca tatt                                    24

<210> SEQ ID NO 63
<211> LENGTH: 25
<212> TYPE: DNA
<213> ORGANISM: Homo sapiens

<400> SEQUENCE: 63
ttccacaagc acaaacttta cacat                                   25

<210> SEQ ID NO 64
<211> LENGTH: 30
<212> TYPE: DNA
<213> ORGANISM: Homo sapiens

<400> SEQUENCE: 64
gtgaaactga gttttgtata acctctcagt                              30

<210> SEQ ID NO 65
<211> LENGTH: 22
<212> TYPE: DNA
<213> ORGANISM: Homo sapiens

<400> SEQUENCE: 65
accagattga ccatattgat ga                                      22

<210> SEQ ID NO 66
<211> LENGTH: 19
<212> TYPE: DNA
<213> ORGANISM: Homo sapiens

<400> SEQUENCE: 66
ggacagatcc agctcaacc                                          19

<210> SEQ ID NO 67
<211> LENGTH: 20
<212> TYPE: DNA
<213> ORGANISM: Homo sapiens

<400> SEQUENCE: 67
aggcaagcaa aggagatgaa                                         20

<210> SEQ ID NO 68
<211> LENGTH: 20
<212> TYPE: DNA
<213> ORGANISM: Homo sapiens

<400> SEQUENCE: 68
tggtgttctg agaggcacag                                         20

<210> SEQ ID NO 69
<211> LENGTH: 27
<212> TYPE: DNA
<213> ORGANISM: Homo sapiens

<400> SEQUENCE: 69
actgagtcat ttgcagtgtt ttctgcc                                 27

<210> SEQ ID NO 70
<211> LENGTH: 21
<212> TYPE: DNA
<213> ORGANISM: Homo sapiens

<400> SEQUENCE: 70
gtgggctgat cccctccagg t                                              21

<210> SEQ ID NO 71
<211> LENGTH: 20
<212> TYPE: DNA
<213> ORGANISM: Homo sapiens

<400> SEQUENCE: 71
tggcactgca ctgggtagga                                                20

<210> SEQ ID NO 72
<211> LENGTH: 20
<212> TYPE: DNA
<213> ORGANISM: Homo sapiens

<400> SEQUENCE: 72
aaggctggga gcccgtcact                                                20

<210> SEQ ID NO 73
<211> LENGTH: 20
<212> TYPE: DNA
<213> ORGANISM: Homo sapiens

<400> SEQUENCE: 73
tgagtcctca agcctcctgt                                                20

<210> SEQ ID NO 74
<211> LENGTH: 20
<212> TYPE: DNA
<213> ORGANISM: Homo sapiens

<400> SEQUENCE: 74
cctctgtctc cttgcaggtc                                                20

<210> SEQ ID NO 75
<211> LENGTH: 20
<212> TYPE: DNA
<213> ORGANISM: Homo sapiens

<400> SEQUENCE: 75
ggccgggaga ccgtgtgttg                                                20

<210> SEQ ID NO 76
<211> LENGTH: 20
<212> TYPE: DNA
<213> ORGANISM: Homo sapiens

<400> SEQUENCE: 76
tggggctcgc ggtccagtaa                                                20

<210> SEQ ID NO 77
<211> LENGTH: 20
<212> TYPE: DNA
<213> ORGANISM: Homo sapiens

<400> SEQUENCE: 77

```
tacgcctgga gagtggggcg                                             20

<210> SEQ ID NO 78
<211> LENGTH: 20
<212> TYPE: DNA
<213> ORGANISM: Homo sapiens

<400> SEQUENCE: 78
tggggctcgc ggtccagtaa                                             20

<210> SEQ ID NO 79
<211> LENGTH: 20
<212> TYPE: DNA
<213> ORGANISM: Homo sapiens

<400> SEQUENCE: 79
tcgtgggtcc caggggtgaa                                             20

<210> SEQ ID NO 80
<211> LENGTH: 20
<212> TYPE: DNA
<213> ORGANISM: Homo sapiens

<400> SEQUENCE: 80
gacctggagg gccctgtgcg                                             20

<210> SEQ ID NO 81
<211> LENGTH: 20
<212> TYPE: DNA
<213> ORGANISM: Homo sapiens

<400> SEQUENCE: 81
tgctgcccca tctgcccaac                                             20

<210> SEQ ID NO 82
<211> LENGTH: 20
<212> TYPE: DNA
<213> ORGANISM: Homo sapiens

<400> SEQUENCE: 82
cctgcaggtc cctgaggccc                                             20

<210> SEQ ID NO 83
<211> LENGTH: 20
<212> TYPE: DNA
<213> ORGANISM: Homo sapiens

<400> SEQUENCE: 83
agggccagga tgtccggcaa                                             20

<210> SEQ ID NO 84
<211> LENGTH: 20
<212> TYPE: DNA
<213> ORGANISM: Homo sapiens

<400> SEQUENCE: 84
tctgccacga ggtccagggg                                             20

<210> SEQ ID NO 85
<211> LENGTH: 20
<212> TYPE: DNA
<213> ORGANISM: Homo sapiens

<400> SEQUENCE: 85
```

| | |
|---|---|
| cggggcgatg gcacctttgt | 20 |

<210> SEQ ID NO 86
<211> LENGTH: 20
<212> TYPE: DNA
<213> ORGANISM: Homo sapiens

<400> SEQUENCE: 86

| | |
|---|---|
| gatagaggcg gtgggggcca | 20 |

<210> SEQ ID NO 87
<211> LENGTH: 20
<212> TYPE: DNA
<213> ORGANISM: Homo sapiens

<400> SEQUENCE: 87

| | |
|---|---|
| acaatgacgg agtccctgac | 20 |

<210> SEQ ID NO 88
<211> LENGTH: 20
<212> TYPE: DNA
<213> ORGANISM: Homo sapiens

<400> SEQUENCE: 88

| | |
|---|---|
| tctgcatcaa agtcgtcctg | 20 |

<210> SEQ ID NO 89
<211> LENGTH: 20
<212> TYPE: DNA
<213> ORGANISM: Homo sapiens

<400> SEQUENCE: 89

| | |
|---|---|
| gagtcagaga cggaacagcc | 20 |

<210> SEQ ID NO 90
<211> LENGTH: 20
<212> TYPE: DNA
<213> ORGANISM: Homo sapiens

<400> SEQUENCE: 90

| | |
|---|---|
| agtcccagag actgagccaa | 20 |

<210> SEQ ID NO 91
<211> LENGTH: 20
<212> TYPE: DNA
<213> ORGANISM: Homo sapiens

<400> SEQUENCE: 91

| | |
|---|---|
| gcgcaagtga aggctcgtat | 20 |

<210> SEQ ID NO 92
<211> LENGTH: 23
<212> TYPE: DNA
<213> ORGANISM: Homo sapiens

<400> SEQUENCE: 92

| | |
|---|---|
| gtttggagga gatgctctgt ttg | 23 |

<210> SEQ ID NO 93
<211> LENGTH: 19
<212> TYPE: DNA
<213> ORGANISM: Homo sapiens

```
<400> SEQUENCE: 93
agtgttggga gccagattg                                              19

<210> SEQ ID NO 94
<211> LENGTH: 20
<212> TYPE: DNA
<213> ORGANISM: Homo sapiens

<400> SEQUENCE: 94
cctctgtctc cttgcaggtc                                             20

<210> SEQ ID NO 95
<211> LENGTH: 20
<212> TYPE: DNA
<213> ORGANISM: Homo sapiens

<400> SEQUENCE: 95
ggactctcca tgggacaaga                                             20

<210> SEQ ID NO 96
<211> LENGTH: 20
<212> TYPE: DNA
<213> ORGANISM: Homo sapiens

<400> SEQUENCE: 96
ctgggccttt ggcctgcctt                                             20

<210> SEQ ID NO 97
<211> LENGTH: 20
<212> TYPE: DNA
<213> ORGANISM: Homo sapiens

<400> SEQUENCE: 97
aggggtctac atggcaactg                                             20

<210> SEQ ID NO 98
<211> LENGTH: 24
<212> TYPE: DNA
<213> ORGANISM: Homo sapiens

<400> SEQUENCE: 98
tttggctgta agtttattca atgc                                        24

<210> SEQ ID NO 99
<211> LENGTH: 20
<212> TYPE: DNA
<213> ORGANISM: Homo sapiens

<400> SEQUENCE: 99
ctctcgtcgg tgactgttca                                             20

<210> SEQ ID NO 100
<211> LENGTH: 18
<212> TYPE: DNA
<213> ORGANISM: Homo sapiens

<400> SEQUENCE: 100
tggcctgaga cagcatga                                               18

<210> SEQ ID NO 101
<211> LENGTH: 20
<212> TYPE: DNA
<213> ORGANISM: Homo sapiens
```

```
<400> SEQUENCE: 101
tgagtcctca agcctcctgt                                               20

<210> SEQ ID NO 102
<211> LENGTH: 20
<212> TYPE: DNA
<213> ORGANISM: Homo sapiens

<400> SEQUENCE: 102
atccgtagag agcacggaga                                               20

<210> SEQ ID NO 103
<211> LENGTH: 20
<212> TYPE: DNA
<213> ORGANISM: Homo sapiens

<400> SEQUENCE: 103
gggcctcaat ggacccaccg                                               20

<210> SEQ ID NO 104
<211> LENGTH: 20
<212> TYPE: DNA
<213> ORGANISM: Homo sapiens

<400> SEQUENCE: 104
ggcctccaag gagtaagacc                                               20

<210> SEQ ID NO 105
<211> LENGTH: 19
<212> TYPE: DNA
<213> ORGANISM: Homo sapiens

<400> SEQUENCE: 105
atttggtcgt ggacgtggt                                                19

<210> SEQ ID NO 106
<211> LENGTH: 20
<212> TYPE: DNA
<213> ORGANISM: Homo sapiens

<400> SEQUENCE: 106
aaacgattgc agggtttcac                                               20
```

METHODS AND FORMULATIONS FOR ORTHOPEDIC CELL THERAPY

This application is a national stage application of PCT Application No. PCT/US12/46564 and claims priority to U.S. Provisional Application No. 61/507,041 filed on Jul. 12, 2011 and U.S. Provisional Application No. 61/601,499 filed on Feb. 21, 2012 all of which are incorporated by reference in their entirety.

FIELD OF THE INVENTION

The invention relates to the filed of pluripotent cell biology and to clonal progenitor cell lines and methods of making the same.

BACKGROUND

Advances in stem cell technology, such as the isolation and propagation in vitro of primordial stem cells, including embryonic stem cells ("ES" cells including human ES cells ("hES" cells)) and related primordial stem cells including but not limited to, iPS, EG, EC, ICM, epiblast, or ED cells (including human iPS, EG, EC, ICM, epiblast, or ED cells), constitute an important new area of medical research. hES cells have a demonstrated potential to be propagated in the undifferentiated state and then to be induced subsequently to differentiate into likely any and all of the cell types in the human body, including complex tissues. In addition, many of these primordial stem cells are naturally telomerase positive in the undifferentiated state, thereby allowing the cells to be expanded indefinitely. This expansion potential allows these primordial cells to be genetically modified followed by clonal expansion, thus permitting the production of numerous homogeneous populations of genetically modified primordial stem cells. Since the telomere length of many of these cells is comparable to that observed in sperm DNA (approximately 10-18 kb TRF length), differentiated cells derived from these immortal lines once they begin differentiation (generally associated with the repression of the expression of the catalytic component of telomerase (TERT)) display a long initial telomere length providing the cells with a long replicative capacity compared to fetal or adult-derived tissue. This has led to the suggestion that many diseases resulting from the dysfunction of cells may be amenable to treatment by the administration of hES-derived cells of various differentiated types (Thomson et al., Science 282:1145-1147 (1998)). Nuclear transfer studies have demonstrated that it is possible to transform a somatic differentiated cell back to a primordial stem cell state such as that of embryonic stem ("ES") cells (Cibelli et al., Nature Biotech 16:642-646 (1998)) or embryo-derived ("ED") cells. The development of technologies to reprogram somatic cells back to a totipotent ES cell state, such as by the transfer of the genome of the somatic cell to an enucleated oocyte and the subsequent culture of the reconstructed embryo to yield ES cells, often referred to as somatic cell nuclear transfer ("SCNT") or through analytical reprogramming technology, offers methods to transplant ES-derived somatic cells with a nuclear genotype of the patient (Lanza et al., Nature Medicine 5:975-977 (1999)).

In addition to SCNT, other techniques exist to address the problem of transplant rejection, including the use of gynogenesis and androgenesis (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US00/29551, filed Oct. 27, 2000; the disclosures of which are incorporated by reference in their entirety). In the case of a type of gynogenesis designated parthenogenesis, pluripotent stem cells may be manufactured without antigens foreign to the gamete donor and therefore useful in manufacturing cells that can be transplanted without rejection. In addition, parthenogenic stem cell lines can be assembled into a bank of cell lines homozygous in the HLA region (or corresponding MHC region of nonhuman animals) to reduce the complexity of a stem cell bank in regard to HLA haplotypes.

In addition, cell lines or a bank of said cell lines can be produced that are hemizygous in the HLA region (or corresponding MHC region of nonhuman animals; see PCT application Ser. No. PCT/US2006/040985 filed Oct. 20, 2006 entitled "Totipotent, Nearly Totipotent or Pluripotent Mammalian Cells Homozygous or Hemizygous for One or More Histocompatibility Antigen Genes", incorporated herein by reference). A bank of hemizygous cell lines provides the advantage of not only reducing the complexity inherent in the normal mammalian MHC gene pool, but it also reduces the gene dosage of the antigens to reduce the expression of said antigens without eliminating their expression entirely, thereby not stimulating a natural killer response.

In addition to SCNT, parthenogenesis, and the construction of banks of cells with homozygous or hemizygous HLA alleles, other techniques exist to address the problem of transplant rejection, including the use of technologies to reprogram somatic cells using transcriptional regulators (see PCT application Ser. No. PCT/US20061030632 filed on Aug. 3, 2006 and titled "Improved Methods of Reprogramming Animal Somatic Cells", incorporated herein by reference).

In regard to differentiating primordial stem cells into desired cell types, the potential to clonally isolate lines of human embryonic progenitor (hEP) cell lines provides a means to propagate novel highly purified cell lineages useful in the production of diverse secreted factors, for research, and for the manufacture of cell-based therapies (see PCT application Ser. No. PCT/US2006/013519 filed on Apr. 11, 2006 and titled "Novel Uses of Cells With Prenatal Patterns of Gene Expression"; U.S. patent application Ser. No. 11/604,047 filed on Nov. 21, 2006 and titled "Methods to Accelerate the Isolation of Novel Cell Strains from Pluripotent Stem Cells and Cells Obtained Thereby"; U.S. patent application Ser. No. 12/504,630 filed on Jul. 16, 2009 and titled "Methods to Accelerate the Isolation of Novel Cell Strains from Pluripotent Stem Cells and Cells Obtained Thereby"; and PCT application Ser. No. PCT/US2011/037969 filed on May 25, 2011 and entitled "Improved Methods of Screening Embryonic Progenitor Cell Lines", each incorporated herein by reference).

Nevertheless, there remains a need for improved methods to discover the differentiation potential of said hEP cell lines when exposed to diverse differentiation-inducing factors or other differentiation conditions that induce such differentiation under conditions which are compatible in either a general laboratory setting or in a good manufacturing processes ("GMP") cell manufacturing facility where there is adequate documentation as to the purity and genetic normality of the cells at advanced passages (>18-21 doublings of clonal expansion). In particular, there remains a need for improved methods of differentiating said hEP cell lines using BMP growth factor family members.

SUMMARY OF THE INVENTION

We have previously demonstrated that the long initial telomere length of hES cells, together with the unexpected robust proliferative capacity of primitive hES-derived progenitor cell types, facilitates the industrial expansion and characterization of >140 diverse and scalable clonal lineages with diverse defined homeobox gene expression as well as diverse transcriptional regulators (West et al., 2008, Regenerative Medicine vol. 3(3) pp. 287-308, incorporated herein by reference, including supplemental information; and U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety). The robustness of these clonally-purified lines, their ability to expand for >40 passages while maintaining their pattern of gene expression, lack of tumorigenicity, and their embryonic pattern of gene expression offers novel compositions and methods for modeling numerous differentiation pathways for the first time in vitro, and for the manufacture of purified product not existing in such a purified state in nature or using other manufacturing modalities. We disclose novel compositions and methods related to these cells, including novel screening methods and conditions that differentiate human embryonic progenitors into numerous terminally-differentiated cell types of use in medical research and therapy in the presence of BMP factor family members including TGFB3, BMP2, BMP4, BMP6, BMP7, and GDF5, and combinations thereof. Suitable concentrations for each of the following factors TGFB3, BMP2, BMP4, BMP6, BMP7, and GDF5, range from about 1 ng/ml to about 200 ng/ml, from about 5 ng/ml to about 150 ng/ml; from about 10 ng/ml to about 100 ng/ml. In some embodiments a suitable concentration of TGFβ3 is about 1-20 ng/ml. In some embodiments a suitable concentration of BMP2 is about 10-200 ng/ml. In some embodiments a suitable concentration of BMP4 is about 1-100 ng/ml. In some embodiments a suitable concentration of BMP6 is about 1-200 ng/ml. In some embodiments a suitable concentration of BMP7 is about 20-300 ng/ml. In some embodiments a suitable concentration of GDRF is about 20-300 ng/ml.

In some embodiments the invention provides an isolated progenitor cell line chosen from the cell lines disclosed in Table 1.

In certain embodiments the invention provides an isolated clonal cell progenitor line expressing one or more markers expressed by chondrocytes. The clonal cell progenitor line may be the in vitro differentiated progeny of a pluripotent stem cell.

In some embodiments the invention provides an isolated cell progenitor line expressing the markers COL2A1 and CCRTAC1. The cells may express little or no COL10A.

In other embodiments the invention provides the cell line 4D20.8.

In certain embodiments the invention provides an isolated cell progenitor line expressing one or more markers expressed by tendons.

In some embodiments the invention provides an isolated cell progenitor line expressing the marker TNMD. The cells may express little or no COL2A1.

In other embodiments the invention provides the cell line 7PEND24.

In certain embodiments the invention provides an isolated cell progenitor line expressing one or more markers expressed by bone forming cells.

In some embodiments the invention provides an isolated cell progenitor line expressing the markers bone sialoprotein II.

In other embodiments the invention provides the cell line SM30.

In other embodiments the invention provides the cell line MEL2.

In certain embodiments the invention provides a method of making chondrocyte progenitor cell comprising obtaining a clonal progenitor cell differentiated from a pluripotent stem cell and contacting the clonal progenitor cell with a differentiation cocktail comprising one or more BMP family members thereby making a chondrocyte progenitor cell.

In other embodiments the invention provides a method of making progenitor cell expressing one or more markers chosen from COL2A1 and CRTAC1 comprising obtaining a clonal progenitor cell differentiated from a pluripotent stem cell and contacting the clonal progenitor cell with a differentiation cocktail comprising one or more BMP family members thereby making a progenitor cell expressing one or more markers chosen from COL2A1 and CRTAC.

In still other embodiments the invention provides a method of making a chondrocyte progenitor cell comprising contacting the clonal progenitor cell line 4D20.8 with one or more members of the BMP family thereby making a chondrocyte progenitor cell.

In yet other embodiments the invention provides a method of making a progenitor cell expressing one or more markers chosen from COL2A1 and CRTAC1 comprising contacting the clonal progenitor cell line 4D20.8 with one or more members of the BMP family thereby making a progenitor cell expressing one or more markers chosen from COL2A1 and CRTAC.

In certain embodiments the invention provides a method of making tendon progenitor cell comprising obtaining a clonal progenitor cell differentiated from a pluripotent stem cell and contacting the clonal progenitor cell with a differentiation cocktail comprising one or more BMP family members thereby making a tendon progenitor cell.

In other embodiments the invention provides a method of making progenitor cell expressing TMND comprising obtaining a clonal progenitor cell differentiated from a pluripotent stem cell and contacting the clonal progenitor cell with a differentiation cocktail comprising one or more BMP family members thereby making a progenitor cell expressing TMND.

In still other embodiments the invention provides a method of making a tendon progenitor cell comprising contacting the clonal progenitor cell line 7PEND24 with one or more members of the BMP family thereby making a chondrocyte progenitor cell.

In yet other embodiments the invention provides a method of making a progenitor cell expressing TMND comprising contacting the clonal progenitor cell line 7PEND with one or more members of the BMP family thereby making a progenitor cell expressing TMND.

In certain embodiments the invention provides a method of making bone progenitor cell comprising obtaining a clonal progenitor cell differentiated from a pluripotent stem cell and contacting the clonal progenitor cell with a differentiation cocktail comprising one or more BMP family members thereby making a bone progenitor cell.

In other embodiments the invention provides a method of making a progenitor cell expressing one or more markers chosen from IBSP, COL2A1 and COL10A comprising obtaining a clonal progenitor cell differentiated from a pluripotent stem cell and contacting the clonal progenitor cell with a differentiation cocktail comprising one or more BMP family members thereby making a progenitor cell expressing one or more markers chosen from IBSP, COL2A1 and COL10A.

In still other embodiments the invention provides a method of making a bone progenitor cell comprising contacting the clonal progenitor cell line chosen from MEL2 and SM30 with one or more members of the BMP family thereby making a bone progenitor cell.

In yet other embodiments the invention provides a method of making a progenitor cell expressing one or more markers chosen from IBSP, COL2A1 and COL10A comprising contacting a clonal progenitor cell line chosen from MEL2 and SM30 with one or more members of the BMP family thereby making a progenitor cell expressing one or more markers chosen from IBSP, COL2A1 and COL10A.

In some embodiments the invention provides a method of making a progenitor cell chosen from a chondrocyte progenitor, a tendon cell progenitor and a bone cell progenitor comprising obtaining at least one clonal cell line recited in table I and contacting the one clonal cell line with one or more members of the BMP family thereby making a progenitor cell chosen from a chondrocyte progenitor, a tendon cell progenitor and a bone cell progenitor.

In other embodiments the invention provides a method of making a progenitor cell expressing one or more markers chosen from COL2A, CRTAC1, TNMD and IBSP comprising obtaining at least one clonal cell line recited in table I and contacting the one clonal cell line with one or more members of the BMP family thereby making a progenitor cell expressing one or more markers chosen from COL2A, CRTAC1, TNMD and IBSP.

In still other embodiments the invention provides a kit for making a progenitor cell chosen from a chondrocyte progenitor cell, a bone progenitor cell and a tendon progenitor cell comprising at least one clonal progenitor cell recited in Table I and at least one member of the BMP family.

In yet other embodiments the invention provides a system for generating progenitor cells comprising a pluripotent stem cell, such as an iPS cell, an hES cell or the like and a differentiated clonal progenitor cell. The differentiated clonal progenitor cell may, under appropriate conditions be induced to differentiate into a progenitor cell chosen from a chondrocyte progenitor cell, a bone progenitor cell and a tendon progenitor cell.

The BMP family member suitable for use in the methods recited infra may include one or more of TGFβ3, TGFβ10, BMP4, BMP6, BMP7 and GDF5.

The cell lines and cell progenitors described above may be the in vitro progeny of a pluripotent stem cell such as an iPS cell or a human embryonic stem cell, such as an established human embryonic stem cell line obtained from a commercial cell bank. As such the cell lines and progenitor cell lines may have essentially the same genome as their parental cell. Thus the cells may have a genome that is at least 95%, at least 96%, at least 97% at least 99%, at least 99.5%, at least 99.9% identical to its parental cell, such as an established line of pluripotent stem cells, such as human embryonic stem cells (hES cells) or an induced pluriptotent stem cell (iPS cell).

The cell lines and cell progenitors described above may proliferate in culture for at least 20 passages. The cell lines and cell progenitors described above may proliferate in culture for about 20 passages.

DETAILED DESCRIPTION OF THE INVENTION

Abbreviations

Figure 1A:
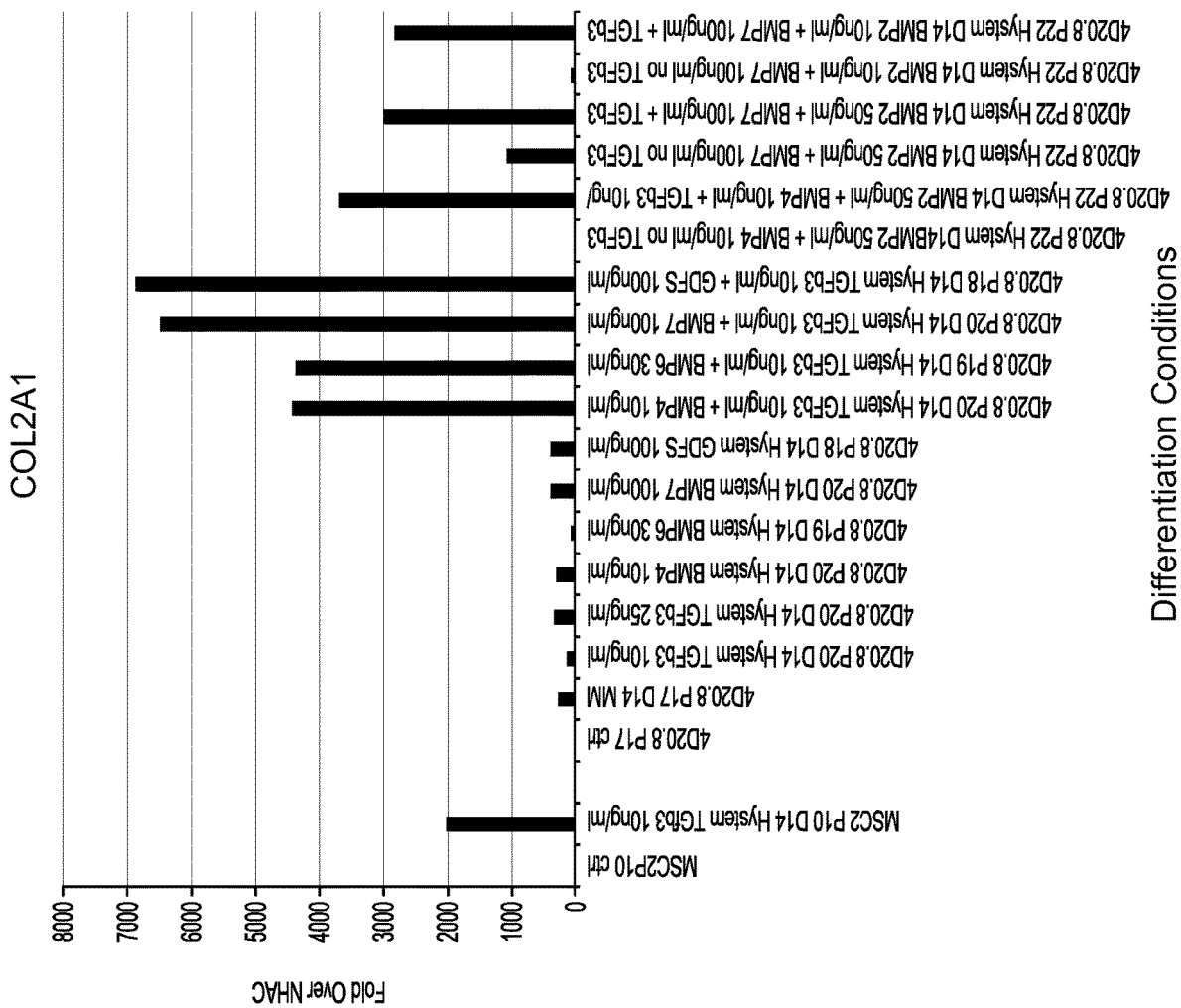
FIGS. 1A, B and C: Levels of induction of genes in control MSCs and the clonal embryonic progenitor cell line 4D20.8 in the presence of diverse BMP family members. Values shown are relative expression compared to cultured normal human articular chondrocytes (NHACs) as determined by qPCR. A) Levels of COL2A1 expression. B) Levels of COL10A1 expression. C) Levels of CRTAC1 expression.

AFP—Alpha fetoprotein
BMP—Bone Morphogenic Protein
BRL—Buffalo rat liver
BSA—Bovine serum albumin
CD—Cluster Designation
cGMP—Current Good Manufacturing Processes
CNS—Central Nervous System
DMEM—Dulbecco's modified Eagle's medium
DMSO—Dimethyl sulphoxide
DPBS—Dulbecco's Phosphate Buffered Saline
EC—Embryonal carcinoma
EC Cells—Embryonal carcinoma cells; hEC cells are human embryonal carcinoma cells
ECAPCs—Embryonic cutaneous adipocyte progenitor cells
ECM—Extracellular Matrix
ED Cells—Embryo-derived cells; hED cells are human ED cells
EDTA—Ethylenediamine tetraacetic acid
EG Cells—Embryonic germ cells; hEG cells are human EG cells EP Cells—Embryonic progenitor cells are cells derived from primordial stem cells that are more differentiated than primordial stem cells, in that they no longer display markers such as SSEA4, TRA1-60 or TRA-1-81 seropositivity in the case of the human species, but have not fully differentiated. Embryonic progenitor cells correspond to the embryonic stages as opposed to the postnatal stage of development.

ES Cells—Embryonic stem cells; hES cells are human ES cells

FACS—Fluorescence activated cell sorting

FBS—Fetal bovine serum

GFP—Green Fluorescent Protein

GMP—Good Manufacturing Practices hED Cells—Human embryo-derived cells hEG Cells—Human embryonic germ cells are stem cells derived from the primordial germ cells of fetal tissue.

hEP Cells—Human embryonic progenitor cells are embryonic progenitor cells from the human species.

hiPS Cells—Human induced pluripotent stem cells are cells with properties similar to hES cells obtained from somatic cells after exposure to hES-specific transcription factors such as SOX2, KLF4, OCT4, MYC, or NANOG, LUN28, OCT4, and SOX2, HSE—Human skin equivalents are mixtures of cells and biological or synthetic matrices manufactured for testing purposes or for therapeutic application in promoting wound repair.

HUVEC—Human umbilical vein endothelial cell

ICM—Inner cell mass of the mammalian blastocyst-stage embryo.

iPS Cells—Induced pluripotent stem cells are cells with properties similar to hES cells obtained from somatic cells after exposure to ES-specific transcription factors such as SOX2, KLF4, OCT4, MYC, or NANOG, LIN28, OCT4, and SOX2.

LOH—Loss of Heterozygosity

MEM—Minimal essential medium miRNA—Micro RNA

MSC—Mesenchymal Stem Cell

NHACs—Cultured Normal Human Articular Chondrocytes

NT—Nuclear Transfer

PBS—Phosphate buffered saline

PEGDA—Polyethylene glycol diacrylate

PS fibroblasts—Pre-scarring fibroblasts are fibroblasts derived from the skin of early gestational skin or derived from ED cells that display a prenatal pattern of gene expression in that they promote the rapid healing of dermal wounds without scar formation.

RA—Retinoic acid

RFU—Relative Fluorescence Units

SCNT—Somatic Cell Nuclear Transfer

SFM—Serum-Free Medium

SPF—Specific Pathogen-Free

SV40—Simian Virus 40

Tag—Large T-antigen

T-EDTA—Trypsin EDTA

Definitions

The term "analytical reprogramming technology" refers to a variety of methods to reprogram the pattern of gene expression of a somatic cell to that of a more pluripotent state, such as that of an iPS, ES, ED, EC or EG cell, wherein the reprogramming occurs in multiple and discrete steps and does not rely simply on the transfer of a somatic cell into an oocyte and the activation of that oocyte (see U.S. application No. 60/332,510, filed Nov. 26, 2001; Ser. No. 10/304,020, filed Nov. 26, 2002; PCT application no. PCT/US02/37899, filed Nov. 26, 2003; U.S. application No. 60/705,625, filed Aug. 3, 2005; U.S. application No. 60/729,173, filed Aug. 20, 2005; U.S. application No. 60/818,813, filed Jul. 5, 2006, PCT/US06/30632, filed Aug. 3, 2006, the disclosure of each of which is incorporated by reference herein).

The term "blastomere/morula cells" refers to blastomere or morula cells in a mammalian embryo or blastomere or morula cells cultured in vitro with or without additional cells including differentiated derivatives of those cells.

The term "cell expressing gene X", "gene X is expressed in a cell" (or cell population), or equivalents thereof, means that analysis of the cell using a specific assay platform provided a positive result. The converse is also true (i.e., by a cell not expressing gene X, or equivalents, is meant that analysis of the cell using a specific assay platform provided a negative result). Thus, any gene expression result described herein is tied to the specific probe or probes employed in the assay platform (or platforms) for the gene indicated.

The term "cell line" refers to a mortal or immortal population of cells that is capable of propagation and expansion in vitro.

The term "cellular reconstitution" refers to the transfer of a nucleus of chromatin to cellular cytoplasm so as to obtain a functional cell.

The term "clonal" refers to a population of cells obtained b the expansion of a single cell into a population of cells all derived from that original single cell and not containing other cells.

The term "colony in situ differentiation" refers to the differentiation of colonies of cells (e.g., hES, hEG, hiPS, hEC or hED) in situ without removing or disaggregating the colonies from the culture vessel in which the colonies were propagated as undifferentiated stem cell lines. Colony in situ differentiation does not utilize the intermediate step of forming embryoid bodies, though embryoid body formation or other aggregation techniques such as the use of spinner culture may nevertheless follow a period of colony in situ differentiation.

The term "cytoplasmic bleb" refers to the cytoplasm of a cell bound by an intact or permeabilized but otherwise intact plasma membrane, but lacking a nucleus.

The term "differentiated cells" when used in reference to cells made by methods of this invention from pluripotent stem cells refer to cells having reduced potential to differentiate when compared to the parent pluripotent stem cells. The differentiated cells of this invention comprise cells that could differentiate further (i.e., they may not be terminally differentiated).

The term "direct differentiation" refers to process of differentiating: blastomere cells, morula cells, ICM cells, ED cells, or somatic cells reprogrammed to an undifferentiated state (such as in the process of making iPS cells but before such cells have been purified in an undifferentiated state) directly without the intermediate state of propagating isolated undifferentiated stem cells such as hES cells as undifferentiated cell lines. A nonlimiting example of direct differentiation would be the culture of an intact human blastocyst into culture and the derivation of ED cells without the generation of a human ES cell line as was described (Bongso et al, 1994. Human Reproduction 9:2110).

The term "embryonic stem cells" (ES cells) refers to cells derived from the inner cell mass of blastocysts, blastomeres, or morulae that have been serially passaged as cell lines while maintaining an undifferentiated state (e.g. expressing TERT, OCT4, and SSEA and TRA antigens specific for ES cells of the species). The ES cells may be derived from fertilization of an egg cell with sperm or DNA, nuclear transfer, parthenogenesis, or by means to generate hES cells with hemizygosity or homozygosity in the MHC region. While ES cells have historically been defined as cells capable of differentiating into all of the somatic cell types as well as germ line when transplanted into a preimplantation embryo, candidate ES cultures from many species, including human, have a more flattened appearance in culture and typically do not contribute to germ line differentiation, and are therefore called "ES-like cells." It is commonly believed that human ES cells are in reality "ES-like", however, in this application we will use the term ES cells to refer to both ES and ES-like cell lines.

The term "histotypic culture" refers to cultured cells that are aggregated to create a three-dimensional structure with tissue-like cell density such as occurs in the culture of some cells over a layer of agar or such as occurs when cells are cultured in three dimensions in a collagen gel, sponge, or other polymers such as are commonly used in tissue engineering.

The term "human embryo-derived" ("hED") cells refers to blastomere-derived cells, morula-derived cells, blastocyst-derived cells including those of the inner cell mass, embryonic shield, or epiblast, or other totipotent or pluripotent stem cells of the early embryo, including primitive endoderm, ectoderm, mesoderm, and neural crest and their derivatives up to a state of differentiation correlating to the equivalent of the first eight weeks of normal human development, but excluding cells derived from hES cells that have been passaged as cell lines (see, e.g., U.S. Pat. Nos. 7,582,479; 7,217,569; 6,887,706; 6,602,711; 6,280,718; and U.S. Pat. No. 5,843,780 to Thomson, incorporated herein by reference). The hED cells may be derived from preimplantation embryos produced by fertilization of an egg cell with sperm or DNA, nuclear transfer, or chromatin transfer, an egg cell induced to form a parthenote through parthenogenesis, analytical reprogramming technology, or by means to generate hES cells with hemizygosity or homozygosity in the HLA region.

The term "human embryonic germ cells" (hEG cells) refer to pluripotent stem cells derived from the primordial germ cells of fetal tissue or maturing or mature germ cells such as oocytes and spermatogonial cells, that can differentiate into various tissues in the body. The hEG cells may also be derived from pluripotent stem cells produced by gynogenetic or androgenetic means, i.e., methods wherein the pluripotent cells are derived from oocytes containing only DNA of male or female origin and therefore will comprise all female-derived or male-derived DNA (see U.S. application No. 60/161,987, filed Oct. 28, 1999; Ser. No. 09/697,297, filed Oct. 27, 2000; Ser. No. 09/995,659, filed Nov. 29, 2001; Ser. No. 10/374,512, filed Feb. 27, 2003; PCT application no. PCT/US/00/29551, filed Oct. 27, 2000; the disclosures of which are incorporated herein in their entirety).

The term "human embryonic stem cells" (hES cells) refers to human ES cells.

The term "human iPS cells" refers to cells with properties similar to hES cells, including the ability to form all three germ layers when transplanted into immunocompromised mice wherein said iPS cells are derived from cells of varied somatic cell lineages following exposure to de-differentiation factors, for example hES cell-specific transcription factor combinations: KLF4, SOX2, MYC, and OCT4 or SOX2, OCT4, NANOG, and LIN28. Any convenient combination of de-differentiation factors may be used to produce iPS cells. Said iPS cells may be produced by the expression of these genes through vectors such as retroviral, lentiviral or adenoviral vectors as is known in the art, or through the introduction of the factors as proteins, e.g., by permeabilization or other technologies. For descriptions of such exemplary methods see: PCT application number PCT/US20061030632, filed on Aug. 3, 2006; U.S. application Ser. No. 11/989,988; PCT Application PCT/US2000/018063, filed on Jun. 30, 2000; U.S. application Ser. No. 09/736,268 filed on Dec. 15, 2000; U.S. application Ser. No. 10/831,599, filed Apr. 23, 2004; and U.S. Patent Publication 20020142397 (App. Ser. No. 10/015,824, entitled "Methods for Altering Cell Fate"); U.S. Patent Publication 20050014258 (App. Ser. No. 10/910,156, entitled "Methods for Altering Cell Fate"); U.S. Patent Publication 20030046722 (App. Ser. No. 10/032,191, entitled "Methods for cloning mammals using reprogrammed donor chromatin or donor cells"); and U.S. Patent Publication 20060212952 (App. Ser. No. 11/439,788, entitled "Methods for cloning mammals using reprogrammed donor chromatin or donor cells") all of which are incorporated herein by reference in their entirety.

The term "ICM cells" refers to the cells of the inner cell mass of a mammalian embryo or the cells of the inner cell mass cultured in vitro with or without the surrounding trophectodermal cells.

The term "oligoclonal" refers to a population of cells that originated from a small population of cells, typically 2-1000 cells, that appear to share similar characteristics such as morphology or the presence or absence of markers of differentiation that differ from those of other cells in the same culture. Oligoclonal cells are isolated from cells that do not share these common characteristics, and are allowed to proliferate, generating a population of cells that are essentially entirely derived from the original population of similar cells.

The term "organotypic culture" refers to cultured cells that are aggregated to create a three-dimensional structure with tissue-like cell density such as occurs in the culture of some cells over a layer of agar, cultured as teratomas in an animal, otherwise grown in a three dimensional culture system but wherein said aggregated cells contain cells of different cell lineages, such as, by way of nonlimiting examples, the combination of epidermal keratinocytes and dermal fibroblasts, or the combination of parenchymal cells with their corresponding tissue stroma, or epithelial cells with mesenchymal cells.

The term "pluripotent stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Pluripotent stem cells may be genetically modified or not genetically modified. Genetically modified cells may include markers such as fluorescent proteins to facilitate their identification within the egg.

The term "pooled clonal" refers to a population of cells obtained by combining two or more clonal populations to generate a population of cells with a uniformity of markers such as markers of gene expression, similar to a clonal population, but not a population wherein all the cells were derived from the same original clone. Said pooled clonal lines may include cells of a single or mixed genotypes. Pooled clonal lines are especially useful in the cases where clonal lines differentiate relatively early or alter in an undesirable way early in their proliferative lifespan.

The term "primordial stem cells" refers to animal cells capable of differentiating into more than one differentiated cell type. Such cells include hES cells, blastomere/morula cells and their derived hED cells, hiPS cells, hEG cells, hEC cells, and adult-derived cells including mesenchymal stem cells, neuronal stem cells, and bone marrow-derived stem cells. Primordial stem cells may be genetically modified or not genetically modified. Genetically modified cells may include markers such as fluorescent proteins to facilitate their identification in vitro or in vivo.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

In addition to the methods described below, methods that find use in the production and use of the cell lines described herein can be found in the following: U.S. Patent Publication 20080070303, entitled "Methods to accelerate the isolation of novel cell strains from pluripotent stem cells and cells obtained thereby"; U.S. patent application Ser. No. 12/504,630 filed on Jul. 16, 2009 and titled "Methods to Accelerate the Isolation of Novel Cell Strains from Pluripotent Stem Cells and Cells Obtained Thereby"; U.S. provisional application Ser. No. 61/226,237 filed on Jul. 16, 2009 and titled "Methods and Compositions Useful for In Vitro and In Vivo Chondrogenesis Using Embryonic Progenitor Cell Lines"; PCT Application PCT/US2006/013519, filed on Apr. 11, 2006, entitled "NOVEL USES OF CELLS WITH PRENATAL PATTERNS OF GENE EXPRESSION"; and PCT application Ser. No. PCT/US2011/037969 filed on May 25, 2011 and entitled "Improved Methods of Screening Embryonic Progenitor Cell lines", each of which is incorporated by reference herein in its entirety.

hES Cell Culture and Generation of Candidate Cultures.

The hES cell lines used were previously described H9 (National Institutes of Health-registered as WA09) and the line (MA03) derived at Advanced Cell Technology (West et al., 2008, *Regenerative Medicine* vol. 3(3) pp. 287-308). hES cells were routinely cultured in hES medium (KO-DMEM (Invitrogen, Carlsbad, Calif.), 1× nonessential amino acids (Invitrogen, Carlsbad, Calif.), 1× Glutamax-1 (Invitrogen, Carlsbad, Calif.), 55 uM beta-mercaptoethanol (Invitrogen, Carlsbad, Calif.), 8% Knock-Out Serum Replacement (Invitrogen, Carlsbad, Calif.), 8% Plasmanate, 10 ng/ml LIF (Millipore, Billerica, Mass.), 4 ng/ml bFGF (Millipore, Billerica, Mass.), 50 unit/ml Penicillin-50 units/ml Streptomycin (Invitrogen, Carlsbad, Calif.). The hES cell lines were maintained at 37 deg C. in an atmosphere of 10% CO2 and 5% O2 on Mitomycin-C treated mouse embryonic fibroblasts (MEFs) and passaged by trypsinization or periodic manual selection of colonies. For the production of clonal embryonic progenitors, hES cells were plated at 500-10,000 cells per 15 cm dish and then differentiated under a two-step protocol, the first step being the differentiation of hES cells under an array of conditions to yield diverse heterogeneous cultures of cells called "candidate cultures." The generation of candidate cultures was performed with either adherent hES cells grown on MEFs (colony in situ differentiation) or with hES-derived embryoid bodies (EB). For colony in situ differentiation experiments, hES cells were allowed to grow to confluence and differentiated by a variety of methods (as described in Supplementary Table I from West et al., 2008, *Regenerative Medicine* vol. 3(3) pp. 287-308, which is incorporated by reference herein in its entirety). By way of nonlimiting example, in the case of colony in situ differentiation in DMEM with 10% FCS, culture medium was aspirated from cultures of hES cell colonies on mouse feeders, and the media was replaced with DMEM medium containing 10%

FBS for differentiation and after various time periods (1, 2, 3, 4, 5, 7, and 9 days in differentiation medium). The cells were then dissociated with 0.25% trypsin (Invitrogen, Carlsbad, Calif.) and plated in 150 cm² flasks for expansion. The candidate cells from each time point in the 150 cm² flasks were plated out for cloning and expansion as described below. For EB differentiation experiments, confluent hES cultures were treated for 15 minutes at 37 deg C. with 1 mg/ml Collagenase IV (in DMEM, Invitrogen, Carlsbad, Calif.) to release the colonies. The detached, intact colonies were scraped and collected by centrifugation (150×g for 5 minutes), resuspended in differentiation medium described in Supplementary Table I (from West et al., 2008, *Regenerative Medicine* vol. 3(3) pp. 287-308, which is incorporated by reference herein in its entirety) and transferred to a single well of a 6-well Ultra-Low Binding plate (Corning, distributed by Fisher Scientific, Pittsburgh, Pa.) containing the same differentiation medium. The Ebs were allowed to differentiate, depending on the experiment, from 4-7 days and the differentiated Ebs dissociated with 0.25% trypsin, plated in 6-well plates containing various expansion medium. The candidate cultures in the 6 well plates are allowed to grow to confluence and plated out for cloning and expansion as described below.

Isolation and Expansion of Clonal Cell Lines.

The partially differentiated candidate cell cultures described above were dissociated with 0.25% trypsin to single cells and plated onto duplicate 15 cm gelatin coated plates at cloning densities of approximately 500 and/or 1,000 and/or 2,000 and/or 5,000 cells per plate for further differentiation and expansion in a variety of growth media shown in Supplementary Table I (from West et al., 2008, *Regenerative Medicine* vol. 3(3) pp. 287-308, which is incorporated by reference herein in its entirety). The clonal density cells were allowed to grow, undisturbed, for 10-14 days and colonies that develop were identified and collected with cloning cylinders and trypsin using standard techniques. The cloned colonies were transferred onto gelatin-coated 24 well plates for expansion. As the clones become confluent in the 24 well plates (but without letting the cells remain confluent for more than 2 days), they were sequentially expanded to 12 well, 6 well, T-25 flask, T-75 flask, T-150 or T-225 flasks and, finally, roller bottles. Clonal cell lines that expand to the roller bottle stage are assigned a unique ACTC identification number, photographed and cryopreserved in aliquots for later use. Once cells reached a confluent 6 well dish, they were passaged to a T-25 flask and a fraction of the cells (5×10⁵) were removed for plating in a gelatinized 6 cm dish for gene expression profile analysis. Alternatively, some cells were first passaged to T-225 flasks, then a fraction of the cells (5×10⁵) were removed for plating in a gelatinized 6 cm dish for gene expression profile analysis. The population doublings that the cells had undergone were therefore determined to be 18-21 PDs. Following removal of the cell clones from the cloning plates, remaining colonies were visualized by Crystal violet staining (Sigma HT9132-1L) in 100% ethanol per manufacturer's instructions. Cell Culture media utilized in experiments and described in text: Smooth muscle cell basal medium (Cat #C-22062B) and growth supplement (Cat #C-39267), Skeletal muscle basal medium (Cat #C-22060B) and growth supplement (Cat #C-39365), Endothelial cell basal medium (Cat #C-22221) and growth supplement (Cat #C-39221), Melanocyte cell basal medium (Cat #C-24010B) and growth supplement (Cat #C-39415) were obtained from PromoCell GmbH (Heidelberg, Germany). Epi-Life, calcium free/phenol red free medium (Cat #M-EPIcf/PRF-500) and low serum growth supplement (Cat #S-003-10) were purchased from Cascade Biologics (Portland, Oreg.). Mesencult basal medium (Cat #05041) and supplement (Cat #5402) were obtained from Stem Cell Technologies (Vancouver, BC). Dulbecco's modified Eagle's medium (Cat #11960-069) and Fetal bovine serum (Cat #SH30070-03) were purchased from Invitrogen (Carlsbad, Calif.) and Hyclone (Logan, Utah) respectively. Medium and supplements were combined according to manufacturer's instructions.

Clonal Embryonic Progenitor Line Nomenclature:

The cell lines of the present invention along with their alternative designations are listed in Table III along with synonyms that represent minor modifications that result from the manipulation of the names resulting from bioinformatics analysis, including the substitution of "-"for"." and vice versa, the inclusion of an "x" before cell line names beginning with an arabic number, and suffixes such as "bio1" or "bio2" that indicate biological replicates of the same line which are examples of cases where a frozen ampule of the same line was thawed, propagated, and used in a parallel analysis and "Rep1" or "Rep2" which indicate technical replicates wherein RNA isolated from a given cell line is utilized a second time for a repeat analysis without thawing or otherwise beginning with a new culture of cells. Passage number (which is the number of times the cells have been trypsinized and replated) for the cell lines is usually designated by the letter "P" followed by an arabic number, and in contrast, the population doubling number (which refers to the number of estimated doublings the cell lines have undergone in clonal expansion from one cell) is designated by the letters "PD" followed by an arabic number. The number of PDs in a passage varied from experiment to experiment but generally each trypsinization and replating was at a 1:3 to 1:4 ratio (corresponding to an increase of PDs of 1.5 and 2 respectively). In the expansion of clones, the original colonies were removed from tissue culture plates with cloning cylinders, and transferred to 24-well plates, then 12-well, and 6-well as described above. First confluent 24 well is designated P1, the first confluent 12 well culture is P2, the first 6-well culture is P3, then the six well culture was then split into a second 6 well plate (P4) and a T25 (P4). The second 6 well at P4 is utilized for RNA extraction (see U.S. patent application Ser. No. 12/504,630 filed on Jul. 16, 2009 and titled "Methods to Accelerate the Isolation of Novel Cell Strains from Pluripotent Stem Cells and Cells Obtained Thereby", incorporated herein by reference in its entirety) and represents about 18-21 PD of clonal expansion. Typical estimated subsequent passages and PDs are the following split to a T75 flask (19.5-22.5 PD), the P6 passage of the cells to a T225 flask (21-24 PD), then P7 being the transfer of the cells to a roller bottle (850 cm², 23-26 PD), and P8 the split into 4 rollers (25-28 PD). The ranges shown above in parenthesis represent estimated ranges in cell counts due to cell sizes, attachment efficiency, and counting error.

Propagation of Clonal, Pooled Clonal, Oligoclonal, and Pooled Oligoclonal Cell Lines.

Aspects of the invention provide methods for identifying and differentiating embryonic progenitor cell lines that are derived from a single cell (clonal) or cell lines that are "pooled clonal" meaning that cell lines cloned have indistinguishable markers, such as gene expression markers, and are combined to produce a single cell culture often for the purpose of increasing the number of cells in a culture, or are oligoclonal wherein a line is produced from a small number, typically 2-1,000 similar cells and expanded as a cell line, or "pooled oligoclonal" lines which are lines produced by combining two or more oligoclonal cell lines that have indistinguishable markers such as patterns of gene expression. Said clonal, pooled clonal, oligoclonal, or pooled oligoclonal cell lines are then propagated in vitro through removal of the cells from the substrate to which they are affixed, and the re-plating of the cells at a reduced density of typically ⅓ to ¼ of the original number of cells, to facilitate further proliferation. Examples of said cell lines and their associated cell culture media is disclosed in U.S. patent application Ser. No. 12/504,630 filed on Jul. 16, 2009 and titled "Methods to Accelerate the Isolation of Novel Cell Strains from Pluripotent Stem Cells and Cells Obtained Thereby"; and West et al., 2008, Regenerative Medicine vol. 3(3) pp. 287-308, both of which are incorporated herein by reference, including supplemental information. The compositions and methods of the present invention relate to said cell lines cultured as described but for greater than 21 doublings of clonal expansion.

Gene Expression Analysis

To reduce variations in gene expression due to cell cycle artifacts, and to capture an early gene expression profile of the cells, upon being expanded to six well plates, on the day the cells reached confluence, the cells were placed in media with a reduction of serum to 0.5% in the case where the original serum concentration was >5%. In all other cases, serum and/or other growth factors was reduced to 10% of their original values. These quiescence conditions were imposed for five days and all cultures were re-fed two days prior to harvest to reduce feeding difference artifacts. So, by way of example, if the original media was DMEM medium with 10% FCS, then the quiescence synchronization media was DMEM with 0.5% FCS. Total RNA was extracted directly from cells growing in 6-well or 6 cm tissue culture plates using Qiagen Rneasy mini kits according to the manufacturer's instructions. RNA concentrations were measured using a Beckman DU530 or Nanodrop spectrophotometer and RNA quality determined by denaturing agarose gel electrophoresis or an Agilent 2100 bioanalyzer. Whole-genome expression analysis was carried out using Affymetrix Human Genome U133 Plus 2.0 GeneChip® system, Illumina Human-6 v1 and HumanRef-8 v1 Beadchips (Illumina 1), and Illumina Human-6 v2 Beadchips (Illumina 2), and RNA levels for certain genes were confirmed by quantitative PCR. For Illumina BeadArrays, total RNA was linearly amplified and biotin-labeled using Illumina Total-Prep kits (Ambion), and cRNA was quality controlled using an Agilent 2100 Bioanalyzer. cRNA was hybridized to Illumina BeadChips, processed, and read using a BeadStation array reader according to the manufacturer's instructions (Illumina). Relative Fluorescence Unit (RFU) values for all of the cell lines with common probe sets were quantile normalized. In Supplementary Tables II-IV (from West et al., 2008, Regenerative Medicine vol. 3(3) pp. 287-308, which are incorporated by reference herein in their entirety) the genes are displayed in rank order (highest-lowest) for the ratio of (highest RFU value observed for the gene in the entire set of cell lines–Average RFU value)/Ave RFU value. In Supplementary Table V (from West et al., 2008, Regenerative Medicine vol. 3(3) pp. 287-308, which is incorporated by reference herein in its entirety) the top 45 differentially expressed genes rank ordered (highest-lowest) for the ratio of (highest RFU value observed for the gene in the individual cell line/Ave RFU value for all cell lines. In Supplementary Table VI (from West et al., 2008, Regenerative Medicine vol. 3(3) pp. 287-308, which is incorporated by reference herein in its entirety) the genes corresponding to recognized CD antigens are displayed in rank order (highest-lowest) and also (lowest to highest) for the ratio of highest RFU value observed for the gene in the entire set of cell lines/Ave RFU value and lowest RFU value observed for the gene in the entire set of cell lines/Ave RFU value respectively. In Supplementary Table VII (from West et al., 2008, Regenerative Medicine vol. 3(3) pp. 287-308, which is incorporated by reference herein in its entirety) the genes corresponding to secreted proteins are displayed in rank order (highest-lowest) for the ratio of highest RFU value observed for the gene in the entire set of cell lines/Ave RFU value.

Low Throughput Screening and qPCR

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 1, 2, 3, 4, 5, or preferably 10 or more diverse differentiation conditions. Said differentiation conditions may include without limitation, all combinations of the human embryonic progenitor cell lines listed in Table I (showing gene expression markers at 18-21 doublings of clonal expansion), together with culture conditions as listed in Table II, exposed to the culture media listed and supplemented factors described herein. The cells are cultured in said differentiation conditions for 1-6 weeks, most preferably two to four weeks.

The readout of the assay can be mRNA markers of differentiation, e.g., as measured by hybridization to arrayed target sequences, including but not limited to microarrays or by PCR. Detection can also be at the level of peptides or proteins that may be detected through the use of specific antibodies, through the use of enzyme assays, mass spectroscopy, or other similar means well known in the art.

In the case of qPCR, protocols may vary and are well-known in the art. By way of nonlimiting example, samples for testing are prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat #4367659) incorporating AmpliTaq Gold DNA polymerase in a total reaction volume of 25 ul. Real-Time qPCR is run using Applied Biosystems 7500 Real-Time PCR System employing SDSv1.2 software. Amplification conditions are set at 50° C. for 2 min. (stage 1), 95° C. for 10 min. (stage 2), 40 cycles of 95° C. for 15 sec then 60° C. for 1 min (stage 3), with a dissociation stage at 95° C. for 15 sec, 60° C. for 1 min, and 95° C. for 15 sec (stage 4). Ct values for amplification products of genes of interest are normalized to the average Ct value of 3 housekeeping genes (GAPD, RPS10, and GUSB).

Medium Throughput Screen of the Fate Space of Clonal or Oligoclonal Embryonic Progenitors.

The clonal, oligoclonal, or pooled clonal or pooled oligoclonal embryonic progenitor cell lines of the present invention at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion (since before 29 doublings of clonal expansion the cells are available only in limited quantities, and beyond 70 doublings the cells normally approach senescence) are screened simultaneously in 10, 20, 30, 40, 50, or preferably 100 or more diverse differentiation conditions. Said differentiation conditions may include without limitation, all combinations of the human embryonic progenitor cell lines listed in Table I (showing gene expression markers at 18-21 doublings of clonal expansion), together with culture conditions that include BMP family members including TGFB1, TGFB2, TGFB3, BMP2, BMP4 (1-100 ng/mL, preferably 10 ng/mL), BMP6 (3-300 ng/mL, preferably 30 ng/mL), BMP7 (10-1,000 ng/mL, preferably 100 ng/mL), and GDF5 (10-1,000 ng/mL, preferably 100 ng/mL) or combinations of these BMP family members. The cells are cultured in said differentiation conditions for 1-6 weeks, most preferably two weeks.

The readout of the assay can be mRNA markers of differentiation, e.g., as measured by hybridization to arrayed target sequences, including but not limited to microarrays or PCR. Detection can also be at the level of peptides or proteins that may be detected through the use of specific antibodies, through the use of enzyme assays, mass spectroscopy, or other similar means well known in the art.

Medium Throughput qPCR Screen of hEP Cell Differentiation

The clonal, oligoclonal, or pooled clonal or pooled oligoclonal embryonic progenitor cell lines of the present invention, including but not limited to those shown in Table I, at either <21 or preferably >21 doublings of clonal or oligoclonal expansion, most preferably at 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 doublings of clonal expansion are plated in 6 well culture plates with each well having 10 micromasses of 250,000 cells (i.e. 2.5 million cells per well). Alternatively the cells are treated with other culture conditions as listed in Table II using the same number of cells, exposed to any combination of culture media and/or supplemented factors, or cultured as described in the exemplary protocols listed in Table V. The cells are cultured in said differentiation conditions for 1-6 weeks, most preferably four weeks.

RNA is prepared from cell lysates using the Rneasy mini kits (Qiagen) according to the manufacturer's instructions. Briefly, cell cultures (micromasses) are rinsed in PBS, then lysed in a minimal volume of the RLT lysis buffer. After incubation on ice, the cell debris is removed by centrifugation and the lysate is mixed with RLT buffer, after which ethanol is added to the mixture. The combined mixture is then loaded onto the Rneasy spin column and centrifuged; the loaded column is then washed and the purified RNA is released from the column with a minimal volume of DEPC-treated water (typically 30 ul or less). The concentration of RNA in the final eluate is determined by absorbance at 260 nm.

cDNA synthesis is performed using the SuperScript First Strand cDNA kit (InVitrogen; Carlsbad, Calif.). Briefly, 2.5 ug of purified RNA is heat denatured in the presence of random hexamers. After cooling, the first strand reaction is completed using SuperSript reverse transcriptase enzyme and associated reagents from the kit. The resulting product is further purified using QIAquick PCR Purification kits (Qiagen) according to the manufacturer's instructions. Briefly, PB buffer is added to the first strand cDNA reaction products, then the mixture is loaded onto the QIAquick spin column and centrifuged. The column is washed with PE buffer and the purified cDNA is eluted from the column using a minimal volume of water (20 ul).

qPCR primer pairs are synthesized for each target gene. Briefly, primer pairs for a target gene are designed to amplify only the target mRNA sequence and optimally have annealing temperatures for their target sequences that lie in the range of 65-80° C. and unique amplification products in the size range of 100-500 bp. Primer pairs are supplied at working concentrations (10 uM) to BioTrove, Inc. (Woburn, Mass.) for production of a custom qPCR Open Array plate. OpenArray plates are designed to accommodate 56-336 primer pairs and the final manufactured plate with dried down primer pairs is provided to the service provider. Purified cDNA reaction products (2.) and Syber green master mix are loaded into individual wells of the OpenArray plate using OpenArray autoloader device (BioTrove). The plate is sealed and the qPCR and loaded into the NT Imager/Cycler device (BioTrove) for amplification. Ct values for each sample are calculated using the OpenArray application software.

Markers of differentiation are not those present in embryonic progenitor cell lines, but are present in later stages of differentiation. It is not obvious to what an effective array of such markers would be. For example, COL2A1 is not expressed in the clonal embryonic progenitor cell lines, but is markedly induced >100-fold in a subset of the cell lines of the present invention. Previous attempts to invent an array of differentiation markers were not useful in the context of the present invention because they included a majority of markers that were expressed in both embryonic progenitor cell types and in terminally-differentiated cell types (Luo, Y., Cai, J., Ginis, I., Sun, Y., Lee, S., Yu, S. X., Hoke, A., and Rao, M. 2003. Designing, testing, and validating a focused stem cell microarray for characterization of neural stem cells and progenitor cells. Stem Cells, 21:575-587). An example of a list of said markers useful in determining that a particular differentiation condition induced terminal differentiation in embryonic progenitor cell lines a majority of which are not expressed in embryonic progenitor cell lines are shown in Table Ill.

Isolation of Secreted or Extracellular Matrix Proteins

Secreted Protein Isolation Protocol 1—Conditioned Medium

Cells were grown in either their normal propagation medium (West et al., 2008, *Regen Med* vol. 3(3) pp. 287-308) or the differentiation conditions described herein. To obtain conditioned medium on a smaller scale (typically 1-2 L or less), the cells were grown in monolayer cultures in T150, T175 or T225 flasks (Corning or BD Falcon) in a 37° C. incubator with 10% $CO_2$ atmosphere. For larger volume medium collections, the cells were typically grown either in 2 L roller bottles, on microcarrier suspensions (porous such as Cytodex varieties from Sigma-Aldrich, St. Louis, Mo., or non-porous such as from SoloHill Engineering, Ann Arbor, Mich.) in spinner flasks or other bioreactors, or in hollow fiber cartridge bioreactors (GE Healthcare, Piscataway, N.J.). Prior to conditioned medium collection, the cultures were rinsed twice with PBS and then incubated for 2 hours at 37° C. in the presence of serum-free medium wherein the medium is the same basal medium as described herein for the propagation or differentiation of the cells, in order to remove fetal serum proteins. The serum-free medium was then removed and replaced with fresh medium, followed by continued as described herein at 37° C. for 24-48 hours.

The culture-conditioned medium was then collected by separation from the cell-bound vessel surface or matrix (e.g., by pouring off directly or after sedimentation) and processed further for secreted protein concentration, enrichment or purification. As deemed appropriate for the collection volume, the culture medium was first centrifuged at 500 to 10,000×g to remove residual cells and cellular debris in 15 or 50 ml centrifuge tubes or 250 ml bottles. It was then passaged through successive 1 µm or 0.45 µm and 0.2 µm filter units (Corning) to remove additional debris, and then concentrated using 10,000 MW cutoff ultrafiltration in a stirred cell or Centricon centrifuge filter (Amicon-Millipore) for smaller volumes, or using a tangential flow ultrafiltration unit (Amicon-Millipore) for larger volumes. The retained protein concentrate was then dialyzed into an appropriate buffer for subsequent purification of specific proteins, and further purified using a combination of isoelectric focusing, size exclusion chromatography, ion exchange chromatography, hydrophobic or reverse phase chromatography, antibody affinity chromatography or other well-known methods appropriate for the specific proteins. During the various steps in the purification process, collection fractions were tested for the presence and quantity of the specific secreted protein by ELISA (e.g., using BMP-2 or BMP-7 ELISA kits from R&D Systems, Minneapolis, Minn.). The purified proteins were then kept in solution or lyophilized and then stored at 4 or minus 20-80° C.

Secreted Protein Isolation Protocol 2—Urea-Mediated Protein Extraction

In the case of some secreted proteins, interactions with the cell or ECM components may reduce the simple diffusion of factors into the medium as described above in Secreted Protein Isolation Protocol 1. A simple comparison of the yield in the two protocols will suffice to determine which protocol provides the highest yield of the desired factors. In the case of Secreted Protein Isolation Protocol 2, a low concentration of urea is added to facilitate the removal of factors. In the case of the examples provided, all urea extractions were performed two days subsequent to feeding. On the second day, cell monolayers in T-150 cell culture flasks were rinsed twice with CMF-PBS and then incubated for two hours at 37° C. in the presence of serum-free medium. The rinse with CMF-PBS and the incubation in serum-free medium together aid in the removal of fetal serum proteins from the surface of the cells. The serum-free medium was then removed and 10 ml/T150 of freshly made 200 mM urea in CMF-PBS was added. The flasks were then placed on a rocker at 37° C. for 6.0 hours. The urea solution was then removed and immediately frozen at −70° C.

Extracellular Matrix Isolation Protocol 1—DOC-Mediated Preparation

Extracellular matrix proteins can be extracted using the method of Hedman et al, 1979 (Isolation of the pericellular matrix of human fibroblast cultures. J. Cell Biol. 81: 83-91). Cell layers are rinsed three times with CMF-PBS buffer at ambient temperature and then washed with 30 mL of 0.5% sodium deoxycholate (DOC), 1 mM phenylmethylsulfonylfluoride (PMSF, from 0.4M solution in EtOH), CMF-PBS buffer 3×10 min. on ice while on a rocking platform. The flasks were then washed in the same manner with 2 mM Tris-HCl, pH 8.0 and 1 mM PMSF 3×5 min. The protein remaining attached to the flask was then removed in 2 mL of gel loading buffer with a rubber policeman.

Screening of Secreted or Extracellular Matrix Proteins for Biological Activity

The cell lines of the present invention are also useful as a means of screening diverse embryonic secretomes for varied biological activities. The cell lines of the present invention cultured at 18-21 doublings of clonal expansion express a wide array of secreted soluble and extracellular matrix genes (see US Patent Application Publication 2010/0184033 entitled "METHODS TO ACCELERATE THE ISOLATION OF NOVEL CELL STRAINS FROM PLURIPOTENT STEM CELLS AND CELLS OBTAINED THEREBY" filed on Jul. 16, 2009, incorporated herein by reference). At 21 or more doublings of clonal expansion, the cells of the present invention differentially express secreted soluble and extracellular matrix genes. These proteins, proteoglycans, cytokines, and growth factors may be harvested from the cell lines of the present invention by various techniques known in the art including but not limited to Secreted Protein Isolation Protocol 1 or 2. These pools of secreted and extracellular matrix proteins may be further purified or used as mixtures of factors and used in varied in vitro or in vivo assays of biological activity as is known in the art.

Applications

The disclosed methods for the culture of animal cells and tissues are useful in generating cells or progeny thereof in mammalian and human cell therapy, such as, but not limited to, generating human cells useful in treating orthopedic disorders in humans and nonhuman animals.

In certain embodiments of the invention, single cell-derived and oligoclonal cell-derived cells derived by methods of this invention, are utilized in research and treatment of disorders relating to cell biology, cell-based drug discovery and in cell therapy. The single cell-derived cell populations derived using the methods of the present invention may already have received the requisite signals to be directed down a differentiation pathway. For example, some paraxial or somatopleuric single cell-derived populations of cells may express genes consistent with dermal fibroblast gene expression, in particular, a prenatal pattern of gene expression useful in promoting scarless wound repair and in promoting elastogenesis. Such cells include, for example, including but not limited to: cells of the heart; cells of the musculo-skeletal system; cells of the nervous tissue; cells of the respiratory system; cells of the endocrine system including preadipocytes or adipocytes including but not limited to cutaneous white and brown preadipocytes or adipocytes capable of causing weight loss, increasing insulin sensitivity, lowering blood glucose, and thereby reducing the risk of vascular disease a other symptoms of Type II diabetes, in a human or nonhuman mammal; cells of the vascular system; cells of the hematopoietic system; cells of the integumentary system; cells of the urinary system; cells of the joint such as articular chondrocytes, tendons, synovial membrane, and meniscus; or cells of the gastrointestinal system. Such cells may be stably grafted in a histocompatible host when the cells are grafted into the tissue into which the cells would normally differentiate. Such tissues include, but are not limited to: endoderm-embryonic tissues; mesoderm-embryonic tissues; ectoderm-embryonic tissues; or extraembryonic cells.

In certain embodiments of the invention, single cell-derived and oligoclonal cell-derived cells are introduced into the tissues in which they normally reside in order to exhibit therapeutic utility. In certain embodiments of the invention, single cell-derived and oligoclonal cell-derived cells, derived by methods of this invention, are utilized in inducing the differentiation of other pluripotent stem cells. The generation of single cell-derived populations of cells capable of being propagated in vitro while maintaining an embryonic pattern of gene expression is useful in inducing the differentiation of other pluripotent stem cells. Cell-cell induction is a common means of directing differentiation in the early embryo. Many potentially medically-useful cell types are influenced by inductive signals during normal embryonic development, including spinal cord neurons, cardiac cells, pancreatic beta cells, and definitive hematopoietic cells. Single cell-derived populations of cells capable of being propagated in vitro while maintaining an embryonic pattern of gene expression can be cultured in a variety of in vitro, in ovo, or in vivo culture conditions to induce the differentiation of other pluripotent stem cells to become desired cell or tissue types. Induction may be carried out in a variety of methods that juxtapose the inducer cell with the target cell. By way of nonlimiting examples, the inducer cells may be plated in tissue culture and treated with mitomycin C or radiation to prevent the cells from replicating further. The target cells are then plated on top of the mitotically-inactivated inducer cells. Alternatively, single cell-derived inducer cells may be cultured on a removable membrane from a larger culture of cells or from an original single cell-derived colony and the target cells may be plated on top of the inducer cells or a separate membrane covered with target cells may be juxtaposed so as to sandwich the two cell layers in direct contact. The resulting bilayer of cells may be cultured in vitro, transplanted into a SPF avian egg, or cultured in conditions to allow growth in three dimensions while being provided vascular support (see, for example, international patent publication number WO/2005/068610, published Jul. 28, 2005, the disclosure of which is hereby incorporated by reference). The inducer cells may also be from a source of pluripotent stem cells, including hES or hED cells, in which a suicide construct has been introduced such that the inducer cells can be removed at will. Cell types useful in single cell-derived and oligoclonal cell-derived induction may include cases of induction well known in the art to occur naturally in normal embryonic development. In certain embodiments of the invention, single cell-derived cells and oligoclonal cell-derived cells, derived by methods of this invention, are used as "feeder cells" to support the growth of other cell types, including pluripotent stem cells. The use of single cell-derived cells and oligoclonal cell-derived cells of the present invention as feeder cells alleviates the potential risk of transmitting pathogens from feeder cells derived from other mammalian sources to the target cells. The feeder cells may be inactivated, for example, by gamma ray irradiation or by treatment with mitomycin C, to limit replication and then co-cultured with the pluripotent stem cells.

In certain embodiments of the invention, the extracellular matrix (ECM) of single cell-derived and oligoclonal cell-derived cells, derived by methods of this invention, may be used to support less differentiated cells (see Stojkovic et al., Stem Cells (2005) 23(3):306-14). Certain cell types that normally require a feeder layer can be supported in feeder-free culture on a matrix (Rosler et al., Dev Dyn. (2004) 229(2):259-74). The matrix can be deposited by preculturing and lysing a matrix-forming cell line (see WO 99/20741), such as the STO mouse fibroblast line (ATCC Accession No. CRL-1503), or human placental fibroblasts.

In certain embodiments of the invention, the conditioned media of single cell-derived and oligoclonal cell-derived cell cultures may be collected, pooled, filtered and stored as conditioned medium. This conditioned medium may be formulated and used for research and therapy. The use of conditioned medium of single cell-derived and oligoclonal cell-derived cell cultures may be advantageous in reducing the potential risk of exposing cultured cells to non-human animal pathogens derived from other mammalian sources (i.e. xenogeneic free).

Our discovery that various single cell-derived and oligoclonal cell-derived cells in early embryonic lineages may be propagated without the loss of their embryonic phenotype allows numerous types of embryonic mesodermal and neural crest-derived mesenchymal cells with a prenatal pattern of gene expression to be cryogenically stored, retrieved, scaled, and used in assays as described herein to discover novel differentiation protocols for these novel and site-specific cell types. Uses for the derived cells and the differentiation methods described herein may also be used for research, drug discovery, and cell-based therapy.

In certain embodiments of the invention, the single cell-derived and oligoclonal cell-derived cells, derived by methods of this invention, may be used to generate skin equivalents, as well as to reconstitute full-thickness human skin, according to the methods described in U.S. application Ser. No. 09/037,191, filed Mar. 9, 1998 (U.S. publication no. 2001/0048917, published Dec. 6, 2001); Ser. No. 10/013,124, filed Dec. 7, 2001 (U.S. publication no. 2002/0120950, published Aug. 29, 2002); Ser. No. 10/982,186, filed Nov. 5, 2004 (U.S. publication no. 2005/0118146, published Jun. 2, 2005); the disclosure of each of which is incorporated herein by reference. For example, the single cell-derived and oligoclonal cell-derived cells may be incorporated into a layered cell sorted tissue that includes a discrete first cell layer and a discrete second cell layer that are formed in vitro by the spontaneous sorting of cells from a homogenous cell mixture. The first cell layer may include any cell type, but preferably includes epithelial cells, in particular, keratinocytes. Other cell types that may be used in the first cell layer are CaCo2 cells, A431 cells, and HUC18 cells. The second cell layer may also include cells of any type, but preferably includes mesenchymal cells, in particular, fibroblasts. The layered cell sorted tissue possesses an epidermal-dermal junction that is substantially similar in structure and function to its native counterpart. That is, the tissue expresses the necessary integral proteins such as hemidesmosomes and collagen I, collagen IV, and collagen VII, to attach the epidermal and dermal layers with the proper basement membrane morphology. The single cell-derived and oligoclonal cell-derived cells may then sort to form an epidermal layer that contacts the connective tissue component. The layered cell sorted tissues comprising the single cell-derived and oligoclonal cell-derived cells may be used as a skin graft that could be used on graft sites such as traumatic wounds and burn injury.

In another embodiment of the invention, single cell-derived and oligoclonal cell-derived cells of this invention may be used as a means to identify and characterize genes that are transcriptionally activated or repressed as the cells undergo differentiation. For example, libraries of gene trap single cell-derived or oligoclonal cell-derived cells may be made by methods of this invention, and assayed to detect changes in the level of expression of the gene trap markers as the cells differentiate in vitro and in vivo. The methods for making gene trap cells and for detecting changes in the expression of the gene trap markers as the cells differentiate are reviewed in Durick et al. (Genome Res. (1999) 9:1019-25), the disclosure of which is incorporated herein by reference). The vectors and methods useful for making gene trap cells and for detecting changes in the expression of the gene trap markers as the cells differentiate are also described in U.S. Pat. No. 5,922,601 (Baetscher et al.), U.S. Pat. No. 6,248,934 (Tessier-Lavigne) and in U.S. patent publication No. 2004/0219563 (West et al.), the disclosures of which are also incorporated herein by reference. Methods for genetically modifying cells, inducing their differentiation in vitro, and using them to generate chimeric or nuclear-transfer cloned embryos and cloned mice are developed and known in the art. To facilitate the identification of genes and the characterization of their physiological activities, large libraries of gene trap cells having gene trap DNA markers randomly inserted in their genomes may be prepared. Efficient methods have been developed to screen and detect changes in the level of expression of the gene trap markers as the cells differentiate in vitro or in vivo. In vivo methods for inducing single cell-derived or oligoclonal cell-derived cells to differentiate further include injecting one or more cells into a blastocyst to form a chimeric embryo that is allowed to develop; fusing a stem cell with an enucleated oocyte to form a nuclear transfer unit (NTU), and culturing the NTU under conditions that result in generation of an embryo that is allowed to develop; and implanting one or more clonogenic differentiated cells into an immune-compromised or a histocompatible host animal (e.g., a SCID mouse, or a syngeneic nuclear donor) and allowing teratomas comprising differentiated cells to form. In vitro methods for inducing single cell-derived or oligoclonal cell-derived cells to differentiate further include culturing the cells in a monolayer, in suspension, or in three-dimensional matrices, alone or in co-culture with cells of a different type, and exposing them to one of many combinations of chemical, biological, and physical agents, including co-culture with one or more different types of cells, that are known to capable of induce or allow differentiation.

In another embodiment of the invention, cell types that do not proliferate well under any known cell culture conditions may be induced to proliferate such that they can be isolated clonally or oligoclonally according to the methods of this invention through the regulated expression of factors that overcome inhibition of the cell cycle, such as regulated expression of SV40 virus large T-antigen (Tag), or regulated E1a and/or E1b, or papillomavirus E6 and/or E7, or CDK4 (see, e.g., U.S. patent application Ser. No. 11/604,047 filed on Nov. 21, 2006 and titled "Methods to Accelerate the Isolation of Novel Cell Strains from Pluripotent Stem Cells and Cells Obtained Thereby", incorporated herein by reference).

In another embodiment of the invention, the factors that override cell cycle arrest may be fused with additional proteins or protein domains and delivered to the cells. For example, factors that override cell cycle arrest may be joined to a protein transduction domain (PTD). Protein transduction domains, covalently or non-covalently linked to factors that override cell cycle arrest, allow the translocation of said factors across the cell membranes so the protein may ultimately reach the nuclear compartments of the cells. PTDs that may be fused with factors that override cell cycle arrest include the PTD of the HIV transactivating protein (TAT) (Tat 47-57) (Schwarze and Dowdy 2000 *Trends Pharmacol. Sci.* 21: 45-48; Krosl et al. 2003 *Nature Medicine* (9): 1428-1432). For the HIV TAT protein, the amino acid sequence conferring membrane translocation activity corresponds to residues 47-57 (Ho et al., 2001, *Cancer Research* 61: 473-477; Vives et al., 1997, *J. Biol. Chem.* 272: 16010-16017). These residues alone can confer protein translocation activity.

In another embodiment of the invention, the PTD and the cycle arrest factor may be conjugated via a linker. The exact length and sequence of the linker and its orientation relative to the linked sequences may vary. The linker may comprise, for example, 2, 10, 20, 30, or more amino acids and may be selected based on desired properties such as solubility, length, steric separation, etc. In particular embodiments, the linker may comprise a functional sequence useful for the purification, detection, or modification, for example, of the fusion protein.

In another embodiment of the invention, single cell-derived or oligoclonal cell-derived cells of this invention may be reprogrammed to an undifferentiated state through novel reprogramming technique, as described in U.S. application No. 60/705,625, filed Aug. 3, 2005, U.S. application No. 60/729,173, filed Oct. 20, 2005; U.S. application No. 60/818,813, filed Jul. 5, 2006, the disclosures of which are incorporated herein by reference. Briefly, the cells may be reprogrammed to an undifferentiated state using at least a two, preferably three-step process involving a first nuclear remodeling step, a second cellular reconstitution step, and finally, a third step in which the resulting colonies of cells arising from step two are characterized for the extent of reprogramming and for the normality of the karyotype and quality. In certain embodiments, the single cell-derived or oligoclonal cell-derived cells of this invention may be reprogrammed in the first nuclear remodeling step of the reprogramming process by remodeling the nuclear envelope and the chromatin of a differentiated cell to more closely resemble the molecular composition of an undifferentiated or a germ-line cell. In the second cellular reconstitution step of the reprogramming process, the nucleus, containing the remodeled nuclear envelope of step one, is then fused with a cytoplasmic bleb containing requisite mitotic apparatus which is capable, together with the transferred nucleus, of producing a population of undifferentiated stem cells such as ES or ED-like cells capable of proliferation. In the third step of the reprogramming process, colonies of cells arising from one or a number of cells resulting from step two are characterized for the extent of reprogramming and for the normality of the karyotype and colonies of a high quality are selected. While this third step is not required to successfully reprogram cells and is not necessary in some applications, the inclusion of the third quality control step is preferred when reprogrammed cells are used in certain applications such as human transplantation. Finally, colonies of reprogrammed cells that have a normal karyotype but not sufficient degree of programming may be recycled by repeating steps one and two or steps one through three.

In another embodiment of the invention, the single cell-derived and oligoclonal cell-derived cells may be used to generate ligands using phage display technology (see U.S. application No. 60/685,758, filed May 27, 2005, and PCT US2006/020552, filed May 26, 2006, the disclosures of which are hereby incorporated by reference).

In another embodiment of the invention, the single cell-derived or oligoclonal cell-derived cells of this invention may exhibit unique patterns of gene expression such as high levels of factors, e.g. secreted factors, that promote the development or formation of specific tissue types either in vitro or in vivo (e.g., angiogenic factors, neurotrophic factors, etc).

As another example, a cell produced by the methods of this invention could produce large amounts of BMP2, BMP7, BMP3b or other members of the BMP family, and this cell could therefore be useful in inducing bone formation (as described below).

The expression of genes of the cells of this invention may be determined. Measurement of the gene expression levels may be performed by any known methods in the art, including but not limited to, microarray gene expression analysis, bead array gene expression analysis and Northern analysis. The gene expression levels may be represented as relative expression normalized to the ADPRT (Accession number NM_001618.2), GAPD (Accession number NM_002046.2), or other housekeeping genes known in the art. The gene expression data may also be normalized by a median of medians method. In this method, each array gives a different total intensity. Using the median value is a robust way of comparing cell lines (arrays) in an experiment. As an example, the median was found for each cell line and then the median of those medians became the value for normalization. The signal from the each cell line was made relative to each of the other cell lines. Based on the gene expression levels, one would expect the expression of the corresponding proteins by the cells of the invention. For example, in the case of cell clone ACTC60 (or B-28) of Series 1, relatively high levels of DKK1, VEGFC and IL1R1 were observed. Therefore, the ability to measure the bioactive or growth factors produced by said cells may be useful in research and in the treatment of disease.

In another embodiment of the invention, the single cell-derived or oligoclonal cell-derived cells of this invention may express unique patterns of CD antigen gene expression, which are cell surface antigens. The differential expression of CD antigens on the cell surface may be useful as a tool, for example, for sorting cells using commerically available antibodies, based upon which CD antigens are expressed by the cells. The expression profiles of CD antigens of some cells of this invention are shown in West et al., 2008, *Regene Med* vol. 3(3) pp. 287-308, incorporated herein by reference, including supplemental information. For example, there are CD antigens that are expressed in ES cells and not (or in some cases, at reduced levels) in the relatively more differentiated cell lines of this invention. This could be a very useful tool for selecting, sorting, purifying and/or characterizing ES cells. Since the CD antigens are expressed on the cell surface and antibodies to them are, generally speaking, commercially available, antibodies (or specific combinations of them) can be used to purify pure populations of ES cells or cells of this invention out of a heterogeneous mixture of cells. This could be useful in various strategies to grow ES cells or cells of this invention, or prepare these cells for various commercial purposes. There are several CD antigens that are robustly expressed in the relative more differentiated cells of this invention, but are not expressed in ES cells (or in some cases at markedly reduced levels). The antigens that fall into this category include: CD73, CD97, CD140B, CD151, CD172A, CD230, CD280, CDw210b. These antigens may be useful in a negative selection strategy to grow ES cells.

In another embodiment of the invention, the single cell-derived and oligoclonal cell-derived cells, derived by methods of this invention, may be injected into mice to raise antibodies to differentiation antigens. Antibodies to differentiation antigens would be useful for both identifying the cells to document the purity of populations for cell therapies, for research in cell differentiation, as well as for documenting the presence and fate of the cells following transplantation. In general, the techniques for raising antibodies are well known in the art.

In another embodiment of the invention, the single cell-derived and oligoclonal cell-derived cells may be used for the purpose of generating increased quantities of diverse cell types with less pluripotentiality than the original stem cell type, but not yet fully differentiated cells. mRNA or miRNA can then be prepared from these cell lines and microarrays of their relative gene expression can be performed as described herein. In another embodiment of the invention, the single cell-derived and oligoclonal cell-derived cells may be used in animal transplant models, e.g. transplanting escalating doses of the cells with or without other molecules, such as ECM components, to determine whether the cells proliferate after transplantation, where they migrate to, and their long-term differentiated fate in safety studies.

In another embodiment of the invention, the single cell-derived and oligoclonal cell-derived cells generated according to the methods of the present invention are useful for harvesting mRNA, microRNA, and cDNA from either single cells or a small number of cells (i.e., clones) to generate a database of gene expression information. This database allows researchers to identify the identity of cell types by searching for which cell types in the database express or do not express genes at comparable levels of the cell type or cell types under investigation. For example, the relative expression of mRNA may be determined using microarray analysis as is well known in the art. The relative values may be imported into a software such as Microsoft Excel and gene expression values from the different cell lines normalized using various techniques well known in the art such as mean, mode, median, and quantile normalization. Hierarchical clustering with the single linkage method may be performed with the software such as The R Project for Statistical Computing as is well known in the art. An example of such documentation may be found at http(colon)//sekhon(dot)berkeley(dot)edu/stats/html/hclust.html. A hierarchical clustering analysis can then be performed as is well known in the art. These software programs perform a hierarchical cluster analysis using a group of dissimilarities for the number of objects being clustered. At first, each object is put in its own cluster, then iteratively, each similar cluster is joined until there is one cluster. Distances between clusters are computed by Lance-Williams dissimilarity update formula (Becker, R. A., Chambers, J. M. and Wilks, A. R. (1988) The New S Language. Wadsworth & Brooks/Cole. (S version.); Everitt, B. (1974). Cluster Analysis. London: Heinemann Educ. Books). Typically the vertical axis of the dendograms displays the extent of similarity of the gene expression profiles of the cell clones. That is, the farther down they branch apart, the more similar they are. The vertical axis is a set of n−1 non-decreasing real values. The clustering height is the value of the criterion associated with the clustering method for the particular agglomeration. In order to determine if a new cell line is identical to existing cell lines, two types of replicates are performed: biological and technical replicates. Biological replicates require that new cell lines be grown, mRNA harvested, and then the analysis compared. Technical replicates, on the other hand, analyze the same RNA twice. A line cutoff is then drawn just above where the replicates branch such that cells branching below the cutoff line are considered the same cell type. Another source of data for the database described above may be microRNA profiles of the single cell-derived and oligoclonal cell-derived cells generated according to the methods of the present invention. MicroRNAs (miRNA) are endogenous RNAs of ~22 nucleotides that play important regulatory roles in animals & plants by targeting mRNAs for cleavage or translational repression. More than 700 miRNAs have been identified across species. Their expression levels vary among species and tissues. Low abundant miRNAs have been difficult to detect based on current technologies such as cloning, Northern hybridization, and the modified Invader® assay. In the present invention, an alternative approach using a new real-time quantitation method termed looped-primer RT-PCR was used for accurate and sensitive detection of miRNAs as well as other non-coding RNA (ncRNA) molecules present in human embryonic stem cells and in cell lines differentiated from human embryonic stem cells.

In another embodiment of the invention, gene expression analysis may be used to identify the developmental pathways and cell types for in vitro differentiated hES cells. Gene expression analysis of single cells or a small number of cells from human or nonhuman embryonic or fetal tissues provides another means to generate a database of unique gene expression profiles for distinct populations of cells at different stages of differentiation. Gene expression analysis on single cells isolated from specific tissues may be performed as previously described by Kurimoto et al., Nucleic Acids Research (2006) Vol. 34, No. 5, e42. Thus, cellular miRNA profiles on their own or in conjunction with gene expression profiles, immunocytochemistry, and proteomics provide molecular signatures that can be used to identify the tissue and developmental stage of differentiating cell lines. This technique illustrates that the database may be used to accurately identify cell types and distinguish them from other cell types.

The cells of the present invention are also useful in providing a subset of gene expression markers that are expressed at relatively high levels in some cell lines while not be expressed at all in other cell lines as opposed to genes expressed in all cell lines but at different levels of expression. This subset of "all-or none" markers can be easily identified by comparing the levels of expression as measured for instance through the use of oligonucleotide probes or other means know in the art, and comparing the level of a gene's expression in one line compared to all the other lines of the present invention. Those genes that are expressed at relatively high levels in a subset of lines, and not at all in other lines, are used to generate a short list of gene expression markers. When applied to the cells and gene expression data described herein, where negative expression in Illumina 1 is <70 RFU and positive expression is >100 RFU.

Safranin O Staining Assay

The well-known techniques of staining of formalin-fixed, paraffin-embedded tissue sections with Safranin O are commonly used in the detection of cartilage-related proteoglycans, however, the assay is not absolutely specific to cartilage since it also stains mucin, mast cell granules, and likely other substances in other cell types. A nonlimiting example of the protocol where cartilage and mucin will be stained orange to red, and the nuclei will be stained black and the background stained green uses formalin-fixed micromasses, pellets, or similar aggregations of cells. Reagents used include Weigert's Iron Hematoxylin Solution: in which Stock Solution A composed of 1 gram of Hematoxylin in 100 ml of 95% Alcohol; Stock Solution B composed of 4 ml of 29% Ferric chloride in water diluted in 95 ml of Distilled water and 1.0 ml of concentrated Hydrochloric acid; Weigert's Iron Hematoxylin Working Solution composed of equal parts of stock solution A and B and used within four weeks; 0.001% Fast Green (FCF) Solution composed of 0.01 gram of Fast green, FCF, C.I.42053 in 1000 ml Distilled water; 1% Acetic Acid Solution composed of 1.0 ml glacial acetic acid in 99 ml Distilled water; and 0.1% Safranin O Solution composed of 0.1 gram Safranin O, C.I.50240 in 100 ml Distilled water. Samples are Deparaffinized and hydrated with distilled water. They are stained with Weigert's iron hematoxylin working solution for 10 minutes, then washed in running tap water for 10 minutes, stained with fast green (FCF) solution for 5 minutes, rinsed quickly with 1% acetic acid solution for no more than 10-15 seconds, stained in 0.1% safranin O solution for 5 minutes, dehydrated and cleared with 95% ethyl alcohol, absolute ethyl alcohol, and xylene, using 2 changes each, 2 minutes each, mounted using resinous medium, and imaged and analyzed for stains as described above. Cartilage-related proteoglycan stains dark red-orange.

Human Embryonic Chondrogenic Progenitor Line Markers

The gene expression markers of the human embryonic progenitor cell lines capable of differentiating into chondroblasts and then chondrocytes expressing higher levels of COL2A1 than normal early passage cultured human articular chondrocytes when said human embryonic progenitor cell lines have undergone 18-21 doublings of clonal expansion following isolation from human ES or similar human primordial stem cell-derived cells are described in: International application PCT/US2006/045352 published as WO/2007/062198; U.S. Application No. 60/981,424; U.S. application No. 61/128,497 and U.S. application Ser. No. 12/504,630 published as 2010-0184033; the disclosures of which applications are herein incorporated by reference.

The cell line SM30 is positive for the markers: COL15A1, CRYAB, DYSF, FST, GDF5, HTRA3, TMEM119, MMP1, MSX1, MSX2, MYL4, POSTN, SERPINA3, SRCRB4D and ZIC2 and is negative for the markers: ACTC, AGC1, AKR1C1, ALDH1A1, ANXA8, APCDD1, AQP1, ATP8B4, CFB, C3, C6, C7, C20orf103, CD24, CDH3, CLDN11, CNTNAP2, COMP, DIO2, METTL7A, DKK2, DLK1, DPT, FGFR3, TMEM100, FMO1, FMO3, FOXF2, GABRB1, GJB2, GSC, HOXA5, HSD11B2, HSPA6, ID4, IFI27, IL1R1, KCNMB1, KIAA0644, KRT14, KRT17, KRT34, IGFL3, LOC92196, MEOX1, MEOX2, MGP, MYBPH, MYH3, MYH11, NLGN4X, NPPB, OGN, OLR1, OSR2, PAX2, PAX9, PDE1A, PENK, PRG4, PROM1, PRRX1, PTN, RARRES1, RASD1, RELN, RGS1, SLTRK6, SMOC1, SMOC2, SNAP25, STMN2, TAC1, RSPO3, TNFSF7, TNNT2, TRH, TUBB4, UGT2B7 and WISP2.

The cell line 4D20.8, sometimes referred to as X4D20.8 is positive for the markers: BARX1, CNTNAP2, COL21A1, CRIP1, CRYAB, DIO2, DKK2, GAP43, ID4, LAMC2, LHX8, MMP1, MSX2, S100A4, SOX11 and THY1 and is negative for the markers: AGC, ALDH1A1, AREG, ATP8B4, CFB, C3, C7, C20orf103, CDH3, CLDN11, COP1, CRLF1, DLK1, DPT, FMO1, FMO3, GDF10, GJB2, GSC, HOXA5, HSD11B2, HSD17B2, HSPA6, HSPB3, ICAM5, IFI27, IGF2, KRT14, KRT17, KRT34, MASP1, MEOX2, MSX1, MX1, MYBPH, MYH3, MYH11, TAGLN3, NPAS1, NPPB, OGN, OLR1, PAX2, PDE1A, PRG4, PROM1, PTN, PTPRN, RARRES1, RGS1, SNAP25, STMN2, TAC1, TNNT2, TRH, TUBB4, WISP2, ZIC1 and ZIC2.

The cell line SK11 is positive for the markers: BEX1, COL21A1, FST, ICAM5, IL1R1, TMEM119, PTPRN, SERPINA3, SFRP2 and ZIC1 and are negative for the markers: ACTC, AGC1, ALDH1A1, AQP1, ATP8B4, C6, C20orf103, CCDC3, CDH3, CLDN11, CNTNAP2, DIO2, DKK2, EMID1, GABRB1, GSC, HOXA5, HSPA6, IFI27, INA, KRT14, KRT34, IGFL3, LOC92196, MEOX1, MEOX2, MMP1, MX1, MYH3, MYH11, IL32, NLGN4X, NPPB, OLR1, PAX2, PAX9, PDE1A, PENK, PROM1, PTN, RARRES1, RASD1, RELN, RGS1, SMOC1, SMOC2, STMN2, TAC1, TFPI2, RSPO3, TNFSF7, TNNT2, TRH and TUBB4.

The cell line MEL2 is positive for the markers: AKR1C1, AQP1, COL21A1, CRYAB, CXADR, DIO2, METTL7A, DKK2, DLK1, DLX5, HAND2, HSD17B2, HSPB3, MGP, MMP1, MSX2, PENK, PRRX1, PRRX2, S100A4, SERPINA3, SFRP2, SNAP25, SOX11, TFPI2 and THY1 and is negative for the markers: ACTC, ALDH1A1, AREG, CFB, C3, C20orf103, CD24, CDH3, CDH6, CNTNAP2, COL15A1, COMP, COP1, CRLF1, FGFR3, FMO1, FMO3, FOXF2, FST, GABRB1, GAP43, GDF5, GDF10, GJB2, GSC, HOXA5, HSD11B2, HSPA6, ICAM5, KCNMB1, KRT14, KRT17, KRT19, KRT34, MASP1, MEOX1, MEOX2, MYBPH, MYH3, MYH11, TAGLN3, NPAS1, NPPB, OLR1, PAX2, PDE1A, PITX2, PRG4, PTN, PTPRN, RASD1, RELN, RGS1, SMOC1, STMN2, TAC1, TNFSF7, TRH, TUBB4, WISP2, ZIC1 and ZIC2.

The cell line X7SMOO32 is positive for the markers: ACTC, BEX1, CDH6, COL21A1, CRIP1, CRLF1, DIO2, DLK1, EGR2, FGFR3, FOXF1, FOXF2, FST, GABRB1, IGFBP5, KIAA0644, KRT19, LAMC2, TMEM119, MGP, MMP1, MSX1, MSX2, PODN, POSTN, PRG4, PRRX2, PTN, RGMA, S100A4, SERPINA3, SOX11 and SRCRB4D and is negative for the markers: AGC, AKR1C1, ALDH1A1, ANXA8, APCDD1, AREG, ATP8B4, BMP4, C3, C6, C7, PRSS35, C20orf103, CCDC3, CD24, CLDN11, CNTNAP2, COL15A1, COP1, CXADR, METTL7A, DKK2, DPT, EMID1, TMEM100, FMO1, FMO3, GDF5, GDF10, GJB2, GSC, HOXA5, HSD11B2, HSD17B2, HSPA6, HSPB3, HTRA3, ICAM, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, IL32, NLGN4X, NPPB, OGN, OLR1, OSR2, PAX2, PAX9, PDE1A, PITX2, PRELP, PROM1, PTPRN, RASD1, RGS1, SFRP2, SMOC1, SMOC2, SOD3, STMN2, SYT12, TAC1, RSPO3, TNFSF7, TNNT2, TRH, TSLP, TUBB4, UGT2B7, WISP2, ZD52F10, ZIC1 and ZIC2.

The cell line E15 is positive for the markers: ACTC, BEX1, PRSS35, CRIP1, CRYAB, GAP43, GDF5, HTRA3, KRT19, MGP, MMP1, POSTN, PRRX1, S100A4, SOX11, SRCRB4D and THY1 and are negative for the markers: AGC1, AKR1C1, ALDH1A1, ANXA8, APCDD1, AQP1, AREG, ATP8B4, CFB, C3, C6, C7, C20orf103, CDH3, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IFIT3, IGF2, INA, KRT14, TMEM119, IGFL3, LOC92196, MFAP5, MASP1, MEOX1, MEOX2, MSX1, MX1, MYBPH, MYH3, MYL4, NLGN4X, TAGLN3, NPAS1, NPPB, OGN, OLR1, PAX2, PAX9, PDE1A, PENK, PITX2, PRG4, PROM1, PTPRN, RARRES1, RASD1, RELN, RGS1, SLITRK6, SMOC1, SMOC2, SNAP25, STMN2, TAC1, TFPI2, RSPO3, TNFSF7, TNNT2, TRH, TSLP, TUBB4, UGT2B7, WISP2, ZD52F10 and ZIC1.

The cell line EN7 in the undifferentiated state propagated in media such as Promocell MV2 endothelial medium is positive for the mRNA markers: RGS1, NEFM, KBTBD10, CLDN5, GPR44, ATP1A2, KCND2, DLK1, FOXF1, and ZIC2, with most distal HOX gene expression being HOXB2, HOXA2, and is negative for the markers: ACTC, AJAP1, ALDH1A1, ALDH1A2, ANXA8, BARX1, C3, CCDC3, CD24, CD74, CDH3, CNTNAP2, COMP, CRYAB, DKK2, GSC, HAND2, HOXA5, HSD11B2, HSPB3, INA, KRT14, KRT17, LHX1, LHX8, MFAP5, MEOX1, MEOX2, MGP, MMP1, MYH3, MYH11, NPAS1, NPPB, OLR1, PAX2 (Illumina Probe 6450767), PAX9, PENK, PITX1, PITX2, PROM, RELN, SFRP2, SMOC2, STMN2, TAC1, TBX15, TRH, and TUBB4 as determined by Illumina microarray analysis described herein.

Below is a list of exemplary human embryonic chondrocyte progenitor cell lines according to aspects of the present invention and certain gene expression markers of interest (positive and negative markers). These human embryonic progenitor cell lines are capable of differentiating into chondrocytes expressing higher levels of COL2A1 than normal early passage cultured human articular chondrocytes (NHACs) when the progenitors have undergone 22 or more doublings of clonal expansion following isolation from human ES or similar human primordial stem cell-derived cells.

Gene expression markers of the cell line MEL2 in the range of P22-28 include the genes: PIP, ENPP2, DLX5, CXADR, NPTX2, CLDN23, SFRP2, HSPB3, HAND2, HSD17B2, RCAN2, EBF3, GPM6B, RNF1 75, PPARGC1A, RGS1 6, GPM6B, SOX17, EPHB6, and BAPX1. The most specific of these markers being expressed in the cell line MEL2 in the range of P22-28 are: PIP (Illumina probe ID 4010519), SOX17 (Illumina probe ID 3610193), DLX5 (Illumina probe ID 3370767), GPM6B (Illumina probe ID 2630279), RGS16 (Illumina probe ID 1030102), EPHB6 (Illumina probe ID 7400017), and HAND2 (Illumina probe ID 4640563) and negative expression of: TBX15 (Illumina probe ID 6060113), HOXA2 (Illumina probe ID 2060471), AJAP1 (Illumina ID 1300647), and HOXB2 (Illumina probe ID 3460097).

Gene expression markers of the cell line SM30 in the range of P13-15 include the genes: COL15A1, DYSF, FST, ITGB4, TMEM1 19, MSX1, NDST3, NTRK1, and ZIC2. The most specific of these gene expression markers being expressed in cell line SM30 in the range of P1 3-15 are: NTRK1 (Illumina probe ID 7050113), NDST3 (Illumina probe ID 670537), ZIC2 (Illumina probe ID 510368), ITGB4 (Illumina probe ID 3940132), and negative expression of PIP (Illumina probe ID 4010519), NNAT (Illumina probe ID 4010709), HOXA2 (Illumina probe ID 2060471), TBX1 5 (Illumina probe ID 6060113), and HAND2 (Illumina probe ID 4640563).

Gene expression markers of the cell line 7SMOO32 in the range of P1 1-18 include the genes: EGFL6, FGF13, BEX2, CHRNA3, NCAM2, BBOX1, and DLK1. The most specific of these gene expression markers being expressed in 7SMOO32 are: EGFL6 (Illumina probe ID 6330079), FGF13 (Illumina probe ID 7380239), CHRNA3 (Illumina probe ID 4280180), BBOX1 (Illumina probe ID 3400386), and negative for the expression of the genes: TBX5 (Illumina probe ID 6060113), NNAT (Illumina probe ID 4010709), NTRK1 (Illumina probe ID 7050113), HAND2 (Illumina probe ID 4640563), and HOXA2 (Illumina probe ID 2060471).

Gene expression markers of the cell line SK11 in the range of P 12-17 include the genes: PITX1, TBX15, NCAM1, COL21A, CYYR1, LAMP3, MEGF1O, RNF165 and GDF1O. The most specific of these gene expression markers being expressed in SK11 are: TBX15 (Illumina probe ID 6060113), COL21A1 (Illumina probe ID 3440747), GDF1O (Illumina probe ID 5690095), PITX1 (Illumina probe ID 2000373), and negative for the expression of the genes: NNAT (Illumina probe ID 4010709), HAND2 (Illumina probe ID 4640563), F0XF2 (Illumina probe ID 1660470), FOXG1 (Illumina probe ID 4200458), HOXA2 (Illumina probe ID 2060471) HOXB2 (Illumina probe ID 3460097), and AJAP1 (Illumina ID 1300647).

Gene expression markers of the cell line 7PEND24 in the range of P15-26 include the genes: TBX15, PAX9, CA9, SPAG16, SUSD2, TBXAS1, AIF1, SLITRK5, FOXF2, AADAC, and FOXG1. The most specific of these gene expression markers being expressed in 7PEND24 are: AADAC (Illumina probe ID 6200619), TBX15 (Illumina probe ID 6060113), SPAG16 (Illumina probe ID 4390537), AIR (Illumina probe ID 3800047), and negative for the expression of the genes: NNAT (Illumina probe ID 4010709), PITX1 (Illumina probe ID 2000373), SOX17 (Illumina probe ID 3610193), and AJAP1 (Illumina ID 1300647).

Gene expression markers of the cell line E15 in the range of P14-15 include the genes: ENPP2, ABCA6, TBX15, BAB, CNTN3, TSPYL5, GAP43, AJAP1, CYFIP2, H0XA2 (Illumina probe ID 2060471) HOXB2 (Illumina probe ID 3460097), and NNAT The most specific of these gene expression markers being expressed in E15 are: AJAP1 (Illumina probe ID 1300647), BAB (Illumina probe ID 5690301), NNAT (Illumina probe ID 4010709), ABCA6 (Illumina probe ID 5810209), and negative for the expression of the gene: PITX1 (Illumina probe ID 2000373) and is negative for the gene expression markers: HAND2 (Illumina probe ID 4640563) and SOX17 (Illumina probe ID 3610193). Gene expression markers of the cell line 4D20.8 in the range of P12-17 include the genes: LHX8, HAPLN1, LING02, FGF18, GPR126, BBOX1, ITGA4, SHISA3, and BARX1 and is negative for the gene expression markers: NNAT and HAND2. The most specific of these gene expression markers being expressed in 4D20.8 are: SHISA3 (Illumina probe ID 5670286), LHX8 (Illumina probe ID 2900343), BARX1 (Illumina probe ID 6450040), LING02 (Illumina probe ID 1110291), and negative for the expression of the genes: PITX1 (Illumina probe ID 2000373), SOX17 (Illumina probe ID 3610193), and AJAP1 (Illumina ID 1300647).

Gene expression markers of the cell line EN7 in the range of P12 include: Expression of RGS1, NEFM, KBTBD10, CLDN5, GPR44, ATP1A2, KCND2, DLK1, FOXF1, and ZIC2, with most distal HOX gene expression being HOXB2, HOXA2, and no expression as determined by Illumina microarray for the expression of the genes: CD74 Illumina Probe ID (1240070), TBX15 (Illumina probe ID 6060113), LHX1, LHX8 (Illumina probe ID 2900343), PITX1 (Illumina probe ID 2000373), HAND2 (Illumina probe ID 4640563), or AJAP1 (Illumina ID 1300647).

As noted above, the embryonic chondrocyte progenitor cells of the present invention find use in methods for generating differentiated cells in the presence of BMP family members and are described below and in the Examples section).

Tissue Engineered Constructs

In certain embodiments, cells of the present invention are employed in therapeutic applications to repair, replace, or enhance tissue function in a subject (e.g, a mammal, e.g., a human patient). A number of therapies that employ cells incorporated in engineered matrices have been described, a few of which are summarized below. The cells of the present invention may be embedded in such matrices to provide form and function as is well-known in the art.

In certain embodiments, synthetic matrices or biological resorbable immobilization vehicles (sometimes referred to as "scaffolds") may be impregnated with cells of the present invention. A variety of synthetic carrier matrices have been used to date and include: three-dimensional collagen gels (U.S. Pat. No. 4,846,835; Nishimoto (1990) Med. J. Kinki University 15; 75-86; Nixon et al. (1993) Am. J. Vet. Res. 54:349-356; Wakitani et al. (1989) J. Bone Joint Surg. 71B:74-80; Yasui (1989) J. Jpn. Ortho. Assoc. 63:529-538); reconstituted fibrin-thrombin gels (U.S. Pat. Nos. 4,642,120; 5,053,050 and 4,904,259); synthetic polymer matrices containing polyanhydride, polyorthoester, polyglycolic acid and copolymers thereof (U.S. Pat. No. 5,041,138); hyaluronic acid-based polymers (Robinson et al. (1990) Calcif. Tissue Int. 46:246-253); and hyaluronan and collagen-based polymers such as HyStem-C (BioTime), e.g., as described in U.S. Pat. Nos. 7,981,871 and 7,928,069, the disclosures of which are herein incorporated by reference. HyStem-C may be employed in numerous applications where the prevention of undesired inflammation or fibrosis is desired, such as in the repair of traumatic orthopedic injuries such as tears to rotator cuff tendons, carpal tunnel syndrome, and trauma to tendons generally.

For example, the cells of the present invention may be employed in tissue reconstruction as described in Methods of Tissue Engineering (2002), edited by Anthony Atala and Robert P. Lanza and published by Academic Press (London), incorporated by reference herein for its description of tissue reconstruction (see, e.g, pages 1027 to 1039). As described therein, cells may be placed into a molded structure (e.g., by injection molding) and transplanted into an animal. Over time, tissue produced by the cells of the present invention will replace the molded structure, thereby producing a formed structure (i.e., in the shape of the initial molded structure). Exemplary mold materials for the molded structure include hydrogels (e.g., alginate, agarose, polaxomers (Pluronics)) and natural materials (e.g., type I collagen, type II collagen, and fibrin).

In certain embodiments, cells of the present invention may be cultured in vitro to form a synthetic tissue-like material. The resulting tissue may be implanted subsequently into a subject at the site of the defect. This type of approach has the advantage that the development of the synthetic tissue may be monitored prior to implantation. In addition, the resulting tissue may be characterized biochemically and morphologically prior to implantation. Numerous different procedures have been developed for growing synthetic tissue in vitro, including growing cells in an anchorage-dependent or an anchorage-independent manner.

In the anchorage-independent manner, cells may be cultured as colonies within an agarose gel. See for example: Benya et al. (1982) Cell 30:215-224; Aydlotte et al. (1990) in Methods and Cartilage Research Chapter 23:pp. 90-92; Aulthouse et al. (1989) In Vitro Cellular and Developmental Biology 25:659-668; Delbruck et al. (1986) Connective Tissue Res. 15:1550-172; and Bohme et al. (1992) J. Cell Biol. 116:1035-1042. Alternatively, in another anchorage-independent method, cells may be cultured as colonies in suspension culture. See for example, Franchimont et al. (1989) J. Rheumatol. 16:5-9; and Bassleer et al. (1990) in "Methods and Cartilage Research", Academic Press Ltd., Chapter 24.

In the anchorage-dependent method, primary cultures of cells may be grown as monolayers attached to the surface of a cell culture flask. See for example: Yoshihashi (1983) J. Jpn. Ortho. Assoc. 58:629-641; and U.S. Pat. No. 4,356,261, incorporated by reference herein in its entirety.

In certain embodiments, a cartilage therapy of the invention includes those described in U.S. Pat. Nos. 5,723,331 and 5,786,217 (entitled "Methods and compositions for the repair of articular cartilage defects in mammals", both of which are incorporated by reference herein in their entirety). These patents describe methods for preparing in vitro a synthetic cartilage patch for the repair of a cartilage defect. When the cartilage-producing cells of the present invention are employed, the methods include the steps of: (1) seeding cartilage-producing cells of the present invention into a pre-shaped well having a cell contacting, cell adhesive surface; and (2) culturing the cartilage-producing cells of the present invention in the well for a time sufficient to permit the cells to secrete an extracellular matrix, thereby to form a three-dimensional, multi cell-layered patch of synthetic cartilage. The resulting synthetic cartilage (e.g., synthetic articular cartilage), contains cartilage-producing cells of the present invention dispersed within an endogenously produced and secreted extracellular matrix. The resulting synthetic cartilage patch may be used subsequently for the repair (or replacement) of a cartilage defect in a subject (e.g., a mammal).

The cells of the present invention thus find use in numerous therapeutic applications for treating diseases or conditions characterized by tissue damage or degeneration as well as for complete replacement of those tissues. Diseases and conditions include, but are not limited to: osteoarthritis, chondromalacia, chondromalacia patella, hallux rigidus, hip labral tear, torn meniscus, cartilage replacement (ear, nose), nervous disorders, endocrine disorders, muscle disease, injuries to tendons and ligaments, etc.

Direct Injection of Cells to Impart Tissue Regeneration

Direct injection of cells, such as the cell lines of the present invention are also of therapeutic utility. Doses and formulation will vary depending on the route of administration, tissue type, and nature of the pathology to be treated as is known in the art, but in the case of humans and most veterinary animals species, the dosage will be between $10^2$-$10^6$ cells and the formulation can be, by way of non-limiting example, a cell suspension in isosmotic buffer or a monolayer of cells attached to an layer of extracellular matrix such as contracted gelatin. Cellular compositions of the present invention may further comprise an acceptable carrier, such as a hydrophilic, e.g., pharmaceutically acceptable, carrier.

Systems and Kits

Also provided by the subject invention are systems and kits that include the cells of the invention for use in various applications, as described herein. The systems and kits may further include reagents and materials for the propagation and use of the cells for research and/or therapeutic applications as described herein.

Biological Deposits

Cell lines described in this application have been deposited with the American Type Culture Collection ("ATCC"; P.O. Box 1549, Manassas, Va. 20108, USA) under the Budapest Treaty. The cell line 4D20.8 (also known as ACTC84) was deposited at the ATCC at passage 11 on Jul. 23, 2009 and has ATCC Accession No. PTA-10231. The cell line SM30 (also known as ACTC256) was deposited at the ATCC on Jul. 23, 2009 at passage 12 and has ATCC Accession No. PTA-10232. The cell line 7SMOO32 (also known as ACTC278) was deposited at the ATCC at passage 12 on Jul. 23, 2009 and has ATCC Accession No. PTA-10233. The cell line E15 (also known as ACTC98) was deposited at the ATCC at passage number 20 on Sep. 15, 2009 and has ATCC Accession No. PTA-10341. The cell line MEL2 (also known as ACTC268) was deposited at the ATCC at passage number 22 on Jul. 1, 2010 and has ATCC Accession No. PTA-11150. The cell line SK11 (also known as ACTC250) was deposited at the ATCC at passage number 13 on Jul. 1, 2010 and has ATCC Accession No. PTA-1152. The cell line 7PEND24 (also known as ACTC283) was deposited at the ATCC at passage number 11 on Jul. 1, 2010 and has ATCC Accession No. PTA-11149.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Cartilage Markers in Differentiating 4D20.8 Cells in the Presence of Diverse BMPs as Determined by qPCR MSCs at passage 10 (Lonza) were differentiated in HyStem hydrogel which is a PEGDA crosslinked polymer of hyaluronic acid and gelatin according to manufacturers instructions (Glycosan) for 14 days in the presence of 10 ng/mL of TGFB3 and the cell line of the present invention designated 4D20.8 was expanded in vitro >21 doublings of clonal expansion since they were isolated from hES-derived cells, synchronized in quiescence by growing to confluence and replacing the media with media supplemented with a 10-fold reduction in serum or other mitogens as described herein (CTRL), or differentiated in micromass conditions as described herein (MM), or differentiated in HyStem hydrogel which is a PEGDA crosslinked polymer of hyaluronic acid and gelatin according to manufacturers instructions (Glycosan) for 14 days in the presence of either 10 ng/mL of TGFB3, 25 ng/mL TGFB3, 10 ng/mL BMP4, 30 ng/mL BMP6, 100 ng/mL BMP7, 100 ng/mL GDF5, or combinations of these growth factors. RNA was extracted from these cells, the RNA was converted to cDNA and then examined for expression of genes commonly associated with chondrogenesis desired in the joint (i.e. COL2A1, COL10A, and CRTAC1). Gene-specific primer pair probes were obtained from Invitrogen. Samples for testing were prepared in standard Optical 96-well reaction plates (Applied Biosystems Carlsbad, Calif., PN 4306737) consisting of 30 ng of RNA equivalent of cDNA, 0.4 uM per primer, Ultra-Pure distilled water (Invitrogen), diluted 1:1 with 12.5 ul of Power SYBR Green PCR Master Mix (Applied Biosystems Carlsbad, Calif., Cat #4367659) incorporating AmpliTaq Gold DNA polymerase in a total reaction volume of 25 ul. Real-Time qPCR was run using Applied Biosystems 7500 Real-Time PCR System employing SDSv1.2 software. Amplification conditions were set at 50° C. for 2 min. (stage 1), 95° C. for 10 min. (stage 2), 40 cycles of 95° C. for 15 sec then 60° C. for 1 min (stage 3), with a dissociation stage at 95° C. for sec, 60° C. for 1 min, and 95° C. for 15 sec (stage 4). Ct values for amplification products of genes of interest were normalized to the average Ct value of 3 housekeeping genes (GAPD, RPS10, and GUSB), and gene expression analyzed relative to that of early passage knee-Normal Human Articular Chondrocytes (Lonza) and cultured human bone marrow mesenchymal stem cells.

The primer sets used to detect chondrogenic genes were ("f" is forward primer; "r" is reverse primer):

| Gene symbol | | Sequence 5' → 3' | SEQ ID NO |
|---|---|---|---|
| COMP | f2 | CCGACAGCAACGTGGTCTT | 1 |
| COMP | r2 | CAGGTTGGCCCAGATGATG | 2 |
| CRTL1 | f1 | TGCTCAGATTGCAAAAGTGG | 3 |

| Gene symbol | | Sequence 5' → 3' | SEQ ID NO |
|---|---|---|---|
| CRTL1 | r1 | TATCTGGGAAACCCACGAAG | 4 |
| CILP | f1 | CCTGGTCCTGGAAGTCACAT | 5 |
| CILP | r1 | CCATGTTGTCCACTCACCAG | 6 |
| CEP68 | f1 | ATCCGTAGAGAGCACGGAGA | 7 |
| CEP68 | r1 | GGACTCTCCATGGGACAAGA | 8 |
| COL2A1 | f3 | GGCAATAGCAGGTTCACGTACA | 9 |
| COL2A1 | r3 | CGATAACAGTCTTGCCCCACTT | 10 |
| COL2A1 | f4 | TGGCCTGAGACAGCATGA | 11 |
| COL2A1 | r4 | AGTGTTGGGAGCCAGATTG | 12 |
| CEP68 | f1 | ATCCGTAGAGAGCACGGAGA | 13 |
| CEP68 | r1 | GGACTCTCCATGGGACAAGA | 14 |
| SOX9 | f1 | TACGACTACACCGACCACCA | 15 |
| SOX9 | r1 | TCAAGGTCGAGTGAGCTGTG | 16 |
| SCXA | f1 | TCCAGCTACATCTCGCACCT | 17 |
| SCXA | r1 | CGGTCCTTGCTCAACTTTCT | 18 |
| BARX2 | f1 | GGACTTGGCTCAGTCTCTGG | 19 |
| BARX2 | r1 | TGGGGATGGAGTTCTTCTTG | 20 |
| GAPDH | f2 | GGCCTCCAAGGAGTAAGACC | 21 |
| GAPDH | r2 | AGGGGTCTACATGGCAACTG | 22 |
| RPS10 | f1 | ATTTGGTCGTGGACGTGGT | 23 |
| RPS10 | r1 | TTTGGCTGTAAGTTTATTCAATGC | 24 |
| GUSB | f1 | AAACGATTGCAGGGTTTCAC | 25 |
| GUSB | r1 | CTCTCGTCGGTGACTGTTCA | 26 |
| COL2A1 | f1 | TCTACCCCAATCCAGCAAAC | 27 |
| COL2A1 | r1 | GTTGGGAGCCAGATTGTCAT | 28 |
| COL2A1 | f2 | CACACTGGTAAGTGGGCAAGACCG | 29 |
| COL2A1 | r2 | ACGAGGTCCTCACTGGTGAA | 30 |
| ACAN | f1 | TGAGTCCTCAAGCCTCCTGT | 31 |
| ACAN | r1 | TGGTCTGCAGCAGTTGATTC | 32 |
| ACAN | f2 | ACAGCTGGGACATTAGTGG | 33 |
| ACAN | r2 | GTGGAATGCAGAGGTGGTTT | 34 |
| COL10A1 | f1 | GCTAAGGGTGAAAGGGGTTC | 35 |
| COL10A1 | r1 | CTCCAGGATCACCTTTTGGA | 36 |
| BGN | f1 | GGACTCTGTCACACCCACCT | 37 |
| BGN | r1 | AGCTCGGAGATGTCGTTGTT | 38 |
| COL9A2 | f1 | AGCATCATTCGGCTGTTACC | 39 |
| COL9A2 | r1 | CTGAGGGGTGGAACTGTAGC | 40 |
| CDMP1 | f1 | CCCATCAGCATCCTCTTCAT | 41 |
| CDMP1 | r1 | TGTAGATGCTCCTGCCACAG | 42 |
| VERSICAN | f1 | ACCACGCTTCCTATGTGACC | 43 |
| VERSICAN | r1 | TGTTGTAACTGGGTGGCAAA | 44 |
| COL11A1 | f1 | TCGAGGGTTTGATGGACTTC | 45 |
| COL11A1 | r1 | CATCTTCTCCCCTCATTCCA | 46 |
| DCN | f1 | TGGCAACAAAATCAGCAGAG | 47 |
| DCN | r1 | GCCATTGTCAACAGCAGAGA | 48 |
| FMOD | f1 | CCTCCAAGGCAATAGGATCA | 49 |
| FMOD | r1 | GCTGCGCTTGATCTCGTTC | 50 |
| LUM | f1 | TGATCTGCAGTGGCTCATTC | 51 |
| LUM | r1 | AAAAGAGCCCAGCTTTGTGA | 52 |
| COL1A1 | f1 | GTGCTAAAGGTGCCAATGGT | 53 |
| COL1A1 | r1 | ACCAGGTTCACCGCTGTTAC | 54 |
| COL1A1 | f2 | GTGCTAAAGGTGCCAATGGT | 55 |
| COL1A1 | r2 | CTCCTCGCTTTCCTTCCTCT | 56 |
| PRELP | f1 | TCCCAATCTTGCCTTCATTC | 57 |
| PRELP | r1 | GTCATGGAACGCCACTAGGT | 58 |
| ACAN | f3 | TCGAGGACAGCGAGGCC | 59 |
| ACAN | r3 | TCGAGGGTGTAGCGTGTAGAGA | 60 |
| COL10A1 | f2 | CAAGGCACCATCTCCAGGAA | 61 |
| COL10A1 | r2 | AAAGGGTATTTGTGGCAGCATATT | 62 |
| CRTL1 | f2 | TTCCACAAGCACAAACTTTACACAT | 63 |
| CRTL1 | r2 | GTGAAACTGAGTTTTGTATAACCTCTCAGT | 64 |
| LUM | f2 | ACCAGATTGACCATATTGATGA | 65 |
| LUM | r2 | GGACAGATCCAGCTCAACC | 66 |
| SOX9 | f2 | AGGCAAGCAAAGGAGATGAA | 67 |
| SOX9 | r2 | TGGTGTTCTGAGAGGCACAG | 68 |
| SOX9 | f3 | ACTGAGTCATTTGCAGTGTTTTCTGCC | 69 |
| SOX9 | r3 | GTGGGCTGATCCCCTCCAGGT | 70 |
| SOX5 | f1 | TGGCACTGCACTGGGTAGGA | 71 |
| SOX5 | r1 | AAGGCTGGGAGCCCGTCACT | 72 |
| AGC1/ACAN | f4 | TGAGTCCTCAAGCCTCCTGT | 73 |
| AGC1/ACAN | r4 | CCTCTGTCTCCTTGCAGGTC | 74 |
| IHH | f1 | GGCCGGGAGACCGTGTTG | 75 |
| IHH | r1 | TGGGGCTCGCGGTCCAGTAA | 76 |
| IHH | f2 | TACGCCTGGAGAGTGGGCG | 77 |
| IHH | r2 | TGGGGCTCGCGGTCCAGTAA | 78 |
| COL2A1 | f5 | TCGTGGGTCCCAGGGGTGAA | 79 |

-continued

| Gene symbol | | Sequence 5' → 3' | SEQ ID NO |
|---|---|---|---|
| COL2A1 | r5 | GACCTGGAGGGCCCTGTGCG | 80 |
| COL2A1 | f6 | TGCTGCCCCATCTGCCCAAC | 81 |
| COL2A1 | r6 | CCTGCAGGTCCCTGAGGCCC | 82 |
| COL2A1 | f7 | AGGGCCAGGATGTCCGGCAA | 83 |
| COL2A1 | r7 | TCTGCCACGAGGTCCAGGGG | 84 |
| CRTAC1 (CEP-68) | f2 | CGGGGCGATGGCACCTTTGT | 85 |
| CRTAC1 (CEP-68) | r2 | GATAGAGGCGGTGGGGGCCA | 86 |
| COMP | f1 | ACAATGACGGAGTCCCTGAC | 87 |
| COMP | r1 | TCTGCATCAAAGTCGTCCTG | 88 |
| BARX2 | f2 | GAGTCAGAGACGGAACAGCC | 89 |
| BARX2 | r2 | AGTCCCAGAGACTGAGCCAA | 90 |
| CHM1 (LECT1) | f1 | GCGCAAGTGAAGGCTCGTAT | 91 |
| CHM1 (LECT1) | r1 | GTTTGGAGGAGATGCTCTGTTTG | 92 |

Figure 1B:
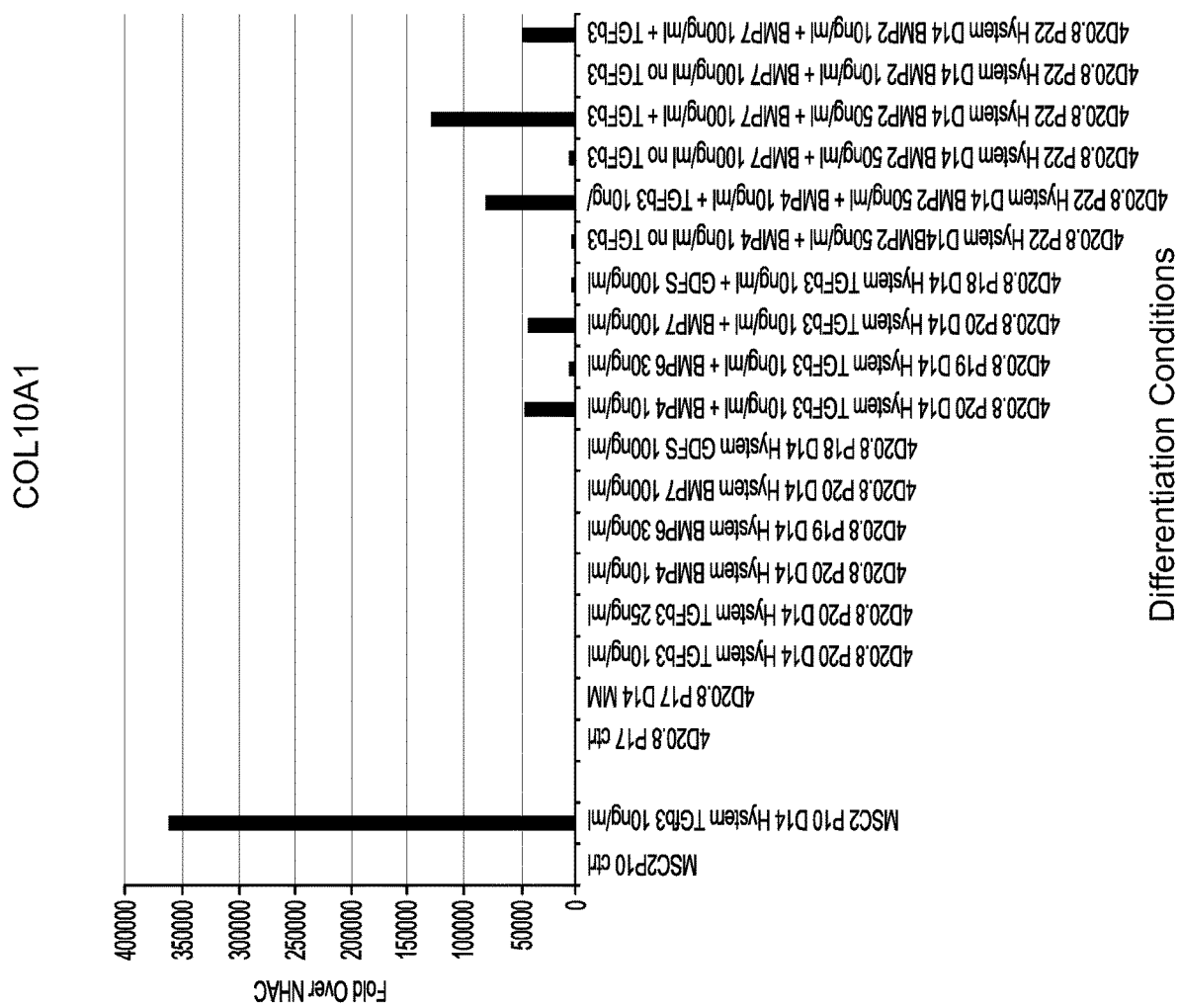
Figure 1C:
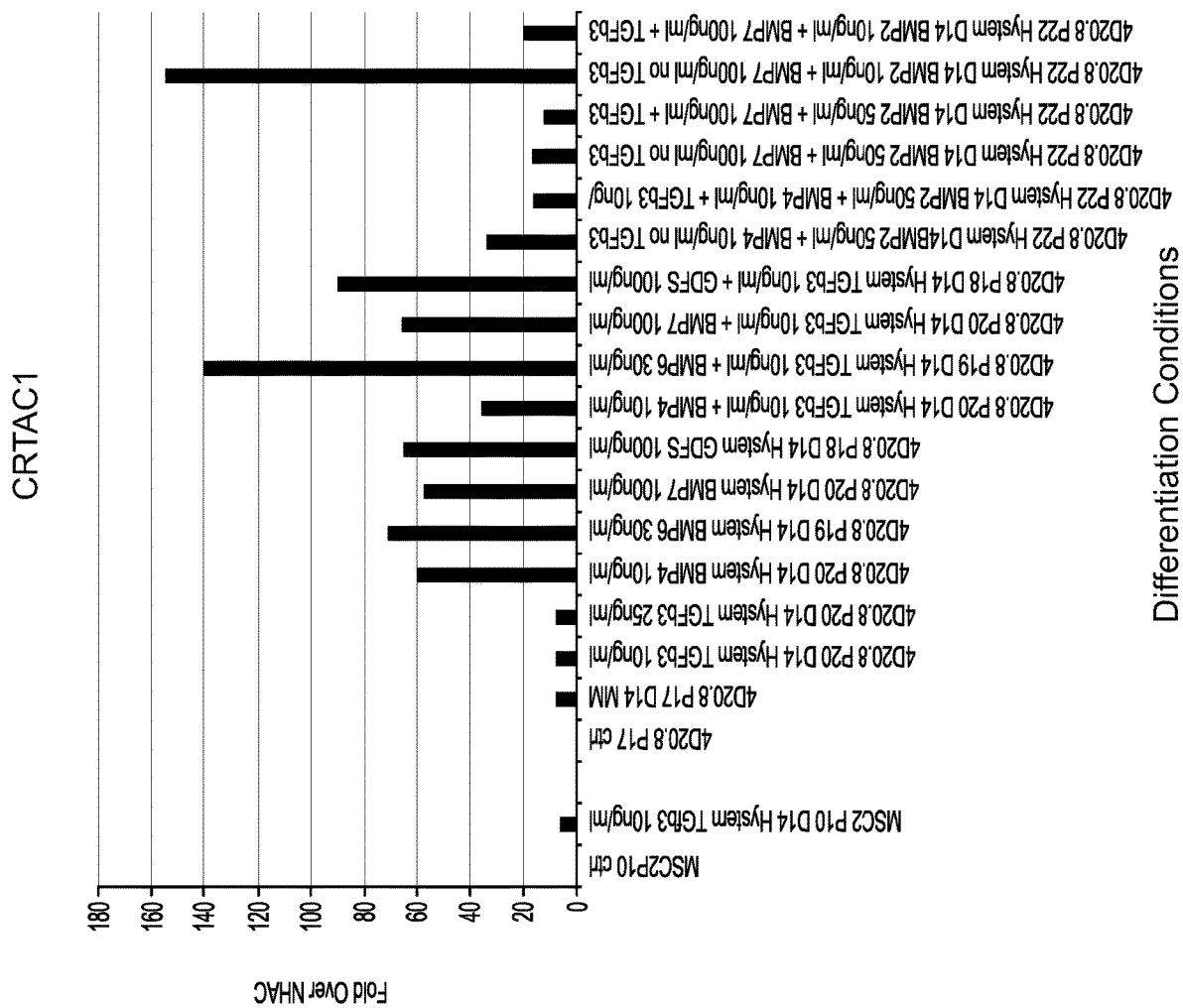

As shown in FIG. 1A-C, combinations of BMPs with TGFB3 increased COL2A1 expression. In the case of treating joint disease, it is desirable to identify conditions that increase COL2A1 expression while minimizing COL10A1 expression to minimize the conversion of chondrocyte progenitors into hypertrophic cells leading to bone formation. Also, it is desirable to increase CRTAC1 expression which is a marker of definitive cartilage. The combination of TGFB3 at 10 ng/mL together with GDF5 at 100 ng/mL in HyStem matrix optimized COL2A1 and CRTAC1 expression while minimizing COL10A1 expression. This optimized differentiation protocol in useful in preconditioning cells with a pattern of gene expression similar to 4D20.8 such that the preconditioned cells when implanted in vivo will differentiate into cells useful in reconstituting joint histology.

Figure 2:
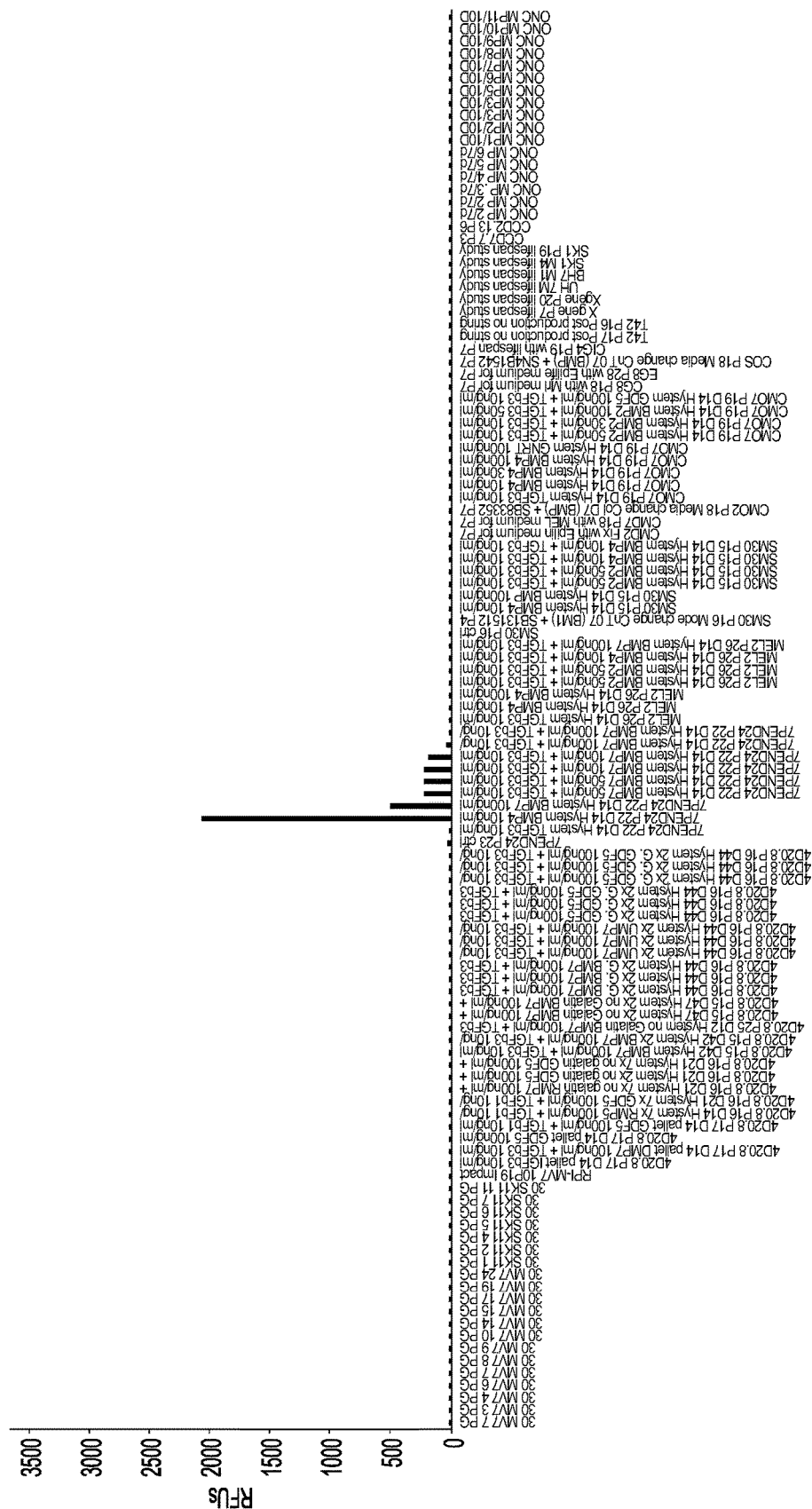
FIG. 2 provides graphical representations of the expression level of Tenomodulin in cell progenitor lines treated with BMP family members as determined by qPCR.

Example 2. Tendon Markers in Differentiating 7PEND24 Cells in the Presence of Diverse BMP4 as Determined by Illumina Gene Expression Microarrays The cell line 7PEND24 (passage 22) was differentiated in HyStem hydrogel which is a PEGDA crosslinked polymer of hyaluronic acid and gelatin according to manufacturers instructions (Glycosan) for 14 days in the presence of 10 ng/mL of TGFB3 and the cell line of the present invention designated 7PEND24 was expanded in vitro >21 doublings of clonal expansion since they were isolated from hES-derived cells, synchronized in quiescence by growing to confluence and replacing the media with media supplemented with a 10-fold reduction in serum or other mitogens as described herein (CTRL), or differentiated in micromass conditions as described herein (MM), or differentiated in HyStem hydrogel which is a PEGDA crosslinked polymer of hyaluronic acid and gelatin according to manufacturers instructions (Glycosan) for 14 days in the presence of either 10 ng/mL of TGFB3, 25 ng/mL TGFB3, 10 ng/mL BMP4, 30 ng/mL BMP6, 100 ng/mL BMP7, 100 ng/mL GDF5, or combinations of these growth factors. In brief, the hydrogel/cell formulation was prepared as follows: HyStem (Glycosan, Salt Lake, Utah, Hystem-CSS Cat #GS319) was reconstituted following manufacturer's instructions. Briefly, Hystem (thiol modified hyaluronan, 10 mg) was dissolved in 1 ml degassed deionized water (taking about 20 minutes) to prepare a 1% solution. Gelin-S(thiol modified gelatin, 10 mg) was dissolved in 1 ml degassed deionized water to prepare a 1% solution, and PEGSSDA (disulfide-containing PEG diacrylate, 10 mg) was dissolved in 0.5 ml degassed deionized water to prepare a 2% solution. Then HyStem (1 ml, 1%) is mixed with Gelin-S (1 ml, 1%) without creating air bubbles, immediately before use. Pelleted cells were resuspended in recently prepared HyStem Gelin-S(1:1) mix described above. Upon the addition of crosslinker PEGSSDA (disulfide containing polyethelene glycol diacrylate), 100 ul of the cell suspension, at a final concentration of 20×10e6 cells/ml, is aliquoted into multiple 24 well plate, 6.5 mm polycarbonate (0.4 uM pore size) transwell inserts (Corning 3413). Following gelation in about 20 minutes, chondrogenic medium is added to each well. Plates are then placed in humidified incubator at 37° C., ambient O2, 10% CO2, and cells are fed three times weekly. RNA was extracted from these cells, the RNA was converted to cDNA and hybridized to Illumina gene expression microarrays. As can be seen in FIG. 2, the 7PEND24 cell line unexpectedly, in the presence of 10.0 ng/mL BMP4, expressed relatively high levels of tenomodulin (TNMD), a molecular marker of tendon cells (tenocytes). Lesser, but nevertheless elevated levels of TNMD expression were observed in parallel cultures incubated in the presence of 100 ng/mL BMP7. Therefore, unlike when cultured in the presence of other BMP family members where COL2A1 expression is induced, little or no COL2A1 expression, but relatively high TNMD expression was observed when 7PEND24 was differentiated as described herein in HyStem hydrogels and in the presence of 10 ng/mL BMP4.

Figure 3:
FIG. 3 provides graphical representations of the expression level of bone sialoprotein II in cell progenitor lines treated with BMP family members as determined by qPCR

Example 3. Bone Markers in Differentiating SM30 Cells in the Presence of Diverse BMPs as Determined by Illumina Gene Expression Microarrays The cell line SM30 (passage 22) was differentiated in HyStem hydrogel which is a PEGDA crosslinked polymer of hyaluronic acid and gelatin according to manufacturers instructions (Glycosan) for 14 days in the presence of 10 ng/mL of TGFB3 and the cell line of the present invention designated SM30 was expanded in vitro >21 doublings of clonal expansion since they were isolated from hES-derived cells, synchronized in quiescence by growing to confluence and replacing the media with media supplemented with a 10-fold reduction in serum or other mitogens as described herein (CTRL), or differentiated in micromass conditions as described herein (MM), or differentiated in HyStem hydrogel which is a PEGDA crosslinked polymer of hyaluronic acid and gelatin according to manufacturers instructions (Glycosan) for 14 days in the presence of either 10 ng/mL of TGFB3, 25 ng/mL TGFB3, 10 ng/mL BMP4, 30 ng/mL BMP6, 100 ng/mL BMP7, 100 ng/mL GDF5, or combinations of these growth factors. In brief, the hydrogel/cell formulation was prepared as follows: HyStem (Glycosan, Salt Lake, Utah, Hystem-CSS Cat #GS319) was reconstituted following manufacturer's instructions. Briefly, Hystem (thiol modified hyaluronan, 10 mg) was dissolved in 1 ml degassed deionized water (taking about 20 minutes) to prepare a 1% solution. Gelin-S(thiol modified gelatin, 10 mg) was dissolved in 1 ml degassed deionized water to prepare a 1% solution, and PEGSSDA (disulfide-containing PEG diacrylate, 10 mg) was dissolved in 0.5 ml degassed deionized water to prepare a 2% solution. Then HyStem (1 ml, 1%) is mixed with Gelin-S(1 ml, 1%) without creating air bubbles, immediately before use. Pelleted cells were resuspended in recently prepared HyStem Gelin-S(1:1) mix described above. Upon the addition of crosslinker PEGSSDA (disulfide containing polyethelene glycol diacrylate), 100 ul of the cell suspension, at a final concentration of 20×10e6 cells/ml, is aliquoted into multiple 24 well plate, 6.5 mm polycarbonate (0.4 uM pore size) transwell inserts (Corning 3413). Following gelation in about 20 minutes, chondrogenic medium is added to each well. Plates are then placed in humidified incubator at 37° C., ambient O2, 10% CO2, and cells are fed three times weekly. RNA was extracted from these cells, the RNA was converted to cDNA and hybridized to Illumina gene expression microarrays. As can be seen in FIG. 3, the cell line SM30 like bone marrow MSCs, unexpectedly, in the presence of 50.0 ng/mL BMP2 and 10 ng/mL TGFB3, and 10 ng/mL BMP4 and 10 ng/mL TGFB3 expressed relatively high levels of bone sialoprotein II (IBSP) a molecular marker of bone-forming cells and very high levels of COL2A1 and COL10A1, suggesting intermediate hypertrophic chondrocyte formation (i.e. endochondral ossification). Lesser, but nevertheless elevated levels of IBSP expression was also observed in the cell line MEL2 in pellet culture in 10 ng/mL TGFB3. Since IBSP is a molecular marker and a component of bone mineralization, SM30 and MEL2 have utility in studying novel molecular mechanisms of bone embryology, in the case of SM30 in particular, of ZIC2+ bone forming cells of the head and face, and in bone repair therapies.

Example 4: qPCR Analysis of Progenitor Cell Lines Treated with BMP Family Members Progenitor cells lines used as starting material in this experiment were derived from NIH registered hES cell line H9 as described by West et al., 2008 (The ACTCellerate initiative: large-scale combinatorial cloning of novel human embryonic stem cell derivatives, *Regen. Med.*, 3(3), 287-308). They were cultured in Corning tissue culture treated polystyrene culture-ware coated with 0.1% gelatin prepared from 2% gelatin, (Sigma Cat #G1393) using appropriate growth media supplemented with 2 mM glutamax and penicillin:streptomycin (100 IU/ml:100 ug/ml). They were placed in a humidified incubator at 37° C., 5% O2, and 10% CO2. Cells were fed by replacing media every 2-3 days and split 1:3 at or near confluence using 0.25% Trypsin/EDTA (Invitrogen 25200-114) diluted 1:3 with PBS, Ca Mg free.

The progenitor cell lines obtained according to the previous paragraph were cultured in the following media supplemented with BMP family members: line 4D20.8 was grown in DMEM 20% FBS; the E15 progenitor line was also cultured in DMEM supplemented with 20% FBS; the SM30 progenitor cell line was cultured in PromoCell smooth muscle media; the SK11 progenitor cell line was cultured in PromoCell skeletal muscle media; the Mel2 progenitor cell line was cultured in PromoCell melanocyte media; 7SMOO32 was cultured in PromoCell smooth muscle media; the MSC progenitor cell line was cultured in Promocell mesenchymal media. All of the above media were supplemented with penocyllin/streptomycin and glutamine.

Figure 4:
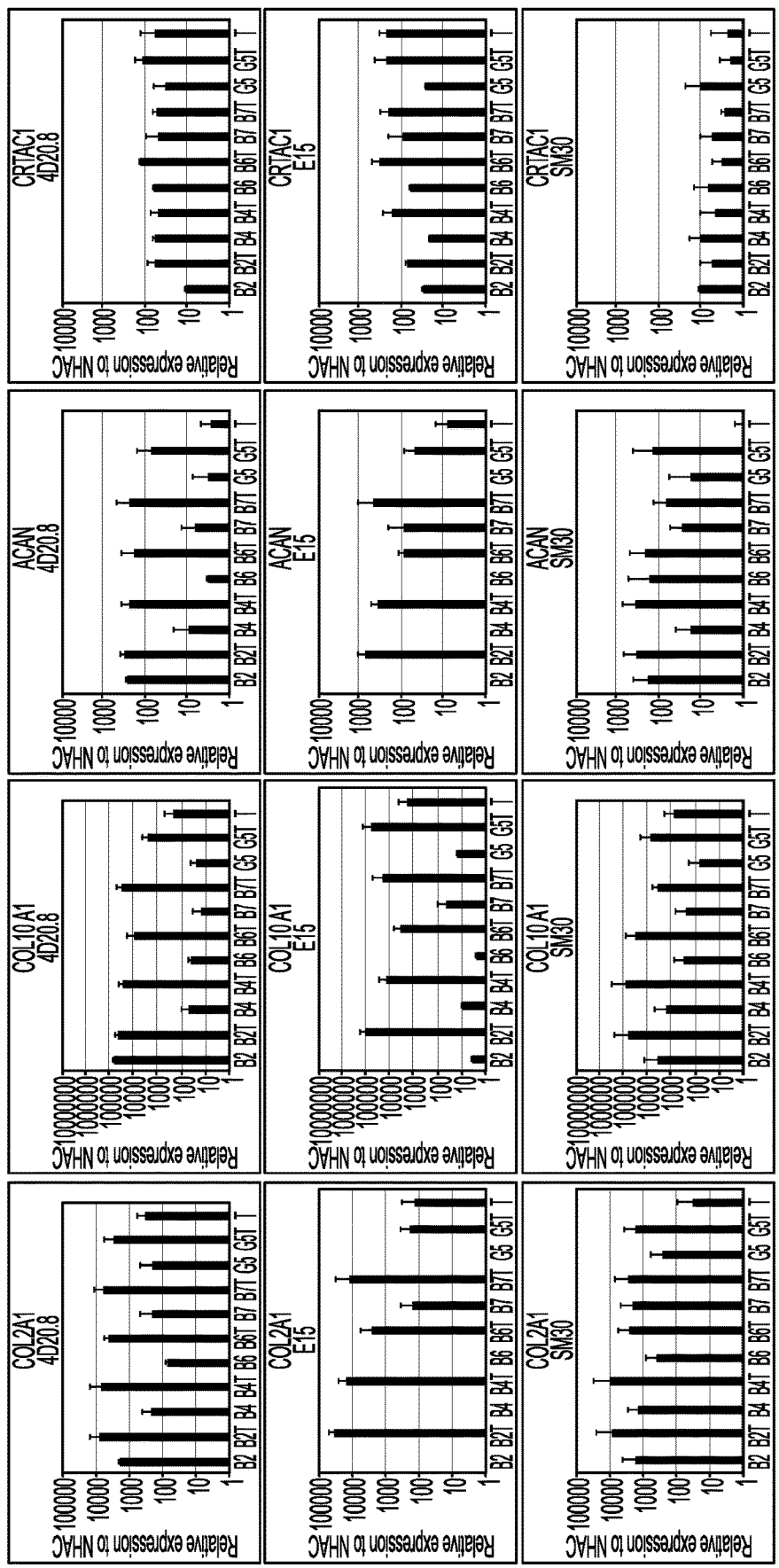
FIG. 4 shows a graphs showing the expression of a variety of genes (noted in bold at the top of each graph) and a variety of clonal progenitor cell lines (each line is noted just below the gene name at the top of the individual graphs. The cells were cultured with BMP family members to induce differentiation and gene expression. B2=BMP2; B2T+BMP2/TGFβ; B4=BMP4; B4T=BMP4/TGFβ; B6=BMP6; B6T=BMP6/TGFβ; B7=BMP7; B7T=BMP7/TGFβ; G5=GDF5; G5T=GDF5/TGFβ; T=TGFβ. The factors were used at the following concentrations: BMP2—50 ng/ml; BMP4—10 ng/ml; BMP6—30 ng/ml; BMP7-100 ng/ml; TGFβ 10 ng/ml; GDF5 100 ng/ml. With the exception of the 7PEND24 cell line treated with G5, the absence of a bar indicates the specific marker was not detectable. In the case of G5 treated 7PEND24 the cells were not treated, thus no result is reported.
Figure 4:
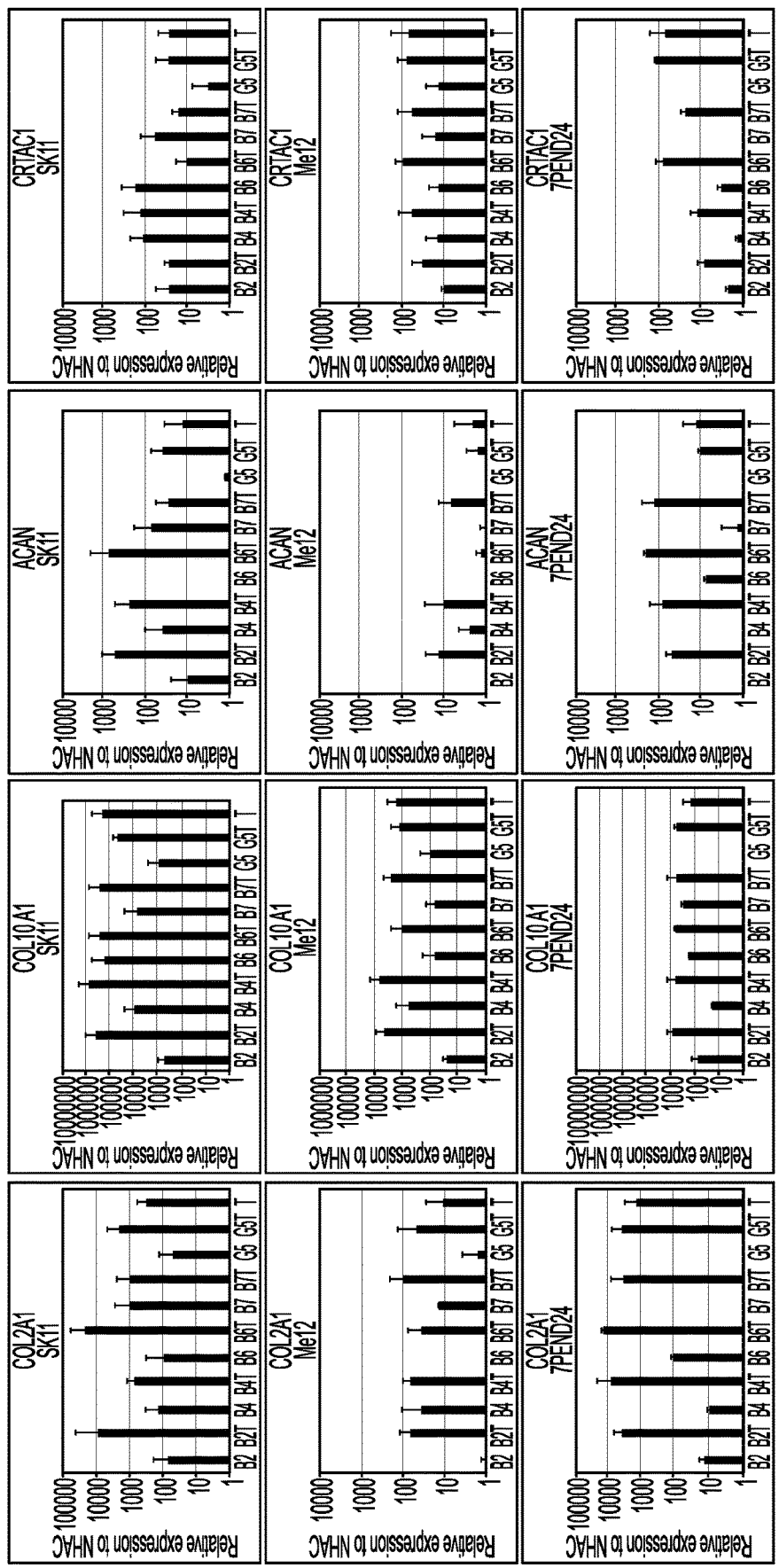
Figure 4:
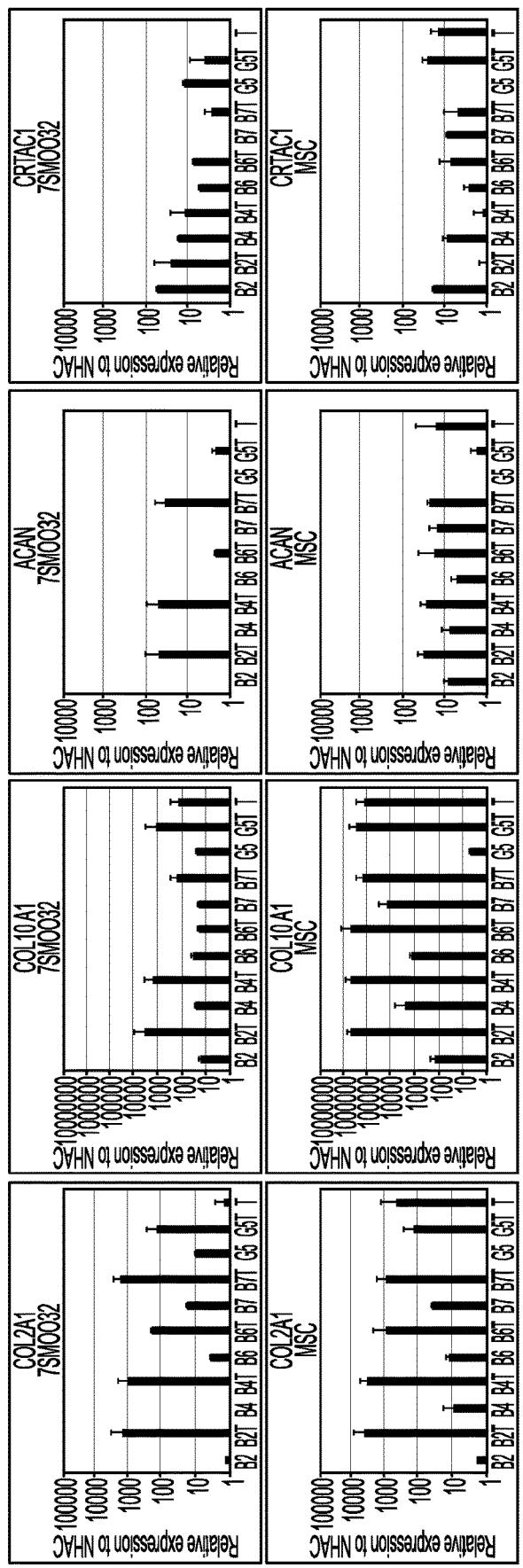

The specific BMP factors along with their respective concentrations are provided in the brief description of FIG. 4.

Hystem C (Glycosan Biosystems, subsidiary of BioTime Inc), hydrogel components consists of 3 primary reagents: (1) Hystem (thiol modified hyaluronan, 10 mg) which is dissolved in 1 ml degassed deionized water (taking about 20 minutes) to prepare a 1% solution. (2) Gelin-S (thiol modified gelatin, 10 mg) which was dissolved in 1 ml degassed deionized water to prepare a 1% solution, and PEGDA extralink crosslinker (PEG diacrylate, 10 mg) which was dissolved in 0.5 ml degassed deionized water to prepare a 2% solution. Hystem (1 ml, 1%) was mixed with Gelin-S(1 ml, 1%) without creating air bubbles, immediately before use. After suspending cells, to gelate, 0.5 ml extralink crosslinker is added.

Cultured cells were detached from the 0.1% gelatin coated surfaces of T225 flasks (Corning) using Trypsin, which was deactivated using growth medium containing FBS. The cells were counted, and then spun at 150 g for 5 min. They were resuspended at 20×10e6-30×10e6 cells/ml in Hystem-C:Gelin-S(1:1). Extralink was added and the evenly distributed cell suspension gradually became more viscous. Before gelation 25 ul aliquots were placed in multiple wells of a 6 well plate. Following complete gelation in about 5 min the encapsulated cells were fed chondro media, and re-fed every other day. On day 14 cells were lysed and RNA harvested.

For total RNA extraction Qiagen RNeasy Mini Kits (Qiagen, Cat #74106) was used. On day 14, the medium was removed, hydrogel-cell constructs are washed with PBS, then exposed to lysis buffer RLT (Qiagen, Valencia Calif. Cat #79216) with 1% beta mercaptoethanol following manufacturers instructions, placed in labeled RNase DNase free 1.5 ml eppendorf tubes and frozen at −80° C. Later, thawed samples, were vortexed, briefly spun, and further homogenized using QIAshredder (Cat #79694). RNA was then extracted using the RNeasy mini-kits following manufactures instruction and RNA concentration measured using a Nanodrop 1000.

cDNA was prepared using SuperScript III first strand kits with random hexamers (Invitrogen, Carlsbad Calif., Cat. 18080-051), following manufacturer's instructions. cDNA clean-up to remove nucleotides, primers, salts and polymerases was carried out using QIAquick PCR purification kits (Qiagen, Valencia Calif. Cat. #28104) following manufacturer's instructions.

Samples for testing (template) were prepared in standard Optical 96-well reaction plates (Applied Biosystems Carlsbad, Calif., PN 4306737) consisting of 30 ng of RNA equivalent of cDNA, 0.8 uM per gene-specific custom oligonucleotide primer set (Invitrogen), ultra-pure distilled water (Invitrogen Cat. #10977015), diluted 1:1 with 12.5 ul of Power SYBR Green PCR Master Mix (Applied Biosystems Carlsbad, Calif., Cat. #4367659) incorporating AmpliTaq Gold DNA polymerase in a total reaction volume of 25 ul. Real-Time qPCR was run using Applied Biosystems 7500 Real-Time PCR System employing SDSv1.2 software. Amplification conditions were set at 50° C. for 2 min. (stage 1), 95° C. for 10 min. (stage 2), 40 cycles of 95° C. for 15 sec then 60° C. for 1 min (stage 3), with a dissociation stage (stage 4) at 95° C. for 15 sec, 60° C. for 1 min, and 95° C. for 15 sec. Ct values of amplicons were normalized to the average Ct value of 3 housekeeping genes (GAPD, RPS10, and GUSB), and normalized gene expression of samples calculated relative to that of early passage knee-Normal Human Articular Chondrocytes (Lonza).

Primers Used:

```
COL2A1 (NM_001844.4)
                                   (SEQ ID NO: 100)
f. TGGCCTGAGACAGCATGA (SEQ ID NO: 93)
r. AGTGTTGGGAGCCAGATTG (373 bp)

ACAN (NM_013227.2)
                                   (SEQ ID NO: 101)
f. TGAGTCCTCAAGCCTCCTGT (SEQ ID NO: 94)
r. CCTCTGTCTCCTTGCAGGTC (185 bp)

CEP-68 (CRTAC1) (NM_018058.4)
                                   (SEQ ID NO: 102)
f. ATCCGTAGAGAGCACGGAGA (SEQ ID NO: 95)
r. GGACTCTCCATGGGACAAGA (144 bp)

COL10A1 (NM_000493.3)
                                   (SEQ ID NO: 103)
f. GGGCCTCAATGGACCCACCG (SEQ ID NO: 96)
r. CTGGGCCTTTGGCCTGCCTT (150 bp)

GAPDH (NM_002046.3)
                                   (SEQ ID NO: 104)
f. GGCCTCCAAGGAGTAAGACC (SEQ ID NO: 97)
r. AGGGGTCTACATGGCAACTG (147 bp)

RPS10 (NM_001014.3)
                                   (SEQ ID NO: 105)
f. ATTTGGTCGTGGACGTGGT (SEQ ID NO: 98)
r. TTTGGCTGTAAGTTTATTCAATGC (77 bp)

GUSB (NM_000181.2)
                                   (SEQ ID NO: 106)
f. AAACGATTGCAGGGTTTCAC (SEQ ID NO: 99)
r. CTCTCGTCGGTGACTGTTCA (171 bp)
```

The results are presented in Table 4 and show that BMP family members effectively induce chondrocyte associated gene expression in many of the tested clonal progenitor lines.

Example 5: Histological Analysis of Chondrocytes Obtained from Various Progenitor Cell Lines Progenitor cells lines were derived from NIH registered hES cell line H9 as described by West et al., 2008 (The ACTCellerate initiative: large-scale combinatorial cloning of novel human embryonic stem cell derivatives, Regen. Med., 3(3), 287-308). They were cultured in Corning tissue culture treated polystyrene culture-ware coated with 0.1% gelatin prepared from 2% gelatin, (Sigma Cat #G1393) using appropriate growth media supplemented with 2 mM glutamax and penicillin:streptomycin (100 IU/ml:100 ug/ml). They were placed in a humidified incubator at 37° C., 5% O2, and 10% CO2. Cells are fed by replacing media every 2-3 days and split 1:3 at or near confluence using 0.25% Trypsin/EDTA (Invitrogen 25200-114) diluted 1:3 with PBS, Ca Mg free. Progenitor cell lines so obtained were treated as described below to induce differentiation to chondrocytes or chondrocyte progenitors.

Pellets were prepared according to the method described by Johnstone 1998 (Johnstone, B., Hering T. M., Caplan A. I., Goldberg, V. M. and Yoo J. U. In Vitro Chondrogenesis of Bone Marrow-Derived Mesenchymal Progenitor Cells. Exptl. Cell Res. 238, 265-272, 1998). Briefly, pellet micromasses were prepared by aliquoting 500,000 cells in 500 ul (i.e. $1 \times 10^6$ cells/ml) chondrogenic media into individual 15 ml sterile conical tubes, spinning at 150×g for 5 minutes at 23° C., and placing pellets in a humidified incubator at 37° C., 10% $CO_2$, 5% $O_2$ with tube caps loosened. Pellets are fed every other day over a 5 day period (i.e. 3 times).

Chondrogenic media was DMEM (CellGro Cat. No. 15-013-CV, or PromoCell, Heidelberg Germany C-71219), high glucose, Pyruvate, 1 mM (Gibco Cat. 11360), Pen:Strep 100U/ml:100 ug/ml (Gibco Cat. No. 504284), Glutamax 2 mM (Gibco Cat. No. 35050), Dexamethasone 0.1 uM (Sigma, St. Louis, Mo., Cat. No. D1756-100), L-Proline 0.35 mM (Sigma Cat. No. D49752), 2-phospho-L-Ascorbic Acid 0.17 mM (Sigma, Cat. No. 49792, Fluka), ITS Premix (BD, Franklin Lakes, N.J., sterile Cat. No. 47743-628) final concentration 6.25 ug/ml insulin, 6.25 ug/ml transferrin, 6.25 ng/ml selenious acid, serum albumin 1.25 mg/ml, 5.35 ug/ml linoleic acid and TGFb3 10 ng/ml (R&D systems, Minneapolis Minn., Cat. No. 243-B3-010). Supplements of other BMP family members was as shown in captions of FIG. 5

All samples were fixed with 10% neutral buffered formalin. Fixed samples are paraffin embedded, sectioned 4-5 um, deparaffinized, hydrated and stained with H&E, Safranin-O, and COL2 immunostain (Millipore, Cat. #MAB8887 Anti-Collagen Type II, clone 6B3).

Figure 5:
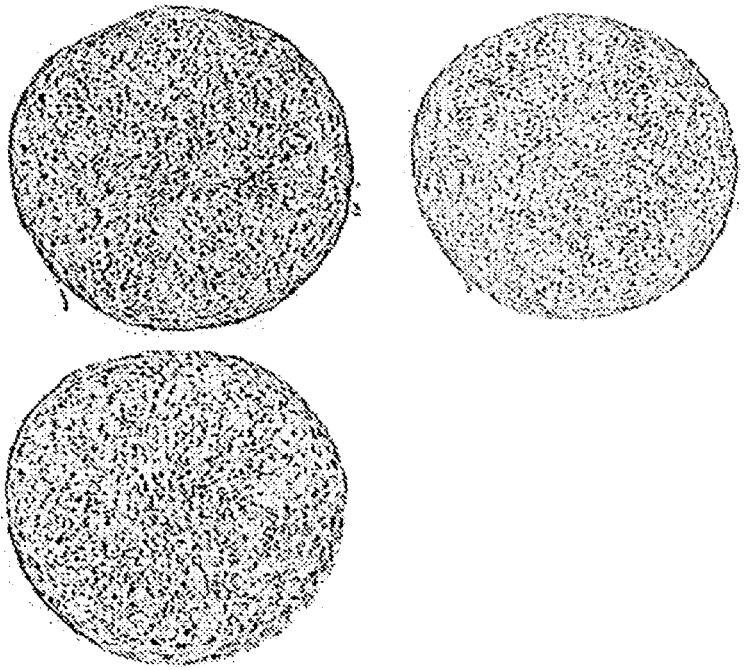
FIG. 5 shows histological sections of pellet cultures of various clonal progenitors cultured with BMP family members. Sections on the left side of each row are stained with hemotoxylin and eosin; the middle column is stained with safranin O (detecting glyocosamino glycan found on chondrocytes) and collagen 2 staining is shown on the far right.
Figure 5:
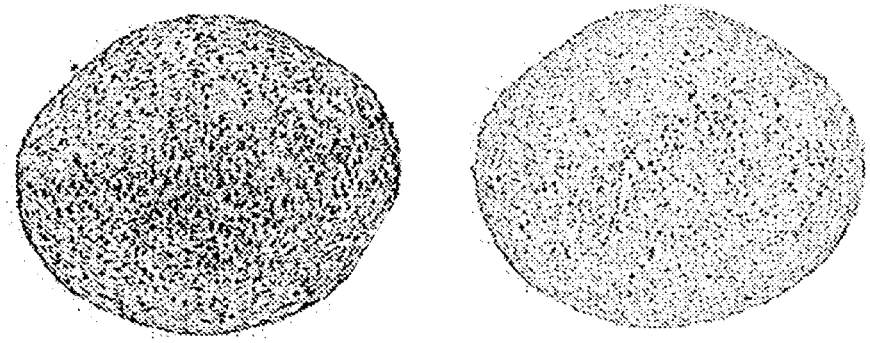
Figure 5:
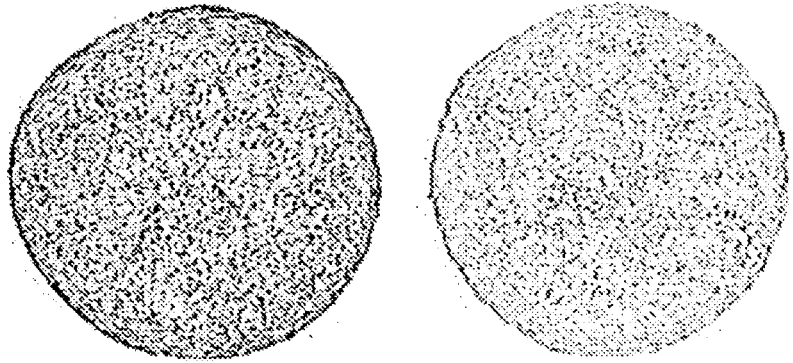
Figure 5:
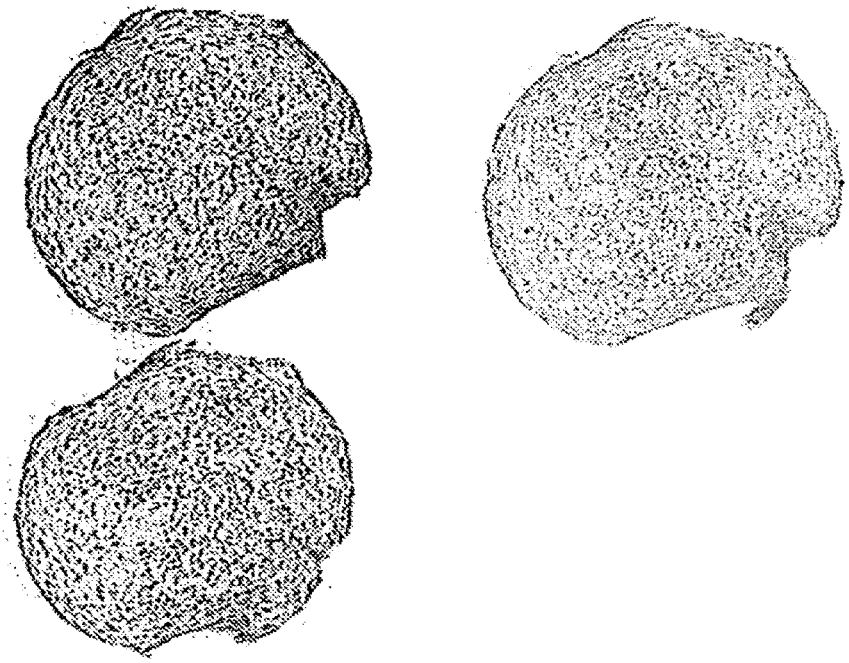
Figure 5:
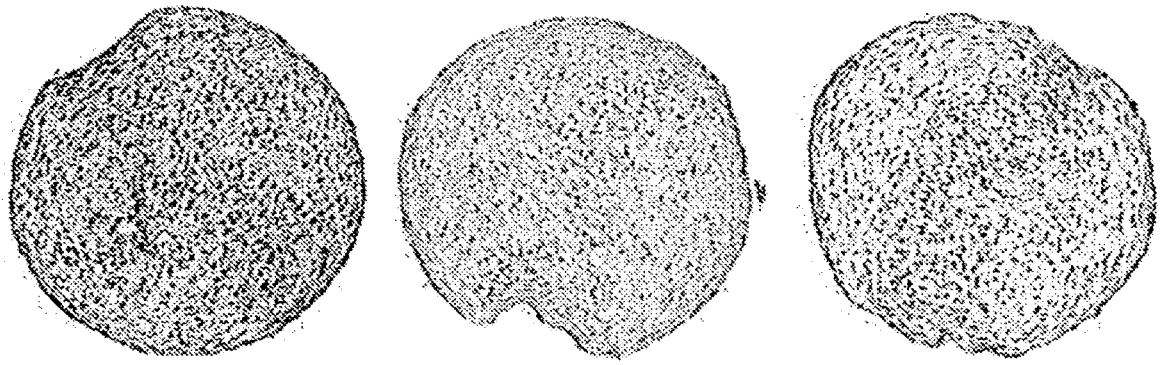
Figure 5:
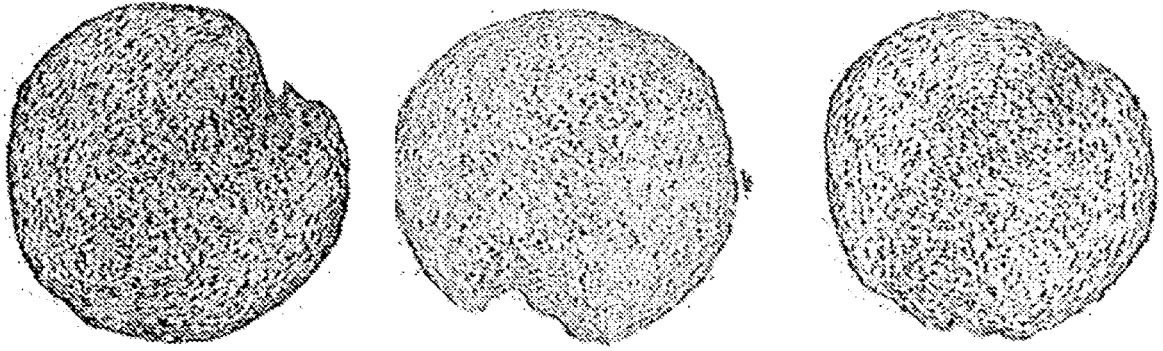
Figure 5:
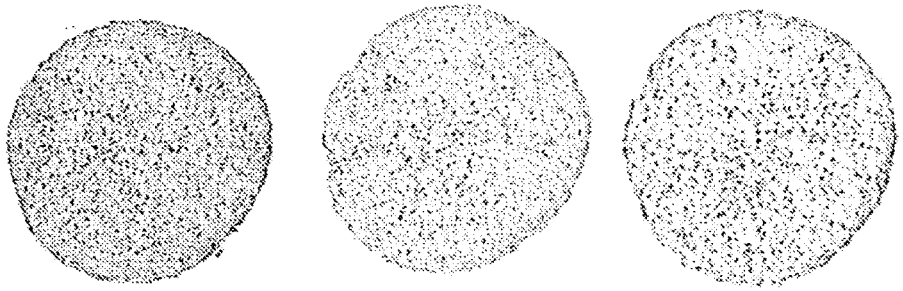
Figure 5:
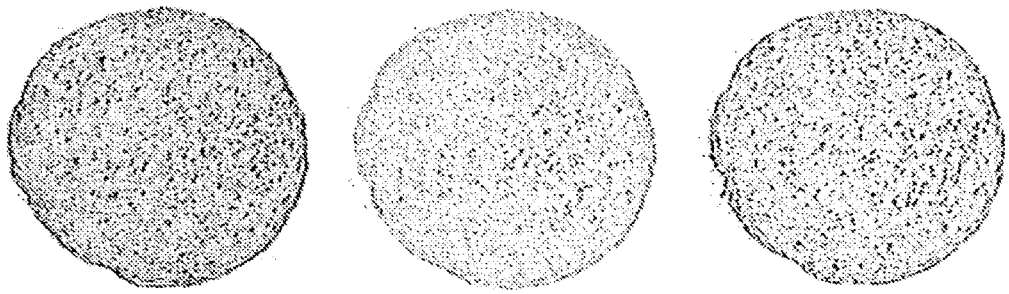
Figure 5:
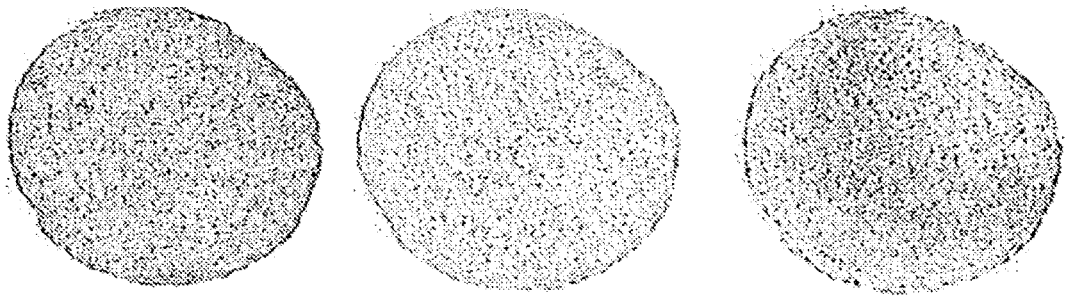
Figure 5:
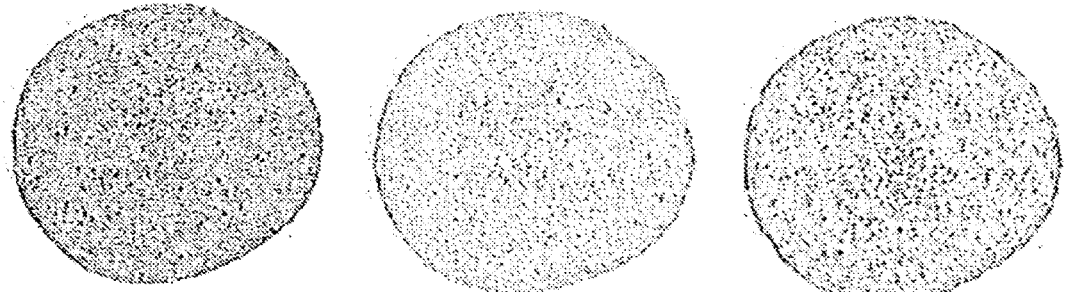
Figure 5:
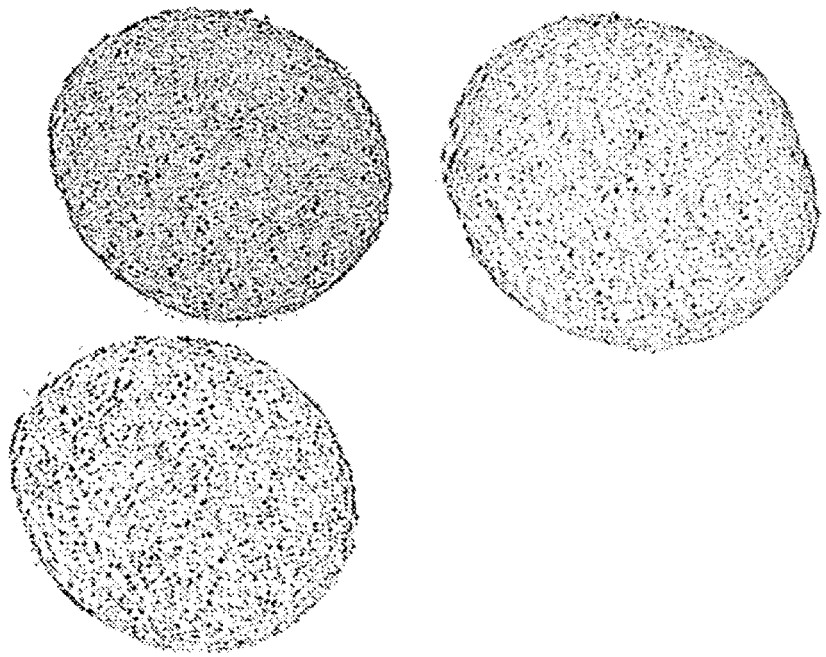
Figure 5:
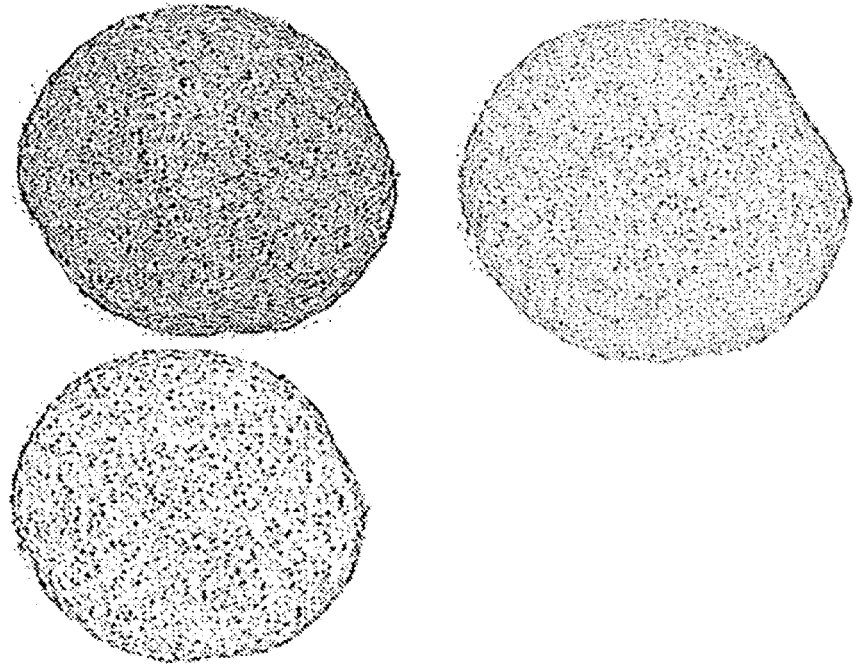
Figure 5:
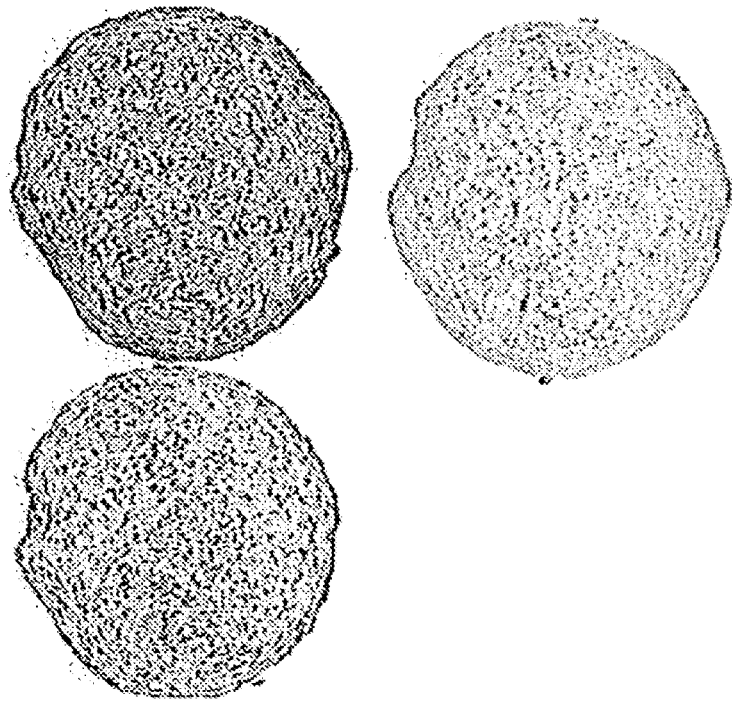
Figure 5:
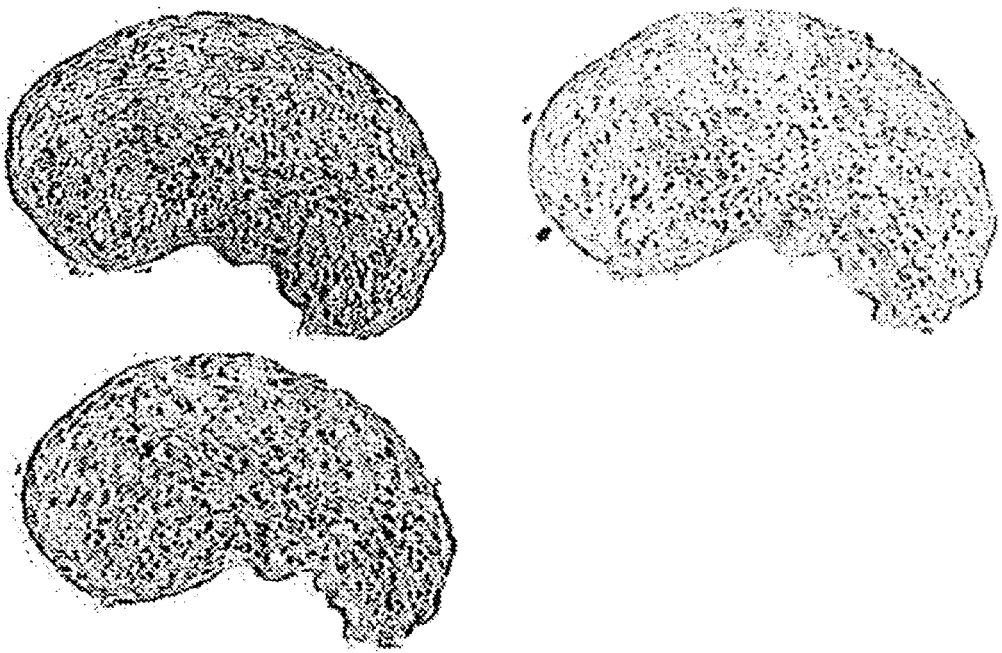
Figure 5:
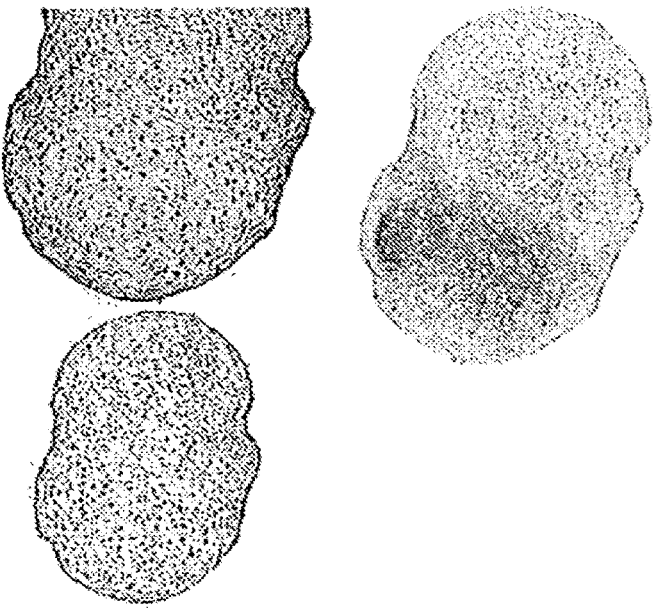
Figure 5:
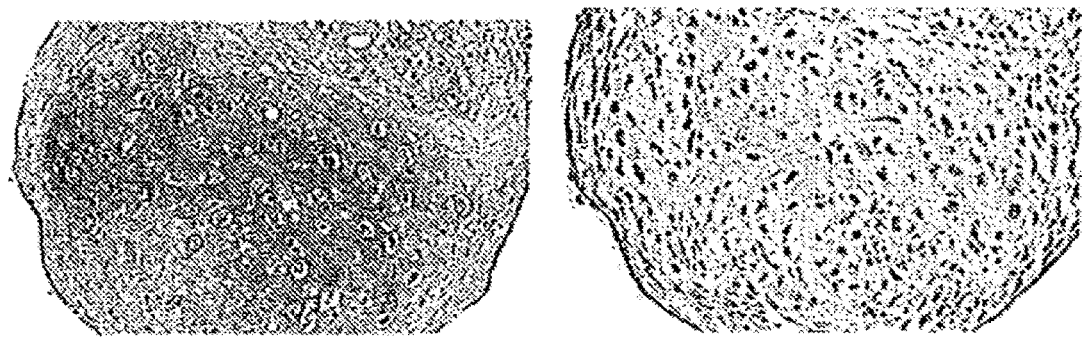
Figure 5:
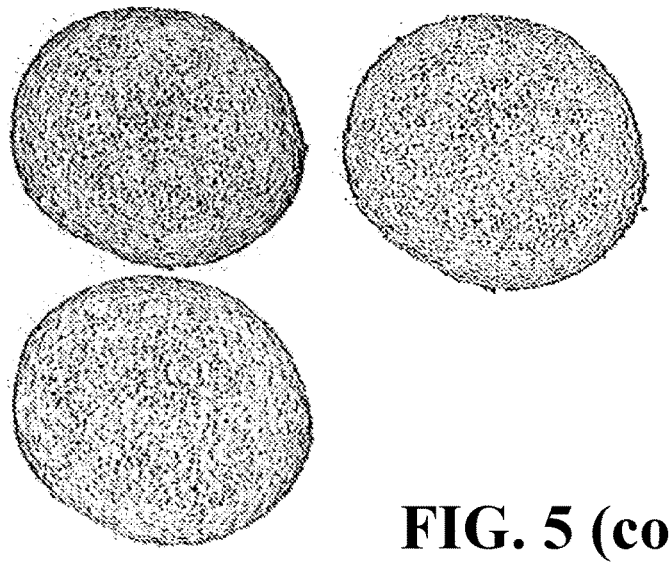
Figure 5:
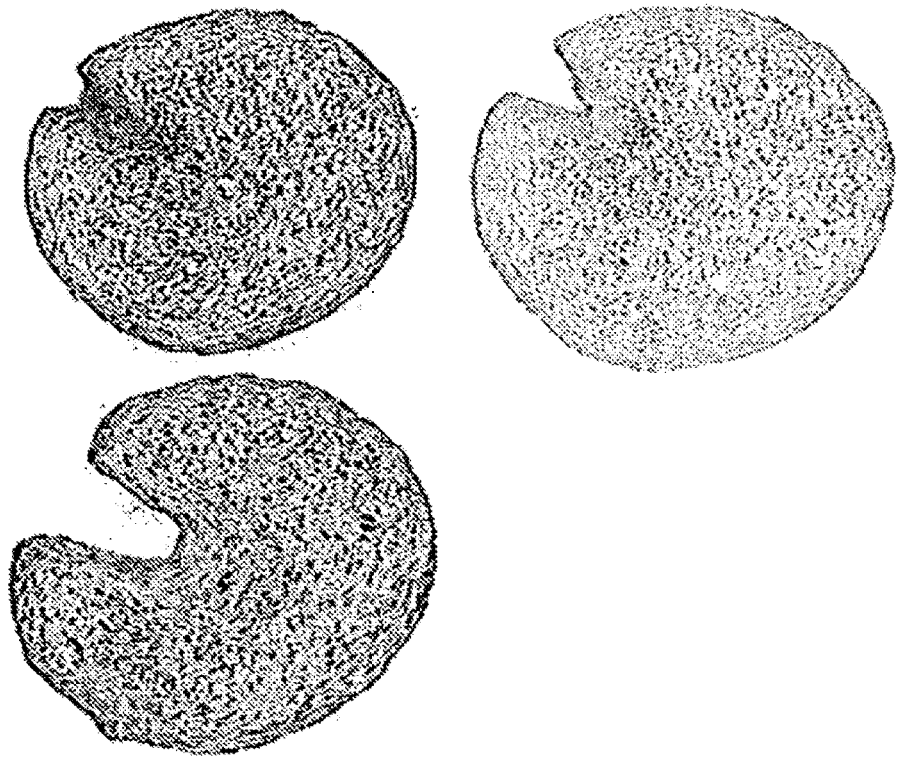
Figure 5:
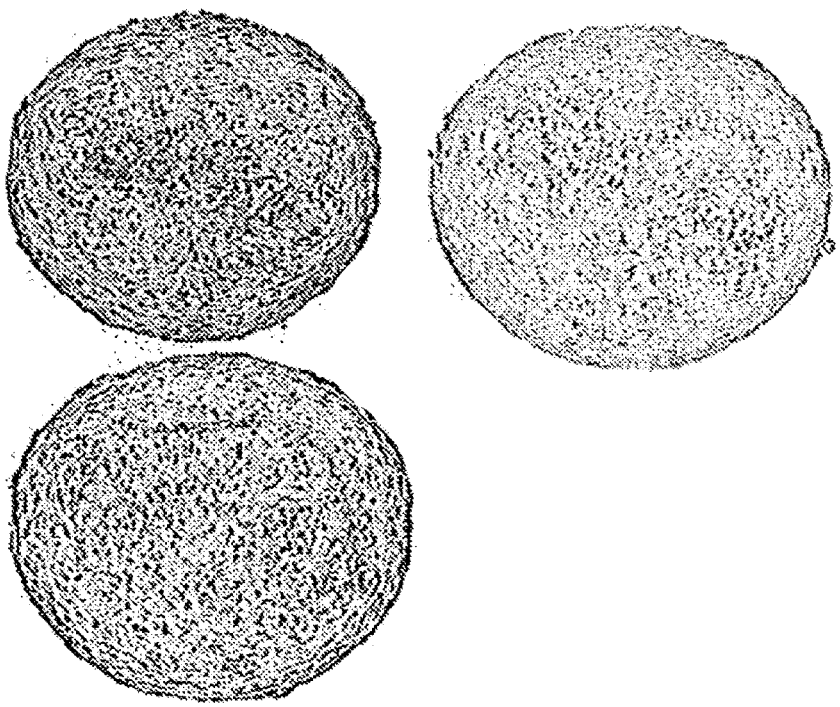
Figure 5:
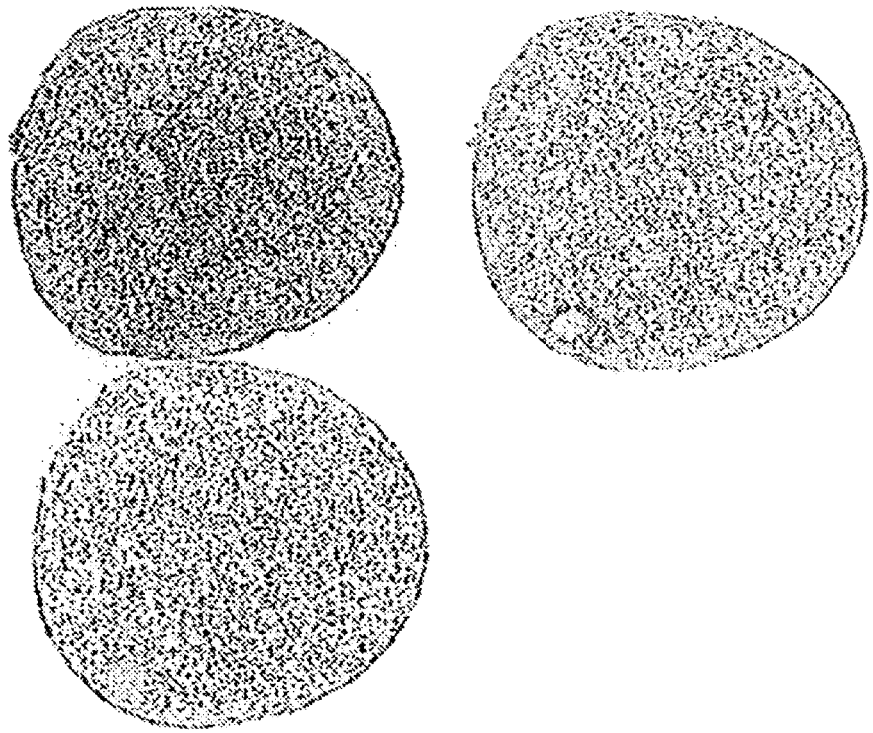
Figure 5:
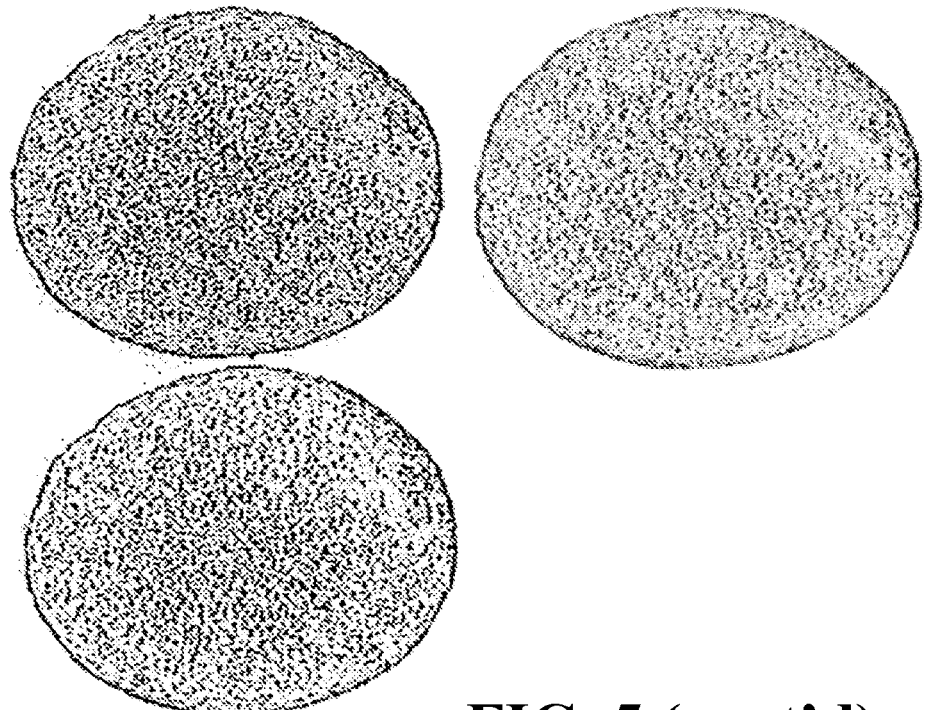
Figure 5:
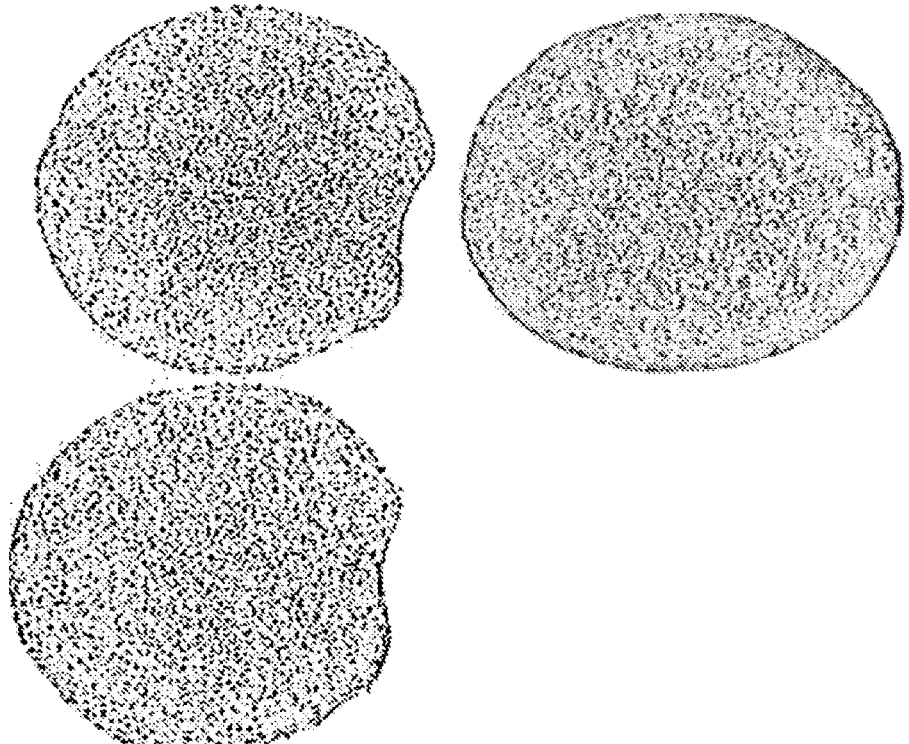
Figure 5:
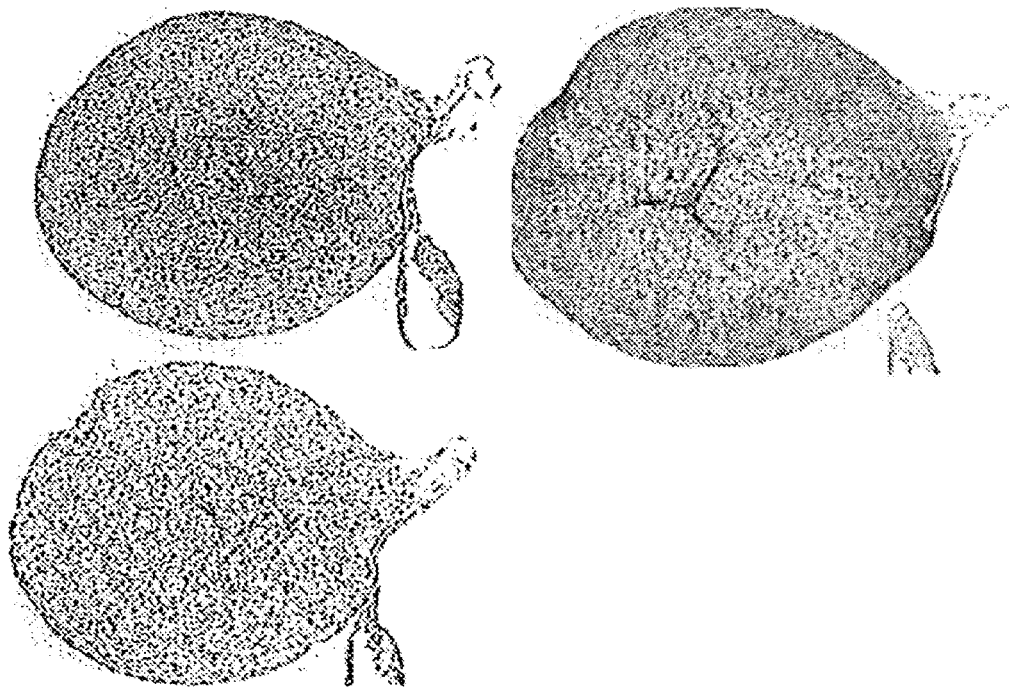
Figure 5:
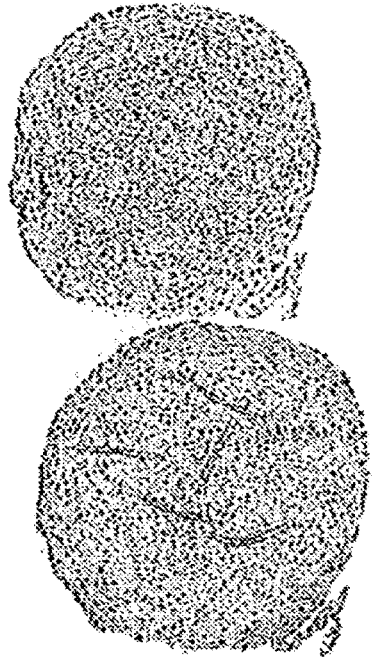
Figure 5:
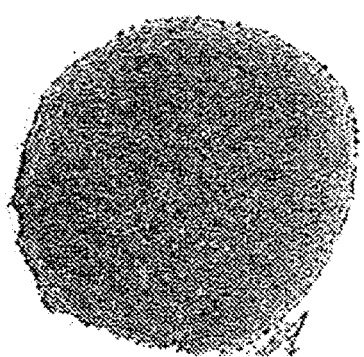
Figure 5:
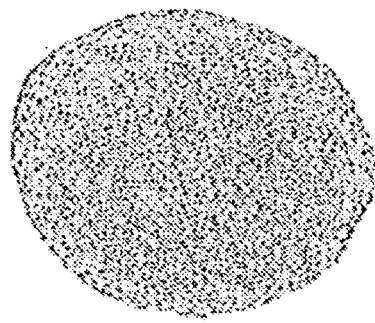
Figure 5:
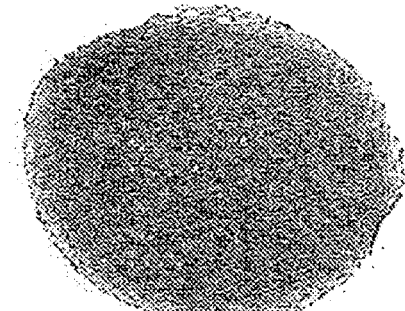
Figure 5:
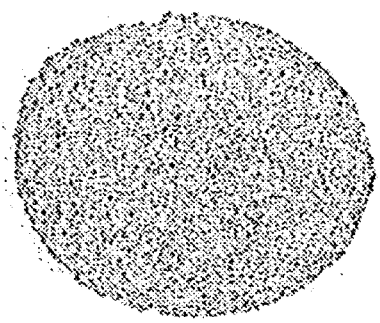
Figure 5:
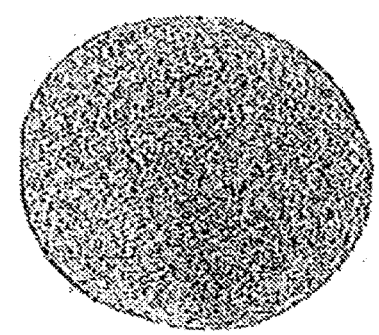
Figure 5:
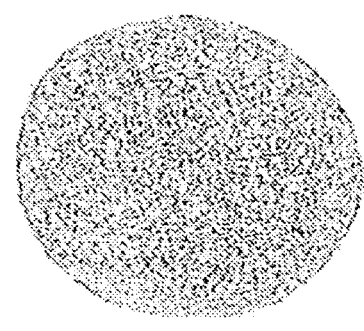
Figure 5:
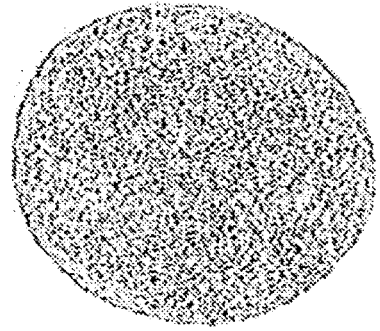
Figure 5:
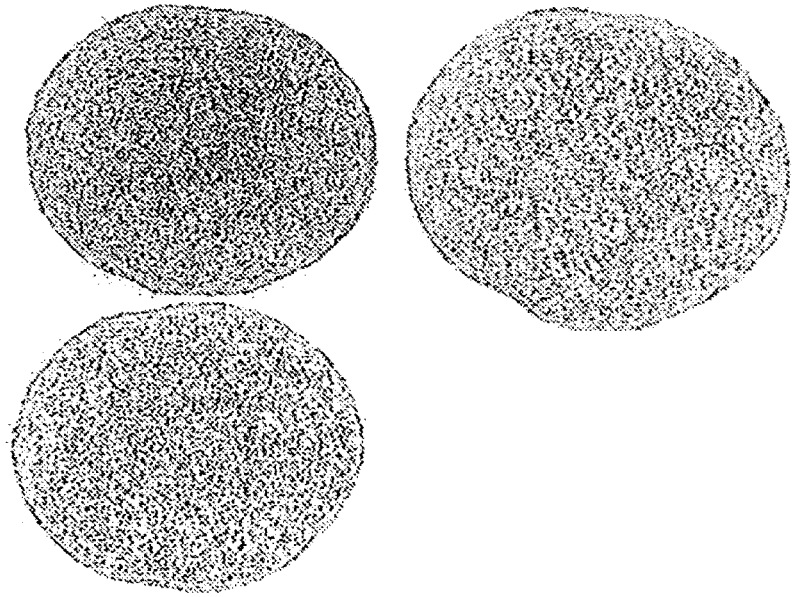
Figure 5:
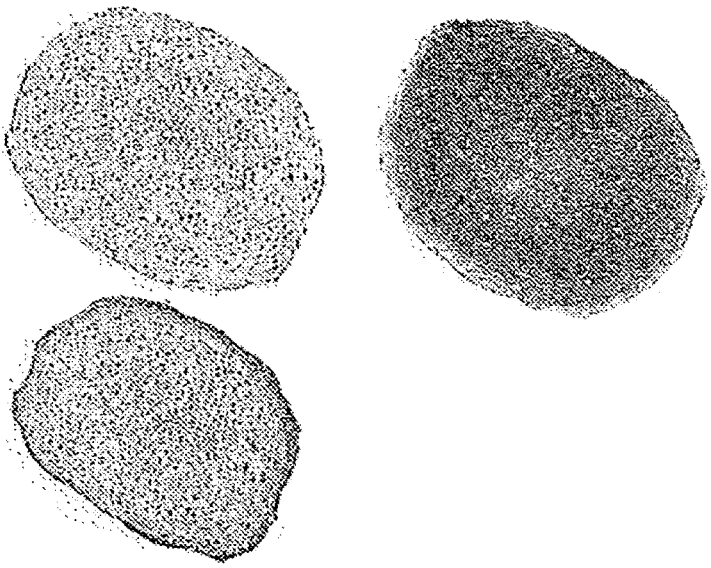
Figure 5:
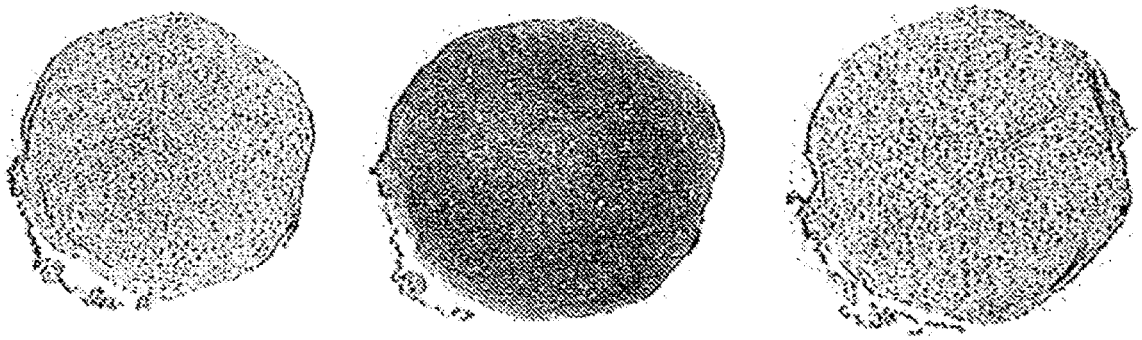
Figure 5:
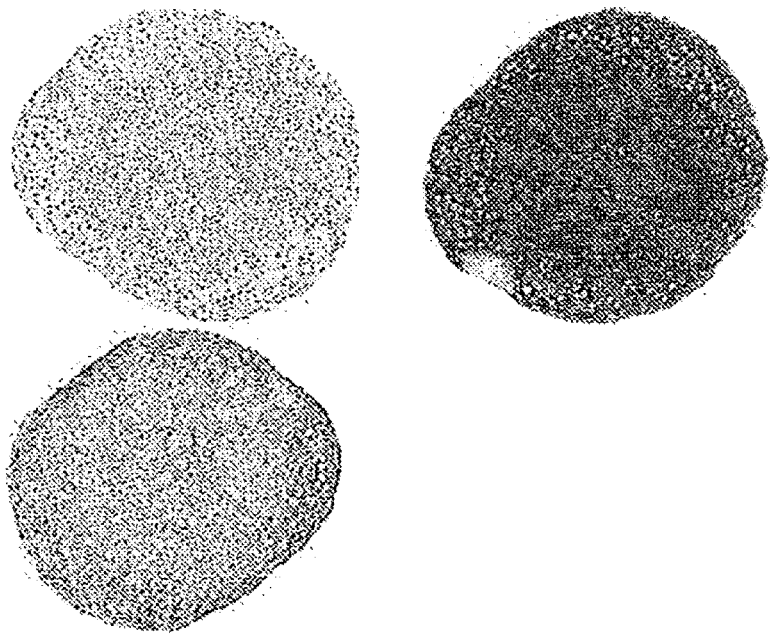
Figure 5:
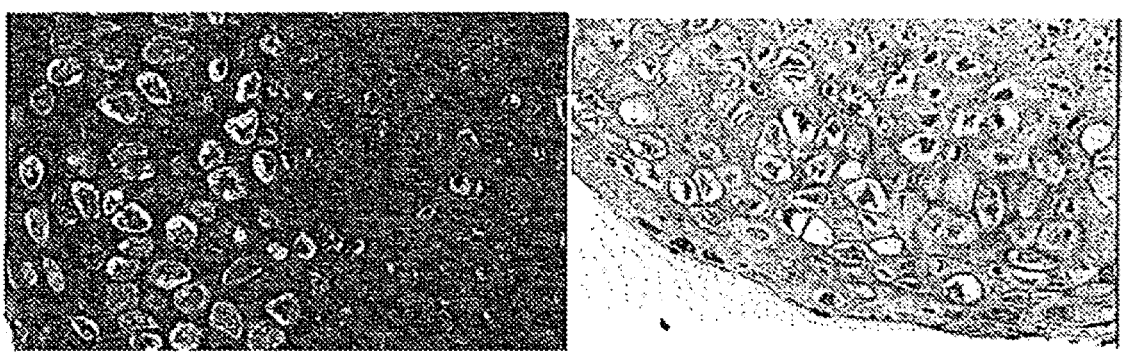
Figure 5:
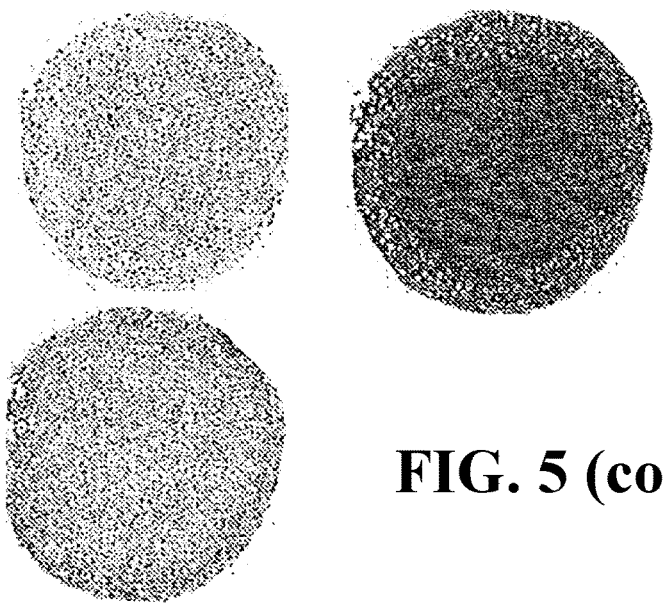
Figure 5:
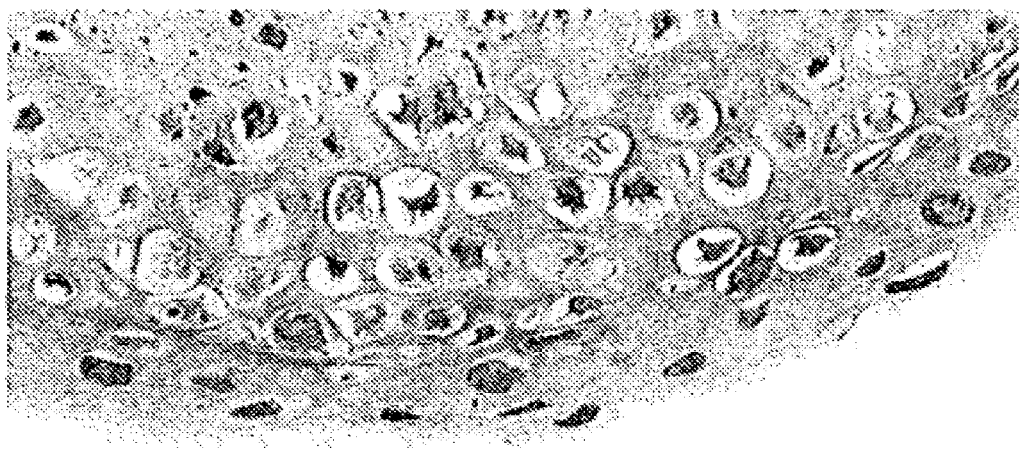
Figure 5:
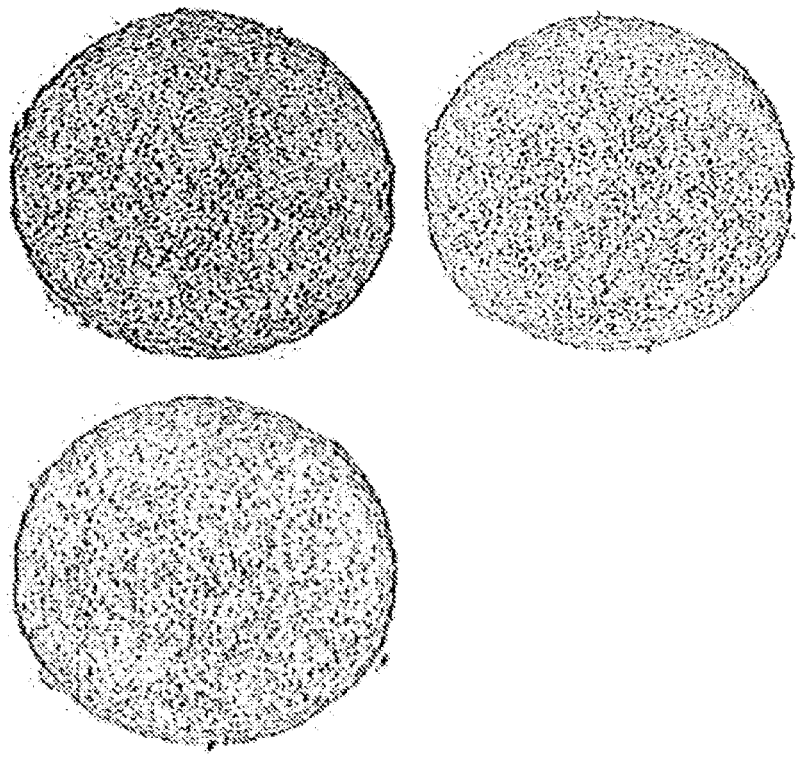
Figure 5:
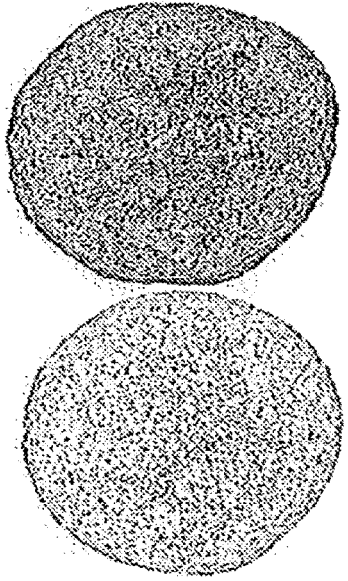
Figure 5:
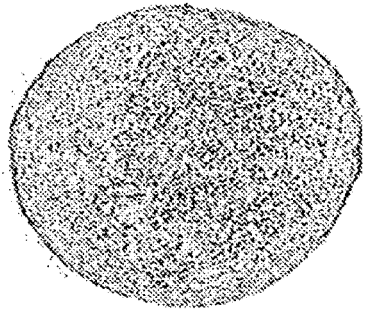
Figure 5:
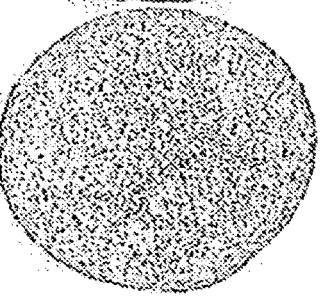
Figure 5:
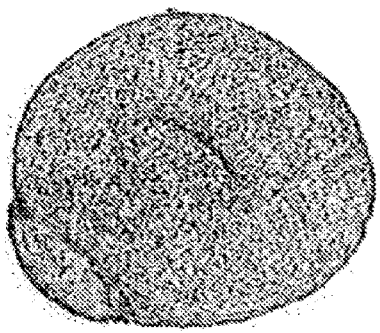
Figure 5:
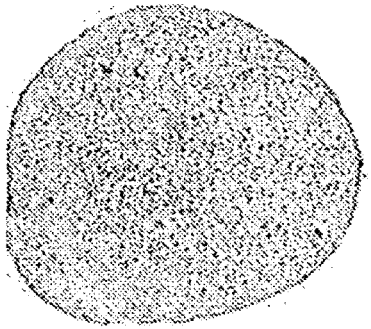
Figure 5:
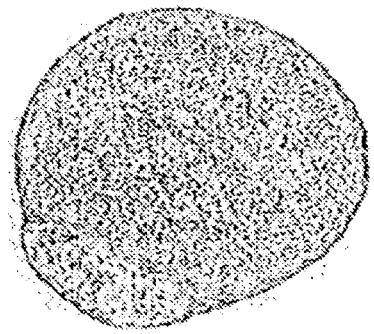
Figure 5:
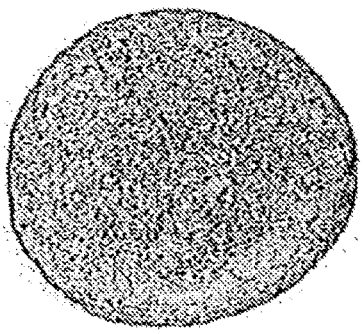
Figure 5:
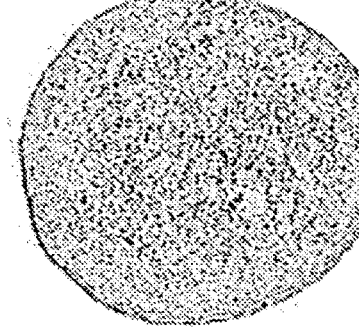
Figure 5:
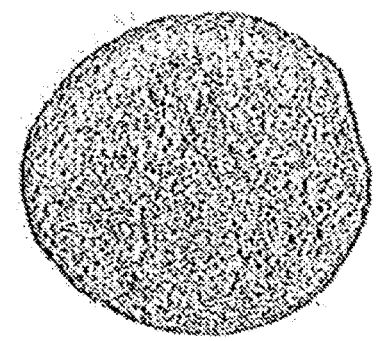
Figure 5:
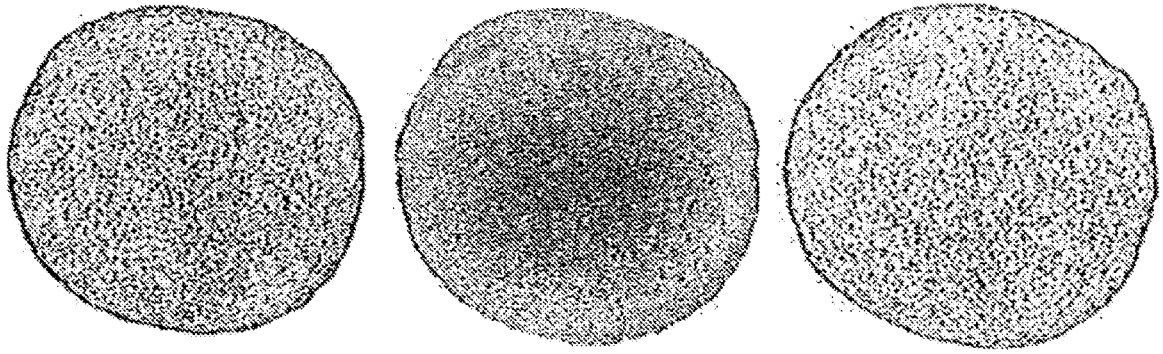
Figure 5:
Figure 5:
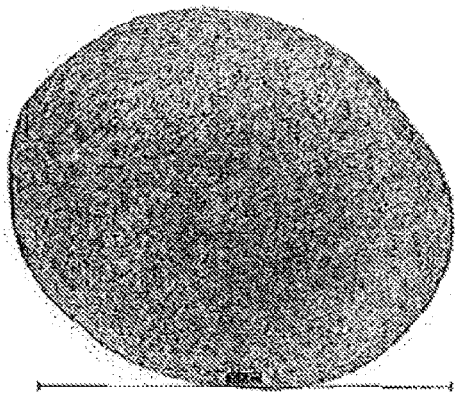
Figure 5:
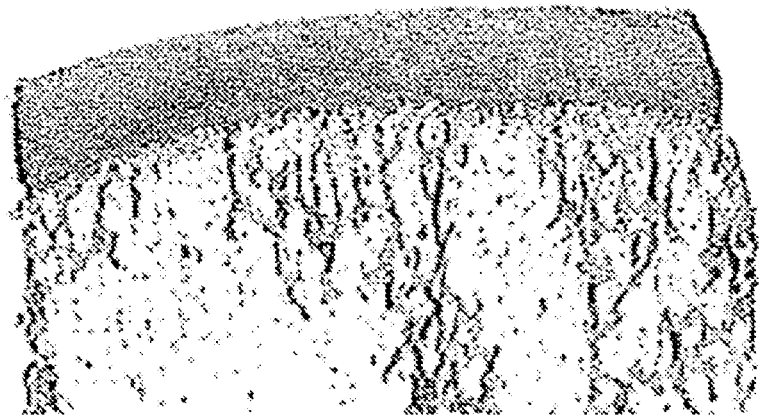
Figure 5:
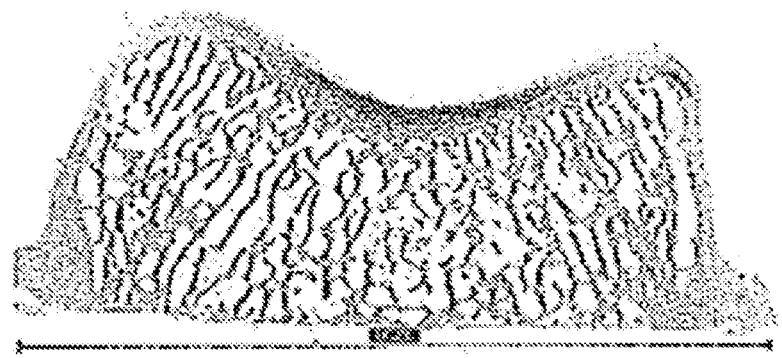
Figure 5:
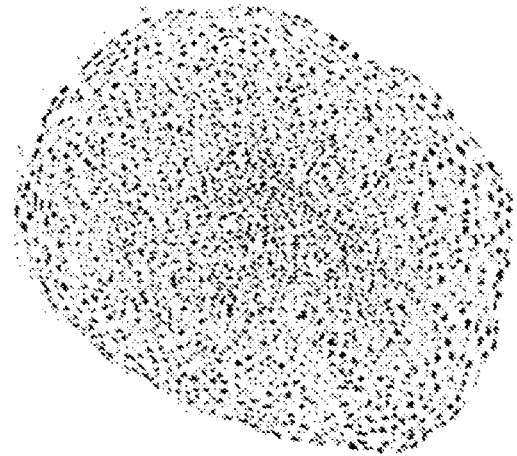

The results of the histological analysis are shown in FIG. 5 and indicate that clonal progenitor cells were induced to differentiate to chondrocytes as measured by Saf O staining and collagen 2 staining.

Example 6: Chondrogenic Potential of a ZIC2, RGS1 Positive Clonal Embryonic Progenitor Cells Line in Response to BMP4 but not TGFB3

Figure 6:
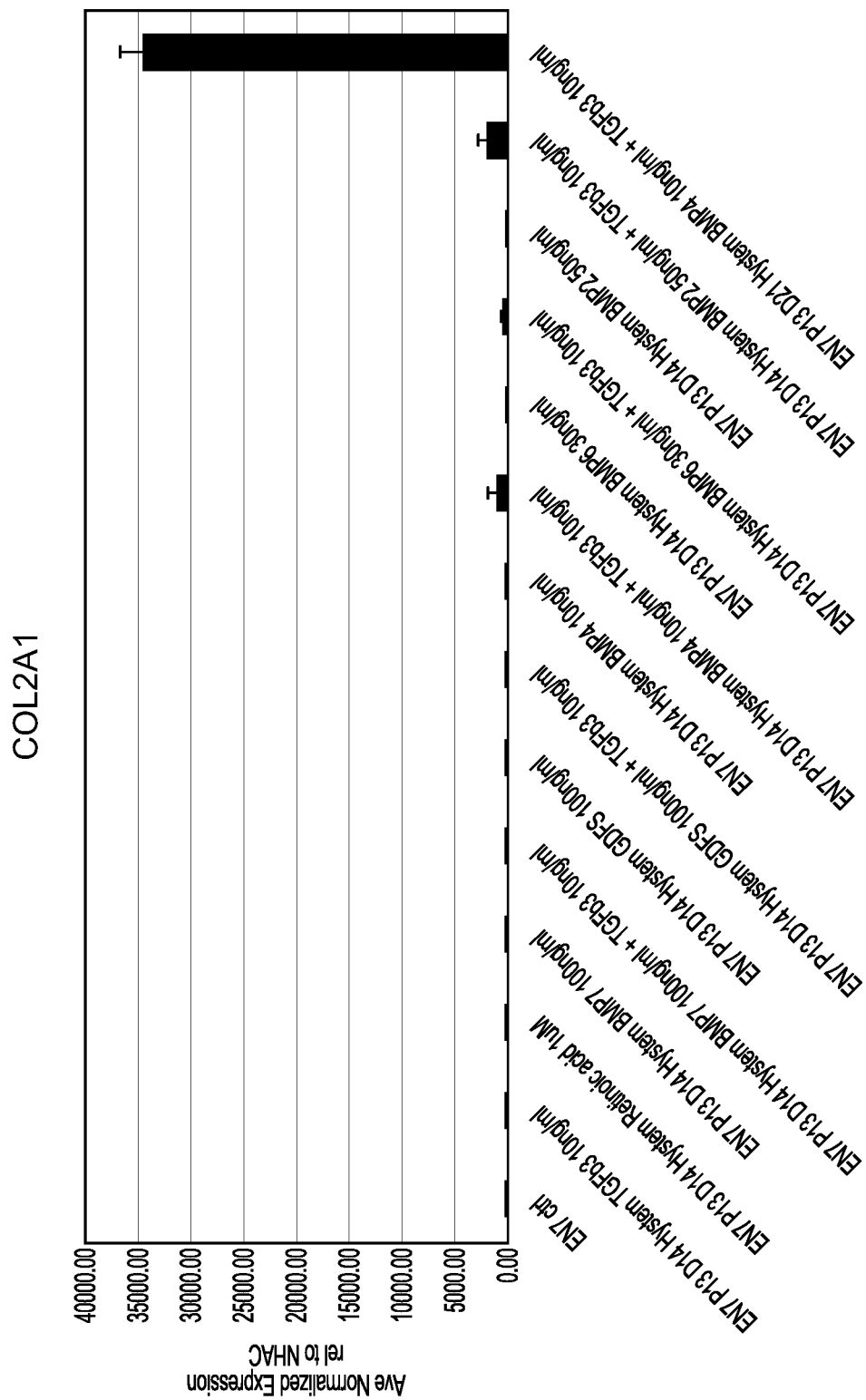
FIG. 6 shows the relative expression of COL2A1 as determined by qPCR in the human clonal embryonic progenitor cell line EN7 in the control undifferentiated state vs differentiation in HyStem pellets supplemented with the shown concentrations of TGF beta family members. Values shown are fold-expression relative to cultured NHACs.

The cell line EN7 in the undifferentiated state propagated in media such as Promocell MV2 endothelial medium is positive for the mRNA markers: RGS1, NEFM, KBTBD10, CLDN5, GPR44, ATP1A2, KCND2, DLK1, FOXF1, and ZIC2, with most distal HOX gene expression being HOXB2, HOXA2, and is negative for the markers: ACTC, AJAP1, ALDH1A1, ALDH1A2, ANXA8, BARX1, C3, CCDC3, CD24, CD74, CDH3, CNTNAP2, COMP, CRYAB, DKK2, GSC, HAND2, HOXA5, HSD11B2, HSPB3, INA, KRT14, KRT17, LHX1, LHX8, MFAP5, MEOX1, MEOX2, MGP, MMP1, MYH3, MYH11, NPAS1, NPPB, OLR1, PAX2 (Illumina Probe 6450767), PAX9, PENK, PITX1, PITX2, PROM, RELN, SFRP2, SMOC2, STMN2, TAC1, TBX15, TRH, and TUBB4 as determined by Illumina microarray analysis described herein. The Gene RGS1 (NM_002922.3) was not observed to be expressed in cultured normal human articular chondrocytes (NHACs), human dermal fibroblasts, Adipose stem cells (cultured stromal fraction), human dental pulp stem cells (DPSCs), human bone marrow-derived mesenchymal stem cells (MSCs), or the other chondrogenic cell lines described herein such as 4D20.8, 7PEND24, SM30, E15, MEL2, 7SMOO32, or SK11. The cell line was differentiated in the presence of TGF beta family members in HyStem pellets as described herein and the resulting RNAs were analyzed by Illumina microarray and qPCR as described herein for the presence of chondrogenic, osteogenic, and tendon markers (FIG. 6). Surprisingly, while there was no evidence of COL2A1 expression in EN7 in the presence of to TGFB3 in micromass conditions as described herein (Sternberg et al, A human embryonic stem cell-derived clonal progenitor cell line with chondrogenic potential and makers of craniofacial mesenchyme. Regen Med 2012 Apr. 23. [Epub ahead of print], 2012), indeed, only seven of 100 clonal progenitor cell lines responded to TGFB3 in micromass conditions with chondrogenic differentiation, nevertheless, in the presence of 10 ng/mL of BMP4 together with 10 ng/mL of TGFB3, there was an average of 1,164 time more COL2A1 expression as determined by qPCR than cultured NHACs, and by 21 days, there was an average of 34,608 fold more COL2A1 than cultured NHACs. In addition to COL2A1, other markers of cartilage were observed by microarray analysis including markedly elevated expression of COL9A2, and CHAD, but unlike other chondrogenic lines described herein, EN7 differentiated for 21 days in the presence of 10 ng/mL of BMP4 together with 10 ng/mL of TGFB3 expressed relatively high levels of transcripts for the secretory leukocyte peptidase inhibitor SLPI which is useful as a therapeutic agent in diseases mediated by leukocyte elastase-antielastase imbalances or bacterial-induced inflammation and articular cartilage destruction (J Exp Med. 1999 Aug. 16; 190(4):535-42), and the protease legumain (LGMN).

Said cells with gene expression markers of EN7 derived from pluripotent stem cells such as hES or iPS cells, including wherein said cells are expandable populations of cells such as clonal, oligoclonal, or pooled clonal or pooled oligoclonal cell lines, may be used not only to repair injured cartilaginous tissues, but also to secrete proteins such as SLPI or LGMN to produce a therapeutic effect, such as the prevention of inflammatory arthritic processes or similar inflammatory processes damaging tissues. Other secreted proteins include Cyt11. Nonlimiting examples of such therapeutic applications include osteoarthritis, bacterial and rheumatoid arthritis, and the repair of cartilage particularly susceptible to damage from lack of SLPI such as intervertebral cartilage. Additional uses include formulating it with an injectable matrix such as Hystem as imaging agent and/or a therapeutic.

TABLE I

Exemplary progenitor cell lines and associated gene expression markers at 18-21 doublings of clonal expansion The group of cell lines X2.1 (also known as 2.1 and ACTC63), X2.2 (also known as X2.2Rep1 and X2.2Rep2 and 2.2 and ACTC62) are positive for the markers: CFB, CLDN11, COMP, CRLF1, EGR2, FST, KRT14, KRT19, KRT34, MFAP5, MGP, PENK, PITX2, POSTN, PTGS2, RARRES1, S100A4, SOD3, TFPI2, THY1 and ZIC1 and are negative for the markers: AGC1, ALDH1A1, APCDD1, AREG, ATP8B4, C6, C7, C20orf103, CCDC3, CDH3, CDH6, CNTNAP2, COP1, CXADR, DIO2, METTL7A, DKK2, DLK1, EMID1, FGFR3, FMO3, FOXF1, FOXF2, GABRB1, GDF10, GSC, HSD11B2, HSD17B2, HSPA6, HSPB3, ID4, IGF2, IGFBP5, INA, KCNMB1, IGFL3, LOC92196, MEOX1, MSX2, MX1, MYBPH, MYU11, MYL4, NLGN4X, NPPB, PAX2, PAX9, PDE1A, PRELP, PROM1, RASD1, RELN, RGS1, RPS4Y2, SFRP2, SMOC1, SMOC2, SNAP25, SYTI2, TAC1, RSPO3, TUBB4, UGT2B7, WISP2, ZD52F10 and ZIC2.
The cell line B1 is positive for the markers: CD24, CDH6, HTRA3, INA, KRT17, KRT19, LAMC2, MMP1, IL32, TAGLN3, PAX2, RELN, UGT2B7 and ZIC2 and is negative for the markers: ACTC, AGC1, ALDH1A1, APCDD1, ATP8B4, BEX1, CFB, C3, C6, C7, PRSS35, C20orf103, CCDC3, CDH3, CNTNAP2, COL15A1, COL21A1, COP1, CRLF1, DIO2, METTL7A, DKK2, DLK1, DPT, EGR2, EMID1, FGFR3, TMEM100, FMO1, FMO3, FOXF1, FOXF2, FST, GABRB1, GAP43, GDF10, GSC, HOXA5, HSD11B2, HSD17B2, HSPA6, ID4, IFI27, IGF2, KCNMB1, KIAA0644, KRT14, TMEM119, IGFL3, LOC92196, MFAP5, MASP1, MEOX2, MGP, MYBPH, MYH3, MYH11, MYL4, NPAS1, OGN, OLR1, OSR2, PAX9, PDE1A, PENK, POSTN, PRELP, PRG4, PROM1, PRRX1, PRRX2, PTN, PTPRN, RARRES1, RASD1, RGMA, RGS1, SERPINA3, SLITRK6, SMOC1, SMOC2, SNAP25, SOD3, STMN2, TAC1, RSPO3, TNNT2, TRH, TSLP, TUBB4, WISP2 and ZIC1.
The group of cell lines X4.1, X4.3 and B10 are positive for the markers: MMP1, AQP1, CDH6, HTRA3, INA, KRT19, LAMC2, IL32, TAGLN3, NPPB and UGT2B7 and are negative for the markers: AGC1, ALDH1A1, APCDD1, AREG, ATP8B4, CFB, C3, C6, C7, C20orf103, CNTNAP2, COL21A1, COMP, COP1, CRLF1, DIO2, METTL7A, DKK2, DLK1, DPT, EMID1, TMEM100, FMO1, FMO3, FOXF1, FOXF2, GABRB1, GAP43, GSC, HOXA5, HSD11B2, HSD17B2, HSPA6, ID4, IFI27, IFIT3, IGF2, KRT14, TMEM119, LOC92196, MASP1, MEOX2, MGP, MYBPH, MYH3, MYL4, OGN, OSR2, PAX9, PDE1A, PENK, PRELP, PRRX2, PTN, RARRES1, RGMA, RGS1, RPS4Y2, SERPINA3, SLITRK6, SMOC1, SMOC2, TAC1, RSPO3, TNNT2, TRH, TUBB4 and WISP2.
The group of cell lines B11, B25, B26 and B3 are positive for the markers: AKR1C1, CFB, BMP4, CLDN11, FST, GDF5, HTRA3, IL1R1, KRT14, KRT19, KRT34, MGP, MMP1, PODN, POSTN, PRG4, RARRES1, S100A4, THY1 and ZIC1 and are negative for the markers: ACTC, ALDH1A1, APCDD1, C6, C7, C20orf103, CCDC3, CD24, CXADR, DIO2, DKK2, DLK1, EMID1, FGFR3, FMO1, FMO3, FOXF1, FOXF2, GABRB1, GDF10, HSD11B2, HSD17B2, HSPA6, HSPB3, ID4, IGF2, INA, KCNMB1, IGFL3, LOC92196, MEOX1, MSX1, MYBPH, MYH3, MYH11, MYL4, NLGN4X, TAGLN3, NPPB, OLR1, PAX2, PAX9, PROM1, RASD1, RGS1, RPS4Y2, SLITRK6, SMOC1, SMOC2, SNAP25, TAC1, RSPO3, TUBB4, UGT2B7, ZD52F10 and ZIC2.
The group of cell lines B12 and B4 are positive for the markers: CLDN11, FST, GDF5, HTRA3, KRT19, KRT34, MFAP5, MGP, MMP1, POSTN, PTGS2, S100A4, THY1 and ZIC1 and are negative for the markers: AGC1, ALDH1A1, APCDD1, AREG, ATP8B4, C3, C6, C7, C20orf103, CCDC3, CDH3, CNTNAP2, COP1, CXADR, DIO2, DKK2, DLK1, DPT, EMID1, FMO1, FMO3, FOXF1, FOXF2, GABRB1, GDF10, HOXA5, HSD11B2, HSD17B2, HSPA6, HSPB3, IGFBP5, IGFL3, LOC92196, MEOX1, MYBPH, MYH3, MYH11, MYL4, NPAS1, NPPB, OLR1, PAX2, PAX9, PITX2, PROM1, RGS1, SLITRK6, SMOC1, SMOC2, SNAP25, TAC1, RSPO3, TNNT2, TRH, TUBB4, ZD52F10 and ZIC2.
The group of cell lines B20 and B15 are positive for the markers: BMP4, CD24, CRIP1, HTRA3, KRT19, LAMC2, MGP, MMP1, POSTN, RELN, S100A4, THY1 and UGT2B7 and are negative for the markers: AGC1, ALDH1A1, ANXA8, AREG, ATP8B4, CFB, C6, C7, C20orf103, CNTNAP2, DIO2, METTL7A, DLK1, DPT, EMID1, TMEM100, FMO1, FMO3, FOXF2, GABRB1, GSC, HOXA5, HSD11B2, HSD17B2, HSPA6, ID4, IFI27, KRT14, KRT34, IGFL3, MASP1, MEOX1, MEOX2, MYBPH, MYH3, MYL4, NPAS1, NPPB, OGN, OLR1, OSR2, PAX9, PDE1A, PENK, PROM1, PRRX2, RGS1, SL1TRK6, SMOC1, SMOC2, STMN2, TAC1, TNNT2, TRH, TUBB4, WISP2 and ZIC1.
The group of cell lines B16Bio1b, B16Bio2b, E72 and E75 are positive for the markers: AKR1C1, BMP4, CLDN11, FST, GDF5, HTRA3, IL1R1, KRT19, KRT34, MFAP5, MGP, MMP1, OSR2, PODN, POSTN, PRG4, PRRX1, RARRES1, S100A4, SOD3, THY1 and ZIC1 and are negative for the markers: ACTC, AGC1,

TABLE I-continued

Exemplary progenitor cell lines and associated gene expression markers at 18-21 doublings of clonal expansion ALDH1A1, AREG, C6, C7, C20orf103, CCDC3, CDH3, CNTNAP2, DKK2, EM1D1, FGFR3, FMO3, FOXF1, FOXF2, GABRB1, GDF10, HSD11B2, HSD17B2, HSPA6, ID4, IGF2, INA, LAMC2, IGFL3, LOC92196, MEOX1, MSX1, MYBPH, MYH11, MYL4, NLGN4X, NPAS1, NPPB, OLR1, PAX2, PAX9, PROM1, PTPRN, RASD1, RGS1, SLITRK6, SMOC1, SMOC2, SNAP25, TAC1, RSPO3, TNNT2, TUBB4, ZD52F10 and ZIC2.
The group of cell lines B17Bio1b, B17Bio2c and B17Bio3c are positive for the markers: BEX1, COL15A1, CRIP1, CRYAB, HTRA3, KCNMB1, KRT19, MGP, POSTN, S100A4, SFRP2, THY1 and TNFSF7 and are negative for the markers: , AGC1, ALDH1A1, APCDD1, AREG, ATP8B4, C6, C7, CNTNAP2, METTL7A, DLK1, DPT, EMID1, FMO1, FMO3, FOXF1, GABRB1, GSC, HOXA5, HSD11B2, HSD17B2, HSPA6, IFI27, KRT14, KRT34, IGFL3, MASP1, MEOX2, MYBPH, MYH3, MYL4, NPPB, OGN, PAX9, PDE1A, PENK, PROM1, RASD1, RGS1, SLITRK6, SMOC1, SMOC2, STMN2, TAC1, TRH, TSLP, TUBB4 and ZIC1.
The group of cell lines B2, B7 and X6.1 are positive for the markers: AKR1C1, CFB, BMP4, C3, CLDN11, COL21A1, FST, GDF5, HTRA3, ICAM5, IL1R1, KRT19, MGP, MMP1, PENK, PODN, POSTN, PRG4, RARRES1, RGMA, S100A4, SERPINA3, SOD3, STMN2, THY1 and WISP2 and are negative for the markers: ACTC, AGC1, ALDH1A1, C6, C7, C20orf103, CCDC3, CD24, CDH3, CXADR, DIO2, DLK1, EMID1, FGFR3, FMO3, FOXF1, FOXF2, GABRB1, GDF10, HSD11B2, HSD17B2, HSPA6, HSPB3, ID4, IGF2, INA, IGFL3, LOC92196, MEOX1, MYH11, MYL4, NLGN4X, TAGLN3, NPAS1, NPPB, OLR1, PAX2, PAX9, PITX2, PROM1, PTPRN, RASD1, RGS1, RPS4Y2, SLITRK6, SMOC1, SMOC2, SNAP25, SOX11, TAC1, RSPO3, TUBB4, UGT2B7, ZD52F10 and ZIC2.
The group of cell lines B22, CM30.2 and X6 are positive for the markers: BMP4, CLDN11, CRIP1, CRYAB, HTRA3, KRT19, S100A4, SFRP2, SRCRB4D, THY1 and UGT2B7 and are negative for the markers: AGC1, ALDH1A1, APCDD1, AREG, ATP8B4, C3, C6, C7, C20orf103, CDH3, CNTNAP2, COL21A1, COP1, DIO2, METTL7A, DKK2, DLK1, DPT, FMO1, FMO3, FOXF1, FOXF2, GABRB1, GSC, HOXA5, HSD11B2, HSPA6, IFI27, IFIT3, IGF2, KRT14, MASP1, MEOX2, MYBPH, MYH3, MYH11, NPPB, OGN, OLR1, OSR2, PAX9, PDE1A, PENK, PROM1, RGS1, SMOC1, SNAP25, STMN2, TAC1, TRH, TSLP, TUBB4 and WISP2.
The group of cell lines B27, B9, CM10.1, X2, X4.2 and X4.4 are positive for the markers: HTRA3, KRT19, LAMC2, IL32, TAGLN3, PAX2, RELN and UGT2B7 and are negative for the markers: AGC1, ALDH1A1, APCDD1, AREG, ATP8B4, CFB, C3, C6, C7, C20orf103, CCDC3, CDH3, CNTNAP2, COL21A1, COP1, CRLF1, DIO2, METTL7A, DLK1, DPT, EMID1, TMEM100, FMO1, FMO3, FOXF1, FOXF2, GABRB1, GAP43, GSC, HOXA5, HSD11B2, HSD17B2, HSPA6, IFI27, IGF2, KIAA0644, KRT14, IGFL3, LOC92196, MASP1, MEOX2, MGP, MYH3, MYH11, MYL4, NPAS1, OGN, OLR1, OSR2, PAX9, PDE1A, PENK, PRELP, PTN, RARRES1, RGMA, RGS1, SERPINA3, SLITRK6, SMOC1, SMOC2, SNAP25, SOD3, STMN2, TAC1, RSPO3, TNNT2, TRH, TUBB4 and WISP2.
The cell line B28 is positive for the markers: CFB, BMP4, COL15A1, CRIP1, CRYAB, FST, GAP43, IL1R1, KCNMB1, KRT14, KRT19, KRT34, MFAP5, MGP, MMP1, IL32, PODN, POSTN, S100A4, THY1 and ZIC1 and are negative for the markers: ACTC, ALDH1A1, ANXA8, AREG, ATP8B4, BEX1, C3, C6, C7, C20orf103, CCDC3, CNTNAP2, CXADR, DIO2, METTL7A, DKK2, DLK1, EMID1, FGFR3, FMO1, FMO3, FOXF1, FOXF2, GABRB1, GDF10, HOXA5, HSD11B2, HSD17B2, HSPA6, ID4, IFI27, IGF2, IGFBP5, INA, IGFL3, LOC92196, MASP1, MEOX1, MYBPH, MYH3, MYL4, NLGN4X, NPAS1, NPPB, OLR1, PAX9, PDE1A, PITX2, PROM1, PTPRN, RASD1, RGS1, RPS4Y2, SLITRK6, SMOC1, SMOC2, SNAP25, STMN2, TAC1, TRH, TSLP, TUBB4, ZD52F10 and ZIC2.
The cell line B29 is positive for the markers: ANXA8, AQP1, CD24, CDH6, CRIP1, GJB2, HTRA3, KRT17, KRT19, LAMC2, IL32, TAGLN3, PAX2, RELN, S100A4, SFRP2, SRCRB4D, THY1, TNFSF7, UGT2B7, ZD52F10 and ZIC2 and are negative for the markers: AGC1, ALDH1A1, APCDD1, AREG, ATP8B4, BEX1, C3, C6, C7, C20orf103, CCDC3, CLDN11, CNTNAP2, COL21A1, COP1, CRLF1, DIO2, METTL7A, DLK1, DPT, EMID1, TMEM100, FMO1, FMO3, FOXF1, FOXF2, GABRB1, GAP43, GDF10, GSC, HOXA5, HSD11B2, HSD17B2, HSPA6, HSPB3, IFI27, IFIT3, IGF2, KRT14, KRT34, IGFL3, MFAP5, MASP1, MEOX2, MMP1, MSX1, MYBPH, MYH3, MYL4, NPAS1, NPPB, OGN, OLR1, OSR2, PAX9, PDE1A, PENK, PITX2, POSTN, PRG4, PROM1, PRRX2, PTPRN, RARRES1, RASD1, RGS1, RPS4Y2, SERPINA3, SLITRK6, SMOC1, SMOC2, SNAP25, SOD3, STMN2, TAC1, RSPO3, TRH, TSLP, TUBB4, WISP2 and ZIC1.
The cell line B30 is positive for the markers: PRSS35, CDH6, COL21A1, CRIP1, CRYAB, DKK2, GAP43, KCNMB1, KRT17, KRT19, PRRX1, PTN, RGMA, S100A4, SOX11 and ZIC2 and are negative for the markers: ACTC, AGC1, AKR1C1, ALDH1A1, ANXA8, APCDD1, AQP1, AREG, ATP8B4, CFB, C3, C6, C7, C20orf103, CD24, CDH3, CLDN11, CNTNAP2, COL15A1, COMP, COP1, CRLF1, METTL7A, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IFIT3, IGF2, KRT34, LAMC2, IGFL3, LOC92196, MFAP5, MASP1, MEOX1, MEOX2, MSX1, MYBPH, MYH3, MYL4, NLGN4X, NPPB, OGN, OLR1, PAX2, PAX9, PDE1A, PENK, PITX2, PRG4, PROM1, PTPRN, RARRES1, RASD1, RELN, RGS1, RPS4Y2, SFRP2, SLITRK6, SMOC1, SNAP25, STMN2, TAC1, TFPI2, TNFSF7, TNNT2, TRH, TSLP, TUBB4, UGT2B7, WISP2, ZD52F10 and ZIC1.
The cell line B6 is positive for the markers: CCDC3, CDH6, COL15A1, CRIP1, DKK2, FST, GDF10, HTRA3, KRT19, LOC92196, MYL4, NLGN4X, S100A4, SOX11, SRCRB4D, THY1, ZIC1 and ZIC2 and are negative for the markers: AGC1, AKR1C1, ALDH1A1, AREG, ATP8B4, BEX1, CFB, C3, C6, C7, CNTNAP2, COMP, COP1, DIO2, METTL7A, DLK1, DPT, EMID1, TMEM100, FMO3, FOXF1, FOXF2, GABRB1, GSC, HOXA5, HSD11B2, HSPA6, HSPB3, ID4, IFI27, IFIT3, KRT14, TMEM119, MFAP5, MASP1, MEOX1, MEOX2, MGP, MMP1, MSX2, MYBPH, MYH3, NPAS1, NPPB, OGN, OLR1, OSR2, PAX2, PAX9, PDE1A, PENK, PRG4, PROM1, PTPRN, RASD1, RGS1, RPS4Y2, SLITRK6, SMOC1, SNAP25, STMN2, TAC1, TRH, TSLP, TUBB4, UGT2B7, WISP2 and ZD52F10.
The cell line C4ELS5.1 is positive for the markers: AKR1C1, C7, CDH6, COL15A1, DIO2, FMO1, FMO3, FOXF2, IGF2, IL1R1, KRT19, LAMC2, TMEM119, PODN, PRRX1, PRRX2, RGMA, SFRP2, TAC1, TFPI2 and RSPO3 and are negative for the markers: ACTC, AGC1, ALDH1A1, ANXA8, APCDD1, AQP1, AREG, ATP8B4, BEX1, CFB, BMP4, C3, C20orf103, CCDC3, CDH3, CLDN11, CNTNAP2, COMP, COP1, CRLF1, CRYAB, CXADR, DKK2, DLK1, EGR2, EMID1, FGFR3, FOXF1, GABRB1, GAP43, GDF10, GJB2, HOXA5, HSD17B2, HSPA6, HSPB3, ICAM5, ID4, IFI27, KRT14, KRT17, KRT34, IGFL3, LOC92196, MFAP5, MEOX1, MEOX2, MGP, MMP1, MSX1, MSX2, MX1, MYBPH, MYH3, MYH11, MYL4, IL32, NLGN4X, TAGLN3, NPAS1, NPPB, OLR1, PAX2, PAX9, PENK, PITX2, POSTN, PRELP, PROM1, PTPRN, RARRES1, RELN, RGS1, RPS4Y2, SMOC1, SMOC2, STMN2, THY1, TNFSF7, TNNT2, TRH, TUBB4, UGT2B7, ZD52F10, ZIC1 and ZIC2.

TABLE I-continued

Exemplary progenitor cell lines and associated gene expression markers at 18-21 doublings of clonal expansion The cell line C4ELS5.5 is positive for the markers: BEX1, BMP4, C7, PRSS35, CDH6, DKK2, FMO3, FOXF2, FST, GDF10, HSD17B2, IGF2, TMEM119, PITX2, PODN, PRRX1, SERPINA3, SFRP2, TFPI2 and ZIC2 and are negative for the markers: AGC1, ALDH1A1, APCDD1, AQP1, AREG, ATP8B4, C3, C6, C20orf103, CD24, CDH3, CNTNAP2, COMP, COP1, CRLF1, CXADR, DLK1, DPT, EMID1, FGFR3, TMEM100, FOXF1, GJB2, HOXA5, HSD11B2, HSPA6, HSPB3, ID4, IFI27, KCNMB1, KRT14, KRT17, KRT34, IGFL3, MFAP5, MEOX1, MEOX2, MGP, MMP1, MSX2, MX1, MYBPH, MYH3, MYH11, IL32, NLGN4X, TAGLN3, NPPB, OGN, OLR1, OSR2, PAX2, PAX9, PDE1A, PENK, PRELP, PRG4, PTPRN, RARRES1, RASD1, RELN, RGS1, SMOC2, STMN2, TAC1, THY1, TNFSF7, TNNT2, TRH, TSLP, TUBB4, WISP2, ZD52F10 and ZIC1.
The cell line C4ELSR.12 is positive for the markers: C7, CDH6, COL21A1, DIO2, FMO1, FMO3, FOXF2, FST, IGF2, IL1R1, TMEM119, PRRX1, PRRX2, PTN, RGMA, SFRP2, SRCRB4D, TAC1, TFPI2, RSPO3, UGT2B7 and ZIC2 and are negative for the markers: ACTC, AGC1, ALDH1A1, ANXA8, APCDD1, AQP1, ATP8B4, C3, C20orf103, CD24, CDH3, CNTNAP2, COMP, COP1, CRLF1, CXADR, DPT, ENID1, FGFR3, TMEM100, FOXF1, GABRB1, GAP43, GJB2, HOXA5, HSPA6, HSPB3, ICAM5, IFI27, INA, KRT14, KRT17, KRT34, IGFL3, MFAP5, MEOX1, MEOX2, MGP, MMP1, MX1, MYBPH, MYH11, MYL4, IL32, NLGN4X, NPAS1, NPPB, OLR1, OSR2, PAX2, PAX9, PENK, POSTN, PRELP, PROM1, PTPRN, RARRES1, RASD1, RELN, RGS1, SLITRK6, SMOC2, STMN2, SYT12, THY1, TNFSF7, TNNT2, TRH, TSLP, TUBB4, WISP2, ZD52F10 and ZIC1.
The group of cell lines C4ELSR2, C4ELSR2Bio2 and C4ELSR2Bio2.1 are positive for the markers: C7, CDH6, COL21A1, DKK2, FMO3, FST, GSC, IGF2, TMEM119, PITX2, SFRP2, TFPI2 and ZIC2 and are negative for the markers: ACTC, AGC1, ALDH1A1, APCDD1, AQP1, ATP8B4, CFB, C3, C6, CCDC3, CD24, CDH3, CLDN11, CNTNAP2, COMP, COP1, CRLF1, CRYAB, DLK1, DPT, EMID1, FGFR3, TMEM100, FOXF1, GABRB1, GJB2, HOXA5, HSD11B2, HSD17B2, HSPA6, HSPB3, ID4, IFI27, KIAA0644, KRT14, KRT17, KRT34, IGFL3, MFAP5, MEOX1, MGP, MSX2, MX1, MYBPH, MYH3, MYH11, IL32, NLGN4X, NPAS1, NPPB, OLR1, PAX2, PAX9, PDE1A, PENK, POSTN, PRELP, PROM1, PTPRN, RARRES1, RASD1, RELN, RGS1, SMOC1, SMOC2, STMN2, THY1, TNFSF7, TRH, TSLP, TUBB4, ZD52F10 and ZIC1.
The group of cell lines CMO.2 and E31 are positive for the markers: AQP1, CD24, CDH6, HTRA3, KRT19, KRT34, TAGLN3, RELN, S100A4, SFRP2, SRCRB4D and UGT2B7 and are negative for the markers: AGC1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GAP43, GSC, HOXA5, HSD11B2, HSPA6, HSPB3, IFI27, IFIT3, IGF2, KRT14, MFAP5, MASP1, MEOX2, MYH3, NPAS1, OGN, OLR1, OSR2, PAX9, PDE1A, PENK, PRG4, PROM1, PTPRN, RARRES1, RASD1, RGS1, SERPINA3, SLITRK6, SMOC1, SMOC2, SNAP25, SOD3, STMN2, TAC1, TRH, TSLP, TUBB4 and WISP2.
The group of cell lines CMO.2, CMO.5 and CM50.5 are positive for the markers: PRSS35, CLDN11, CRIP1, CRYAB, FST, KRT19, KRT34, MFAP5, MEOX2, MGP, MMP1, PODN, POSTN, PRRX1, S100A4, THY1 and ZIC1 and are negative for the markers: ACTC, ALDH1A1, APCDD1, AREG, ATP8B4, BEX1, C3, C6, C7, C20orf103, CCDC3, CDH3, CNTNAP2, CXADR, DIO2, DKK2, DLK1, EMID1, TMEM100, FMO1, FMO3, FOXF1, FOXF2, GABRB1, GDF10, GJB2, GSC, HSD11B2, HSD17B2, HSPA6, IGF2, IGFBP5, INA, LAMC2, IGFL3, LOC92196, MEOX1, MX1, MYBPH, MYL4, NLGN4X, NPAS1, NPPB, PAX2, PAX9, PDE1A, PENK, PITX2, PROM1, PTPRN, RASD1, RGS1, SLITRK6, SMOC1, SMOC2, SNAP25, STMN2, TAC1, RSPO3, TRH, TSLP, TUBB4, ZD52F10 and ZIC2.
The group of cell lines CM10.4, CM20.4, CM30.5 and X2.3 are positive for the markers: CLDN11, COMP, CRIP1, FST, KRT19, KRT34, MFAP5, MGP, PITX2, POSTN, S100A4 and THY1 and are negative for the markers: ACTC, ALDH1A1, AQP1, ATP8B4, C6, C7, C20orf103, CCDC3, CDH3, CNTNAP2, COP1, CXADR, METTL7A, DLK1, DPT, EMID1, FGFR3, TMEM100, FMO1, FMO3, FOXF1, FOXF2, GABRB1, GDF10, HSD11B2, HSD17B2, HSPA6, HSPB3, IGF2, IGFL3, LOC92196, MEOX1, MX1, MYBPH, MYH3, MYH11, MYL4, NLGN4X, TAGLN3, NPPB, PAX2, PAX9, PDE1A, PRELP, PROM1, PTPRN, RASD1, RELN, RGS1, SLITRK6, SMOC2, SNAP25, STMN2, TAC1, RSPO3, TUBB4, UGT2B7, WISP2, ZD52F10 and ZIC2.
The group of cell lines E111 and E111Bio2 are positive for the markers: CD24, CDH6, GRIP1, HTRA3, INA, TAGLN3, SFRP2, SRCRB4D, UGT2B7 and ZIC2 and are negative for the markers: AGC1, AKR1C1, ALDH1A1, APCDD1, AREG, ATP8B4, CFB, C3, C6, C7, C20orf103, CDH3, CNTNAP2, COP1, CRLF1, DIO2, METTL7A, DLK1, DPT, EMID1, TMEM100, FMO1, FMO3, FOXF1, FOXF2, GABRB1, GAP43, GSC, HOXA5, HSD1B2, HSD17B2, HSPA6, HSPB3, ID4, IFI27, IFIT3, IGF2, KRT14, LAMC2, MASP1, MEOX2, MX1, MYBPH, MYH3, MYH11, NPAS1, OGN, OLR1, PAX9, PDE1A, PENK, PRG4, PROM1, PRRX2, PTPRN, RARRES1, RASD1, RGMA, RGS1, SLITRK6, SMOC1, SMOC2, SNAP25, STMN2, TAC1, TNNT2, TRH, TUBB4 and WISP2.
The cell line E120 is positive for the markers: ACTC, BEX1, CLDN11, COL15A1, CRIP1, CRYAB, FST, GDF10, GJB2, HTRA3, IGFL3, MGP, MX1, IL32, POSTN, S100A4, SFRP2, THY1, TNFSF7, ZD52F10 and ZIC2 and are negative for the markers: AGC1, AKR1C1, ALDH1A1, APCDD1, AQP1, AREG, ATP8B4, BMP4, C3, C6, C7, PRSS35, C20orf103, CD24, CDH3, CNTNAP2, COL21A1, COMP, COP1, CRLF1, CXADR, DIO2, METTL7A, DKK2, DLK1, EMID1, FGFR3, FMO1, FMO3, FOXF1, FOXF2, GABRB1, GAP43, GDF5, GSC, HOXA5, HSD11B2, HSD17B2, HSPA6, HSPB3, IFI27, IGF2, INA, KRT14, LAMC2, TMEM119, MASP1, MEOX2, MMP1, MSX2, MYBPH, MYH3, MYH11, NLGN4X, TAGLN3, NPAS1, NPPB, OGN, OLR1, OSR2, PAX2, PAX9, PDE1A, PENK, PITX2, PODN, PRG4, PROM1, RASD1, RELN, RGMA, RGS1, SLITRK6, SMOC1, SMOC2, SNAP25, STMN2, SYT12, TAC1, RSPO3, TNNT2, TRH, TUBB4, UGT2B7 and WISP2.
The cell line E15 is positive for the markers: ACTC, BEX1, PRSS35, CRIP1, CRYAB, GAP43, GDF5, HTRA3, KRT19, MGP, MMP1, POSTN, PRRX1, S100A4, SOX11, SRCRB4D and THY1 and are negative for the markers: AGC1, AKR1C1, ALDH1A1, ANXA8, APCDD1, AQP1, AREG, ATP8B4, CFB, C3, C6, C7, C20orf103, CDH3, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IFIT3, IGF2, INA, KRT14, TMEM119, IGFL3, LOC92196, MFAP5, MASP1, MEOX1, MEOX2, MSX1, MX1, MYBPH, MYH3, MYL4, NLGN4X, TAGLN3, NPAS1, OGN, OLR1, PAX2, PAX9, PDE1A, PENK, PITX2, PRG4, PROM1, PTPRN, RARRES1, RASD1, RELN, RGS1, SLITRK6, SMOC1, SMOC2, SNAP25, STMN2, TAC1, TFPI2, RSPO3, TNFSF7, TNNT2, TRH, TSLP, TUBB4, UGT2B7, WISP2, ZD52F10 and ZIC1.
The cell line E164 is positive for the markers: AQP1, CD24, CDH6, CRIP1, HTRA3, KRT17, KRT19, IL32, TAGLN3, PAX2, RELN, S100A4, SFRP2, SRCRB4D, THY1, TNFSF7, UGT2B7, ZD52F10 and ZIC2 and are negative for the markers: ACTC, AGC1, ALDH1A1, ANXA8, APCDD1, AREG, ATP8B4, C3, C6, C7, TABLE I-continued Exemplary progenitor cell lines and associated gene expression markers at 18-21 doublings of clonal expansion C20orf103, CCDC3, CDH3, CLDN11, CNTNAP2, COL15A1, COL21A1, COMP, COP1, CRLF1, DIO2, METTL7A, DKK2, DLK1, DPT, EGR2, EMID1, TMEM100, FMO1, FMO3, FOXF1, FOXF2, GABRB1, GAP43, GDF5, GSC, HOXA5, HSD11B2, HSD17B2, HSPA6, HSPB3, ID4, IFI27, KCNMB1, KRT14, KRT34, TMEM119, MFAP5, MASP1, MEOX2, MGP, MSX2, MYBPH, MYH3, MYH11, MYL4, NPAS1, NPPB, OGN, OLR1, PAX9, PDE1A, PENK, PITX2, POSTN, PRELP, PRG4, PRRX1, PRRX2, PTGS2, PTPRN, RARRES1, RASD1, RGMA, RGS1, SERPINA3, SLITRK6, SMOC1, SMOC2, SNAP25, SOD3, STMN2, TAC1, TNNT2, TRH, TUBB4 and WISP2.

The group of cell lines E69 and E169 are positive for the markers: BEX1, CDH6, CRIP1, FST, GDF5, HTRA3, MMP1, POSTN, PTN, S100A4 and ZIC2 and are negative for the markers: AGC1, ALDH1A1, APCDD1, AQP1, AREG, ATP8B4, BMP4, C3, C6, C7, C20orf103, CDH3, CNTNAP2, COMP, CRLF1, CXADR, DLK1, DPT, EGR2, EMID1, FMO1, FMO3, FOXF1, FOXF2, GABRB1, GJB2, GSC, HOXA5, HSD11B2, HSD17B2, HSPA6, HSPB3, IFI27, IGF2, INA, KRT14, IGFL3, LOC92196, MASP1, MEOX1, MEOX2, MYBPH, MYH3, MYH11, MYL4, NLGN4X, TAGLN3, NPAS1, NPPB, OGN, OLR1, PAX2, PAX9, PDE1A, PENK, PITX2, PROM1, RARRES1, RASD1, RELN, RGS1, SL1TRK6, SMOC1, SMOC2, SNAP25, STMN2, SYT12, TAC1, RSPO3, TNNT2, TRH, TUBB4, UGT2B7 and ZD52F10.

The cell line E19 is positive for the markers: ACTC, BEX1, PRSS35, CLDN11, CRIP1, CRYAB, DKK2, HTRA3, ICAM5, KRT17, KRT19, KRT34, MX1, POSTN, THY1, ZIC1 and ZIC2 and are negative for the markers: AGC1, AKR1C1, ALDH1A1, APCDD1, AQP1, AREG, ATP8B4, CFB, BMP4, C3, C6, C7, C20orf103, CNTNAP2, COL21A1, COP1, CXADR, METTL7A, DLK1, DPT, EGR2, EMID1, TMEM100, FMO1, FMO3, FOXF1, FOXF2, GABRB1, GAP43, GDF10, GJB2, GSC, HOXA5, HSD11B2, HSD17B2, HSPA6, IGF2, IL1R1, KIAA0644, TMEM119, IGFL3, LOC92196, MASP1, MEOX1, MEOX2, MGP, MYBPH, MYH3, NLGN4X, TAGLN3, OGN, PAX2, PAX9, PDE1A, PENK, PRG4, PROM1, PRRX2, RARRES1, RASD1, RELN, RGMA, RGS1, SFRP2, SLITRK6, SMOC1, SMOC2, SNAP25, SOD3, STMN2, SYT12, TAC1, TFPI2, RSPO3, TNFSF7, TNNT2, TRH, TSLP, TUBB4, UGT2B7, WISP2 and ZD52F10.

The group of cell lines E3, E30, E20Bio2, E67, E73, E57 and E84 are positive for the markers: KRT19, KRT34, MFAP5, MGP, MMP1, S100A4, THY1 and ZIC1 and are negative for the markers: ALDH1A1, AREG, ATP8B4, C7, C20orf103, CDH3, CNTNAP2, DKK2, DLK1, DPT, FMO1, FMO3, FOXF1, FOXF2, GDF10, GSC, HOXA5, HSD17B2, IGF2, MEOX1, TAGLN3, NPPB, PAX9, PROM1, PTPRN, RGS1, SMOC1, SNAP25, STMN2, TAC1, TUBB4 and ZIC2.

The cell line E33 is positive for the markers: AQP1, PRSS35, CD24, CDH6, CLDN11, CRIP1, CRYAB, DKK2, HTRA3, KRT17, KRT19, KRT34, LOC92196, MFAP5, MGP, MYH11, TAGLN3, POSTN, S100A4, SRCRB4D, UGT2B7, ZIC1 and ZIC2 and are negative for the markers: AGC1, AKR1C1, ALDH1A1, APCDD1, AREG, ATP8B4, CFB, C3, C6, C7, C20orf103, CDH3, CNTNAP2, COMP, COP1, CRLF1, DIO2, METTL7A, DLK1, DPT, EMID1, TMEM100, FMO1, FMO3, FOXF1, FOXF2, GABRB1, GDF5, GJB2, GSC, HOXA5, HSD11B2, HSPA6, HSPB3, IFI27, IFIT3, IGF2, TMEM119, IGFL3, MASP1, MX1, MYBPH, NPAS1, NPPB, OGN, OLR1, OSR2, PAX9, PDE1A, PENK, PITX2, PRG4, PROM1, PTPRN, RARRES1, RASD1, RGMA, RGS1, SERPINA3, SFRP2, SLITRK6, SMOC1, SMOC2, SNAP25, STMN2, TAC1, RSPO3, TRH, TSLP, TUBB4, WISP2 and ZD52F10.

The cell line E40 is positive for the markers: BEX1, CDH6, CLDN11, GRIP1, CRYAB, DKK2, FST, HTRA3, KRT17, KRT19, MMP1, POSTN, S100A4, SRCRB4D and ZIC2 and are negative for the markers: AGC1, AKR1C1, ALDH1A1, APCDD1, AQP1, AREG, ATP8B4, CFB, BMP4, C3, C6, C7, C20orf103, CDH3, CNTNAP2, COMP, COP1, CRLF1, CXADR, METTL7A, DLK1, DPT, EGR2, EMID1, TMEM100, FMO1, FMO3, FOXF1, FOXF2, GABRB1, GJB2, GSC, HOXA5, HSD11B2, HSD17B2, HSPA6, HSPB3, IFIT3, IGF2, KIAA0644, KRT14, IGFL3, LOC92196, MASP1, MEOX1, MEOX2, MGP, MX1, MYBPH, MYH3, NLGN4X, TAGLN3, NPAS1, NPPB, OGN, OLR1, OSR2, PAX2, PAX9, PDE1A, PENK, PITX2, PRG4, PROM1, PRRX2, PTPRN, RARRES1, RASD1, RELN, RGS1, SLITRK6, SMOC1, SMOC2, SNAP25, STMN2, SYT12, TAC1, TFPI2, RSPO3, TNFSF7, TNNT2, TRH, TSLP, TUBB4, WISP2, ZD52F10 and ZIC1.

The cell line E44 is positive for the markers: BEX1, CLDN11, CRIP1, FST, GDF5, HTRA3, IFI27, IFIT3, MGP, MMP1, MSX1, MX1, IL32, PRRX2, PTN, S100A4, SOD3 and ZIC2 and are negative for the markers: ACTC, AGC1, ALDH1A1, AQP1, AREG, ATP8B4, BMP4, C6, C7, C20orf103, CDH3, CDH6, CNTNAP2, COL21A1, COMP, CRLF1, DKK2, DPT, EGR2, EMID1, FGFR3, FMO1, FMO3, FOXF2, GABRB1, GDF10, GSC, HOXA5, HSD11B2, HSD17B2, HSPA6, HSPB3, IGF2, INA, KCNMB1, KRT14, KRT34, TMEM119, IGFL3, LOC92196, MFAP5, MEOX1, MEOX2, MYBPH, MYH3, MYH11, MYL4, NLGN4X, NPAS1, NPPB, OGN, OLR1, PAX2, PAX9, PDE1A, PENK, PITX2, POSTN, PRELP, PRG4, PROM1, RASD1, RELN, RGMA, RGS1, RPS4Y2, SFRP2, SLITRK6, SMOC1, SMOC2, SNAP25, SRCRB4D, STMN2, SYT12, TAC1, RSPO3, TNNT2, TRH, TUBB4, UGT2B7, ZD52F10 and ZIC1.

The cell line E45 is positive for the markers: AQP1, CD24, CDH6, COL21A1, CRIP1, DKK2, HTRA3, KRT17, KRT19, MGP, TAGLN3, PRRX1, S100A4, SOX11, UGT2B7, ZIC1 and ZIC2 and are negative for the markers: AGC1, ALDH1A1, ANXA8, APCDD1, AREG, ATP8B4, BEX1, BMP4, C3, C6, C7, C20orf103, CDH3, CNTNAP2, COL15A1, COMP, COP1, CRLF1, METTL7A, DLK1, DPT, EMID1, TMEM100, FMO1, FMO3, FOXF1, FOXF2, GABRB1, GAP43, GJB2, GSC, HOXA5, HSD11B2, HSPA6, HSPB3, ID4, IFI27, KRT14, LAMC2, IGFL3, MFAP5, MASP1, MEOX1, MEOX2, MMP1, MYBPH, MYH3, MYH11, NPAS1, NPPB, OGN, OLR1, OSR2, PAX9, PDE1A, PENK, PITX2, PRG4, PROM1, PTPRN, RARRES1, RASD1, RELN, RGS1, SERPINA3, SFRP2, SLITRK6, SMOC1, SMOC2, SNAP25, STMN2, TAC1, RSPO3, TRH, TSLP, TUBB4, WISP2 and ZD52F10.

The cell line E50 is positive for the markers: ACTC, BEX1, CD24, CDH6, COL21A1, CRIP1, CRYAB, DKK2, FST, KRT17, KRT19, LOC92196, POSTN, PTN, S100A4, SFRP2, SRCRB4D, ZIC1 and ZIC2 and are negative for the markers: AGC1, AKR1C1, ALDH1A1, APCDD1, AQP1, AREG, ATP8B4, CFB, BMP4, C6, C7, C20orf103, CDH3, CLDN11, CNTNAP2, COMP, COP1, CRLF1, METTL7A, DLK1, DPT, EMID1, TMEM100, FMO3, FOXF1, FOXF2, GABRB1, GSC, HOXA5, HSD11B2, HSD17B2, HSPA6, HSPB3, IFI27, IFIT3, KRT14, KRT34, LAMC2, TMEM119, IGFL3, MFAP5, MASP1, MEOX1, MEOX2, MMP1, MYH3, NLGN4X, NPAS1, NPPB, OGN, OLR1, PAX2, PAX9, PENK, PRG4, PROM1, PTGS2, PTPRN, RARRES1, RASD1, RELN, RGS1, SERPINA3, SLITRK6, SMOC1, SMOC2, STMN2, SYT12, TAC1, TFPI2, RSPO3, TRH, TSLP, TUBB4, UGT2B7, WISP2 and ZD52F10.

The cell line E51 is positive for the markers: PRSS35, CCDC3, CDH6, CRIP1, CRYAB, DIO2, DKK2, HTRA3, ID4, KCNMB1, KRT17, KRT19, KRT34, MGP, MYH11, POSTN, PRRX1, S100A4, SOX11 and ZIC2 and are negative for the markers: AGC1, AKR1C1, ALDH1A1, APCDD1, AREG, ATP8B4, BMP4, C3, C6, C7, TABLE I-continued Exemplary progenitor cell lines and associated gene expression markers at 18-21 doublings of clonal expansion C20orf103, CDH3, CNTNAP2, COP1, CRLF1, CXADR, METTL7A, DLK1, DPT, EMID1, FMO1, FMO3, FOXF1, FOXF2, GABRB1, GSC, HOXA5, HSD17B2, HSPA6, HSPB3, IFI27, IFIT3, IGF2, IGFBP5, TMEM119, IGFL3, LOC92196, MASP1, MEOX1, MEOX2, MX1, MYBPH, MYH3, MYL4, NLGN4X, TAGLN3, NPAS1, NPPB, OGN, OLR1, PAX2, PAX9, PDE1A, PENK, PRG4, PROM1, PTPRN, RARRES1, RASD1, RELN, RGS1, SFRP2, SMOC1, SMOC2, SNAP25, STMN2, SYT12, TAC1, TFPI2, TNFSF7, TNNT2, TRH, TUBB4, UGT2B7, WISP2 and ZD52F10.

The group of cell lines E68 and E68Bio2 are positive for the markers: CD24, CRIP1, CRYAB, HTRA3, KRT17, KRT19, TAGLN3, UGT2B7, ZIC1 and ZIC2 and are negative for the markers: AGC1, AREG, ATP8B4, C6, C7, CDH3, COP1, CRLF1, DLK1, DPT, TMEM100, FMO1, FMO3, FOXF1, FOXF2, GSC, HOXA5, HSD11B2, HSPA6, HSPB3, IGF2, LAMC2, IGFL3, MEOX1, MEOX2, MMP1, MYBPH, MYH3, NPAS1, OGN, PAX9, PITX2, PRG4, PROM1, RARRES1, RGS1, SMOC2, TAC1, RSPO3, TRH, TSLP and WISP2.

The group of cell lines C4ELS5.6 and C4ELS5.6Bio2 are positive for the markers: BMP, COP1, METTL7A, TMEM100, FOXF1, HSD17B2, HTRA3, IGF2, IGFBP5, IL1R1, KRT19, MASP1, OLR1, PITX2, PODN and TSLP and are negative for the markers: ACTC, AGC1, ALDH1A1, AQP1, CFB, C6, C7, C20orf103, CDH3, CDH6, CLDN11, CNTNAP2, COL21A1, COMP, CRLF1, DKK2, DPT, EGR2, EMID 1, FMO3, FOXF2, GABRB1, GAP43, GDF10, GSC, HOXA5, HSPA6, HSPB3, ID4, IFI27, INA, KRT17, KRT34, LAMC2, TMEM119, IGFL3, LOC92196, MFAP5, MEOX1, MEOX2, MGP, MSX1, MYH3, MYH11, MYL4, IL32, NLGN4X, TAGLN3, NPAS1, NPPB, OGN, PAX2, PAX9, PDE1A, PENK, PRG4, PROM1, PRRX1, PRRX2, PTPRN, RARRES1, RASD1, RELN, RGMA, RGS1, SFRP2, SMOC1, SMOC2, SNAP25, SOD3, SYT12, TAC1, RSPO3, THY1, TNFSF7, TNNT2, TRH, TUBB4, UGT2B7, WISP2, ZD52F10, ZIC1 and ZIC2.

The cell line C4ELS5.8 is positive for the markers: AKR1C1, ALDH1A1, BMP4, C3, COP1, METTL7A, TMEM100, FOXF1, HSD17B2, HTRA3, ICAM5, IFIT3, IGF2, IGFBP5, IL1R1, KRT19, MASP1, MX1, OLR1, PODN, STMN2, TFPI2 and THY1 and are negative for the markers: ACTC, AGC1, APCDD1, BEX1, C6, C7, PRSS35, C20orf103, CCDC3, CD24, CDH3, CLDN11, CNTNAP2, COL21A1, COMP, CRIP1, CRLF1, DKK2, DLK1, DPT, EMID1, FGFR3, FMO3, FOXF2, GABRB1, GAP43, GDF10, GSC, HOXA5, HSD11B2, HSPA6, HSPB3, ID4, INA, KCNMB1, KRT14, KRT17, TMEM119, IGFL3, LOC92196, MFAP5, MEOX1, MEOX2, MGP, MSX2, MYH3, MYH11, MYL4, IL32, NLGN4X, TAGLN3, NPPB, OGN, PAX2, PAX9, PDE1A, PENK, POSTN, PRRX1, PRRX2, PTPRN, RARRES1, RASD1, RELN, RGMA, RGS1, SLITRK6, SMOC1, SMOC2, SOD3, SOX11, SYT12, TAC1, RSPO3, TNFSF7, TNNT2, TRH, TUBB4, UGT2B7, WISP2, ZD52F10, ZIC1 and ZIC2.

The cell line C4ELSR13 is positive for the markers: AKR1C1, ANXA8, AREG, BMP4, C3, COP1, METTL7A, FMO3, FOXF1, HTRA3, IFI27, IFIT3, IGF2, IL1R1, KRT19, MASP1, MX1, MYBPH, OLR1, PITX2, PODN, S100A4 and TFPI2 and are negative for the markers: AGC1, APCDD1, AQP1, ATP8B4, C6, C20orf103, CD24, CDH3, CDH6, CLDN11, CNTNAP2, COL15A1, COL21A1, COMP, CRIP1, CRLF1, CRYAB, DKK2, DLK1, DPT, EGR2, EMID1, FGFR3, TMEM100, FMO1, FOXF2, GABRB1, GAP43, GDF10, GSC, HOXA5, HSD11B2, HSD17B2, HSPA6, HSPB3, ID4, INA, KIAA0644, KRT14, KRT17, IGFL3, LOC92196, MFAP5, MEOX1, MEOX2, MGP, MSX1, MSX2, MYH3, MYH11, MYL4, IL32, NLGN4X, TAGLN3, NPAS1, NPPB, OGN, OSR2, PAX2, PAX9, PDE1A, PENK, POSTN, PROM1, PRRX1, PTPRN, RARRES1, RASD1, RELN, RGMA, RGS1, RPS4Y2, SERPINA3, SLITRK6, SMOC2, SNAP25, SOD3, SOX11, STMN2, SYT12, TAC1, RSPO3, THY1, TNNT2, TRH, TUBB4, UGT2B7, ZD52F10, ZIC1 and ZIC2.

The cell line C4ELSR18 is positive for the markers: AQP1, BEX1, BMP4, C20orf103, CDH6, FST, HOXA5, IGF2, IGFBP5, OLR1, OSR2, PDE1A, PRRX2, S100A4, SFRP2, SLITRK6, TFPI2 and ZIC2 and are negative for the markers: AGC1, ALDH1A1, ANXA8, APCDD1, ATP8B4, CFB, C6, CCDC3, CD24, CDH3, CLDN11, CNTNAP2, COL15A1, COMP, COP1, CRLF1, CRYAB, DLK1, DPT, EGR2, EMID1, TMEM100, FOXF1, GABRB1, GAP43, GDF10, GSC, HSD11B2, HSD17B2, HSPA6, HSPB3, ID4, IFI27, IFIT3, KCNMB1, KRT14, KRT17, KRT34, TMEM119, IGFL3, LOC92196, MFAP5, MASP1, MEOX1, MEOX2, MSX1, MSX2, MX1, MYH3, MYH11, MYL4, IL32, NPAS1, NPPB, OGN, PAX2, PAX9, PITX2, PODN, PRG4, PTPRN, RARRES1, RASD1, RELN, RGS1, SERPINA3, SMOC1, SMOC2, SOD3, SOX11, STMN2, SYT12, TAC1, THY1, TNFSF7, TNNT2, TRH, TUBB4, UGT2B7, ZD52F10 and ZIC1.

The group of cell lines EN11 and W10 are positive for the markers: DLK1, FOXF1, FST, GABRB1, GDF5, HTRA3, IGF2, IGFBP5, IL1R1, POSTN, PTN, SOX11, SRCRB4D and TFPI2 and are negative for the markers: ACTC, AGC1, ALDH1A1, ANXA8, APCDD1, AQP1, AREG, CFB, BMP4, C3, C6, C7, CCDC3, CD24, CDH6, CLDN11, CNTNAP2, COL15A1, COMP, COP1, CRYAB, DKK2, DPT, EGR2, EMID1, FGFR3, FMO1, FMO3, FOXF2, GAP43, GDF10, GSC, HSD11B2, HSD17B2, HSPA6, HSPB3, ID4, IFI27, INA, KCNMB1, KRT14, KRT17, KRT34, IGFL3, LOC92196, MEOX1, MEOX2, MX1, MYBPH, MYH3, MYH11, MYL4, IL32, NLGN4X, NPAS1, NPPB, OLR1, PAX2, PAX9, PENK, PITX2, PRELP, PROM1, RARRES1, RASD1, RELN, RGS1, SMOC1, SMOC2, STMN2, SYT12, TAC1, THY1, TNFSF7, TNNT2, TRH, TUBB4, UGT2B7, WISP2, ZIC1 and ZIC2.

The group of cell lines EN7, EN13Bio1b, EN13Bio2c and EN13Bio3c are positive for the markers: CDH6, DLK1, FOXF1, FST, HTRA3, IGF2, IL1R1, MSX1, POSTN, SOD3, ZIC1 and ZIC2 and are negative for the markers: ACTC, ALDH1A1, ANXA8, ATP8B4, BMP4, C3, C20orf103, CCDC3, CD24, CDH3, CLDN11, CNTNAP2, COMP, CRYAB, DIO2, DKK2, GSC, HOXA5, HSD11B2, HSD17B2, HSPA6, HSPB3, IFI27, INA, KRT14, KRT17, KRT34, IGFL3, LOC92196, MFAP5, MEOX1, MEOX2, MGP, MMP1, MX1, MYH3, MYH11, MYL4, IL32, NPAS1, NPPB, OLR1, PAX2, PAX9, PDE1A, PENK, PITX2, PROM1, RELN, SFRP2, SMOC2, STMN2, TAC1, RSPO3, THY1, TNFSF7, TNNT2, TRH, TUBB4 and ZD52F10.

The cell line EN16 is positive for the markers: COL15A1, DIO2, DPT, FMO3, FOXF1, FOXF2, FST, HSPB3, HTRA3, IGF2, IL1R1, TMEM119, MGP, MMP1, PODN and PRRX2 and are negative for the markers: ACTC, AGC1, AKR1C1, ALDH1A1, ANXA8, AQP1,, AREG, ATP8B4, BEX1, CFB, C3, C6, C7, C20orf103, CCDC3, CD24, CDH3, CLDN11, CNTNAP2, COMP, CRIP1, CRLF1, DKK2, EMID1, FGFR3, TMEM100, GABRB1, GAP43, GDF5, GDF10, GJB2, GSC, HOXA5, HSD11B2, HSD17B2, HSPA6, ID4, IFI27, KCNMB1, KRT14, KRT17, KRT34, LAMC2, IGFL3, LOC92196, MFAP5, MEOX1, MEOX2, MYBPH, MYH3, MYH11, MYL4, IL32, NLGN4X, TAGLN3, NPAS1, NPPB, PAX2, PAX9, PENK, PITX2, POSTN, PTGS2, PTPRN, RARRES1, RASD1, RGS1, SMOC1, SMOC2, SNAP25, STMN2, TAC1, RSPO3, THY1, TNFSF7, TNNT2, TRH, TUBB4, UGT2B7, ZD52F10, ZIC1 and ZIC2.

The group of cell lines EN1, EN1Bio2 and EN18 are positive for the markers: DIO2, DLK1, FOXF1, GDF5, HTRA3, IGF2, IL1R1, MGP, POSTN, PRRX2 and SRCRB4D and are negative for the markers: ACTC, AGC1, ALDH1A1, ANXA8, AQP1, CFB, C20orf103, CCDC3, CD24, CLDN11, CNTNAP2, CRYAB, CXADR, DKK2,

TABLE I-continued

Exemplary progenitor cell lines and associated gene expression markers at 18-21 doublings of clonal expansion GABRB1, GAP43, GDF10, GSC, HSD11B2, HSD17B2, HSPA6, IFI27, INA, KCNMB1, KRT14, KRT17, KRT34, IGFL3, LOC92196, MFAP5, MEOX1, MEOX2, MX1, MYH3, MYH11, MYL4, NPAS1, NPPB, PAX2, PAX9, PENK, PITX2, PROM1, RASD1, RGS1, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN19 is positive for the markers: CDH6, COL15A1, COL21A1, DLK1, FOXF1, FST, GDF5, IGF2, TMEM119, MSX1, RGMA, SERPINA3, SOD3, ZIC1 and ZIC2 and are negative for the markers: ACTC, AGC1, ANXA8, AQP1, ATP8B4, C3, C6, C7, C20orf103, CD24, CDH3, CLDN11, CNTNAP2, CRIP1, CXADR, DIO2, DKK2, EMID1, TMEM100, GABRB1, GAP43, GJB2, GSC, HOXA5, HSD11B2, HSD17B2, HSPA6, HSPB3, IFI27, INA, KCNMB1, KRT14, KRT17, KRT19, KRT34, IGFL3, LOC92196, MFAP5, MEOX1, MEOX2, MGP, MX1, MYH3, MYH11, MYL4, IL32, NLGN4X, NPPB, OLR1, OSR2, PAX2, PAX9, PDE1A, PENK, PROM1, RARRES1, RASD1, RELN, RGS1, SLITRK6, SMOC1, SMOC2, SNAP25, STMN2, SYT12, TAC1, RSPO3, THY1, TNFSF7, TNNT2, TRH, TUBB4, UGT2B7 and ZD52F10.

The cell line EN2 is positive for the markers: FST, GDF5, HTRA3, IGF2, IGFBP5, IL1R1, PRRX2, PTN, SFRP2, SOX11, SRCRB4D, TFPI2 and RSPO3 and are negative for the markers: ACTC, AGC1, AKR1C1, ALDH1A1, ANXA8, APCDD1, AREG, ATP8B4, CFB, C3, C6, C7, PRSS35, C20orf103, CCDC3, CD24, CDH6, CLDN11, COMP, COP1, CRLF1, CXADR, DKK2, DPT, EGR2, EMID1, TMEM100, FMO1, FOXF2, GAP43, GDF10, GJB2, GSC, HOXA5, HSD11B2, HSD17B2, HSPA6, HSPB3, ICAM5, IFI27, INA, KRT14, KRT17, KRT19, KRT34, TMEM119, IGFL3, LOC92196, MFAP5, MEOX1, MEOX2, MX1, MYBPH, MYH3, MYH11, MYL4, NLGN4X, TAGLN3, NPAS1, NPPB, OGN, OLR1, PAX2, PAX9, PDE1A, PENK, PITX2, POSTN, PRELP, PRG4, PTGS2, RARRES1, RASD1, RELN, RGS1, SMOC1, SMOC2, SNAP25, STMN2, SYT12, TAC1, THY1, TNFSF7, TNNT2, TRH, TSLP, TUBB4, UGT2B7, ZD52F10, ZIC1 and ZIC2.

The cell line EN25 is positive for the markers: CDH6, CNTNAP2, COL15A1, COL21A1, DLK1, FOXF1, FST, HTRA3, IGF2, SERPINA3, SRCRB4D, TFPI2, ZIC1 and ZIC2 and are negative for the markers: ACTC, AGC1, AKR1C1, ALDH1A1, AQP1, ATP8B4, C3, C6, C7, C20orf103, CCDC3, CD24, CDH3, CLDN11, CRIP1, DIO2, DKK2, EMID1, FOXF2, GSC, HOXA5, HSD11B2, HSD17B2, HSPA6, HSPB3, IFI27, IFIT3, INA, KCNMB1, KRT14, KRT17, KRT34, IGFL3, LOC92196, MFAP5, MEOX1, MGP, MMP1, MX1, MYBPH, MYH3, MYH11, MYL4, IL32, NLGN4X, NPPB, OLR1, PAX2, PAX9, PENK, PITX2, PRELP, PROM1, PRRX1, PTN, RARRES1, RASD1, RELN, SFRP2, SLITRK6, SMOC2, STMN2, TAC1, RSPO3, THY1, TNFSF7, TNNT2, TRH, TUBB4, UGT2B7 and ZD52F10.

The cell line EN26 is positive for the markers: DIO2, DPT, FMO3, FOXF1, FOXF2, FST, GDF5, HTRA3, IGF2, IL1R1, TMEM119, PODN, PRRX1, PRRX2, SFRP2, SOD3 and SRCRB4D and are negative for the markers: ACTC, AGC1, AKR1C1, ALDH1A1, ANXA8, AQP1, ATP8B4, BEX1, C3, C6, C7, C20orf103, CCDC3, CD24, CLDN11, CNTNAP2, COL21A1, COMP, CRIP1, CXADR, DKK2, GABRB1, GAP43, GDF10, GJB2, GSC, HOXA5, HSD11B2, HSD17B2, HSPA6, ID4, IFI27, INA, KCNMB1, KRT14, KRT17, KRT19, KRT34, LAMC2, IGFL3, LOC92196, MFAP5, MEOX1, MEOX2, MMP1, MX1, MYBPH, MYH3, MYH11, MYL4, NLGN4X, NPAS1, NPPB, PAX2, PAX9, PENK, PITX2, PROM1, PTGS2, PTPRN, RARRES1, RASD1, RELN, RGS1, SLITRK6, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN27 is positive for the markers: DIO2, FMO3, FOXF1, FOXF2, FST, HSPB3, HTRA3, IGF2, IL1R1, TMEM119, MSX2, OGN, PODN, PRELP, PRRX2, SERPINA3 and SLITRK6 and are negative for the markers: , ACTC, AGC1, ALDH1A1, ANXA8, AQP1, AREG, ATP8B4, CFB, C3, C6, C7, C20orf103, CCDC3, CD24, CDH3, CDH6, CLDN11, CNTNAP2, CRIP1, CRLF1, DKK2, EMID1, FGFR3, TMEM100, GABRB1, GAP43, GDF10, GJB2, GSC, HOXA5, HSD11B2, HSD17B2, HSPA6, ICAM5, ID4, IFI27, IFIT3, IGFBP5, INA, KCNMB1, KRT14, KRT17, KRT19, KRT34, LAMC2, IGFL3, LOC92196, MFAP5, MASP1, MEOX1, MEOX2, MMP1, MX1, MYBPH, MYH3, MYH11, MYL4, IL32, NLGN4X, NPAS1, NPPB, OLR1, PAX2, PAX9, PENK, PITX2, PROM1, RARRES1, RASD1, RELN, RGS1, SFRP2, SMOC1, SMOC2, STMN2, TAC1, RSPO3, THY1, TNFSF7, TNNT2, TRH, TUBB4, UGT2B7, ZD52F10, ZIC1 and ZIC2.

The cell line EN28 is positive for the markers: COL15A1, COL21A1, DIO2, FOXF1, FOXF2, FST, HSPB3, HTRA3, IGF2, IGFBP5, IL1R1, TMEM119, PODN, PRRX1, PTN, SFRP2 and SOX11 and are negative for the markers: ACTC, AGC1, AKR1C1, ALDH1A1, ANXA8, AQP1, AREG, ATP8B4, CFB, BMP4, C3, C6, C7, C20orf103, CCDC3, CD24, CDH3, CDH6, CLDN11, CNTNAP2, COP1, CRIP1, DKK2, EMID1, TMEM100, GAP43, GDF10, GJB2, GSC, HOXA5, HSD11B2, HSD17B2, HSPA6, ID4, IFI27, INA, KCNMB1, KIAA0644, KRT14, KRT17, KRT34, IGFL3, LOC92196, MFAP5, MEOX1, MEOX2, MGP, MMP1, MX1, MYBPH, MYH3, MYH11, MYL4, IL32, NLGN4X, NPPB, OLR1, OSR2, PAX2, PAX9, PDE1A, PENK, PITX2, POSTN, PRELP, PRG4, PROM1, PTGS2, RARRES1, RELN, RGS1, SLITRK6, SMOC1, SMOC2, STMN2, SYT12, TAC1, RSPO3, TNFSF7, TNNT2, TRH, TSLP, TUBB4, UGT2B7, ZD52F10, ZIC1 and ZIC2.

The cell line EN31 is positive for the markers: CDH6, COL21A1, DLK1, FMO3, FOXF1, FST, GDF5, HTRA3, IGF2, IL1R1, MSX1, MSX2, OGN, OSR2, PRRX2, SERPINA3, SLITRK6, SOD3, TSLP, ZIC1 and ZIC2 and are negative for the markers: ACTC, AGC1, ALDH1A1, ANXA8, AQP1, ATP8B4, BEX1, BMP4, C3, C6, C7, PRSS35, C20orf103, CCDC3, CD24, CDH3, CLDN11, CNTNAP2, COMP, CRIP1, CRLF1, CRYAB, CXADR, DIO2, DKK2, EMID1, TMEM100, GAP43, GDF10, GJB2, GSC, HOXA5, HSD11B2, HSD17B2, HSPA6, HSPB3, ICAM5, ID4, IFI27, INA, KRT14, KRT17, KRT19, KRT34, LAMC2, IGFL3, LOC92196, MFAP5, MEOX1, MEOX2, MGP, MMP1, MX1, MYBPH, MYH3, MYH11, MYL4, IL32, NLGN4X, TAGLN3, NPAS1, NPPB, OLR1, PAX2, PAX9, PENK, PITX2, PROM1, PTGS2, RARRES1, RASD1, RELN, SFRP2, SMOC2, SNAP25, STMN2, SYT12, TAC1, RSPO3, TNFSF7, TNNT2, TRH, TUBB4, UGT2B7 and ZD52F10.

The cell line EN38 is positive for the markers: BEX1, CDH6, COL21A1, DLK1, FOXF1, FST, GDF5, HTRA3, IGF2, IL1R1, TMEM119, MGP, MSX1, OGN, PODN, POSTN, PRRX1, PRRX2, RGMA, SERPINA3, SOD3 and TSLP and are negative for the markers: ACTC, AGC1, AKR1C1, ALDH1A1, ANXA8, AQP1, AREG, ATP8B4, BMP4, C3, C6, C7, C20orf103, CCDC3, CD24, CDH3, CLDN11, CNTNAP2, CRIP1, DIO2, DKK2, DPT, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, IGFL3, LOC92196, MFAP5, MEOX1, MEOX2, MX1, MYBPH, MYH3, MYH11, MYL4, IL32, NLGN4X, NPPB, OLR1, PAX2, PAX9, PDE1A, PENK, PITX2, PRELP, PRG4, PROM1, RASD1, RELN, RGS1, SFRP2, SLITRK6, SMOC1, SMOC2, SNAP25, STMN2, SYT12, TAC1, RSPO3, THY1, TNFSF7, TNNT2, TRH, TUBB4, ZD52F10, ZIC1 and ZIC2.

The cell line EN4 is positive for the markers: COL21A1, DLK1, FMO1, FMO3, FOXF1, FOXF2, FST, GDF5, HTRA3, IGF2, IGFBP5, IL1R1, TMEM119, MGP, MSX1, OGN, PODN, PRRX1, PRRX2, PTN, RGMA, SOD3 and TSLP and are negative for the markers: ACTC, AGC1, AKR1C1, ALDH1A1, ANXA8, AQP1, AREG, CFB, TABLE I-continued Exemplary progenitor cell lines and associated gene expression markers at 18-21 doublings of clonal expansion BMP4, C3, C6, C7, C20orf103, CCDC3, CD24, CDH3, CLDN11, CNTNAP2, CRIP1, DIO2, DKK2, DPT, EMID1, FGFR3, TMEM100, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, LAMC2, IGFL3, LOC92196, MFAP5, MASP1, MEOX1, MEOX2, MX1, MYBPH, MYH3, MYH11, MYL4, IL32, NLGN4X, NPAS1, NPPB, OLR1, PAX2, PAX9, PENK, PROM1, PTGS2, RARRES1, RASD1, RGS1, SFRP2, SMOC1, SMOC2, SNAP25, STMN2, TAC1, RSPO3, THY1, TNFSF7, TNNT2, TRH, TUBB4, UGT2B7 and ZD52F10.
The cell line EN42 is positive for the markers: COL15A1, COL21A1, FMO3, FOXF1, FST, GDF5, HTRA3, IGF2, IL1R1, TMEM119, MGP, OGN, PODN, PRRX1, PRRX2, PTN, RGMA, SERPINA3, SNAP25 and SOD3 and are negative for the markers: ACTC, AGC1, AKR1C1, ALDH1A1, ANXA8, AQP1, ATP8B4, BMP4, C3, C6, C7, C20orf103, CCDC3, CD24, CDH3, CLDN11, CNTNAP2, COMP, CXADR, DIO2, DKK2, DPT, EMID1, FGFR3, TMEM100, GAP43, GDF10, GSC, HOXA5, HSD11B2, HSD17B2, HSPA6, HSPB3, ID4, IF127, INA, KCNMB1, KRT14, KRT17, KRT19, KRT34, LAMC2, IGFL3, LOC92196, MFAP5, MASP1, MEOX1, MEOX2, MMP1, MX1, MYBPH, MYH3, MYH11, MYL4, IL32, NLGN4X, NPAS1, NPPB, OLR1, PAX9, PENK, PITX2, PRG4, PROM1, RARRES1, RASD1, RELN, RGS1, SMOC1, SMOC2, STMN2, RSPO3, THY1, TNFSF7, TNNT2, TRH, TUBB4, UGT2B7, ZD52F10, ZIC1 and ZIC2.
The cell line EN47 is positive for the markers: CDH6, COP1, DLK1, FMO3, FOXF1, FST, HTRA3, IGF2, IL1R1, MSX1, POSTN, PTPRN, RGS1, SOD3, TFPI2, TSLP, ZIC1 and ZIC2 and are negative for the markers: AGC1, ALDH1A1, APCDD1, BMP4, C3, C20orf103, CCDC3, CD24, CDH3, DIO2, DKK2, FOXF2, GSC, HOXA5, HSD11B2, HSD17B2, HSPA6, HSPB3, IF127, INA, KCNMB1, KRT14, KRT17, KRT34, LAMC2, TMEM119, IGFL3, LOC92196, MFAP5, MEOX1, MEOX2, MX1, MYH3, MYH11, MYL4, IL32, NLGN4X, NPAS1, NPPB, OLR1, PAX2, PAX9, PENK, PITX2, PRELP, PROM1, RARRES1, SFRP2, SMOC2, STMN2, TAC1, RSPO3, THY1, TNFSF7, TNNT2, TRH, TUBB4, UGT2B7 and ZD52F10.
The cell line EN5 is positive for the markers: COL21A1, DLK1, FMO3, FOXF1, FOXF2, FST, HTRA3, IGF2, IL1R1, KIAA0644, TMEM119, MGP, MSX1, MSX2, OGN, PRRX1 and PRRX2 and are negative for the markers: ACTC, AGC1, AKR1C1, ALDH1A1, ANXA8, AQP1, AREG, BMP4, C3, C6, C7, C20orf103, CCDC3, CD24, CDH3, CLDN11, CNTNAP2, COMP, CRIP1, CRLF1, CRYAB, CXADR, DKK2, GABRB1, GAP43, GDF10, GJB2, GSC, HOXA5, HSD11B2, HSD17B2, HSPA6, HSPB3, ID4, IFI27, INA, KCNMB1, KRT14, KRT17, KRT34, LAMC2, IGFL3, LOC92196, MFAP5, MEOX1, MEOX2, MMP1, MX1, MYH3, MYH11, MYL4, IL32, NLGN4X, NPAS1, NPPB, PAX2, PAX9, PENK, PITX2, PRELP, PRG4, PROM1, RASD1, RELN, RGS1, SMOC1, SMOC2, STMN2, SYT12, TAC1, TFPI2, RSPO3, THY1, TNFSF7, TNNT2, TRH, TUBB4, UGT2B7, ZD52F10 and ZIC1.
The cell line EN50 is positive for the markers: BEX1, CDH6, COL21A1, DIO2, FMO1, FOXF1, FOXF2, FST, GDF5, HTRA3, IGF2, IGFBP5, IL1R1, KRT19, TMEM119, MASP1, MGP, MSX1, PODN, PRRX2, PTPRN, SERPINA3, SOD3, WISP2, ZIC1 and ZIC2 and are negative for the markers: ACTC, AGC1, ALDH1A1, APCDD1, AQP1, BMP4, C3, C6, C20orf103, CDH3, CLDN11, CNTNAP2, COMP, DKK2, DPT, EGR2, EMID1, TMEM100, GABRB1, GAP43, GDF10, GSC, HOXA5, HSD11B2, HSPA6, HSPB3, IF127, KIAA0644, KRT17, KRT34, IGFL3, LOC92196, MFAP5, MEOX1, MEOX2, MX1, MYBPH, MYH3, MYH11, NLGN4X, NPPB, OGN, OSR2, PAX2, PAX9, PDE1A, PENK, PITX2, PRELP, PROM1, PRRX1, RARRES1, RASD1, RGS1, SMOC2, SNAP25, STMN2, SYT12, TAC1, RSPO3, TNFSF7, TNNT2, TRH, TUBB4, UGT2B7 and ZD52F10.
The cell line EN51 is positive for the markers: CDH6, DLK1, FMO1, FMO3, FOXF1, FST, HTRA3, IGF2, IL1R1, MSX1, MSX2, PTN, SERPINA3, SOD3, TSLP, ZIC1 and ZIC2 and are negative for the markers: ACTC, AGC1, AKR1C1, ALDH1A1, ANXA8, APCDD1, AQP1, ATP8B4, CFB, C3, C6, C20orf103, CCDC3, CD24, CDH3, CLDN11, CRIP1, CRYAB, CXADR, DIO2, DKK2, DPT, EMID1, TMEM100, FOXF2, GABRB1, GSC, HOXA5, HSD11B2, HSD17B2, HSPA6, HSPB3, ID4, IF127, INA, KCNMB1, KRT14, KRT17, KRT19, KRT34, LAMC2, IGFL3, LOC92196, MFAP5, MEOX1, MEOX2, MGP, MMP1, MX1, MYH3, MYH11, MYL4, IL32, NLGN4X, NPAS1, NPPB, OLR1, PAX2, PAX9, PDE1A, PENK, PITX2, PRELP, PROM1, PTGS2, RARRES1, RASD1, RELN, RGS1, SFRP2, SMOC2, STMN2, TAC1, RSPO3, THY1, TNFSF7, TNNT2, TRH, TUBB4, UGT2B7 and ZD52F10.
The cell line EN53 is positive for the markers: BEX1, COL21A1, FST, GDF5, HTRA3, ICAM5, KRTI9, TMEM119, PTPRN, SERPINA3, SOD3 and ZIC2 and are negative for the markers: ACTC, AGC1, ALDH1A1, APCDD1, AQP1, ATP8B4, BMP4, C3, C6, C7, C20orf103, CCDC3, CDII3, CLDN11, CNTNAP2, COP1, CRYAB, DIO2, DKK2, DPT, EMID1, FGFR3, TMEM100, FMO3, FOXF2, GABRB1, GAP43, GJB2, GSC, HOXA5, HSPA6, HSPB3, ID4, IFI27, INA, KCNMB1, KIAA0644, KRT14, KRT17, KRT34, IGFL3, LOC92196, MFAP5, MEOX1, MEOX2, MGP, MMP1, MX1, MYBPH, MYH3, MYH11, MYL4, IL32, NLGN4X, NPPB, OGN, OLR1, OSR2, PAX2, PAX9, PDE1A, PENK, PITX2, POSTN, PRELP, PROM1, PTN, RASD1, RELN, RGS1, SLITRK6, SMOC2, STMN2, SYT12, TAC1, RSPO3, THY1, TNFSF7, TNNT2, TRH, TUBB4, UGT2B7, ZD52F10 and ZIC1.
The cell line EN55 is positive for the markers: DIO2, FOXF1, FOXF2, FST, GDF5, HTRA3, IGF2, IL1R1, KIAA0644, MGP, MSX2, PODN, PRRX2, PTN, SLITRK6 and SRCRB4D and are negative for the markers: ACTC, AGC1, AKR1C1, ALDH1A1, ANXA8, AQP1, ATP8B4, CFB, BMP4, C6, C7, C20orf103, CCDC3, CD24, CDH3, CLDN11, CNTNAP2, CRIP1, CRYAB, DKK2, FGFR3, FMO1, GABRB1, GAP43, GDF10, GSC, HOXA5, HSD11B2, HSD17B2, HSPA6, HSPB3, ICAM5, ID4, IFI27, INA, KCNMB1, KRT14, KRT17, KRT34, LAMC2, IGFL3, LOC92196, MFAP5, MEOX1, MEOX2, MX1, MYBPH, MYH3, MYH11, MYL4, IL32, NLGN4X, NPAS1, NPPB, OLR1, PAX2, PAX9, PENK, PITX2, POSTN, PROM1, PRRX1, PTGS2, RARRES1, RASD1, RELN, RGS1, SFRP2, SMOC1, SMOC2, SOD3, STMN2, SYT12, TAC1, RSPO3, THY1, TNFSF7, TNNT2, TRH, TUBB4, UGT2B7, ZD52F10, ZIC1 and ZIC2.
The group of cell lines H9.Biol and H9.Bio2 are positive for the markers: ACTC, BEX1, CD24, CDH3, CNTNAP2, CXADR, METTL7A, FGFR3, FST, GAP43, INA, KRT19, NLGN4X, PROM1, PTN, PTPRN, RGMA, SFRP2, SOX11, SRCRB4D, ZD52F10 and ZIC2 and are negative for the markers: AGC1, ALDH1A1, ANXA8, APCDD1, AQP1, AREG, ATP8B4, CFB, C6, C7, PRSS35, C20orf103, CDH6, CLDN11, COL15A1, COL21A1, COP1, DIO2, DKK2, DPT, EGR2, TMEM100, FMO1, FMO3, FOXF1, FOXF2, GABRB1, GDF10, GJB2, HSD17B2, HSPA6, HSPB3, IFI27, IFIT3, IGF2, IL1R1, KRT14, KRT17, KRT34, TMEM119, IGFL3, LOC92196, MEOX1, MEOX2, MGP, MMP1, MSX1, MSX2, MX1, MYBPH, MYH3, MYH11, OGN, OLR1, OSR2, PAX2, PAX9, PDE1A, PENK, POSTN, PRELP, PRG4, PRRX1, PTGS2, RARRES1, RELN, RGS1, SERPINA3, SLITRK6, SMOC1, SNAP25, RSPO3, TNFSF7, TNNT2, TRH, TUBB4, UGT2B7 and WISP2.
The cell line J13 is positive for the markers: CDH6, CLDN11, FST, GDF5, IGF2, MMP1, PRRX1, PRRX2, RGMA, SLITRK6, TFPI2 and ZIC2 and are negative for the markers: ACTC, ACG1, ALDH1A1, ANXA8, AQP1, TABLE I-continued Exemplary progenitor cell lines and associated gene expression markers at 18-21 doublings of clonal expansion AREG, ATP8B4, CFB, C3, C6, PRSS35, C20orf103, CCDC3, CD24, CDH3, CNTNAP2, COL15A1, COMP, COP1, CRLF1, CRYAB, DIO2, METTL7A, DKK2, DLK1, DPT, EGR2, EMID1, FGFR3, TMEM100, FMO1, FOXF1, GABRB1, GAP43, GDF10, GSC, HOXA5, HSD11B2, HSD17B2, HSPA6, HSPB3, ID4, IFI27, IGFBP5, KCNMB1, KIAA0644, KRT14, KRT17, KRT34, LAMC2, IGFL3, LOC92196, MFAP5, MEOX1, MEOX2, MGP, MYBPH, MYH3, MYH11, MYL4, IL32, NPAS1, NPPB, OGN, OLR1, PAX2, PAX9, PENK, PITX2, POSTN, PRELP, PRG4, PROM1, PTGS2, PTPRN, RARRES1, RASD1, RELN, RGS1, RPS4Y2, SFRP2, SMOC1, SMOC2, SRCRB4D, STMN2, TAC1, RSPO3, THY1, TNFSF7, TNNT2, TRH, TUBB4, UGT2B7, ZD52F10 and ZIC1.

The cell line J16Bio2 is positive for the markers: BEX1, BMP4, CCDC3, CDH6, CLDN11, COL21A1, CRYAB, FMO3, FST, ICAM5, IGF2, KRT17, TMEM119, POSTN, SERPINA3, SFRP2, SYT12, TFPI2, UGT2B7 and ZIC2 and are negative for the markers: AGC1, ALDH1A1, APCDD1, AQP1, AREG, ATP8B4, C3, C6, C20orf103, CD24, CDH3, CNTNAP2, COMP, CRLF1, METTL7A, DLK1, DPT, EMID1, FGFR3, TMEM100, FMO1, FOXF1, FOXF2, GABRB1, GAP43, GDF10, GJB2, GSC, HOXA5, HSD11B2, HSPA6, HSPB3, HTRA3, ID4, IFI27, KIAA0644, KRT14, KRT34, IGFL3, LOC92196, MEOX1, MEOX2, MSX1, MYBPH, MYH3, NLGN4X, NPPB, OGN, PAX2, PAX9, PDE1A, PENK, PITX2, PRELP, PRG4, PROM1, PTPRN, RARRES1, RASD1, RELN, RGS1, SMOC1, SMOC2, STMN2, TAC1, THY1, TNFSF7, TRH, TUBB4, WISP2 and ZD52F10.

The cell line J8 is positive for the markers: BEX1, BMP4, CLDN11, CRYAB, IGF2, INA, KRT19, MX1, IL32, TAGLN3, SFRP2, TSLP and UGT2B7 and is negative for the markers: AGC1, ALDH1A1, ANXA8, APCDD1, ATP8B4, CFB, C3, C6, C7, C20orf103, CCDC3, CDH3, CNTNAP2, COL15A1, COL21A1, COMP, COP1, CRLF1, DIO2, METTL7A, DKK2, DLK1, DPT, EGR2, EMID1, FGFR3, TMEM100, FMO1, FMO3, FOXF1, FOXF2, GABRB1, GAP43, GSC, HOXA5, HSD11B2, HSPA6, HSPB3, ID4, IFI27, IGFBP5, KCNMB1, KIAA0644, KRT14, KRT34, IGFL3, LOC92196, MFAP5, MASP1, MEOX1, MEOX2, MGP, MMP1, MSX1, MYH3, MYH11, MYL4, NPAS1, NPPB, OGN, OLR1, OSR2, PAX2, PAX9, PENK, PITX2, PRELP, PROM1, PRRX1, PTGS2, PTN, PTPRN, RARRES1, RGMA, RGS1, SLITRK6, SMOC1, SMOC2, SNAP25, STMN2, TAC1, TNNT2, TRH, TUBB4, WISP2 and ZD52F10.

The cell line MW1 is positive for the markers: APCDD1, BEX1, BMP4, C3, CD24, CDH3, CRLF1, CRYAB, DIO2, METTL7A, TMEM100, FOXF1, FST, GJB2, IGF2, IGFBP5, IL1R1, KIAA0644, KRT19, TMEM119, OLR1, PODN, PROM1, SERPINA3, SNAP25, SRCRB4D, STMN2, TFPI2 and THY1 and are negative for the markers: ACTC, AGC1, AKR1C1, ALDH1A1, AQP1, AREG, ATP8B4, C6, C7, PRSS35, C20orf103, CCDC3, CDH6, CLDN11, CNTNAP2, COL15A1, COL21A1, COMP, COP1, CXADR, DKK2, DPT, EGR2, EMID1, FGFR3, FMO1, FMO3, FOXF2, GABRB1, GAP43, GDF5, GDF10, GSC, HOXA5, HSD11B2, HSD17B2, HSPA6, HSPB3, HTRA3, ICAM5, ID4, IFI27, INA, KCNMB1, KRT14, KRT17, KRT34, IGFL3, LOC92196, MFAP5, MASP1, MEOX1, MEOX2, MGP, MMP1, MSX2, MYBPH, MYH3, MYH11, MYL4, IL32, NLGN4X, TAGLN3, NPAS1, NPPB, OGN, OSR2, PAX2, PAX9, PENK, POSTN, PRELP, PRG4, PRRX1, PRRX2, PTGS2, PTPRN, RARRES1, RELN, RGS1, SFRP2, SLITRK6, SMOC1, SMOC2, SOD3, SYT12, TAC1, RSPO3, TNFSF7, TNNT2, TRH, TSLP, TUBB4, UGT2B7, WISP2, ZD52F10, ZIC1 and ZIC2.

The cell line MW2 is positive for the markers: C6, C7, CRLF1, DIO2, METTL7A, FMO1, FMO3, FOXF1, FOXF2, HTRA3, IGF2, IL1R1, TMEM119, MGP, OGN, PRRX2, RGMA, SFRP2, SYT12 and TFPI2 and are negative for the markers: ACTC, AGC1, AKR1C1, ALDH1A1, ANXA8, AQP1, AREG, CFB, C3, C20orf103, CCDC3, CD24, CDH3, CNTNAP2, COMP, COP1, CRYAB, CXADR, DKK2, DLK1, EMID1, FGFR3, GABRB1, GAP43, GDF5, GDF10, GSC, HOXA5, HSD17B2, HSPA6, HSPB3, ICAM5, ID4, IFI27, INA, KCNMB1, KRT14, KRT17, KRT34, LAMC2, IGFL3, LOC92196, MFAP5, MEOX1, MEOX2, MMP1, MSX1, MX1, MYBPH, MYH3, MYH11, MYL4, IL32, NPAS1, NPPB, OLR1, OSR2, PAX2, PAX9, PENK, PITX2, POSTN, PROM1, PRRX1, PTPRN, RASD1, RELN, RGS1, SMOC1, SMOC2, STMN2, THY1, TNFSF7, TNNT2, TRH, TUBB4, UGT2B7, ZD52F10, ZIC1 and ZIC2.

The cell line MW6 is positive for the markers: BEX1, C6, C7, DIO2, DPT, FOXF1, FST, HTRA3, IGF2, IL1R1, TMEM119, PITX2, POSTN, PRRX2, SERPINA3, SFRP2, SRCRB4D and SYT12 and are negative for the markers: AGC1, ALDH1A1, ANXA8, AQP1, ATP8B4, CFB, BMP4, C20orf103, CCDC3, CDH3, CNTNAP2, COP1, CXADR, DKK2, DLK1, EMID1, FGFR3, TMEM100, GABRB1, GDF10, GSC, HSD11B2, HSD17B2, HSPA6, HSPB3, ID4, IFI27, IFIT3, INA, KCNMB1, KRT14, KRT17, KRT34, IGFL3, LOC92196, MFAP5, MEOX1, MEOX2, MMP1, MSX1, MX1, MYH3, MYH11, MYL4, IL32, NLGN4X, NPPB, OLR1, PAX2, PAX9, PENK, PRELP, PROM1, PRRX1, RARRES1, RASD1, RELN, RGS1, SLITRK6, SMOC1, SMOC2, SNAP25, TAC1, TFPI2, THY1, TNFSF7, TNNT2, TRH, TSLP, TUBB4, UGT2B7, ZIC1 and ZIC2.

The cell line Q4 is positive for the markers: AREG, BEX1, CRYAB, FMO1, FST, HTRA3, ICAM5, IGF2, IL1R1, KRT19, TMEM119, PTPRN, SERPINA3, SOD3, SRCRB4D, ZD52F10 and ZIC2 and are negative for the markers: ACTC, AGC1, ALDH1A1, ANXA8, APCDD1, ATP8B4, CFB, BMP4, C20orf103, CCDC3, CDH3, CDH6, CLDN11, CNTNAP2, COL15A1, COMP, COP1, DIO2, DKK2, DPT, EGR2, EMID1, FMO3, GAP43, GDF10, GJB2, GSC, HOXA5, HSD17B2, HSPA6, HSPB3, ID4, IFIT3, INA, KCNMB1, KIAA0644, KRT17, KRT34, IGFL3, LOC92196, MEOX1, MEOX2, MGP, MMP1, MSX2, MX1, MYBPH, MYH3, MYH11, NLGN4X, NPPB, OGN, OLR1, OSR2, PAX2, PAX9, PENK, PROM1, PRRX2, PTGS2, RARRES1, RELN, RGMA, RGS1, SLITRK6, SMOC1, SMOC2, STMN2, SYT12, TAC1, RSPO3, THY1, TNFSF7, TNNT2, TRH, TSLP, TUBB4 and UGT2B7.

The cell line Q6 is positive for the markers: AREG, BEX1, COL21A1, DLK1, FMO1, FST, GDF10, ICAM5, IL1R1, TMEM119, MYL4, OGN, POSTN, SERPINA3, SFRP2, SOD3, SRCRB4D, ZIC1 and ZIC2 and are negative for the markers: AGC1, ALDH1A1, ANXA8, AQP1, ATP8B4, CFB, C3, C6, C20orf103, CD24, CDH3, CDH6, CLDN11, CNTNAP2, COMP, COP1, CXADR, DIO2, DKK2, DPT, EMID1, FGFR3, FMO3, FOXF1, FOXF2, GABRB1, GJB2, GSC, HOXA5, HSD11B2, HSD17B2, HSPA6, IFI27, INA, KCNMB1, KIAA0644, KRT17, KRT19, KRT34, IGFL3, LOC92196, MFAP5, MASP1, MEOX1, MEOX2, MMP1, MX1, MYBPH, MYH3, MYH11, IL32, NLGN4X, NPPB, OLR1, OSR2, PAX2, PAX9, PENK, PITX2, PRELP, PROM1, PTN, PTPRN, RARRES1, RASD1, RELN, RGS1, SMOC1, SMOC2, SYT12, TAC1, TFPI2, RSPO3, THY1, TNFSF7, TNNT2, TRH, TUBB4 and WISP2.

The cell line Q7 is positive for the markers: AREG, BEX1, COL15A1, COL21A1, COMP, EGR2, FST, GDF10, HSD17B2, IGF2, SERPINA3, ZIC1 and ZIC2 and is negative for the markers: ACTC, AGC1, AKR1C1, ALDH1A1, AQP1, ATP8B4, CFB, C3, C6, C7, PRSS35, C20orf103, CCDC3, CD24, CDH3, CLDN11, CNTNAP2, DIO2, DKK2, DLK1, EMID1, FGFR3, TMEM100, FMO1, FMO3, GABRB1, GDF5, GJB2, GSC, HOXA5, HSD11B2, HSPA6, HSPB3, ID4, IFI27, KCNMB1, KIAA0644, KRT14, KRT17, KRT34, IGFL3, LOC92196, MFAP5, MASP1, MEOX1, MEOX2, MGP, MMP1, MSX2, MX1, MYBPH, MYH3, MYH11, IL32, TABLE I-continued Exemplary progenitor cell lines and associated gene expression markers at 18-21 doublings of clonal expansion NLGN4X, NPAS1, NPPB, OGN, OLR1, OSR2, PAX2, PAX9, PDE1A, PENK, P1TX2, PODN, POSTN, PRELP, PROM1, PRRX2, PTGS2, PTN, RARRES1, RASD1, RELN, RGMA, RGS1, SLITRK6, SMOC2, SNAP25, STMN2, TAC1, RSPO3, THY1, TNFSF7, TNNT2, TRH, TUBB4, UGT2B7 and WISP2.

The cell line RAD20.16 is positive for the markers: ACTC, CD24, CRIP1, CRYAB, FST, HOXA5, HTRA3, KRT19, LAMC2, MFAP5, MASP1, MGP, MMP1, MSX1, POSTN, S100A4, SRCRB4D and THY1 and is negative for the markers: AGC1, ALDH1A1, AQP1, AREG, ATP8B4, CFB, C6, C7, C20orf103, CCDC3, CDH3, CLDN11, CNTNAP2, COL15A1, COL21A1, CRLF1, DLK1, DPT, TMEM100, FMO1, FMO3, FOXF2, GABRB1, GDF10, GJB2, GSC, HSD11B2, HSD17B2, HSPA6, HSPB3, IFI27, IGF2, KCNMB1, KRT14, TMEM119, IGFL3, LOC92196, MEOX1, MEOX2, MSX2, MX1, MYH3, MYH11, NLGN4X, NPPB, OGN, OSR2, PAX2, PAX9, PDE1A, PENK, PRG4, PROM1, PRRX1, RARRES1, RASD1, RGS1, SFRP2, SMOC1, SMOC2, SOD3, STMN2, TAC1, TFPI2, RSPO3, TRH, TSLP, TUBB4, UGT2B7, WISP2, ZIC1 and ZIC2.

The cell line RAD20.19 is positive for the markers: ACTC, BEX1, CD24, CRIP1, CRYAB, FST, HOXA5, INA, KRT19, KRT34, LAMC2, MFAP5, MASP1, MMP1, MSX1, NPPB, PTPRN and THY1 and is negative for the markers: AGC1, ALDH1A1, APCDD1, AQP1, AREG, ATP8B4, CFB, C6, C7, C20orf103, CDH3, CNTNAP2, COL15A1, COL21A1, COP1, CRLF1, DIO2, METTL7A, DKK2, DLK1, DPT, EGR2, EMID1, TMEM100, FMO1, FMO3, FOXF2, GABRB1, GDF10, GJB2, GSC, HSD11B2, HSD17B2, HSPA6, HSPB3, ID4, IFI27, IGF2, KIAA0644, KRT14, KRT17, IGFL3, LOC92196, MEOX1, MEOX2, MGP, MX1, MYBPH, MYH3, NLGN4X, OGN, OSR2, PAX2, PAX9, PDE1A, PENK, PROM1, PRRX1, PTN, RARRES1, RASD1, RGMA, RGS1, SFRP2, SLITRK6, SMOC1, SMOC2, SNAP25, STMN2, SYT12, TAC1, RSPO3, TNFSF7, TRH, TSLP, TUBB4, WISP2, ZIC1 and ZIC2.

The cell line RAD20.5 is positive for the markers: AKR1C1, GRIP1, METTL7A, FOXF1, HOXA5, HTRA3, KIAA0644, KRT19, MASP1, MMP1, MSX1, POSTN, PTPRN, S100A4, SRCRB4D and THY1 and is negative for the markers: AGC1, ALDH1A1, ANXA8, APCDD1, AQP1, AREG, ATP8B4, BEA1, CFB, C6, C7, PRSS35, C20orf103, CCDC3, CDH3, CLDN11, CNTNAP2, COL15A1, COL21A1, COMP, CRLF1, CNTNAP2, DKK2, DLK1, DPT, EGR2, EMID1, TMEM100, FMO1, FMO3, FOXF2, GAP43, GDF10, GSC, HSD11B2, HSD17B2, HSPA6, HSPB3, ID4, IGF2, KCNMB1, KRT14, KRT34, IGFL3, LOC92196, MEOX1, MEOX2, MGP, MSX2, MYBPH, MYH3, MYH11, MYL4, IL32, NLGN4X, NPAS1, NPPB, OGN, PAX2, PAX9, PDE1A, PENK, PRELP, PRG4, PROM1, RARRES1, RGMA, RGS1, SFRP2, SLITRK6, SMOC1, SMOC2, SOD3, STMN2, SYT12, TAC1, TRH, TSLP, TUBB4, UGT2B7, WISP2, ZIC1 and ZIC2.

The cell line RAPEND17 is positive for the markers: ANXA8, BEX1, C3, CD24, CRIP1, CRYAB, METTL7A, FST, HOXA5, HTRA3, ICAM5, IFIT3, IGF2, IL1R1, KRT19, LAMC2, MFAP5, MASP1, OLR1, POSTN, PTN, PTPRN and TFPI2 and is negative for the markers: ACTC, AGC1, APCDD1, AQP1, ATP834, CFB, C6, C7, PRSS35, C20orf103, CCDC3, CDH3, CDH6, CLDN11, CNTNAP2, COL15A1, COL21A1, DKK2, DLK1, DPT, EGR2, EMID1, TMEM100, FMO1, FMO3, FOXF2, GABRB1, GAP43, GDF10, GSC, HSD11B2, HSD17B2, HSPA6, HSPB3, ID4, KCNMB1, KRT14, KRT17, IGFL3, LOC92196, MEOX1, MEOX2, MGP, MSX2, MYH3, MYH11, NLGN4X, OGN, OSR2, PAX2, PAX9, PDE1A, PENK, PRELP, PROM1, PRRX1, PRRX2, RARRES1, RELN, RGMA, RGS1, SFRP2, SLITRK6, SMOC1, SMOC2, SOD3, SYT12, TAC1, RSPO3, THY1, TNFSF7, TNNT2, TRH, TSLP, TUBB4, UGT2B7, WISP2, ZD52F10, ZIC1 and ZIC2.

The cell line RASKEL18 is positive for the markers: AREG, CD24, CRYAB, METTL7A, DPT, FST, GJB2, HTRA3, IGF2, IGFBP5, IL1R1, PTN, PTPRN, SERPINA3, SOX11, SRCRB4D and RSPO3 and is negative for the markers: ACTC, AKR1C1, ALDH1A1, ANXA8, AQP1, CFB, C7, PRSS35, C20orf103, CDH6, CLDN11, CNTNAP2, COMP, COP1, DIO2, DKK2, DLK1, EGR2, EMID1, FGFR3, FMO1, FMO3, GAP43, GDF10, GSC, HSD11B2, HSD17B2, HSPA6, HSPB3, IFI27, INA, KCNMB1, KRT14, KRT17, KRT34, TMEM119, IGFL3, LOC92196, MFAP5, MASP1, MEOX1, MEOX2, MMP1, MSX2, MYBPH, MYH3, MYH11, MYL4, IL32, NLGN4X, TAGLN3, NPAS1, NPPB, OGN, OLR1, PAX2, PAX9, PENK, PRELP, PRG4, PROM1, PRRX1, PRRX2, PTGS2, RARRES1, RASD1, RELN, RGMA, RGS1, SLITRK6, SMOC1, SMOC2, STMN2, SYT12, TAC1, TFPI2, THY1, TNFSF7, TNNT2, TRH, TSLP, TUBB4, WISP2, ZIC1 and ZIC2.

The cell line RASKEL6 is positive for the markers: AREG, BEX1, C3, CRLF1, CRYAB, METTL7A, FST, HTRA3, IGF2, IL1R1, TMEM119, PITX2, SERPINA3 and TFPI2 and is negative for the markers: ACTC, AKR1C1, ALDH1A1, ANXA8, AQP1, CFB, BMP4, C6, CCDC3, CDH3, CDH6, CLDN11, CNTNAP2, COL15A1, COMP, COP1, CXADR, DKK2, DLK1, EGR2, EMID1, FMO1, FMO3, FOXF2, GAP43, GDF10, GSC, HSD17B2, HSPA6, ID4, IFI27, IFIT3, IGFBP5, INA, KIAA0644, KRT17, KRT34, LAMC2, IGFL3, LOC92196, MFAP5, MASP1, MEOX1, MEOX2, MMP1, MSX2, MYBPH, MYH3, MYH11, IL32, NLGN4X, TAGLN3, NPAS1, NPPB, OGN, OLR1, OSR2, PAX2, PAX9, PENK, POSTN, PRELP, PROM1, PRRX1, PRRX2, RARRES1, RELN, RGMA, RGS1, SLITRK6, SMOC1, SMOC2, STMN2, SYT12, TAC1, RSPO3, THY1, TNFSF7, TRH, TUBB4, UGT2B7, WISP2, ZIC1 and ZIC2.

The cell line RASKEL8 is positive for the markers: AREG, BEX1, C7, CRIP1, CRLF1, CRYAB, EST, HOXA5, HTRA3, ICAM5, IGF2, IL1R1, KRT19, LAMC2, PITX2, POSTN, PTPRN, SERPINA3 and TFPI2 and is negative for the markers: ACTC, AGC1, ALDH1A1, AQP1, ATP8B4, CFB, C6, PRSS35, C20orf103, CCDC3, CDH3, CDH6, CLDN11, CNTNAP2, COMP, COP1, DKK2, DLK1, DPT, EMID1, FMO1, FMO3, FOXF2, GABRB1, GAP43, GDF10, GSC, HSD11B2, HSD17B2, HSPA6, HSPB3, IFI27, IGFBP5, KCNMB1, KIAA0644, KRT14, KRT17, KRT34, IGFL3, LOC92196, MEOX1, MEOX2, MGP, MMP1, MSX2, MX1, MYH3, MYH11, NLGN4X, TAGLN3, NPPB, OGN, OSR2, PAX2, PAX9, PDE1A, PENK, PRELP, PRG4, PROM1, PRRX1, PRRX2, PTN, RARRES1, RELN, RGMA, RGS1, SFRP2, SLITRK6, SMOC1, SMOC2, SNAP25, STMN2, SYT12, TAC1, RSPO3, TNFSF7, TNNT2, TRH, TSLP, TUBB4, WISP2, ZIC1 and ZIC2.

The cell line SK1 is positive for the markers: AKR1C1, BEX1, C6, C7, COL21A1, CRIP1, METTL7A, DLK1, TMEM100, FMO1, FMO3, FOXF2, FST, HSD11B2, HTRA3, ICAM5, IGF2, IL1R1, TMEM119, MGP, MSX1, PRG4, PTN, PTPRN, S100A4, SERPINA3, SFRP2, SOD3, SOX11, WISP2 and ZIC1 and is negative for the markers: AGC1, ALDH1A1, ANXA8, AQP1, ATP8B4, BMP4, C20orf103, CD24, CDH3, CDH6, CLDN11, CNTNAP2, COMP, COP1, CRLF1, DKK2, EGR2, EMID1, FGFR3, GABRB1, GAP43, GDP10, GJB2, GSC, HOXA5, HSD17B2, HSPA6, ID4, IFI27, IFIT3, INA, KCNMB1, KRT14, KRT17, KRT19, KRT34, LAMC2, IGFL3, LOC92196, MFAP5, MASP1, MEOX1, MEOX2, MMP1, MSX2, MX1, MYBPH, MYH11, IL32, NLGN4X, NPAS1, NPPB, OLR1, PAX2, PAX9, PENK, PITX2, POSTN, PRELP, PROM1, RARRES1, RGS1, SMOC2, SYT12, TFPI2, RSPO3, THY1, TNNT2, TRH, TSLP, TUBB4 and ZIC2.

The group of cell lines SK10Bio1 and SK10Bio2 are positive for the markers: BEX1, COL21A1, FST, ICAM5, ILIR1, TMEM119, SERPINA3 and ZIC2 and are negative for the markers: Acid, AGC1, ALDH1A1, AQP1, CFB, BMP4, C3, C6, C20orf103, CDH3, CLDN11, CNTNAP2, DKK2, DPT, EMID1, TMEM100, FMO3, TABLE I-continued Exemplary progenitor cell lines and associated gene expression markers at 18-21 doublings of clonal expansion GABRB1, GAP43, GSC, HOXA5, HSPA6, ID4, IFI27, KIAA0644, KRT14, KRT34, IGFL3, LOC92196, MFAP5, MEOX1, MEOX2, MX1, MYBPH, MYH3, MYH11, NLGN4X, NPPB, OLR1, PAX2, PAX9, PDE1A, PENK, PROM1, RARRES1, RASD1, RELN, RGS1, SLITRK6, SMOC1, SMOC2, STMN2, SYT12, TAC1, RSPO3, THY1, TNNT2 and TUBB4.

The group of cell lines SK11, SK44, SK50 and SK52 are positive for the markers: BEX1, COL21A1, FST, ICAM5, IL1R1, TMEM119, PTPRN, SERPINA3, SFRP2 and ZIC1 and are negative for the markers: ACTC, AGC1, ALDH1A1, AQP1, ATP8B4, C6, C20orf103, CCDC3, CDH3, CLDN11, CNTNAP2, DIO2, DKK2, EMID1, GABRB1, GSC, HOXA5, HSPA6, IFI27, INA, KRT14, KRT34, IGFL3, LOC92196, MEOX1, MEOX2, MMP1, MX1, MYH3, MYH11, IL32, NLGN4X, NPPB, OLR1, PAX2, PAX9, PDE1A, PENK, PROM1, PTN, RARRES1, RASD1, RELN, RGS1, SMOC1, SMOC2, STMN2, TAC1, TFPI2, RSPO3, TNFSF7, TNNT2, TRH and TUBB4.

The group of cell lines SK14, SK53, SK60 and SK61 are positive for the markers: C7, COL21A1, CRYAB, HTRA3, IL1R1, MGP, PTPRN, RGMA, SERPINA3 and SFRP2 and are negative for the markers: ACTC, AGC1, ALDH1A1, ANXA8, AQP1, ATP8B4, CFB, BMP4, CCDC3, CDH3, CNTNAP2, COP1, CXADR, DKK2, GABRB1, GAP43, GDF10, GJB2, GSC, HOXA5, HSD17B2, IFI27, IFIT3, KRT14, KRT17, KRT34, IGFL3, LOC92196, MFAP5, MEOX1, MEOX2, MMP1, MX1, MYBPH, MYH3, MYH11, IL32, NLGN4X, NPPB, OLR1, PAX2, PAX9, PENK, PROM1, RASD1, RELN, RGS1, SLITRK6, SMOC1, SMOC2, STMN2, TAC1, RSPO3, TNNT2, TRH, TUBB4, UGT2B7, ZIC1 and ZIC2.

The cell line SK17 is positive for the markers: ACTC, APCDD1, BEX1, COL21A1, METTL7A, DLK1, FST, HOXA5, HSPB3, HTRA3, IGF2, IL1R1, KIAA0644, MASP1, MGP, MYBPH, MYH3, NLGN4X, PDE1A, PTN, RGMA, SRCRB4D, STMN2, RSPO3 and TNNT2 and is negative for the markers: AGC1, AKR1C1, ALDH1A1, ANXA8, AQP1, CFB, C6, C20orf103, CCDC3, CDH3, CDH6, CLDN11, CNTNAP2, COL15A1, COMP, COP1, CRLF1, DKK2, DPT, TMEM100, FMO1, FMO3, FOXF2, GABRB1, GDF10, GSC, HSD17B2, HSPA6, ID4, IFI27, INA, KCNMB1, KRT14, KRT34, LAMC2, TMEM119, IGFL3, LOC92196, MFAP5, MEOX1, MEOX2, MMP1, MX1, MYH11, IL32, NPAS1, NPPB, OLR1, PAX2, PAX9, PENK, PITX2, PRELP, RASD1, RELN, RGS1, S100A4, SLITRK6, SMOC1, SMOC2, TAC1, THY1, TNFSF7, TRH, TSLP, TUBB4, UGT2B7, WISP2, ZIC1 and ZIC2.

The cell line SK18 is positive for the markers: APCDD1, COL21A1, METTL7A, FMO1, FOXF1, FST, HTRA3, IGF2, IL1R1, TMEM119, OGN, PITX2, PRRX1, RGMA, SERPINA3, SFRP2, SOD3 and TSLP and is negative for the markers: ACTC, AGC1, AKR1C1, ALDH1A1, ANXA8, AQP1, AREG, ATP8B4, CFB, BMP4, C3, C6, C7, C20orf103, CCDC3, CD24, CDH3, CNTNAP2, COP1, CXADR, DIO2, DKK2, DLK1, DPT, EMID1, TMEM100, GABRB1, GAP43, GDF5, GDF10, GJB2, GSC, HOXA5, HSD17B2, HSPA6, HSPB3, ID4, IEI27, INA, KIAA0644, KRT14, KRT17, KRT19, KRT34, LAMC2, IGFL3, LOC92196, MFAP5, MEOX1, MEOX2, MMP1, MSX1, MX1, MYBPH, MYH3, MYH11, MYL4, IL32, NLGN4X, NPPB, OLR1, OSR2, PAX2, PAX9, PDE1A, PENK, PRELP, PROM1, RARRES1, RASD1, RELN, RGS1, SLITRK6, SMOC1, SMOC2, STMN2, TAC1, TFPI2, RSPO3, THY1, TNFSF7, TNNT2, TRH, TUBB4, UGT2B7, ZIC1 and ZIC2.

The cell line SK26 is positive for the markers: APCDD1, BEX1, COL21A1, CRYAB, FMO1, FOXF2, FST, HTRA3, ICAM5, IL1R1, TMEM119, PRRX1, PTPRN, SERPINA3 and SFRP2 and is negative for the markers: ACTC, AGC1, ALDH1A1, ANXA8, AQP1, AREG, ATP8B4, CFB, BMP4, C3, C6, C7, C20orf103, CCDC3, CD24, CDH3, CLDN11, CNTNAP2, COP1, CXADR, DKK2, DLK1, DPT, EGR2, EMID1, FGFR3, GABRB1, GAP43, GDF10, GJB2, GSC, HOXA5, HSD17B2, HSPA6, IF127, IFIT3, KIAA0644, KRT14, KRT17, KRT34, IGFL3, LOC92196, MFAP5, MEOX1, MEOX2, MMP1, MX1, MYBPH, MYH3, MYH11, MYL4, IL32, NLGN4X, NPPB, OLR1, OSR2, PAX2, PAX9, PDE1A, PENK, PITX2, POSTN, PROM1, PTN, RARRES1, RASD1, RELN, RGS1, SLITRK6, SMOC1, SMOC2, SNAP25, STMN2, TACT, TFP12, RSPO3, THY1, TNFSF7, TNNT2, TRH, TUBB4, UGT2B7 and ZIC1.

The group of cell lines SK27 and T7 are positive for the markers: BEX1, PRSS35, CCDC3, CDH6, COL21A1, CRIP1, CRYAB, GAP43, IGF2, KRT19, LAMC2, POSTN, S100A4, SFRP2, SOX11 and ZIC2 and are negative for the markers: AGC1, ALDH1A1, APCDD1, AREG, ATP8B4, CFB, C3, C7, C20orf103, CDH3, CLDN11, CNTNAP2, COP1, CXADR, DLK1, DPT, EGR2, EMID1, GDF10, GJB2, GSC, HOXA5, HSD11B2, HSD17B2, HSPA6, HSPB3, IEI27, INA, KRT14, IGFL3, LOC92196, MFAP5, MEOX1, MEOX2, MMP1, MYBPH, MYH3, MYL4, NLGN4X, NPPB, OLR1, PAX2, PAX9, PDE1A, PENK, PRG4, PROM1, RARRES1, RASD1, RELN, RGS1, SLITRK6, SMOC1, SMOC2, SNAP25, STMN2, TAC1, TFP12, RSPO3, TNNT2, TRH, TUBB4 and ZIC1.

The group of cell lines SK28 and SK57 are positive for the markers: BEX1, COL21A1, CRYAB, HTRA3, ICAM5, IGF2, ILIR1, PTPRN and SERPINA3 and are negative for the markers: AGC1, ALDH1A1, AQP1, ATP8B4, CFB, BMP4, C20orf103, CCDC3, CDH3, CDH6, CLDN11, CNTNAP2, COP1, CXADR, DIO2, DKK2, EMID1, GABRB1, GAP43, GDF10, GSC, HOXA5, HSD17B2, HSPA6, HSPB3, ID4, IFI27, KCNMB1, KIAA0644, KRT14, KRT17, KRT34, IGFL3, LOC92196, MFAP5, MEOX1, MEOX2, MMP1, MSX2, MX1, MYH3, MYH11, MYL4, IL32, NLGN4X, NPPB, OLR1, OSR2, PAX2, PAX9, PENK, PROM1, PTN, RARRES1, RASD1, RELN, RGS1, SLITRK6, SMOC1, SMOC2, STMN2, TAC1, TFPI2, RSPO3, TNFSF7, TNNT2, TRH, TUBB4 and UGT2B7.

The group of cell lines SK30 and W4 are positive for the markers: BEX1, FST, HTRA3, IGF2, TMEM119, POSTN, SOX11, SRCRB4D, ZIC1 and ZIC2 and are negative for the markers: AGC1, ALDH1A1, ANXA8, AQP1, ATP8B4, C3, C6, C7, C20orf103, CCDC3, CDH3, CLDN11, CRYAB, DIO2, METTL7A, EGR2, EMID1, FMO3, FOXF2, GABRB1, GSC, HOXA5, HSD11B2, HSPA6, HSPB3, ID4, IFI27, INA, KRT14, KRT17, KRT34, IGFL3, LOC92196, MFAP5, MASP1, MEOX1, MEOX2, MMP1, MX1, MYH3, MYH11, NPPB, OLR1, OSR2, PAX2, PAX9, PDE1A, PENK, PRELP, PROM1, RARRES1, RASD1, RELN, SMOC2, STMN2, SYT12, TAC1, RSPO3, TNFSF7, TNNT2 and TUBB4.

The group of cell lines SK31 and SK54 are positive for the markers: BEX1, COL21A1, CRIP1, CRYAB, TMEM100, FMO1, FMO3, FOXF1, FOXF2, IGF2, IGFBP5, IL1R1, KRT19, LAMC2, TMEM119, NPAS1, PDE1A, PRRX2, S100A4, SERPINA3, SNAP25, SOX11, SRCRB4D and WISP2 and are negative for the markers: ACTC, AGC1, AKR1C1, ALDH1A1, ANXA8, AQP1, AREG, ATP8B4, CFB, BMP4, C3, CCDC3, CD24, CDH3, CLDN11, CNTNAP2, COMP, COP1, CXADR, DKK2, DLK1, DPT, EMID1, FGFR3, GABRB1, GAP43, GDF10, GSC, HSD17B2, HSPA6, HTRA3, ID4, IFI27, INA, KCNMB1, KRT14, KRT17, KRT34, IGFL3, LOC92196, MFAP5, MASP1, MEOX1, MEOX2, MMP1, MYH3, MYH11, MYL4, IL32, NLGN4X, NPPB, OGN, OLR1, OSR2, PAX2, PAX9, PENK, PITX2, PRELP, PROM1, PRRX1, RELN, RGS1, SLITRK6, SMOC1, SMOC2, SOD3, STMN2, SYT12, TAC1, TFP12, RSPO3, TNFSF7, TNNT2, TRH, TSLP, TUBB4, ZIC1 and ZIC2.

TABLE I-continued

Exemplary progenitor cell lines and associated gene expression markers at 18-21 doublings of clonal expansion The cell line SK32 is positive for the markers: AKR1C1, BEX1, C6, C7, C20orf103, COL21A1, CRYAB, METTL7A, DPT, GDF5, HTRA3, ICAM5, IL1R1, TMEM119, MGP, OGN, POSTN, PTPRN, RGMA, SERPINA3, SFRP2, SOD3, WISP2 and ZIC1 and is negative for the markers: ACTC, AGC1, ALDH1A1, ANXA8, AQP1, AREG, ATP8B4, CFB, BMP4, C3, CCDC3, CD24, CDH3, CDH6, CLDN11, CNTNAP2, COL15A1, COMP, COP1, CXADR, DIO2, DKK2, EGR2, EMID1, FGFR3, FMO3, FOXF1, FOXF2, GABRB1, GAP43, GDF10, GSC, HOXA5, HSD17B2, HSPA6, HSPB3, ID4, IFI27, IFIT3, INA, KIAA0644, KRT14, KRT17, KRT19, KRT34, IGFL3, LOC92196, MFAP5, MASP1, MEOX1, MEOX2, MMP1, MX1, MYBPH, MYH3, MYH11, MYL4, IL32, NLGN4X, NPPB, OLR1, OSR2, PAX2, PAX9, PENK, PITX2, PRELP, PROM1, PTGS2, RASD1, RELN, RGS1, SLITRK6, SMOC1, SMOC2, STMN2, SYT12, TFPI2, RSPO3, THY1, TNFSF7, TNNT2, TRH, TSLP, TUBB4 and ZIC2.

The group of cell lines SK40 and SK40Bio2 are positive for the markers: BEX1, COL21A1, CRYAB, FMO1, FST, ICAM5, IGFBP5, TMEM119, MSX1, MYL4, PTPRN, SERPINA3, SOD3, ZIC1 and ZIC2 and are negative for the markers: AGC1, AKR1C1, ALDF1A1, AQP1, ATP8B4, BMP4, C3, C20orf103, CCDC3, CD24, CDH3, CLDN11, CNTNAP2, COP1, D102, DKK2, DPT, TMEM100, FMO3, GABRB1, GAP43, GSC, HOXA5, HSPA6, HSPB3, ID4, IFI27, INA, KCNMB1, KIAA0644, KRT14, KRT17, KRT34, IGFL3, LOC92196, MEOX1, MEOX2, MX1, MYBPH, MYH11, NLGN4X, NPPB, OGN, OLR1, PAX2, PAX9, PDE1A, PENK, PITX2, PRELP, PROM1, RARRES1, RASD1, RELN, RGS1, SMOC2, SNAP25, SYT12, TAC1, TFPI2, RSPO3, THY1, TNFSF7, TRH, TSLP and TUBB4

The cell line SK46 is positive for the markers: APCDD1, COL21A1, DIO2, METTL7A, FMO1, FMO3, FOXF1, FOXF2, FST, HTRA3, IGF2, IL1R1, TMEM119, OGN, PRRX1, PRRX2, SERPINA3, SFRP2, SLITRK6, TSLP and ZIC2 and is negative for the markers: ACTC, AGC1, ALDH1A1, ANXA8, AQP1, ATP8B4, CFB, BMP4, C3, C6, C7, C20orf103, CCDC3, CD24, CDH3, CLDN11, CNTNAP2, COP1, GRIP1, CXADR, DKK2, DP1, EMID1, FGFR3, GABRB1, GAP43, GDF5, GDF10, GJB2, GSC, HOXA5, HSD17B2, HSPA6, HSPB3, IFI27, INA, KRT14, KRT17, KRT19, KRT34, LAMC2, IGFL3, LOC92196, MFAP5, MEOX1, MEOX2, MMP1, MX1, MYBPH, MYH3, MYH11, MYL4, IL32, NLGN4X, TAGLN3, NPAS1, NPPB, OLR1, OSR2, PAX2, PAX9, PDE1A, PENK, PITX2, POSTN, PRELP, PROM1, RARRES1, RASD1, RELN, RGS1, SMOC1, SMOC2, STMN2, TFPI2, RSPO3, THY1, TNFSF7, TNNT2, TRH, TUBB4, UGT2B7 and ZIC1.

The cell line SK47 is positive for the markers: BEX1, COL21A1, METTL7A, FMO1, FOXF1, FOXF2, FST, HTRA3, ICAM5, IGF2, ILIR1, KRT19, TMEM119, MSX1, PRRX2, PTPRN, SERPINA3, SOD3 and ZIC1 and is negative for the markers: AGC1, ALDH1A1, AQP1, ATP8B4, CFB, BMP4, C3, C6, C7, C20orf103, CCDC3, CD24, CDH3, CLDN11, CNTNAP2, COL15A1, COP1, CRLF1, DKK2, DPT, EGR2, EMID1, FGFR3, GABRB1, GAP43, GDF10, GJB2, GSC, HOXA5, HSD17B2, HSPA6, HSPB3, ID4, IF127, INA, KCNMB1, KRT14, KRT17, KRT34, IGFL3, LOC92196, MFAP5, MEOX1, MEOX2, MGP, MMP1, MX1, MYBPH, MYH3, MYH11, IL32, NLGN4X, NPPB, OLR1, PAX2, PAX9, PDE1A, PENK, PITX2, POSTN, PRELP, PROM1, RARRES1, RASD1, RELN, RGS1, SL1TRK6, SMOC1, SMOC2, STMN2, SYT12, TAC1, TFPI2, RSPO3, THY1, TNFSF7, TNNT2, TRH, TUBB4 and ZD52F10.

The group of cell lines SK5.Bio1, SK5.Bio2, SK5Bio3 and SK5BioUT are positive for the markers: ACTC, C7, CRLF1, CRYAB, FST, HTRA3, IL1R1, TMEM119, MGP, PTPRN, SERPINA3, SFRP2 and ZIC1 and are negative for the markers: ALDH1A1, ANXA8, CFB, BMP4, C3, C20orf103, CDH3, CLDN11, CNTNAP2, COP1, DKK2, EMID1, FMO3, GABRB1, GDF10, GSC, HSD17B2, HSPB3, IFI27, KRT14, KRT17, KRT34, IGFL3, LOC92196, MFAP5, MEOX1, MEOX2, MYH11, IL32, NPPB, OLR1, OSR2, PAX2, PAX9, PENK, PRELP, PROM1, RARRES1, RELN, RGS1, SLITRK6, SMOC1, SMOC2, STMN2, RSPO3, TNFSF7, TNNT2, TRH, TUBB4 and ZIC2.

The cell line SK8 is positive for the markers: APCDD1, BEX1, COL21A1, CRLF1, FMO1, FMO3, FOXF2, FST, HTRA3, ICAM5, IGF2, IL1R1, TMEM119, MASP1, PTPRN, SERPINA3 and SFRP2 and is negative for the markers: ACTC, AGC1, ALDH1A1, ANXA8, AQP1, ATP8B4, CFB, BMP4, C7, PRSS35, C20orf103, CD24, CDH3, CDH6, CLDN11, CNTNAP2, COP1, DKK2, EMID1, GABRB1, GAP43, GDF10, GJB2, GSC, HOXA5, HSD17B2, HSPA6, HSPB3, IFI27, IFIT3, INA, KIAA0644, KRT14, KRT17, KRT34, IGFL3, LOC92196, MFAP5, MEOX1, MEOX2, MMP1, MX1, MYBPH, MYH3, MYH11, MYL4, IL32, NLGN4X, NPPB, OLR1, OSR2, PAX2, PAX9, PDE1A, PENK, PRELP, PROM1, PTN, RARRES1, RASD1, RELN, RGS1, SMOC1, SMOC2, STMN2, TAC1, RSPO3, THY1, TNFSF7, TNNT2, TRH, TUBB4, ZIC1 and ZIC2.

The cell line SM17 is positive for the markers: BEX1, CD24, CRYAB, EGR2, FOXF1, FST, GDF5, HTRA3, IGFBP5, KRT19, MMP1, MSX1, MSX2, IL32, PODN, POSTN, PRELP, PRRX2, SRCRB4D, TFPI2, TSLP and ZIC1 and is negative for the markers: AGC1, AKR1C1, ALDH1A1, ANXA8, APCDD1, AQP1, AREG, ATP8B4, CFB, BMP4, C6, C7, C20orf103, CCDC3, CDH3, CLDN11, CNTNAP2, COL15A1, DIO2, METTL7A, DKK2, DLK1, DPT, FGFR3, TMEM100, FMO1, FMO3, GABRB1, GAP43, GDF10, GSC, HOXA5, HSD11B2, HSD17B2, HSPA6, IFI27, IGF2, KCNMB1, KRT14, KRT17, KRT34, IGFL3, LOC92196, MFAP5, MEOX1, MEOX2, MYBPH, MYH3, MYH11, NLGN4X, NPPB, OLR1, OSR2, PAX2, PAX9, PDE1A, PENK, PRG4, PROM1, RARRES1, RASD1, RELN, RGS1, SMOC1, SMOC2, SNAP25, STMN2, TAC1, RSPO3, TNFSF7, TNNT2, TRH, TUBB4, UGT2B7, WISP2 and ZIC2.

The cell line SM19 is positive for the markers: BEX1, CNTNAP2, CRYAB, FST, GDF5, MMP1, POSTN, PRRX2, SERPINA3 and SFRP2 and is negative for the markers: ACTC, AGC1, AKR1C1, ALDH1A1, ANXA8, AQP1, AREG, ATP8B4, CFB, BMP4, C3, C6, C7, C20orf103, CDH3, CDH6, CLDN11, COL21A1, COMP, COP1, CRLF1, DIO2, METTL7A, DKK2, DLK1, DPT, EMID1, FGFR3, TMEM100, FMO1, FMO3, FOXF2, GABRB1, GDF10, GSC, HOXA5, HSD11B2, HSD17B2, HSPA6, ID4, IFI27, IGF2, IGFBP5, IL1R1, KCNMB1, KIAA0644, KRT14, KRT17, KRT34, IGFL3, LOC92196, MFAP5, MASP1, MEOX1, MEOX2, MGP, MX1, MYBPH, MYH3, MYH11, NLGN4X, NPPB, OGN, OLR1, OSR2, PAX2, PAX9, PDE1A, PENK, PITX2, PRG4, PROM1, RARRES1, RASD1, RGS1, SLITRK6, SMOC1, SMOC2, SNAP25, STMN2, SYT12, TAC1, TFPI2, RSPO3, THY1, TNFSF7, TNNT2, TRH, UGT2B7, WISP2, ZIC1 and ZIC2.

The cell line SM2 is positive for the markers: CDH6, CNTNAP2, COL15A1, COL21A1, FST, GDF5, TMEM119, MMP1, MSX1, POSTN, PRRX1, SOD3, ZIC1 and ZIC2 and is negative for the markers: ACTC, AGC1, AKR1C1, ALDH1A1, ANXA8, APCDD1, AQP1, AREG, ATP8B4, BEX1, BMP4, C3, C6, C7, PRSS35, C20orf103, CCDC3, CD24, CDH3, CLDN11, COMP, CRIP1, CRYAB, DIO2, DPT, EMID1, FGFR3, TMEM100, FMO3, GDF10, GJB2, GSC, HOXA5, HSD11B2, HSD17B2, HSPA6, HSPB3, ID4, IFI27, INA, KCNMB1, KIAA0644, KRT14, KRT17, KRT19, KRT34, IGFL3, LOC92196, MFAP5, MASP1, MEOX1, MEOX2, MGP, MX1,

TABLE I-continued

Exemplary progenitor cell lines and associated gene expression markers at 18-21 doublings of clonal expansion MYBPH, MYH3, MYH11, MYL4, IL32, NLGN4X, NPAS1, NPPB, OLR1, OSR2, PAX2, PAX9, PDE1A, PENK, PITX2, PROM1, RARRES1, RASD1, RELN, RGS1, SFRP2, SLITRK6, SMOC1, SMOC2, STMN2, SYT12, TAC1, TFPI2, RSPO3, TNFSF7, TNNT2, TRH, TUBB4 and UGT2B7.

The cell line SM22 is positive for the markers: CDH6, CRLF1, DLK1, FOXF1, FST, GDF5, HTRA3, IGFBP5, IL1R1, MGP, MMP1, MSX1, MSX2, OGN, POSTN, PRRX2, PTN, RGMA, SOD3, SRCRB4D, STMN2, TSLP, ZD52F10 and ZIC1 and is negative for the markers: AGC1, ALDH1A1, ANXA8, APCDD1, AQP1, AREG, BMP4, C3, C6, C7, C20orf103, CCDC3, CDH3, CLDN11, CNTNAP2, COL15A1, CRT1, CXADR, DIO2, DKK2, DPT, TMEM100, FMO1, FOXF2, GDF10, GJB2, GSC, HOXA5, HSD11B2, HSD17B2, HSPA6, HSPB3, ICAM5, IFI27, INA, KRT14, KRT17, KRT34, LAMC2, TMEM119, IGFL3, LOC92196, MFAP5, MASP1, MEOX1, MEOX2, MX1, MYBPH, MYH3, MYH11, MYL4, IL32, NLGN4X, NPAS1, NPPB, OLR1, OSR2, PAX2, PAX9, PENK, PITX2, PRG4, PROM1, PTPRN, RARRES1, RASD1, RELN, RGS1, SFRP2, SMOC1, SMOC2, SNAP25, TAC1, RSPO3, TNFSF7, TNNT2, TRH, TUBB4, UGT2B7 and ZIC2.

The group of cell lines SM25 and Z8 are positive for the markers: FOXF1, FST, GDF5, HTRA3, MSX1, MSX2, PRRX2 and SRCRB4D and are negative for the markers: ACTC, AGC1, AKR1C1, ALDH1A1, ANXA8, AQP1, AREG, ATP8B4, BMP4, C6, C7, C20orf103, CD24, CDH3, CLDN11, CNTNAP2, METTL7A, DKK2, EMID1, TMEM100, FMO1, GABRB1, GDF10, GSC, HOXA5, HSD11B2, HSD17B2, HSPA6, ID4, IFI27, KCNMB1, KRT14, KKRT17, KRT34, IGFL3, LOC92196, MFAP5, MEOX1, MEOX2, MYBP11, MYH3, MYH11, MYL4, NLGN4X, NPPB, OLR1, OSR2, PAX2, PAX9, PDE1A, PENK, PITX2, PROM1, RARRES1, RASD1, RGS1, RPS4Y2, SFRP2, SLITRK6, SMOC1, SMOC2, TAC1, RSPO3, TNFSF7, TNNT2, TRH, TUBB4 and UGT2B7.

The cell line SM28 is positive for the markers: COMP, CRLF1, DIO2, EGR2, FOXF1, FOXF2, FST, HSPB3, INA, TMEM119, MGP, MMP1, MSX2, POSTN, PRELP, PRRX2, PTN and SYT12 and is negative for the markers: ACTC, AGC1, AKR1C1, ALDH1A1, ANXA8, APCDD1, AQP1, AREG, ATP8B4, BEX1, CFB, C3, C6, C7, C20orf103, CD24, CDH6, CLDN11, CNTNAP2, COL21A1, CXADR, METTL7A, DKK2, DLK1, FGFR3, TMEM100, FMO1, GABRB1, GAP43, GDF10, GJB2, GSC, HOXA5, HSD11B2, HSD17B2, HSPA6, ID4, IFI27, IFIT3, KCNMB1, KRT14, KRT17, KRT19, KRT34, LAMC2, IGFL3, LOC92196, MFAP5, MEOX1, MEOX2, MX1, MYBPH, MYH3, MYH11, IL32, NLGN4X, TAGLN3, NPPB, OGN, OLR1, OSR2, PAX2, PAX9, PDE1A, PENK, PITX2, PRG4, PROM1, PTGS2, PTPRN, RARRES1, RASD1, RGS1, RPS4Y2, SERPINA3, SFRP2, SMOC1, SMOC2, SNAP25, STMN2, TAC1, RSPO3, TNFSF7, TNNT2, TRH, TUBB4, UGT2B7, WISP2, ZD52E10, ZIC1 and ZIC2.

The cell line SM29 is positive for the markers: FOXF1, FOXF2, FST, HTRA3, IGF2, IGFBP5, IL1R1, MASP1, MGP, MMP1, MSX2, OGN, PODN, POSTN, PRELP, PRRX2, PTN, SRCRB4D and TSLP and is negative for the markers: ACTC, AKR1C1, ALDH1A1, ANXA8, APCDD1, AQP1, CFB, C6, C7, CCDC3, CDH3, CLDN11, CNTNAP2, COL15A1, COL21A1, CRIP1, CRLF1, CRYAB, DKK2, DPT, FGFR3, TMEM100, GDF10, GSC, HOXA5, HSD11B2, HSD17B2, HSPA6, ID4, IFI27, INA, KCNMB1, KRT14, KRT17, KRT34, LAMC2, IGFL3, LOC92196, MFAP5, MEOX1, MEOX2, MX1, MYBPH, MYH3, MYH11, MYL4, IL32, NLGN4X, NPPB, OLR1, OSR2, PAX9, PDE1A, PENK, PITX2, PROM1, RARRES1, RASD1, RELN, RGS1, S100A4, SMOC1, SMOC2, SNAP25, TAC1, RSPO3, TNFSF7, TNNT2, TRH, TUBB4, UGT2B7, WISP2, ZIC1 and ZIC2.

The cell line SM30 is positive for the markers: COL15A1, CRYAB, DYSF, FST, GDF5, HTRA3, TMEM119, MMP1, MSX1, MSX2, MYL4, POSTN, SERPINA3, SRCRB4D and ZIC2 and is negative for the markers: ACTC, AGC1, AKR1C1, ALDH1A1, ANXA8, APCDD1, AQP1, ATP8B4, CFB, C3, C6, C7, C20orf103, CD24, CDH3, CLDN11, CNTNAP2, COMP, DIO2, METTL7A, DKK2, DLK1, DP1, FGFR3, TMEM100, FMO1, FMO3, FOXF2, GABRB1, GJB2, GSC, HOXA5, HSD11B2, HSPA6, ID4, IFI27, IL1R1, KCNMB1, KIAA0644, KRT14, KRT17, KRT34, IGFL3, LOC92196, MEOX1, MEOX2, MGP, MYBPH, MYH3, MYH11, NLGN4X, NPPB, OGN, OLR1, OSR2, PAX2, PAX9, PDE1A, PENK, PRG4, PROM1, PRRX1, PIN, RARRES1, RASD1, RELN, RGS1, SLITRK6, SMOC1, SMOC2, SNAP25, STMN2, TAC1, RSPO3, INFSF7, TNNT2, TRH, TUBB4, UGT2B7 and WISP2.

The cell line SM33 is positive for the markers: BEX1, CDH6, CRLF1, EGR2, FOXF1, FST, IGFBP5, MSX1, MSX2, PRELP, SERPINA3, SRCRB4D, SYT12, TSLP and ZIC2 and is negative for the markers: ACTC, AGC1, AKR1C1, ALDH1A1, ANXA8, APCDD1, AQP1, AREG, ATP8B4, CFB, BMP4, C3, C6, C7, C20orf103, CD24, CDH3, CLDN11, CNTNAP2, COL21A1, CRIP1, DIO2, METTL7A, DLK1, DPT, EMID1, FGFR3, TMEM100, FMO1, GABRB1, GAP43, GSC, HOXA5, HSD11B2, HSPA6, HSPB3, ID4, IFI27, IL1R1, KCNMB1, KRT14, KRT17, KRT34, IGFL3, LOC92196, MFAP5, MEOX1, MEOX2, MX1, MYBPH, MYH3, MYH11, NLGN4X, NPPB, OGN, OSR2, PAX2, PAX9, PDE1A, PENK, PRG4, PROM1, PTGS2, RARRES1, RASD1, RELN, RGS1, RPS4Y2, SFRP2, SMOC1, SMOC2, SNAP25, STMN2, TAC1, RSPO3, THY1, TNFSF7, TRH, TUBB4, UGT2B7, WISP2 and ZIC1.

The cell line SM4 is positive for the markers: HEX1, CCDC3, CDH6, CRLF1, EGR2, FST, GABRB1, GAP43, GDF5, HSPB3, HTRA3, MMP1, MSX1, MSX2, PRELP, PRRX1, PRRX2 and SRCRB4D and is negative for the markers: AGC1, ALDH1A1, ANXA8, APCDD1, AQP1, AREG, ATP8B4, CFB, BMP4, C3, C6, C7, PRSS35, C20orf103, CD24, CDH3, CLDN11, CNTNAP2, COL15A1, COL21A1, COP1, CXADR, METTL7A, DKK2, DLK1, DP1, EMID1, FGFR3, TMEM100, FMO1, FMO3, GDF10, GJB2, GSC, HOXA5, HSD11B2, HSD17B2, HSPA6, ICAM5, ID4, IFI27, IGF2, KRT14, KRT17, KRT19, KRT34, IGFL3, LOC92196, MFAP5, MASP1, MEOX1, MEOX2, MX1, MYBPH, MYH3, MYH11, MYL4, IL32, NLGN4X, TAGLN3, NPAS1, NPPB, OLR1, OSR2, PAX2, PAX9, PDE1A, PENK, PITX2, PRG4, PROM1, RARRES1, RASD1, RELN, RGS1, SFRP2, SLITRK6, SMOC1, SMOC2, SNAP25, STMN2, TAC1, RSPO3, TNFSF7, TNNT2, TRH, TSLP, TUBB4, UGT2B7, WISP2, ZD52F10 and ZIC1.

The cell line SM40 is positive for the markers: BEX1, CD24, CRYAB, FST, HSPB3, IGFBP5, KRT19, MMP1, MYL4, POSTN, PRELP, SRCRB4D and ZD52F10 and is negative for the markers: AGC1, AKR1C1, ALDH1A1, ANXA8, APCDD1, AQP1, AREG, CFB, C6, C7, CDH3, CDH6, CLDN11, CNTNAP2, COL15A1, COL21A1, COMP, CRLF1, DIO2, METTL7A, DKK2, DLK1, DPT, EMID1, FGFR3, TMEM100, FMO1, FMO3, GABRB1, GAP43, GDF10, GJB2, GSC, HOXA5, HSD11B2, HSD17B2, HSPA6, ID4, IFI27, IGF2, KRT14, KRT17, KRT34, IGFL3, LOC92196, MEOX1, MEOX2, MGP, MX1, MYBPH, MYH3, MYH11, NLGN4X, NPPB, OGN, OSR2, PAX9, PDE1A, PENK, PITX2, PROM1, PRRX1, RARRES1, RASD1, RELN, RGMA, RGS1, RPS4Y2, SFRP2, SLITRK6, SMOC1, SMOC2, SOX11, STMN2, TAC1, RSPO3, TNFSF7, TNNT2, TRH, TUBB4, UGT2B7, WISP2, ZIC1 and ZIC2.

The cell line SM42 is positive for the markers: COL15A1, EGR2, FST, GDF5, TMEM119, MMP1, MSX1, MSX2, PRELP, PRRX1, PRRX2, SFRP2, SRCRB4D, ZIC1 and ZIC2 and is negative for the markers: ACTC, AGC1, AKR1C1, ALDH1A1, ANXA8, APCDD1, AQP1, ATP8B4, CFB, BMP4, C3, C6, C7, C20orf103, CCDC3, CD24,

TABLE I-continued

Exemplary progenitor cell lines and associated gene expression markers at 18-21 doublings of clonal expansion CDH3, CLDN11, CNTNAP2, CRIP1, CRYAB, DIO2, METTL7A, DKK2, DLK1, DPT, EMID1, FGFR3, TMEM100, FOXF2, GABRB1, GAP43, GJB2, GSC, HOXA5, HSD11B2, HSPA6, ID4, IFI27, KIAA0644, KRT14, KRT17, KRT19, KRT34, IGFL3, LOC92196, MFAP5, MEOX1, MEOX2, MGP, MX1, MYBPH, MYH3, MYH11, NLGN4X, NPPB, OGN, OLR1, PAX2, PAX9, PDE1A, PENK, PITX2, PRG4, PROM1, RARRES1, RASD1, RELN, RGS1, SLITRK6, SMOC1, SMOC2, SNAP25, STMN2, TAC1, RSPO3, TNFSF7, TNNT2, TRH, TUBB4 and UGT2B7.

The cell line SM44 is positive for the markers: CDH6, COMP, CRLF1, CRYAB, EGR2, FOXF1, FST, GDF5, HTRA3, MGP, MMP1, MSX2, POSTN, PRELP, PRRX2, SYT12 and TSLP and is negative for the markers: ACTC, AGC1, AKR1C1, ALDH1A1, ANXA8, APCDD1, AQP1, AREG, ATP8B4, CFB, BMP4, C3, C6, C7, C20orf103, CD24, CDH3, CLDN11, CNTNAP2, COL15A1, COL21A1, COP1, CXADR, METTL7A, DKK2, DLK1, DPT, EMID1, FGFR3, TMEM100, FMO1, FMO3, FOXF2, GABRB1, GDF10, GJB2, GSC, HOXA5, HSD11B2, HSD17B2, HSPA6, ID4, IFI27, IFIT3, IGF2, KRT14, KRT17, KRT19, KRT34, IGFL3, LOC92196, MFAP5, MEOX1, MEOX2, MX1, MYBPH, MYH3, MYH11, MYL4, NLGN4X, NPPB, OGN, OLR1, OSR2, PAX2, PAX9, PDE1A, PENK, PRG4, PROM1, PTN, PTPRN, RARRES1, RASD1, RELN, RGS1, SFRP2, SLITRK6, SMOC1, SMOC2, SNAP25, STMN2, TAC1, RSPO3, INFSF7, TNNT2, TRH, TUBB4, UGT2B7, WISP2, ZD52F10, ZIC1 and ZIC2.

The cell line SM49 is positive for the markers: FOXF1, FOXF2, FST, GAP43, GDF5, HSPB3, HTRA3, IGFBP5, MGP, MMP1, MSX2, POSTN, PRELP, PRRX2, PTN, RGMA, MOD3, SRCRB4D and SYT12 and is negative for the markers: ACTC, AGC1, AKR1C1, ALDH1A1, ANXA8, APCDD1, AQP1, AREG, CFB, BMP4, C6, C7, C20orf103, CD24, CDH3, CLDN11, CNTNAP2, COL15A1, COL21A1, DIO2, METTL7A, DPT, EMID1, FGFR3, TMEM100, FMO1, GABRB1, GDF10, GJB2, GSC, HOXA5, HSD11B2, HSD17B2, HSPA6, ID4, IFI27, IFIT3, KIAA0644, KRT14, KRT17, KRT19, KRT34, LAMC2, IGFL3, LOC92196, MFAP5, MEOX1, MEOX2, MYBPH, MYH3, MYH11, MYL4, NLGN4X, TAGLN3, NPAS1, NPPB, OGN, OLR1, OSR2, PAX2, PAX9, PDE1A, PENK, PITX2, PRG4, PROM1, RARRES1, RELN, RGS1, SMOC1, SMOC2, SNAP25, TAC1, RSPO3, THY1, TNFSF7, TNNT2, TRH, TUBB4, UGT2B7, WISP2, ZIC1 and ZIC2

The cell line SM8 is positive for the markers: BEX1, CDH6, FOXF1, FST, GDF5, GDF10, IGF2, IGFBP5, MMP1, MSX1, TFPI2, TSLP and ZIC2 and is negative for the markers: ACTC, AGC1, AKR1C1, ALDH1A1, ANXA8, APCDD1, AQP1, ATP8B4, CFB, BMP4, C3, C6, C7, PRSS35, C20orf103, CCDC3, CDH3, CLDN11, COL21A1, COMP, CRYAB, DIO2, METTL7A, DKK2, DLK1, DPT, EMID1, FGFR3, TMEM100, FMO1, FMO3, FOXF2, GABRB1, GJB2, GSC, HOXA5, HSD11B2, HSD17B2, HSPA6, HSPB3, ICAM5, ID4, IFI27, KCNMB1, KIAA0644, KRT14, KRT17, KRT34, TMEM119, IGFL3, LOC92196, MFAP5, MASP1, MEOX1, MEOX2, MGP, MX1, MYBPH, MYH3, MYH11, MYL4, NLGN4X, NPAS1, NPPB, OGN, OLR1, OSR2, PAX2, PAX9, PDE1A, PENK, PITX2, POSTN, PRELP, PRG4, PROM1, PRRX1, PTGS2, RGMA, RGS1, S100A4, SFRP2, SLITRK6, SMOC2, STMN2, TAC1, RSPO3, TNFSF7, TNNT2, TRH, TUBB4, UGT2B7, WISP2 and ZD52F10.

The cell line T14 is positive for the markers: BEX1, PRSS35, CCDC3, COL15A1, CRIP1, CRYAB, FST, HTRA3, IGF2, KCNMB1, KRT17, KRT19, LAMC2, PITX2, POSTN, S100A4, SOX11, THY1 and TNNT2 and is negative for the markers: AGC1, ALDH1A1, AQP1, AREG, ATP8B4, CFB, C3, C6, C7, C20orf103, CDH3, CLDN11, CNTNAP2, COP1, CXADR, METTL7A, DLK1, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IGFBP5, KIAA0644, KRT14, IGFL3, LOC92196, MASP1, MEOX1, MEOX2, MGP, MX1, MYH3, IL32, NLGN4X, TAGLN3, NPPB, OGN, OLR1, OSR2, PAX2, PAX9, PDE1A, PENK, PRG4, PROM1, PTGS2, PTPRN, RARRES1, RASD1, RELN, RGS1, SLITRK6, SMOC1, SMOC2, SNAP25, SOD3, STMN2, TAC1, TFPI2, RSPO3, TNFSF7, TRH, TUBB4, WISP2, ZD52F10, ZIC1 and ZIC2.

The group of cell lines T4 and T23 are positive for the markers: BEX1, CCDC3, DKK2, KRT19 and LAMC2 and are negative for the markers: ALDH1A1, APCDD1, AQP1, CFB, C3, C6, C20orf103, CDH3, CLDN11, CNTNAP2, COL15A1, COMP, CRLF1, METTL7A, DPT, EMID1, TMEM100, FMO3, FOXF2, GDF10, GJB2, GSC, HOXA5, HSD11B2, HSPA6, IFI27, IL1R1, KRT14, IGFL3, LOC92196, MASP1, MEOX1, MEOX2, MGP, MX1, MYBPH, MYH3, MYH11, NLGN4X, NPAS1, OGN, OLR1, PAX2, PAX9, PDE1A, PENK, PROM1, PRRX2, PTPRN, RARRES1, RASD1, RGMA, RGS1, RPS4Y2, SFRP2, SLITRK6, SMOC1, SMOC2, SNAP25, STMN2, SYT12, TAC1, RSPO3, TNFSF7, TRH, WISP2, ZD52F10 and ZIC1.

The group of cell lines T36 and T42 are positive for the markers: BEX1, CCDC3, CDH6, CRIP1, FST, HTRA3, KRT17, PTN, S100A4, SRCRB4D, THY1 and ZIC2 and are negative for the markers: AGC1, ALDH1A1, APCDD1, AREG, ATP8B4, C3, C6, C7, PRSS35, C20orf103, CDH3, CLDN11, CNTNAP2, CRLF1, METTL7A, DLK1, DPT, EMID1, FMO1, FMO3, FOXF2, GJB2, GSC, HOXA5, HSD11B2, HSD17B2, HSPA6, HSPB3, IFI27, KRT14, IGFL3, LOC92196, MFAP5, MASP1, MEOX1, MEOX2, MGP, MMP1, MYBPH, MYH3, NLGN4X, TAGLN3, NPAS1, NPPB, OGN, OLR1, PAX9, PDE1A, PENK, PRG4, PROM1, PTPRN, RARRES1, RASD1, RELN, RGS1, SLITRK6, SMOC2, SNAP25, STMN2, TAC1, RSPO3, TRH, TUBB4 and WISP2.

The group of cell lines T43 and T44 are positive for the markers: BEX1, PRSS35, CCDC3, CDH6, COL21A1, CRIP1, CRYAB, ICAM5, KRT17, LAMC2, POSTN, S100A4, SFRP2 and THY1 and are negative for the markers: AGC1, ALDH1A1, APCDD1, AQP1, AREG, ATP8B4, C3, C6, C7, C20orf103, CDH3, CNTNAP2, COP1, METTL7A, DLK1, DPT, EMID1, FMO1, FMO3, FOXF1, FOXF2, GABRB1, GDF10, GJB2, GSC, HOXA5, HSD11B2, HSD17B2, HSPA6, IFI27, IGFBP5, IGFL3, LOC92196, MEOX1, MEOX2, MGP, NLGN4X, TAGLN3, NPPB, OGN, OLR1, OSR2, PAX2, PAX9, PDE1A, PRG4, PROM1, RARRES1, RASD1, RELN, RGS1, SLITRK6, SMOC1, SMOC2, SNAP25, STMN2, TAC1, TRH, TUBB4, UGT2B7, WISP2, ZD52F10 and ZIC2.

The cell line U18 is positive for the markers: ANXA8, BEX1, PRSS35, CCDC3, CDH6, CRYAB, DKK2, KRT19, MYH11, NPPB, TNNT2 and ZIC2 and is negative for the markers: ACTC, AGC1, ALDH1A1, APCDD1, AQP1, AREG, ATP8B4, CFB, C3, C6, C7, C20orf103, CD24, CDH3, CLDN11, CNTNAP2, COL15A1, COP1, CRLF1, DIO2, METTL7A, DPT, EGR2, EMID1, TMEM100, FMO1, FMO3, FOXF1, FOXF2, GABRB1, GDF10, GJB2, GSC, HOXA5, HSD11B2, HSD17B2, HSPA6, HSPB3, IFI27, IGF2, IGFBP5, KIAA0644, KRT14, TMEM119, IGFL3, LOC92196, MEOX1, MEOX2, MGP, MX1, MYBPH, MYH3, NLGN4X, OGN, OLR1, PAX2, PAX9, PDE1A, PENK, PROM1, PTPRN, RARRES1, RASD1, RELN, RGS1, SFRP2, SLITRK6, SMOC1, SMOC2, SNAP25, SOD3, STMN2, TAC1, TFPI2, RSPO3, THY1, TNFSF7, TRH, TUBB4, WISP2 and ZIC1.

The group of cell lines U30, U30 and U31 are positive for the markers: BEX1, CDH6, CRYAB, KCNMB1, KRT17, MYH11, ZIC1 and ZIC2 and are negative for the markers: ALDH1A1, ATP8B4, C3, C7, C20orf103, CD24, CDH3, CLDN11, CNTNAP2, COP1, CRLF1, METTL7A, DPT, FMO1, FMO3, FOXF1, FOXF2, GABRB1, GSC, HOXA5, HSD11B2, HSD17B2, HSPA6, IFI27, KIAA0644, KRT14, MEOX2, MGP, MYH3, TABLE I-continued Exemplary progenitor cell lines and associated gene expression markers at 18-21 doublings of clonal expansion OGN, OLR1, PAX2, PAX9, PDE1A, PROM1, PTPRN, RASD1, RGS1, SFRP2, SMOC1, SNAP25, TAC1, TNNT2, TRH, TUBB4 and WISP2.
The cell line W11 is positive for the markers: COL15A1, COL21A1, DIO2, DLK1, FMO1, FOXF1, FOXF2, FST, HTRA3, IGF2, IL1R1, TMEM119, OGN, PRRX2, PTN, SERP1NA3, SLITRK6, SOD3, TFPI2 and WISP2 and is negative for the markers: ACTC, AGC1, AKR1C1, ALDH1A1, ANXA8, APCDD1, AQP1, ATP8B4, CFB, C3, C6, C7, C20orf103, CCDC3, CD24, CDH3, CLDN11, CNTNAP2, CRIP1, CRYAB, CXADR, DKK2, EMID1, FGFR3, GAP43, GDF10, GJB2, GSC, HOXA5, HSD11B2, HSD17B2, HSPA6, HSPB3, ID4, IFI27, INA, KRT14, KRT17, KRT19, KRT34, LAMC2, IGFL3, LOC92196, MFAP5, MEOX1, MEOX2, MGP, MMP1, MX1, MYBPH, MYH3, MYH11, MYL4, IL32, NLGN4X, NPAS1, NPPB, OLR1, PAX2, PAX9, PENK, PITX2, POSTN, PRG4, PROM1, RASD1, RELN, RGS1, SMOC1, SMOC2, STMN2, TAC1, RSPO3, THY1, TNFSF7, TNNT2, TRH, TUBB4, UGT2B7, ZD52F10, ZIC1 and ZIC2.
The cell line W2 is positive for the markers: BEX1, CD24, COL21A1, FST, HTRA3, ICAM5, IGF2, IGFBP5, IL1R1, KRT19, LAMC2, TMEM119, MSX1, MSX2, PTN, SERPINA3, SFRP2, SOD3, SOX11, SRCRB4D and ZIC2 and is negative for the markers: AGC1, AKR1C1, ALDH1A1, APCDD1, ATP8B4, BMP4, C6, C7, C20orf103, CCDC3, CDH3, CLDN11, CNTNAP2, COL15A1, COMP, COP1, CRLF1, DKK2, DLK1, DPT, EGR2, EMID1, TMEM100, FMO3, FOXF2, GAP43, GDF10, GSC, HOXA5, HSD11B2, HSPA6, ID4, IFI27, INA, KCNMB1, KIAA0644, KRT14, KRT17, IGFL3, LOC92196, MEOX1, MEOX2, MGP, MYBPH, MYH3, MYH11, NLGN4X, NPPB, OGN, OLR1, OSR2, PAX2, PAX9, PDE1A, PENK, PITX2, PRG4, PROM1, PTGS2, RARRES1, RASD1, RELN, RGMA, RGS1, SLITRK6, SMOC1, SMOC2, STMN2, SYT12, TAC1, TNFSF7, TNNT2, TRH, TSLP, TUBB4 and ZIC1.
The cell line W3 is positive for the markers: BEX1, CRIP1, FOXF1, FST, GDF5, HSPA6, HTRA3, IGF2, IGFBP5, KRT19, LAMC2, MMP1, MSX1, POSTN, PTPRN and TFP12 and is negative for the markers: ACTC, AGC1, ALDH1A1, ANXA8, APCDD1, AQP1, ATP8B4, CFB, BMP4, C6, C7, PRSS35, C20orf103, CCDC3, CDH3, CLDN11, CNTNAP2, COL15A1, COL21A1, COMP, DIO2, METTL7A, DKK2, DLK1, DPT, EGR2, EMID1, FGFR3, FMO1, FMO3, FOXF2, GAP43, GDF10, GJB2, GSC, HOXA5, HSD11B2, HSD17B2, IFI27, IFIT3, INA, KIAA0644, KRT14, KRT17, IGFL3, LOC92196, MEOX1, MEOX2, MGP, MX1, MYBPH, MYH3, MYH11, MYL4, IL32, NLGN4X, NPPB, OGN, OSR2, PAX2, PAX9, PDE1A, PENK, PRELP, PRG4, PROM1, PRRX1, RARRES1, RELN, RGMA, RGS1, SLITRK6, SMOC1, SMOC2, SOX11, SYT12, TAC1, RSPO3, THY1, TNFSF7, TNNT2, TRH, TUBB4, UGT2B7, ZIC1 and ZIC2.
The cell line W8 is positive for the markers: AQP1, CDH6, DIO2, DLK1, EMID1, FOXF1, FOXF2, FST, HTRA3, IL1R1, MSX1, MSX2, PRRX2, PTN, SLITRK6, SRCRB4D, TSLP and ZIC2 and is negative for the markers: ACTC, AGC1, AKR1C1, ALDH1A1, ANXA8, APCDD1, BMP4, C6, C7, C20orf103, CCDC3, CD24, CDH3, CLDN11, CNTNAP2, CRLF1, CRYAB, CXADR, DKK2, DPT, EGR2, FGFR3, TMEM100, GABRB1, GAP43, GDF10, GJB2, GSC, HOXA5, HSD11B2, HSD17B2, HSPA6, HSPB3, ID4, IFI27, IFIT3, INA, KCNMB1, KRT14, KRT17, KRT34, IGFL3, LOC92196, MFAP5, MEOX1, MEOX2, MX1, MYBPH, MYH3, MYH11, MYL4, NLGN4X, NPPB, OLR1, PAX2, PAX9, PENK, PITX2, POSTN, PRELP, PROM1, PRRX1, RARRES1, RASD1, RGMA, RGS1, SMOC1, SMOC2, STMN2, SYT12, TAC1, RSPO3, THY1, TNFSF7, TNNT2, TRH, TUBB4, UGT2B7, WISP2, ZD52F10 and ZIC1.
The cell line X4 is positive for the markers: ACTC, AQP1, BEX1, BMP4, CD24, CDH6, CLDN11 CRYAB, CXADR, HTRA3, INA, KRT17, KRT19, LAMC2, MMP1, IL32, NLGN4X, TAGLN3, NPPB, PAX2, PROM1, RASD1, RELN and UGT2B7 and is negative for the markers: AGC1, ALDH1A1, APCDD1, ATP8B4, CFB, C3, C6, C7, C20orf103, CCDC3, CDH3, CNTNAP2, COL15A1, COL21A1, COMP, COP1, CRLF1, DIO2, METTL7A, DKK2, DLK1, DP1, EGR2, EMID1, TMEM100, FMO1, FMO3, FOXF1, FOXF2, FST, GABRB1, GAP43, GDF10, GJB2, GSC, HOXA5, HSD11B2, HSD17B2, HSPA6, ID4, IFI27, IFIT3, IGF2, IL1R1, KCNMB1, KIAA0644, TMEM119, IGFL3, LOC92196, MFAP5, MASP1, MEOX1, MEOX2, MGP, MX1, MYBPH, MYH3, MYL4, OGN, OSR2, PAX9, PDE1A, PENK, PITX2, PRELP, PRRX1, PRRX2, PTGS2, PTN, RARRES1, RGMA, RGS1, SERPINA3, SLITRK6, SMOC1, SMOC2, SOD3, TAC1, RSPO3, TNNT2, TRH, TUBB4, WISP2, ZD52F10, ZIC1 and ZIC2.
The cell line X5.4 is positive for the markers: ACTC, CD24, CLDN11, CRIP1, CRYAB, HTRA3, KRT19, KRT34, LAMC2, MMP1, IL32, NLGN4X, TAGLN3, NPPB, PAX2, POSTN, RELN, S100A4, SFRP2, SRCRB4D, THY1 and UGT2B7 and is negative for the markers: AGC1, ALDH1A1, APCDD1, AREG, ATP8B4, CFB, C3, C6, C7, C20orf103, CNTNAP2, COL21A1, COMP, COP1, CRLF1, DIO2, METTL7A, DKK2, DLK1, DPT, EMID1, TMEM100, FMO1, FMO3, FOXF1, FOXF2, GABRB1, GAP43, GDF10, GJB2, GSC, HOXA5, HSD11B2, HSD17B2, HSPA6, ID4, IFI27, IFIT3, IGF2, KIAA0644, TMEM119, IGFL3, MASP1, MEOX2, MSX1, MX1, MYBPH, MYH3, MYL4, NPAS1, OGN, OSR2, PAX9, PDE1A, PENK, PRELP, PRRX1, PRRX2, PTPRN, RARRES1, RGMA, RGS1, SLITRK6, SMOC1, SMOC2, SNAP25, SOD3, TAC1, RSPO3, TNNT2, TRH, TUBB4, WISP2, ZD52F10, ZIC1 and ZIC2.
The cell line X5 is positive for the markers: ACTC, AKR1C1, BEX1, CLDN11, COMP, CRIP1, CRYAB, GDF5, HTRA3, KIAA0644, KRT14, KRT19, KRT34, LAMC2, MFAP5, MEOX2, MGP, MMP1, PENK, PITX2, POSTN, PTGS2, S100A4 and THY1 and is negative for the markers: AGC1, ALDH1A1, ANXA8, APCDD1, AQP1, AREG, ATP8B4, C6, C7, C20orf103, CCDC3, CDH6, CNTNAP2, COL15A1, COL21A1, COP1, CXADR, DIO2, DKK2, DLK1, DPT, EMID1, FGFR3, TMEM100, FMO1, FMO3, FOXF1, FOXF2, GAP43, GDF10, HSD11B2, HSD17B2, HSPA6, IFI27, IFIT3, IGF2, IGFL3, LOC92196, MEOX1, MSX1, MSX2, MYBPH, MYH3, MYH11, MYL4, NLGN4X, NPPB, OGN, OLR1, PAX2, PAX9, PDE1A, PROM1, PTPRN, RASD1, RELN, RGS1, SERPINA3, SFRP2, SMOC2, SNAP25, STMN2, SYT12, TAC1, RSPO3, TNNT2, TRH, TUBB4, UGT2B7, WISP2, ZD52F10, ZIC1 and ZIC2.
The group of cell lines X7PEND12 and X7PEND24 are positive for the markers: AQP1, BEX1, CDH3, DIO2, DLK1, FOXF1, FST, GABRB1, IGF2, IGFBP5, IL1R1, KIAA0644, MSX1, PODN, PRRX2, SERPINA3, SOX11, SRCRB4D and TFPI2 and are negative for the markers: ACTC, AGC1, AKR1C1, ALDH1A1, ANXA8, APCDD1, AREG, CFB, C3, C6, C7, PRSS35, CCDC3, CD24, CLDN11, COMP, COP1, CXADR, DKK2, EMID1, FGFR3, FMO1, FMO3, GAP43, GDF10, GSC, HOXA5, HSD11B2, HSPA6, HTRA3, ICAM5, ID4, IFI27, IFIT3, INA, KCNMB1, KRT14, KRT17, KRT34, IGFL3, LOC92196, MFAP5, MASP1, MEOX1, MEOX2, MMP1, MX1, MYBPH, MYH3, MYH11, MYL4, IL32, NLGN4X, NPPB, OGN, OSR2, PAX2, PAX9, PENK, PITX2, PRELP, PRG4, PRRX1, RARRES1, RELN, RGMA, SFRP2, SMOC1, SMOC2, SOD3, SYT12, TAC1, TNESF7, TRH, TSLP, TUBB4, UGT2B7, WISP2, ZD52F10, ZIC1 and ZIC2.
The group of cell lines X7PEND9 and X7PEND16 are positive for the markers: BEX1, CDH6, DLK1, TMEM100, FOXF1, FOXF2, IGF2, IGFBP5, IL1R1, KIAA0644, TMEM119, MGP, MSX1, MSX2, PDE1A, PODN, PRRX2, TABLE I-continued Exemplary progenitor cell lines and associated gene expression markers at 18-21 doublings of clonal expansion PTN, S100A4, SERPINA3, SNAP25, SOX11 and SRCRB4D and are negative for the markers: ACTC, AGC1, AKR1C1, ALDH1A1, ANXA8, AREG, ATP8B4, BMP4, C3, C20orf103, CCDC3, CD24, CDH3, CNTNAP2, COP1, CRYAB, CXADR, METTL7A, DKK2, EMID1, FGFR3, FMO1, GDF10, GSC, HOXA5, HSD11 B2, HSD17B2, HSPA6, HSPB3, ICAM5, ID4, IFI27, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPAS1, NPPB, OLR1, OSR2, PAX2, PAX9, PENK, PITX2, PRELP, PRG4, PROM1, PTPRN, RASD1, RELN, RGS1, SFRP2, SMOC1, SMOC2, SOD3, SYT12, TAC1, RSPO3, THY1, TNFSF7, TNNT2, TRH, TSLP, TUBB4, UGT2B7, ZD52F10, ZIC1 and ZIC2.

The cell line X7PEND30 is positive for the markers: BEX1, PRSS35, CDH6, COL15A1, DIO2, DLK1, DPT, TMEM100, FMO1, FMO3, FOXF1, FOXF2, FST, HSPB3, IGF2, IGFBP5, IL1R1, KIAA0644, KRT19, LAMC2, TMEM119, MGP, MSX1, PDE1A, PODN, PRRX2, S100A4, SERPINA3, SOX11 and SRCRB4D and is negative for the markers: ACTC, AGC1, AKR1C1, ALDH1A1, ANXA8, APCDD1, AQP1, AREG, ATP8B4, C3, C7, C20orf103, CCDC3, CD24, CDH3, CLDN11, CNTNAP2, COP1, CXADR, DKK2, EMID1, FGFR3, GAP43, GDF5, GDF10, GJB2, GSC, HOXA5, HSD11B2, HSD17B2, HSPA6, HTRA3, ICAM5, ID4, IFI27, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OSR2, PAX2, PAX9, PENK, PITX2, PRELP, PRRX1, PTGS2 PTPRN, RELN, RGS1, SFRP2, SMOC1, SMOC2, SOD3, STMN2, SYT12, TAC1, RSPO3, THY1, TNFSF7, TNNT2, TRH, TSLP, TUBB4, UGT2B7, WISP2, ZD52F10, ZIC1 and ZIC2.

The cell line X7SKEL2 is positive for the markers: APCDD1, BEX1, C6, C7, PRSS35, COL21A1, CRIP1, CRLF1, CRYAB, DLK1, TMEM100, FMO1, FOXF2, GDF5, HSD11B2, IGF2, IGFBP5, KRT19, LAMC2, TMEM119, MGP, NPAS1, PRRX2, PTPRN, RGMA, S100A4, SERPINA3, SNAP25 and SOX11 and is negative for the markers: ACTC, AGC1, AKR1C1, ALDH1A1, ANXA8, AQP1, AREG, ATP8B4, CFB, BMP4, C3, C20orf103, CCDC3, CD24, CDH3, CDH6, CLDN11, CNTNAP2, COMP, COPI, CXADR, DIO2, METTL7A, DKK2, DPT, EGR2, EMID1, FGFR3, FOXF1, GABRB1, GDF10, GJB2, GSC, HOXA5, HSD17B2, HSPA6, HTRA3, ID4, IFI27, IFIT3, KCNMB1, KIAA0644, KRT14, KRT17, KRT34, IGFL3, LOC92196, MFAP5, MASP1, MEOX1, MEOX2, MMP1, MSX2, MX1, MYBPH, MYH3, MYH11, MYL4, IL32, NLGN4X, NPPB, OGN, OLR1, OSR2, PAX2, PAX9, PENK, PITX2, POSTN, PRELP, PROM1, PRRX1, PTGS2, PTN, RARRES1, RELN, RGS1, SLITRK6, SMOC1, SMOC2, SOD3, STMN2, SYT12, TAC1, TFPI2, RSPO3, THY1, TNFSF7, TRH, TSLP, TUBB4, UGT2B7, ZIC1 and ZIC2.

The cell line X7SKEL22 is positive for the markers: ACTC, BEX1, C7, PRSS35, COL21A1, CRIP1, CRYAB, DIO2, DPT, EGR2, FMO3, FOXF1, FOXF2, FST, GJB2, HSPB3, IGF2, IGFBP5, IL1R1, KRT19, LAMC2, TMEM119, MGP, NPAS1, PODN, PRRX2, SERPINA3, SOX11 and SRCRB4D and is negative for the markers: AGC1, AKR1C1, ALDH1A1, ANXA8, AQP1, AREG, ATP8B4, CFB, BMP4, C3, C20orf103, CCDC3, CD24, CDH3, CDH6, CLDN11, CNTNAP2, COL15A1, COMP, COP1, CXADR, METTL7A, DKK2, DLK1, EMID1, FGFR3, TMEM100, GABRB1, GAP43, GDF5, GDF10, GSC, HOXA5, HSD17B2, HSPA6, HTRA3, ICAM5, ID4, IFI27, IFIT3, KCNMB1, KRT14, KRT17, KRT34, IGFL3, LOC92196, MFAP5, MASP1, MEOX1, MEOX2, MMP1, MSX1, MSX2, MX1, MYBPH, MYH3, MYH11, IL32, NLGN4X, NPPB, OGN, OLR1, OSR2, PAX2, PAX9, PENK, PITX2, POSTN, PRELP, PRG4, PROM1, PRRX1, PTN, RARRES1, RASD1, RELN, RGS1, SFRP2, SLITRK6, SMOC1, SMOC2, SOD3, STMN2, SYT12, TAC1, TFPI2, RSPO3, TNFSF7, TNNT2, TRH, TSLP, TUBB4, UGT2B7, ZD52F10, ZIC1 and ZIC2.

The group of cell lines X7SKEL4, X7SKEL6 and X7SKEL7 are positive for the markers: BEX1, COL21A1, CRLF1, DLK1, FMO1, FMO3, FOXF1, FOXF2, HSD11B2, IGF2, IGFBP5, IL1R1, TMEM119, PRRX2, RGMA, SERPINA3, SNAP25, SOX11 and SRCRB4D and are negative for the markers: ACTC, AGC1, AKR1C1, ALDH1A1, ANXA8, AQP1, AREG, ATP8B4, CFB, BMP4, C3, C20orf103, CCDC3, CD24, CDH3, CLDN11, CNTNAP2, COL15A1, COMP, COP1, CXADR, DKK2, EMID1, FGFR3, GDF10, GJB2, GSC, HOXA5, HSD17B2, HSPA6, HTRA3, ID4, IFI27, IFIT3, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OLR1, OSR2, PAX2, PENK, PITX2, POSTN, PRELP, PROM1, RELN, RGS1, SFRP2, SLITRK6, SMOC1, SMOC2, SOD3, STMN2, SYT12, TAC1, TFPI2, RSPO3, THY1, TNFSF7, TNNT2, TRH, TSLP, TUBB4 and ZIC1.

The cell line X7SMOO12 is positive for the markers: BEX1, CDH6, COL21A1, CRIP1, DIO2, DLK1, EGR2, FOXF1, FOXF2, FST, IGF2, IGFBP5, TMEM119, MSX1, MSX2, MX1, PODN, POSTN, PRRX2, PTN, S100A4, SERPINA3, SOX11, TFPI2, WISP2 and ZIC2 and is negative for the markers: ACTC, AGC1, AKR1C1, ALDH1A1, ANXA8, APCDD1, AQP1, AREG, CFB, C3, C6, C7, C20orf103, CCDC3, CD24, CLDN11, CNTNAP2, COMP, COP1, CRYAB, CXADR, METTL7A, DKK2, EMID1, FGFR3, TMEM100, GABRB1, GAP43, GDF10, GJB2, GSC, HOXA5, HSD11B2, HSD17B2, HSPA6, HSPB3, HTRA3, ICAM5, ID4, IFI27, IL1R1, KCNMB1, KRT14, KRT17, KRT34, IGFL3, LOC92196, MFAP5, MASP1, MEOX1, MEOX2, MGP, MMP1, MYBPH, MYH3, MYH11, MYL4, IL32, NLGN4X, NPPB, OGN, OSR2, PAX2, PAX9, PDE1A, PENK, PITX2, PRELP, PRG4, PTGS2, RARRES1, RGS1, SFRP2, SMOC1, SMOC2, SOD3, SYT12, TAC1, RSPO3, TNFSF7, TRH, TSLP, TUBB4, UGT2B7, ZD52F10 and ZIC1.

The cell line X7SMOO19 is positive for the markers: BEX1, CDH6, COL15A1, COL21A1, COMP, CRIP1, DLK1, EGR2, FMO1, FMO3, FOXF1, FOXF2, FST, HSPA6, IGF2, IGFBP5, KIAA0644, KRT19, LAMC2, TMEM119, MSX1, MSX2, OGN, PODN, PRRX2, RGMA, S100A4, SERPINA3, SNAP25, SOX11, SRCRB4D, TNNT2 and ZIC2 and is negative for the markers: ACTC, AGC1, AKR1C1, ALDH1A1, ANXA8, APCDD1, AREG, ATP8B4, C3, C6, C7, C20orf103, CCDC3, CD24, CLDN11, COP1, CXADR, DIO2, METTL7A, DKK2, DPT, EMID1, TMEM100, GABRB1, GJB2, GSC, HOXA5, HSD11B2, HSD17B2, HTRA3, ICAM5, ID4, IFI27, IL1R1, INA, KCNMB1, KRT14, KRT17, KRT34, IGFL3, LOC92196, MFAP5, MASP1, MEOX1, MEOX2, MMP1, MYBPH, MYH3, MYH11, MYL4, IL32, NLGN4X, NPPB, OLR1, OSR2, PAX2, PAX9, PENK, PITX2, PRG4, PROM1, PTPRN, RARRES1, RELN, RGS1, SFRP2, SLITRK6, SMOC1, SMOC2, SOD3, STMN2, SYT12, TAC1, RSPO3, TNFSF7, TRH, TSLP, TUBB4, UGT2B7, WISP2, ZD52F10 and ZIC1.

The cell line X7SMOO25 is positive for the markers: AQP1, ATP8B4, BEX1, CDH3, COL21A1, CRIP1, DLK1, FOXF1, FOXF2, FST, GABRB1, HSPB3, IGF2, IGFBP5, IL1R1, KRT19, LAMC2, TMEM119, MSX1, MSX2, PODN, POSTN, PRRX2, PTN, RGMA, S100A4, SERPINA3, SLITRK6, SOX11, SRCRB4D, TFPI2, RSPO3 and THY1 and is negative for the markers: ACTC, AGC1, AKR1C1, ANXA8, APCDD1, AREG, CFB, BMP4, C3, C6, C7, PRSS35, C20orf103, CCDC3, CLDN11, COL15A1, COP1, CXADR, METTL7A, DKK2, EGR2, EMID1, FGFR3, TMEM100, FMO1, FMO3, GDF10, GJB2, GSC, HOXA5, HSD11B2, HSD17B2, HSPA6, HTRA3, ICAM5, ID4, IFI27, INA, KCNMB1, KRT14, KRT17, KRT34, IGFL3, LOC92196, MASP1, MEOX1, MEOX2, MGP, MYBPH, MYH3, MYH11, MYL4, IL32, NLGN4X, NPPB, OGN, OLR1, OSR2, PAX2, PAX9, PDE1A, TABLE I-continued Exemplary progenitor cell lines and associated gene expression markers at 18-21 doublings of clonal expansion PENK, PITX2, PRELP, PRG4, PROM1, PRRX1, PTPRN, RASD1, RELN, RGS1, SFRP2, SMOC1, SMOC2, SOD3, SYT12, TAC1, TNFSF7, TRH, TSLP, TUBB4, UGT2B7, WISP2, ZD52F10, ZIC1 and ZIC2.
The cell line X7SMOO26 is positive for the markers: BEX1, CCDC3, CDH6, COL15A1, COL21A1, COMP, CRIP1, CRLF1, CRYAB, DIO2, EGR2, FOXF1, FOXF2, FST, GDF10, HSPB3, IGF2, IGFBP5, KRT19, LAMC2, TMEM119, MSX1, MSX2, NPAS1, PODN, POSTN, PRRX2, S100A4, SERPINA3, SOX11, SRCRB4D, TNNT2 and ZIC2 and is negative for the markers: ACTC, AGC1, AKR1C1, ALDH1A1, ANXA8, APCDD1, AREG, ATP8B4, CFB, BMP4, C3, C6, C7, C20orf103, CD24, CDH3, CLDN11, COP1, METTL7A, DLK1, DPT, EMID1, FGFR3, TMEM100, FMO1, FMO3, GJB2, GSC, HOXA5, HSD11B2, HSPA6, HTRA3, ICAM5, ID4, IFI27, IL1R1, KCNMB1, KIAA0644, KRT14, KRT34, IGFL3, LOC92196, MFAP5, MASP1, MEOX1, MEOX2, MGP, MMP1, MX1, MYBPH, MYH3, IL32, NLGN4X, OGN, OLR1, OSR2, PAX2, PAX9, PDE1A, PENK, PITX2, PRELP, PRG4, PROM1, PTGS2, PTN, PTPRN, RARRES1, RASD1, RELN, RGS1, SFRP2, SLITRK6, SMOC1, SMOC2, SNAP25, SOD3, STMN2, SYT12, TAC1, TFPI2, RSPO3, THY1, TNFSF7, TRH, TSLP, TUBB4, UGT2B7, WISP2, ZD52F10 and ZIC1.
The group of cell lines X7SMOO9 and X7SMOO29 are positive for the markers: BEX1, COL21A1, CRIP1, CRLF1, DIO2, DLK1, FOXF1, FOXF2, FST, IGF2, IGFBP5, KIAA0644, TMEM119, MSX1, PODN, POSTN, PRRX2, RGMA, S100A4, SERPINA3, SNAP25, SOX11 and SRCRB4D and are negative for the markers: ACTC, AGC1, AKR1C1, ALDH1A1, ANXA8, APCDD1, AQP1, AREG, ATP8B4, C3, C6, C7, PRSS35, C20orf103, CCDC3, CD24, CDH3, CLDN11, COP1, CXADR, METTL7A, DKK2, EMID1, GDF10, GJB2, GSC, HOXA5, HSD11B2, HSD17B2, HSPA6, HTRA3, ICAM5, ID4, IFI27, IL1R1, INA, KCNMB1, KRT14, KRT17, KRT19, KRT34, IGFL3, LOC92196, MFAP5, MASP1, MEOX1, MEOX2, MYH3, MYH11, MYL4, IL32, NLGN4X, NPPB, OLR1, OSR2, PAX2, PAX9, PENK, PITX2, PRELP, PROM1, PTPRN, RASD1, RELN, RGS1, SMOC1, SMOC2, SYT12, TAC1, TNFSF7, TRH, TSLP, TUBB4, UGT2B7, ZD52F10 and ZIC1.
The cell line X7SMOO32 is positive for the markers: ACTC, BEX1, CDH6, COL21A1, CRIP1, CRLF1, DIO2, DLK1, EGR2, FGFR3, FOXF1, FOXF2, FST, GABRB1, IGFBP5, KIAA0644, KRT19, LAMC2, TMEM119, MGP, MMP1, MSX1, MSX2, PODN, POSTN, PRG4, PRRX2, PTN, RGMA, S100A4, SERPINA3, SOX11 and SRCRB4D and is negative for the markers: AGC1, AKR1C1, ALDH1A1, ANXA8, APCDD1, AREG, ATP8B4, BMP4, C3, C6, C7, PRSS35, C20orf103, CCDC3, CD24, CLDN11, CNTNAP2, COL15A1, COP1, CXADR, METTL7A, DKK2, DPT, EMID1, TMEM100, FMO1, FMO3, GDF5, GDF10, GJB2, GSC, HOXA5, HSD11B2, HSD17B2, HSPA6, HSPB3, HTRA3, ICAM5, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, NLGN4X, NPPB, OGN, OLR1, OSR2, PAX2, PAX9, PDE1A, PITX2, PRELP, PROM1, PTPRN, RASD1, RGS1, SFRP2, SMOC1, SMOC2, SOD3, STMN2, SYT12, TAC1, RSPO3, TNFSF7, TNNT2, TRH, TSLP, TUBB4, UGT2B7, WISP2, ZD52F10, ZIC1 and ZIC2.
The cell line X7SMOO6 is positive for the markers: ACTC, BEX1, CNTNAP2, COL15A1, COL21A1, CRIP1, CRLF1, CRYAB, DLK1, EGR2, FMO1, FMO3, FOXF1, FOXF2, FST, HSPB3, IGF2, IGFBP5, KRT19, LAMC2, TMEM119, MGP, MSX1, MSX2, NPAS1, OGN, PODN, POSTN, PRRX2, RGMA, S100A4, SERPINA3, SNAP25, SOX11, SRCRB4D, STMN2 and TNNT2 and is negative for the markers: AGC1, AKR1C1, ALDH1A1, ANXA8, APCDD1, AQP1, AREG, ATP8B4, C3, C6, C7, C20orf103, CCDC3, CD24, CLDN11, COP1, CXADR, DIO2, METTL7A, DKK2, EMID1, TMEM100, GAP43, GDF10, GJB2, GSC, HOXA5, HSD11B2, HSD17B2, HSPA6, HTRA3, ICAM5, ID4, IFI27, IL1R1, INA, KCNMB1, KRT14, KRT17, KRT34, IGFL3, LOC92196, MFAP5, MASP1, MEOX1, MEOX2, MYBPH, MYH3, MYH11, MYL4, IL32, NLGN4X, TAGLN3, NPPB, OSR2, PAX2, PAX9, PDE1A, PENK, PITX2, PRG4, PRRX1, PTGS2, PTPRN, RASD1, RELN, RGS1, SFRP2, SMOC1, SMOC2, SYT12, TAC1, RSPO3, TNFSF7, TRH, TSLP, TUBB4, UGT2B7, ZD52F10, ZIC1 and ZIC2.
The cell line X7SMOO7 is positive for the markers: ACTC, BEX1, CDH6, CRIP1, CRLF1, CRYAB, DLK1, EGR2, FOXF1, FOXF2, FST, HSPA6, IGF2, IGFBP5, INA, LAMC2, MMP1, MSX1, MSX2, TAGLN3, POSTN, PRRX2, PTGS2, PTPRN, RASD1, RELN, S100A4, SNAP25, SOX11, SRCRB4D, TAC1, TFPI2 and RSPO3 and is negative for the markers: AGC1, AKR1C1, ALDH1A1, ANXA8, APCDD1, AQP1, AREG, CFB, BMP4, C3, C6, C7, C20orf103, CCDC3, CDH3, CLDN11, CNTNAP2, COL15A1, COL21A1, COP1, CXADR, METTL7A, DKK2, DPT, EMID1, FMO3, GAP43, GDF5, GDF10, GSC, HOXA5, HSD11B2, HSD17B2, HSPB3, HTRA3, ID4, 1FI27, IFIT3, KCNMB1, KIAA0644, KRT14, KRT17, IGFL3, LOC92196, MFAP5, MASP1, MEOX1, MEOX2, MGP, MYBPH, MYH3, MYH11, MYL4, IL32, NLGN4X, NPPB, OGN, OLR1, OSR2, PAX2, PAX9, PDE1A, PENK, PITX2, PRELP, PRG4, PROM1, PRRX1, PTN, RGMA, RGS1, SFRP2, SLITRK6, SMOC2, SOD3, STMN2, SYT12, TNNT2, TRH, TSLP, TUBB4, WISP2 and ZIC1.
The group of cell lines Z1, Z6 and Z7 are positive for the markers: FST, GDF5, MMP1, MSX1, SRCRB4D, ZIC1 and ZIC2 and are negative for the markers: ACTC, AGC1, AKR1C1, ALDH1A1, ANXA8, APCDD1, AQP1, AREG, ATP8B4, CFB, BMP4, C3, C6, C7, C20orf103, CDH3, CLDN11, CNTNAP2, CRLF1, DIO2, METTL7A, DKK2, DLK1, DPT, EMID1, FGFR3, TMEM100, FMO1, FMO3, FOXF2, GABRB1, GJB2, GSC, HOXA5, HSD11B2, HSPA6, HSPB3, ID4, IFI27, IGF2, KCNMB1, KIAA0644, KRT14, IGFL3, LOC92196, MFAP5, MASP1, MEOX1, MEOX2, MGP, MYBPH, MYH3, MYH11, NLGN4X, NPPB, OGN, OLR1, PAX2, PAX9, PDE1A, PENK, PITX2, PRG4, PROM1, RARRES1, RASD1, RELN, RGS1, SFRP2, SMOC1, SMOC2, SNAP25, STMN2, SYT12, TAC1, RSPO3, TNFSF7, TNNT2, TRH, TUBB4 and WISP2.
The cell line Z11 (also known as Z11Rep1 and Z11Rep2 and ACTCI94) is positive for the markers: ATP8B4, CD24, DLK1, FOXF1, FST, HTRA3, IGF2, IGH3P5, IL1R1, MSX1, NLGN4X, OSR2, PODN, PROM1, PRRX2, PTN, SOD3, SOX11, SRCRB4D, STMN2 and TFPI2 and are negative for the markers: ACTC, AGC1, AKR1C1, ALDH1A1, ANXA8, APCDD1, AREG, CFB, C6, C7, PRSS35, CCDC3, CDH3, CLDN11, CNTNAP2, COMP, CRIP1, CRLF1, DIO2, DKK2, DPT, EMID1, FMO1, FMO3, GAP43, GDF10, GJB2, GSC, HOXA5, HSD11B2, HSPA6, HSPB3, IFI27, INA, KCNMB1, KIAA0644, KRT14, KRT17, KRT34, LAMC2, IGFL3, LOC92196, MFAP5, MEOX1, MEOX2, MX1, MYBPH, MYH3, MYH11, MYL4, IL32, NPPB, OLR1, PAX2, PITX2, RARRES1, RASD1, RGS1, SMOC1, SMOC2, SNAP25, TAC1, TNFSF7, TNNT2, TRH, TUBB4, UGT2B7, WISP2, ZIC1 and ZIC2.
The cell line Z2 is positive for the markers: BEX1, CCDC3, EGR2, FOXF1, FOXF2, FST, GDF5, HSPB3, IGFBP5, INA, TMEM119, MASP1, MMP1, MSX2, POSTN, PRELP, PRRX2, PTN, SRCRB4D, TFPI2 and TSLP and is negative for the markers: ACTC, AGC1, AKR1C1, ALDH1A1, ANXA8, APCDD1, AQP1, AREG, CFB, BMP4, C3, C6, C7, C20orf103, CD24, CDH3, CLDN11, CNTNAP2, COL21A1, DIO2, DKK2, DLK1, DPT, FGFR3, TMEM100, FMO1, FMO3, GABRB1, GAP43, GDF10, GJB2, GSC, HOXA5, HSD11B2, HSD17B2, HSPA6, ID4, IFI27, KCNMB1, KIAA0644, KRT14, KRT17, KRT34, IGFL3, LOC92196, MFAP5, MEOX1, MEOX2, MYBPH, MYH3, MYH11, NLGN4X, NPPB, OGN, OSR2, PAX2, PAX9, PDE1A, PENK, PITX2, TABLE I-continued Exemplary progenitor cell lines and associated gene expression markers at 18-21 doublings of clonal expansion PRG4, PROM1, RARRES1, RASD1, RGS1, SMOC1, SMOC2, SNAP25, STMN2, TAC1, RSPO3, TNFSF7, TNNT2, TRH, TUBB4, WISP2, ZIC1 and ZIC2.
The cell line MEL2 is positive for the markers: AKR1C1, AQP1, COL21A1, CRYAB, CXADR, DIO2, METTL7A, DKK2, DLK1, HSD17B2, HSPB3, MGP, MMP1, MSX2, PENK, PRRX1, PRRX2, S100A4, SERPINA3, SFRP2, SNAP25, SOX11, TFPI2 and THY1 and is negative for the markers: ACTC, ALDH1A1, AREG, CFB, C3, C20orf103, CD24, CDH3, CDH6, CNTNAP2, COL15A1, COMP, COP1, CRLF1, FGFR3, FMO1, FMO3, FOXF2, FST, GABRB1, GAP43, GDF5, GDF10, GJB2, GSC, HOXA5, HSD11B2, HSPA6, ICAM5, KCNMB1, KRT14, KRT17, KRT19, KRT34, MASP1, MEOX1, MEOX2, MYBPH, MYH3, MYH11, TAGLN3, NPAS1, NPPB, OLR1, PAX2, PDE1A, PITX2, PRG4, PTN, PTPRN, RASD1, RELN, RGS1, SMOC1, STMN2, TAC1, TNFSF7, TRH, TUBB4, WISP2, ZIC1 and ZIC2.
The cell line C4ELSR10 is positive for the markers: AKR1C1, ALDH1A1, ANXA8, AREG, CDH6, COP1, DIO2, METTL7A, EGR2, FOXF1, HSD17B2, IGFBP5, KIAA0644, KRT19, KRT34, OLR1, PITX2, S100A4, STMN2 and TFPI2 and is negative for the markers: ACTC, AQP1, C7, C20orf103, CD24, CDH3, CLDN11, CNTNAP2, COMP, CRIP1, CRLF1, DKK2, DLK1, DP1, FGFR3, FMO1, GABRB1, CRLF43, GDF10, GJB2, GSC, HSD11B2, HSPA6, HSPB3, ICAM5, ID4, KRT14, KRT17, LAMC2, MFAP5, MASP1, MEOX1, MEOX2, MGP, MMP1, MSX1, MYBPH, MYH3, MYH11, TAGLN3, NPAS1, NPPB, OGN, PAX2, PAX9, PENK, PRELP, PRG4, PRRX1, PRRX2, PTN, RELN, RGS1, SERPINA3, SFRP2, SMOC1, SNAP25, SOX11, TAC1, TNNT2, TUBB4, WISP2, ZIC1 and ZIC2.
The cell line Z3 is positive for the markers: BEX1, CDH6, COL21A1, CXADR, EGR2, FOXF1, FST, HSD17B2, LAMC2, MMP1, MSX1, MSX2, SERPINA3, ZIC1 and ZIC2 and is negative for the markers: ACTC, ALDH1A1, AQP1, ATP8B4, CFB, C3, C7, C20orf103, CDH3, CLDN11, CNTNAP2, COMP, CRIP1, CRLF1, DIO2, METTL7A, DKK2, DLK1, DPT, FGFR3, FMO1, FMO3, GABRB1, GJB2, GSC, HOXA5, HSD11B2, HSPA6, HSPB3, ICAM5, ID4, IFI27, IGF2, KCNMB1, KIAA0644, KRT14, KRT17, MFAP5, MASP1, MEOX1, MEOX2, MGP, MX1, MYBPH, MYH3, MYH11, NPAS1, OGN, OLR1, PAX2, PAX9, PDE1A, PRG4, PROM1, PRRX2, PTN, PTPRN, RARRES1, RASD1, RGS1, S100A4, SFRP2, SMOC1, SNAP25, STMN2, TAC1, TNFSF7, TUBB4 and WISP2.
The cell line SK15 is positive for the markers: AREG, BEX1, FOXF1, KRT19, LAMC2, MSX1, PITX2, S100A4, SERPINA3 and THY1 and is negative for the markers: AGC1, ALDH1A1, AQP1, ATP8B4, CFB, C3, C7, C20orf103, CD24, CDH3, CDH6, CLDN11, CNTNAP2, COL15A1, COMP, CRIP1, CRLF1, DLK1, DPT, FMO1, FMO3, GABRB1, GDF10, GJB2, GSC, HOXA5, HSD11B2, HSD17B2, HSPA6, HSPB3, ICAM5, ID4, IGF2, IGFBP5, KCNMB1, KIAA0644, KRT14, KRT17, MFAP5, MASP1, MEOX1, MEOX2, MGP, MSX2, MX1, MYBPH, MYH3, MYH11, OGN, OLR1, PAX2, PAX9, PDE1A, PRG4, PROM1, PRRX2, PTN, RARRES1, RGS1, SFRP2, SMOC1, SNAP25, STMN2, TAC1, TNNT2, TRH, TUBB4, WISP2, ZIC1 and ZIC2.
The cell line W8Rep2a is positive for the markers: AQP1, AREG, BEX1, CDH6, COL21A1, COP1, DIO2, METTL7A, DLK1, FMO1, FMO3, FOXF1, FOXF2, MMP1, MSX1, MSX2, PDE1A, PRRX2, SERPINA3, SNAP25, SOX11, TFPI2 and ZIC2 and is negative for the markers: ALDHIA1, ATP8B4, C3, C7, C20orf103, CD24, CLDN11, CNTNAP2, COMP, CRIP1, CRLF1, CXADR, DKK2, DPT, EGR2, GAP43, GDF10, GJB2, GSC, HOXA5, HSD11B2, HSD17B2, HSPA6, HSPB3, ICAM5, ID4, IFI27, KCNMB1, KRT14, KRT17, KRT34, MFAP5, MASP1, MEOX1, MEOX2, MGP, MX1, MYBPH, MYH3, MYH11, NPAS1, NPPB, OLR1, PAX2, PAX9, PITX2, PRG4, PROM1, PRRX1, PTGS2, PIN, PTPRN, RGS1, SFRP2, STMN2, TAC1, THY1, TNNT2, TRH, TUBB4 and ZIC1.
The cell line E55 is positive for the markers: AKR1C1, BEX1, CDH6, COL21A1, DIO2, DKK2, EGR2, GAP43, KRI19, MSX2, PRRX1, S100A4, SOX11, THY1, TNNT2 and ZIC2 and is negative for the markers: ALDH1A1, AQP1, AREG, ATP8B4, C3, C7, C20orf103, CLDN11, CNTNAP2, COMP, CRLF1, CXADR, DLK1, DPT, FMO1, FMO3, FOXF2, GABRB1, GDF10, GJB2, GSC, HOXA5, HSD11B2, HSD17B2, HSPA6, HSPB3, IFI27, IGF2, KRT14, KRT34, LAMC2, MFAP5, MASP1, MEOX1, MEOX2, MGP, MYBPH, MYH3, NPAS1, NPPB, OGN, OLR1, PAX2, PAX9, PDE1A, PENK, PITX2, PRG4, PROM1, PRRX2, PTN, PTPRN, RARRES1, RGS1, SFRP2, SMOC1, SNAP25, STMN2, TAC1, TRH, TUBB4, WISP2 and ZIC1.
The cell line T20 is positive for the markers: ACTC, AKR1C1, BEX1, CDH6, COL21A1, CRYAB, DKK2, EGR2, GAP43, LAMC2, MMP1, MSX2, PITX2, SOX11, THY1 and ZIC2 and is negative for the markers: ALDH1A1, AREG, ATP8B4, CFB, C3, C7, C20orf103, CD24, CDH3, CLDN11, CNTNAP2, COMP, CRLF1, METTL7A, DPT, FMO1, FMO3, FOXF2, GDF10, GJB2, GSC, HOXA5, HSD11B2, HSD17B2, HSPA6, HSPB3, ICAM5, IFI27, IGF2, KIAA0644, KRT14, MASP1, MEOX2, MGP, MX1, MYBPH, MYH3, TAGLN3, NPAS1, NPPB, OGN, OLR1, PAX2, PDE1A, PRG4, PROM1, PRRX2, PTN, PTPRN, RARRES1, RASD1, RGS1, SFRP2, SMOC1, SNAP25, STMN2, TAC1, TFPI2, TNFSF7, TRH, TUBB4, WISP2 and, ZIC1.
The cell line X4D20.8 is positive for the markers: BEX1, CDH6, CNTNAP2, COL21A1, CRIP1, CRYAB, DIO2, DKK2, GAP43, ID4, LAMC2, MMP1, MSX2, S100A4, SOX11 and THY1 and is negative for the markers: AGC1, ALDH1A1, AREG, ATP8B4, CFB, C3, C7, C20orf103, CDH3, CLDN11, COP1, CRLF1, DLK1, DPT, FMO1, FMO3, GDF10, GJB2, GSC, HOXA5, HSD11B2, HSD17B2, HSPA6, HSPB3, ICAM5, IFI27, IGF2, KRT14, KRT17, KRT34, MASP1, MEOX2, MSX1, MX1, MYBPH, MYH3, MYH11, TAGLN3, NPAS1, NPPB, OGN, OLR1, PAX2, PDE1A, PRG4, PROM1, PTN, PTPRN, RARRES1, RGS1, SNAP25, STMN2, TAC1, TNNT2, TRH, TUBB4, WISP2, ZIC1 and ZIC2.
The cell line X4D20.3 is positive for the markers: ACTC, AKR1C1, AQP1, BEX1, CDH6, COL21A1, CRYAB, DKK2, DLK1, GJB2, HSD17B2, KRT17, LAMC2, MYL4, PITX2, S100A4, SOX11, THY1, TNNT2, ZIC1 and ZIC2 and is negative for the markers: AGC1, ALDH1A1, AREG, ATP8B4, CFB, C3, C7, C20orf103, CDH3, CLDN11, CNTNAP2, COMP, COP1, CRLF1, METTL7A, DPT, FGFR3, FMO1, FMO3, FOXF1, GABRB1, GSC, HOXA5, HSD11B2, HSPA6, HSPB3, ICAM5, ID4, IFI27, IGF2, IGFBP5, KIAA0644, KRT14, KRT34, MASP1, MEOX2, MGP, MSX2, MX1, MYBPH, MYH3, MYH11, NPAS1, OGN, OLR1, PAX9, PENK, PRG4, PROM1, PRRX2, PTN, RARRES1, RGS1, SFRP2, SNAP25, STMN2, TAC1, TRH, TUBB4 and WISP2.
The cell line E132 is positive for the markers: ACTC, AKR1C1, AQP1, CD24, CDH6, COL21A1, CRYAB, DKK2, KRT19, TAGLN3, RELN, S100A4, SFRP2, SOX11, THY1 and ZIC2 and is negative for the markers: AGC1, ALDH1A1, AREG, ATP8B4, CFB, C3, C7, C20orf103, CNTNAP2, COL15A1, COMP, COP1, CRLF1, DIO2, METTL7A, DLK1, DPT, FMO1, FMO3, FOXF1, FOXF2, FST, GABRB1, GDF10, GJB2, GSC, HOXA5, HSDI1B2, HSD17B2, HSPA6, HSPB3, ID4, IFI27, IGF2, KCNMB1, KRT14, MFAP5, MASP1, MEOX2, MGP, MYBPH, MYH3, MYH11, NPAS1, NPPB, OGN, OLR1, PDE1A, PRG4, PROM1, PRRX2, PTGS2, PTN, PTPRN, RARRES1, RASD1, RGS1, SERPINA3, SMOC1, SNAP25, STMN2, TAC1, TRH, TUBB4, WISP2 and ZIC1.

TABLE I-continued

Exemplary progenitor cell lines and associated gene expression markers at 18-21 doublings of clonal expansion The cell line M13 is positive for the markers: ACTC, ANXA8, BEX1, CDH6, COL15A1, EGR2, GDF10, GJB2, KRT19, LAMC2, MYL4, TAGLN3, S100A4, SFRP2, SOX11, THY1, ZIC1 and ZIC2 and is negative for the markers: ALDH1A1, AREG, ATP8B4, CFB, C3, C7, C20orf103, CDH3, CLDN11, CNTNAP2, COMP, COP1, CRLF1, DIO2, DLK1, DPT, FGFR3, FMO1, FMO3, FOXF1, GABRB1, GAP43, GSC, HOXA5, HSD11B2, HSD17B2, HSPA6, HSPB3, ICAM5, ID4, IFI27, IGF2, KIAA0644, KRT14, MFAP5, MEOX2, MGP, MMP1, MSX2, MYBPH, MYH3, NPAS1, OGN, OLR1, PDE1A, PRELP, PRG4, PROM1, PRRX2, PTN, PTPRN, RARRES1, RASD1, RELN, RGS1, SMOC1, SNAP25, STMN2, TAC1, TRH, TUBB4 and WISP2.

The cell line M10 is positive for the markers: ACTC, BEX1, CDH6, COL21A1, DIO2, DKK2, EGR2, IGFBP5, PRRX1, S100A4, SFRP2, THY1 and ZIC2 and is negative for the markers: AKR1C1, ALDH1A1, AQP1, AREG, ATP8B4, CFB, C3, C7, C20orf103, CD24, CDH3, CLDN11, CNTNAP2, COMP, COP1, CRLF1, CXADR, METTL7A, DPT, FMO1, FMO3, FOXF1, GABRB1, GJB2, GSC, HOXA5, HSD11B2, HSD17B2, HSPA6, HSPB3, ICAM5, IFI27, IGF2, KIAA0644, KRT14, MEOX1, MEOX2, MOP, MYBPH, MYH3, MYH11, TAGLN3, NPAS1, OGN, OLR1, PAX2, PAX9, PDE1A, PITX2, PRG4, PROM1, PRRX2, PTN, PTPRN, RELN, RGS1, SERPINA3, SMOC1, SNAP25, STMN2, TAC1, TNFSF7, TNNT2, TRH, TUBB4, WISP2 and ZIC1.

The cell line E109 is positive for the markers: ACTC, AKR1C1, BEX1, CDH6, COL15A1, COL21A1, CRIP1, CRYAB, DIO2, DKK2, GAP43, GDF5, ID4, KRT14, KRT19, KRT34, MFAP5, MEOX2, MGP, MMP1, MYH11, S100A4, TFPI2, THY1 and ZIC1 and is negative for the markers: ALDH1A1, AQP1, AREG, ATP8B4, C3, C7, C20orf103, CD24, CDH3, CLDN11, CNTNAP2, COMP, CRLF1, CXADR, METTL7A, DLK1, DPT, FMO1, FMO3, FOXF1, FOXF2, GDF10, GJB2, GSC, HSD11B2, HSD17B2, HSPA6, ICAM5, IGF2, KIAA0644, MASP1, MEOX1, MYBPH, MYH3, TAGLN3, NPAS1, NPPB, OGN, PAX2, PAX9, PDE1A, PITX2, PRG4, PROM1, PRRX2, PTN, RARRES1, RASD1, RGS1, SFRP2, SMOC1, SNAP25, STMN2, TAC1, TRH, TUBB4 and WISP2.

The cell line E34 is positive for the markers: ACTC, AGC1, AQP1, CDH6, COL15A1, COL21A1, CRYAB, DKK2, GAP43, KRT14, KRT17, KRT19, KRT34, MFAP5, MEOX1, MEOX2, MGP, MYH11, TAGLN3, S100A4, THY1, TNNT2, ZIC1 and ZIC2 and is negative for the markers: ALDH1A1, AREG, ATP8B4, C3, C7, C20orf103, CDH3, CLDN11, CNTNAP2, COMP, COP1, CRLF1, CXADR, DIO2, METTL7A, DPT, FMO1, FMO3, FOXF1, FOXF2, FST, GABRB1, GDF10, GJB2, GSC, HOXA5, HSD11B2, HSPA6, IFI27, IGF2, KIAA0644, LAMC2, MASP1, MSX2, MX1, MYBPH, MYH3, NPAS1, OLR1, PAX9, PDE1A, PRG4, PROM1, PRRX2, PTN, RARRES1, RASD1, ROS1, SERPINA3, SFRP2, SMOC1, SNAP25, STMN2, TAC1, TFPI2, TRH, TUBB4 and WISP2.

The cell line E122 is positive for the markers: ACTC, AGC1, AKR1C1, BEX1, CDH6, COL21A1, CRIP1, CRYAB, DIO2, DKK2, GAP43, ID4, KRT19, MFAP5, MYH11, MYL4, OGN, PRRX1, PTGS2, S100A4, SOX11 and THY1 and is negative for the markers: ALDH1A1, AREG, ATP8B4, CFB, C3, C7, C20orf103, CD24, CDH3, CLDN11, CNTNAP2, COL15A1, COP1, CRLF1, METTL7A, DLK1, DPT, FMO1, FMO3, FOXF2, GABRB1, GDF10, GJB2, GSC, HOXA5, HSD11B2, HSD17B2, HSPA6, HSPB3, ICAM5, IFI27, IGF2, KIAA0644, KRT14, KRT17, KRT34, LAMC2, MASP1, MEOX1, MEOX2, MYBPH, NPAS1, NPPB, OLR1, PAX2, PAX9, PDE1A, PRG4, PROM1, RARRES1, RASD1, RGS1, SERPINA3, SFRP2, SMOC1, SNAP25, STMN2, TAC1, TUBB4, WISP2 and ZIC2.

The cell line E65 is positive for the markers: ACTC, AKR1C1, AQP1, BEX1, CD24, CDH6, COL21A1, CRYAB, DKK2, GAP43, KRT17, KRT19, KRT34, TAGLN3, RELN, S100A4, SFRP2, SOX11, THY1 and ZIC2 and is negative for the markers: AGC1, ALDH1A1, ATP8B4, CFB, C3, C7, C20orf103, CDH3, CLDN11, CNTNAP2, COMP, COP1, CRIP1, CRLF1, CXADR, METTL7A, DLK1, DPT, FMO1, FMO3, FOXF2, FST, GABRB1, GDF10, GJB2, GSC, HOXA5, HSD11B2, HSD17B2, HSPA6, HSPB3, ICAM5, IFI27, IGF2, KIAA0644, KRT14, MFAP5, MASP1, MEOX2, MGP, MYBPH, MYH3, NPAS1, OGN, OLR1, PAX9, PDE1A, PITX2, PRG4, PROM1, PRRX2, PTGS2, PTN, RARRES1, RASD1, RGS1, SMOC1, SNAP25, STMN2, TAC1, TRH, TUBB4, WISP2 and ZIC1.

The cell line E76 is positive for the markers: ACTC, BEX1, COL21A1, CRIP1, CRYAB, DIO2, DKK2, EGR2, GAP43, KRT17, KRT19, MMP1, MSX2, PTGS2, S100A4 and THY1 and is negative for the markers: ALDH1A1, AREG, ATP8B4, CFB, C3, C7, C20orf103, CDH3, CLDN11, CNTNAP2, COP1, CRLF1, METTL7A, DPT, FMO1, FMO3, FOXF1, GABRB1, GDF10, GSC, HOXA5, HSD11B2, HSD17B2, HSPA6, ICAM5, IFI27, IGF2, KRT14, MEOX2, MGP, MYBPH, MYH3, NPAS1, NPPB, OGN, OLR1, PAX2, PAX9, PDE1A, PENK, PITX2, PRG4, PROM1, PRRX2, PTN, PTPRN, RARRES1, RGS1, SFRP2, SMOC1, SNAP25, STMN2, TAC1, TFPI2, TNNT2, TRH, TUBB4, WISP2 and ZIC1.

The cell line E108 is positive for the markers: ACTC, BEX1, CDH6, COL21A1, CRIP1, CRYAB, DIO2, DKK2, IGFBP5, KRT17, KRT19, MYH11, S100A4, SOX11, THY1 and ZIC2 and is negative for the markers: ALDH1A1, AQP1, AREG, ATP8B4, CFB, C3, C7, C20orf103, CD24, CDH3, CLDN11, CNTNAP2, COMP, COP1, CRLF1, CXADR, METTL7A, DLK1, DPT, FMO1, FMO3, FOXF1, FOXF2, GABRB1, GDF10, GJB2, GSC, HOXA5, HSD11B2, HSD17B2, HSPA6, ICAM5, IFI27, IGF2, KRT14, KRT34, MASP1, MEOX1, MEOX2, MGP, MYBPH, MYH3, NPAS1, NPPB, OGN, OLR1, PAX2, PAX9, PDE1A, PRG4, PROM1, PTN, PTPRN, RARRES1, RASD1, RGS1, SERPINA3, SFRP2, SMOC1, SNAP25, TAC1, TFPI2, TNNT2, TRH, TUBB4 and WISP2.

The cell line E85 is positive for the markers: ACTC, BEX1, CDH6, COL21A1, CRYAB, DIO2, DKK2, EGR2, FGFR3, ID4, KRT17, KRT19, MFAP5, MGP, MMP1, MYH11, PRELP, S100A4, SOX11, THY1, TNNT2, ZIC1 and ZIC2 and is negative for the markers: ALDH1A1, AQP1, AREG, ATP8B4, CFB, C3, C7, C20orf103, CD24, CDH3, CNTNAP2, COMP, COP1, CRLF1, METTL7A, DPT, FMO1, FMO3, GABRB1, GDF5, GDF10, GJB2, GSC, HOXA5, HSD11B2, HSD17B2, HSPA6, ICAM5, IFI27, IGF2, KRT14, MASP1, MEOX1, MEOX2, MYBPH, MYH3, NPAS1, OGN, OLR1, PAX9, PDE1A, PITX2, PRG4, PROM1, PRRX2, PTN, RARRES1, RASD1, RGS1, SFRP2, SMOC1, STMN2, TAC1, TFPI2, TRH, TUBB4 and WISP2.

The cell line M11 is positive for the markers: BEX1, CDH6, COL21A1, CRYAB, DKK2, GAP43, ID4, MMP1, MYH11, SOX11, THY1 and ZIC1 and is negative for the markers: ALDH1A1, AREG, ATP8B4, C3, C7, C20orf103, CD24, CDH3, CLDN11, CNTNAP2, COMP, COP1, CRLF1, CXADR, METTL7A, DLK1, DPT, FMO1, FMO3, FOXF2, FST, GABRB1, GDF10, GJB2, GSC, HOXA5, HSD11B2, HSD17B2, HSPA6, ICAM5, IGF2, IGFBP5, KCNMB1, KIAA0644, KRT14, MASP1, MEOX1, MEOX2, MSX2, MX1, MYBPH, MYH3, TAGLN3, NPAS1, OLR1, PAX2, PAX9, PDE1A, PENK, PITX2, PRG4, PROM1, PRRX2, PTN, PTPRN, RARRES1, RELN, RGS1, SFRP2, SMOC1, SNAP25, STMN2, TAC1, TFPI2, TNFSF7, TNNT2, TRH, TUBB4, WISP2 and ZIC2.

TABLE I-continued

Exemplary progenitor cell lines and associated gene expression markers at 18-21 doublings of clonal expansion The cell line E8 is positive for the markers: ACTC, BEX1, CDH6, COL21A1, CRIP1, CRYAB, DIO2, DKK2, ID4, KCNMB1, KRT14, KRT17, KRT19, KRT34, MFAP5, MGP, MYH11, PTGS2, S100A4, SOX11 and THY1 and is negative for the markers: ALDH1A1, AREG, ATP8B4, C3, C7, C20orf103, CDH3, CNTNAP2, COMP, COP1, CXADR, METTL7A, DPT, FMO1, FMO3, FOXF1, FOXF2, GABRB1, GDF10, GJB2, GSC, HOXA5, HSD11B2, HSD17B2, HSPA6, HSPB3, ICAM5, IFI27, IGF2, IGFBP5, KIAA0644, LAMC2, MASP1, MEOX1, MSX2, MX1, MYBPH, TAGLN3, NPAS1, NPPB, OLR1, PAX2, PAX9, PDE1A, PRELP, PRG4, PROM1, PRRX2, PTN, PTPRN, RARRES1, RASD1, RGS1, SFRP2, SMOC1, SNAP25, STMN2, TAC1, TFPI2, TNFSF7, TRH, WISP2, ZIC1 and ZIC2.

The cell line E80 is positive for the markers: ACTC, BEX1, CDH6, COL21A1, CRYAB, DKK2, ID4, KRT19, MMP1, MYH11, TAGLN3, SOX11 and THY1 and is negative for the markers: ALDH1A1, AQP1, AREG, ATP8B4, CFB, C3, C7, C20orf103, CDH3, CLDN11, CNTNAP2, COMP, CRIP1, CRLF1, METTL7A, DLK1, DPT, FMO1, FMO3, FOXF1, FOXF2, GABRB1, GDF10, GSC, HOXA5, HSD11B2, HSD17B2, HSPA6, ICAM5, IFI27, IGF2, KIAA0644, KRT14, KRT34, MASP1, MEOX2, MGP, MYBPH, MYH3, NPAS1, OGN, OLR1, PAX9, PDE1A, PRELP, PRG4, PROM1, PRRX2, PTN, RARRES1, RASD1, RGS1, SERPINA3, SMOC1, SNAP25, STMN2, TAC1, TNNT2, TRH, WISP2, ZIC1 and ZIC2.

The cell line RA.D20.24 is positive for the markers: ACTC, BEX1, CRYAB, CXADR, DKK2, FOXF1, GAP43, HOXA5, IGFBP5, KRT19, LAMC2, MFAP5, MMP1, MSX1, MYL4, PITX2, PTGS2, RELN, THY1 and TNNT2 and is negative for the markers: AGC1, ALDH1A1, AQP1, AREG, ATP8B4, CFB, C7, C20orf103, CDH3, CNTNAP2, COL15A1, COMP, COP1, CRLF1, DLK1, DPT, FGFR3, FMO1, FMO3, FOXF2, GDF10, GJB2, GSC, HSD11B2, HSD17B2, HSPA6, HSPB3, ICAM5, ID4, IFI27, IGF2, KCNMB1, KRT14, MASP1, MEOX1, MEOX2, MGP, MSX2, MX1, MYBPH, MYH3, MYH11, NPAS1, OGN, PAX2, PAX9, PDE1A, PRG4, PROM1, PRRX2, PTN, PTPRN, RARRES1, RGS1, SFRP2, SMOC1, SNAP25, STMN2, TAC1, TUBB4, WISP2, ZIC1 and ZIC2.

The cell line RA.D20.6 is positive for the markers: ACTC, CRYAB, CXADR, DKK2, FOXF1, GAP43, HOXA5, IGFBP5, KRT19, LAMC2, MFAP5, MMP1, MSX1, PITX2, PTGS2, SOX11 and THY1 and is negative for the markers: ALDH1A1, ATP8B4, CFB, C3, C7, C20orf103, CDH3, CNTNAP2, COL15A1, COMP, COP1, CRLF1, DIO2, DLK1, DPT, FMO1, FMO3, FOXF2, GDF10, GSC, HSD11B2, HSD17B2, HSPA6, HSPB3, ICAM5, ID4, IGF2, KRT14, MASP1, MEOX1, MEOX2, MGP, MSX2, MX1, MYBPH, MYH3, MYH11, NPAS1, OGN, PAX2, PAX9, PDE1A, PRG4, PROM1, PRRX2, PTN, PTPRN, RARRES1, RGS1, SERPINA3, SFRP2, SMOC1, STMN2, TAC1, TRH, TUBB4, WISP2, ZIC1 and ZIC2.

The cell line RA.SMO10 is positive for the markers: ALDH1A1, BEX1, C3, CDH3, COL21A1, CXADR, METTL7A, EGR2, FMO3, FOXF1, HOXA5, KIAA0644, MGP, RARRES1, SOX11 and STMN2 and is negative for the markers: ACTC, AGC1, ANXA8, AQP1, CFB, C7, C20orf103, CD24, CDH6, CNTNAP2, COL15A1, COMP, COP1, CRIP1, CRLF1, DPT, FOXF2, GAP43, GDF10, GSC, HSD11B2, HSD17B2, HSPA6, HSPB3, ICAM5, ID4, IFI27, KRT14, KRT17, KRT34, MASP1, MEOX1, MEOX2, MSX2, MYBPH, MYH3, MYH11, TAGLN3, NPAS1, NPPB, OGN, PAX2, PAX9, PDE1A, PITX2, PRELP, PRG4, PROM1, PRRX2, PTN, PTPRN, RGS1, S100A4, SERPINA3, SFRP2, SMOC1, TAC1, TFPI2, THY1, TNFSF7, TRH, TUBB4, WISP2, ZIC1 and ZIC2.

The cell line RA.SMO14 is positive for the markers: ACTC, BEX1, CD24, CXADR, FOXF1, GDFS, GJB2, HOXA5, IGFBP5, KRT19, LAMC2, MFAP5, MMP1, RELN, SOX11 and STMN2 and is negative for the markers: AGC1, ALDH1A1, AQP1, ATP8B4, CFB, C3, C7, CDH6, CLDN11, CNTNAP2, COL15A1, COL21A1, COMP, COP1, CRIP1, CRLF1, DIO2, DLK1, DPT, FGFR3, FMO1, FMO3, FOXF2, GABRB1, GDF10, GSC, HSD11B2, HSD17B2, HSPA6, HSPB3, ICAM5, ID4, IFI27, IGF2, KCNMB1, KRT14, KRT17, KRT34, MASP1, MEOX1, MEOX2, MGP, MSX2, MYBPH, MYH3, MYH11, NPAS1, NPPB, OGN, PAX2, PAX9, PDE1A, PITX2, PRELP, PRG4, PROM1, PRRX1, PRRX2, PTN, PTPRN, RGS1, SERPINA3, SFRP2, SMOC1, TAC1, TNFSF7, TUBB4, WISP2, ZIC1 and ZIC2.

The cell line RA.PEND18 is positive for the markers: C3, CDH3, COL21A1, METTL7A, DLK1, EGR2, FOXF1, GABRB1, HOXA5, IGF2, KIAA0644, KRT19, MSX1, PITX2, PROM1, PTGS2, SNAP25 and SOX11 and is negative for the markers: ACTC, AGC1, ALDH1A1, AQP1, BEX1, CFB, C20orf103, CDH6, CNTNAP2, COL15A1, COMP, CRIP1, CRLF1, CXADR, DPT, FMO1, FOXF2, GAP43, GDF10, GSC, HSD11B2, HSD17B2, HSPA6, HSPB3, ICAM5, ID4, IFI27, KCNMB1, KRT14, KRT34, MFAP5, MASP1, MEOX1, MEOX2, MGP, MMP1, MSX2, MYBPH, MYH3, MYH11, TAGLN3, NPAS1, NPPB, PAX2, PAX9, PENK, PRELP, PRG4, PRRX2, PTN, PTPRN, RARRES1, RELN, RGS1, SFRP2, SMOC1, STMN2, TAC1, TNFSF7, TRH, TUBB4, WISP2, ZIC1 and ZIC2.

The cell line RA.PEND10 is positive for the markers: AREG, C3, CDH3, CDH6, COL21A1, METTL7A, DLK1, EGR2, FOXF1, FST, GDF5, HOXA5, IGF2, IGFBP5, KRT19, PDE1A, PITX2, RELN and SOX11 and is negative for the markers: ACTC, AGC1, ALDH1A1, ATP8B4, CFB, C7, C20orf103, CLDN11, CNTNAP2, COL15A1, COMP, CRIP1, CRLF1, CRYAB, DPT, FOXF2, GAP43, GDF10, GSC, HSD11B2, HSD17B2, HSPA6, HSPB3, ICAM5, ID4, IFI27, KCNMB1, KRT14, KRT17, KRT34, MASP1, MEOX1, MEOX2, MMP1, MSX2, MYBPH, MYH3, MYH11, TAGLN3, NPAS1, NPPB, OGN, PAX2, PAX9, PRELP, PRG4, PROM1, PRRX1, PRRX2, PTN, PTPRN, RGS1, S100A4, SERPINA3, SFRP2, SMOC1, STMN2, TAC1, THY1, TNFSF7, TRH, TUBB4, WISP2, ZIC1 and ZIC2.

The cell line RA.SKEL21 is positive for the markers: AREG, BEX1, C3, CD24, COL21A1, COP1, METTL7A, FOXF1, KRT19, MSX1, PITX2, SERPINA3, SOX11 and THY1 and is negative for the markers: ACTC, AGC1, ALDH1A1, AQP1, ATP8B4, CFB, C7, C20orf103, CDH6, CLDN11, CNTNAP2, COL15A1, COMP, CRIP1, CRLF1, DKK2, DPT, FGFR3, FMO1, FMO3, FOXF2, GAP43, GDF10, GSC, HSD11B2, HSD17B2, HSPA6, HSPB3, ICAM5, ID4, IFI27, KCNMB1, KRT14, KRT17, KRT34, MASP1, MEOX1, MEOX2, MGP, MMP1, MSX2, MX1, MYBPH, MYH3, TAGLN3, NPAS1, NPPB, OGN, OLR1, PAX2, PAX9, PDE1A, PENK, PRELP, PRG4, PRRX2, PTGS2, PTN, PTPRN, RARRES1, RASD1, RELN, RGS1, SFRP2, SMOC1, STMN2, TAC1, TNFSF7, TRH, TUBB4 and ZIC2.

The cell line RA.SKEL18Rep2a is positive for the markers: AREG, C3, CD24, CDH3, COL21A1, METTL7A, DPT, GJB2, SERPINA3, SNAP25 and SOX11 and is negative for the markers: ALDH1A1, ATP8B4, CFB, C7, C20orf103, CDH6, CLDN11, CNTNAP2, COMP, COP1, CRIP1, DIO2, DKK2, DLK1, FGFR3, FMO1, FMO3, GDF10, GSC, HSD11B2, HSD17B2, HSPA6, HSPB3, ICAM5, ID4, IFI27, IGF2, KCNMB1, KRT14, KRT17, KRT19, KRT34, MASP1, MEOX1, MEOX2, MGP, MMP1, MSX2, MYBPH, MYH3, MYH11, TAGLN3, TABLE I-continued Exemplary progenitor cell lines and associated gene expression markers at 18-21 doublings of clonal expansion NPAS1, NPPB, OGN, OLR1, PAX2, PAX9, PRELP, PRG4, PROM1, PRRX1, PRRX2, PTGS2, PTN, PTPRN, RARRES1, RELN, RGS1, SFRP2, SMOC1, STMN2, TAC1, THY1, TNFSF7, TNNT2, TRH, WISP2, ZIC1 and ZIC2.

The cell line C4.4 is positive for the markers: AKR1C1, BEX1, CDH6, COP1, DIO2, METTL7A, DKK2, DPT, EGR2, FOXF1, FST, KIAA0644, MMP1, MSX1, RELN, S100A4, TAC1 and THY1 and is negative for the markers: AGC1, ALDH1A1, ANXA8, AQP1, AREG, ATP8B4, CFB, C3, C7, C20orf103, CD24, CDH3, CLDN11, CNTNAP2, COL21A1, COMP, CRIP1, CRLF1, CXADR, FGFR3, FMO1, GAP43, GDF10, GJB2, GSC, HOXA5, HSD11B2, HSD17B2, HSPA6, HSPB3, ICAM5, ID4, IFI27, IGF2, KCNMB1, KRT14, KRT17, KRT19, KRT34, LAMC2, MFAP5, MASP1, MEOX1, MEOX2, MGP, MYBPH, MYH3, MYH11, TAGLN3, NPAS1, NPPB, OGN, PAX2, PAX9, PDE1A, PENK, PITX2, PRG4, PROM1, PTGS2, PTN, PTPRN, RARRES1, RASD1, RGS1, SERPINA3, SFRP2, SMOC1, SNAP25, STMN2, TNFSF7, TNNT2, TRH, TUBB4, ZIC1 and ZIC2.

The cell line W7 is positive for the markers: AREG, C3, COL15A1, COL21A1, COP1, CXADR, DIO2, DLK1, EGR2, FMO1, FOXF1, GDF5, HOXA5, KIAA0644, METTL7A, PITX2, PROM1, S100A4, SERPINA3 and SOX11 and is negative for the markers: AGC1, ALDH1A1, AQP1, ATP8B4, C20orf103, C7, CD24, CDH3, CDH6, CFB, CLDN11, CNTNAP2, COMP, CRIP1, DKK2, DPT, FMO3, GABRB1, GAP43, GDF10, GSC, HSD11B2, HSD17B2, HSPA6, ICAM5, ID4, 1FI27, KCNMB1, KRT14, KRT17, KRT19, KRT34, MASP1, MEOX1, MEOX2, MGP, MMP1, MYBPH, MYH11, MYH3, NPAS1, NPPB, OGN, PAX2, PAX9, PRG4, PRRX2, PTN, PTPRN, RARRES1, RASD1, RELN, RGS1, SFRP2, SMOC1, STMN2, TAC1, TNFSF7, TRH, TUBB4, ZIC1 and ZIC2.

The cell line X4SKEL20 is positive for the markers: AREG, BEX1, C3, C7, COP1, CXADR, FOXF1, FST, KRT19, METTL7A, MGP, MSX1, PITX2, SERPINA3 and TFPI2 and is negative for the markers: ALDH1A1, AQP1, ATP8B4, C20orf103, CD24, CDH3, CDH6, CFB, CLDN11, CNTNAP2, COL15A1, COMP, DKK2, DLK1, DPT, EGR2, FGFR3, FMO1, FOXF2, GABRB1, GAP43, GDF10, GDF5, GJB2, GSC, HOXA5, HSD11B2, HSD17B2, HSPA6, HSPB3, ICAM5, ID4, IFI27, IGF2, IGFBP5, KCNMB1, KRT14, KRT34, MASP1, MEOX1, MEOX2, MFAP5, MMP1, MSX2, MX1, MYBPH, MYH11, MYH3, NPAS1, NPPB, OGN, OLR1, PAX2, PENK, PRG4, PROM1, PRRX1, PRRX2, PTN, PTPRN, RARRES1, RELN, RGS1, SFRP2, SMOC1, SOX11, STMN2, TAC1, TAGLN3, THY1, TNFSF7, TNNT2, TRH, WISP2, ZIC1 and ZIC2.

The cell line C4ELSR6 is positive for the markers: ACTC, BEX1, C7, CDH6, COL21A1, DIO2, METTL7A, DKK2, FOXF1, FOXF2, LAMC2, PITX2, PRRX11, S100A4, SFRP2, SNAP25, SOX11, TAC1 and TFPI2 and is negative for the markers: AGC1, ALDH1A1, AREG, ATP8B4, CFB, C3, C20orf103, CD24, CLDN11, CNTNAP2, COMP, CRIP1, CRLF1, CRYAB, DLK1, DPT, FGFR3, FMO3, GAP43, GDF5, GDF10, GJB2, GSC, HOXA5, HSD11B2, HSD17B2, HSPA6, HSPB3, ICAM5, ID4, IFI27, IGF2, KCNMB1, KRT14, KRT17, KRT34, MFAP5, MASP1, MEOX1, MEOX2, MGP, MMP1, MYBPH, MYH3, MYH11, NPAS1, NPPB, PAX2, PAX9, PENK, PRG4, PTN, PTPRN, RARRES1, RASD1, RGS1, SMOC1, STMN2, TNFSF7, TRH, TUBB4, WISP2 and ZIC1.

The cell line J2 is positive for the markers: ACTC, AKR1C1, BEX1, CDH6, COL15A I, COL21A1, 13102, METTL7A, DKK2, DLK1, FOXF1, KIAA0644, MGP, PDE1A, PRRX1, SFRP2, SNAP25, TNNT2 and ZIC2 and is negative for the markers: AGC1, ALDH1A1, ATP8B4, CFB, C3, C20orf103, CD24, CNTNAP2, COMP, CRIP1, CRLF1, DPT, FGFR3, GABRB1, GDF10, GSC, HOXA5, HSD11B2, HSD17B2, HSPA6, ICAM5, ID4, IFI27, KCNMB1, KRT14, KRT17, KRT19, KRT34, LAMC2, MFAP5, MASP1, MEOX1, MMP1, MSX1, MYBPH, MYH3, MYH11, NPAS1, NPPB, OGN, OLR1, PAX2, PAX9, PENK, PROM1, PRRX2, PTN, PTPRN, RARRES1, RGS1, SMOC1, STMN2, TAC1, TNFSF7, TRH and TUBB4.

The cell line F15 is positive for the markers: BEX1, CDH6, COL15A1, COL21A1, DKK2, DLK1, FOXF1, FST, GDF5, KRTI9, MGP, MMP1, PRRX1, SERPINA3, SNAP25, SOX11, ZIC1 and ZIC2 and is negative for the markers: ACTC, AGC1, ALDH1A1, AQP1, AREG, ATP8B4, CFB, C3, C7, C20orf103, CD24, CDH3, CNTNAP2, COMP, CRLF1, DIO2, DPT, FGFR3, FMO1, FMO3, FOXF2, GABRB1, GDF10, GJB2, GSC, HOXA5, HSD11B2, HSD17B2, HSPA6, HSPB3, ICAM5, ID4, IFI27, IGF2, KCNMBI, KIAA0644, KRTI4, KRT17, MASP1, MEOX1, MEOX2, MYBPH, MYH3, MYH11, NPAS1, NPPB, OGN, OLR1, PAX2, PDE1A, PENK, PITX2, PRG4, PROM1, PRRX2, PTN, PTPRN, RGS1, SFRP2, SMOC1, STMN2, TFPI2, TNNT2, TRH and TUBB4.

The cell line X4SKEL4 is positive for the markers: ANXA8, AREG, BEX1, C3, COL21A1, COP1, CXADR, METTL7A, EGR2, FOXF1, FST, KRT19, LAMC2, MYL4, PITX2 and SERPINA3 and is negative for the markers: ALDH1A1, AQP1, ATP8B4, CFB, C7, C20orf103, CD24, CDH3, CDH6, CLDN11, CNTNAP2, COL15A1, COMP, CRLF1, DKK2, DLK1, DPT, FGFR3, FMO3, FOXF2, GABRB1, GAP43, GDF5, GDF10, GJB2, GSC, HOXA5, HSD11B2, HSD17B2, HSPA6, HSPB3, ICAM5, ID4, IFI27, IGF2, IGFBP5, KIAA0644, KRT14, KRT17, KRT34, MASP1, MEOX1, MEOX2, MGP, MMP1, MSX2, MX1, MYBPH, MYH3, NPAS1, NPPB, OGN, OLR1, PAX2, PAX9, PDE1A, PENK, PRELP, PRG4, PROM1, PRRX2, PTN, PTPRN, RARRES1, RASD1, RGS1, SFRP2, SMOC1, SOX11, STMN2, TAC1, TNNT2, TRH, TUBB4, WISP2 and ZIC1.

The cell line X4SKEL19 is positive for the markers: AREG, COL21A1, COP1, DIO2, METTL7A, EGR2, FOXF1, FST, KIAA0644, KRT19, MGP, PDE1A, PITX2, SERPINA3 and TFPI2 and is negative for the markers: ACTC, AGC1, ALDH1A1, AQP1, ATP8B4, CFB, C20orf103, CD24, CDH3, CDH6, CLDN11, CNTNAP2, COL15A1, COMP, CRIP1, CRLF1, CXADR, DKK2, DLK1, DPT, FGFR3, FMO1, FOXF2, GABRB1, GAP43, GDF5, GDF10, GJB3, GSC, HOXA5, HSD11B2, HSD17B2, HSPA6, HSPB3, ICAM5, ID4, IFI27, IGF2, KCNMB1, KRT14, KRT17, KRT34, MFAP5, MASP1, MEOX1, MEOX2, MMP1, MSX2, MX1, MYBPH, MYH3, MYH11, TAGLN3, NPAS1, NPPB, OGN, OLR1, PAX2, PAX9, PRELP, PRG4, PRRX2, PTN, PTPRN, RELN, SFRP2, SMOC1, SOX11, STMN2, TAC1, THY1, TRH, WISP2, ZIC1 and ZIC2.

The cell line X4SKEL8 is positive for the markers: AREG, BEX1, COL21A1, DIO2, METTL7A, DKK2, EGR2, FMO3, FOXF1, FST, MYL4, PITX2, PIGS2, S100A4 and SERPINA3 and is negative for the markers: ALDH1A1, AQP1, ATP8B4, CFB, C3, C20orf103, CD24, CDH3, CLDN11, CNTNAP2, COMP, CRIP1, CRLF1, DLK1, DPT, FGFR3, FOXF2, GABRB1, GDF5, GDF10, GJB2, GSC, HOXA5, HSD11B2, HSD17B2, HSPA6, HSPB3, ID4, IFI27, IGF2, KRT14, KRT17, KRT34, MFAP5, MASP1, MEOX1, MEOX2, MGP, MMP1, MSX2, MX1, MYBPH, MYH3, MYH11, TAGLN3, NPAS1, NPPB, OGN, OLR1, PAX2, PAX9, PDE1A, PENK, PRG4, PRRX1, PRRX2, PTN, PTPRN, RARRES1, RASD1, RELN, RGS1, SFRP2, SMOC1, STMN2, TAC1, THY1, TNFSF7, TNNT2, TRH, TUBB4, Z1C1 and Z1C2.

The cell line RA.PEND17Bio2a is positive for the markers: AREG, BEX1, CDH6, COL15A1, COL21A1, COP1, METTL7A, DPT, EGR2, FOXF1, FST, GJB2, LAMC2, MSX2, PTGS2, SERPINA3 and SFRP2 and is negative

TABLE I-continued

Exemplary progenitor cell lines and associated gene expression markers at 18-21 doublings of clonal expansion for the markers: ACTC, ALDH1A1, AQP1, ATP8B4, CFB, C20orf103, CD24, CDH3, CNTNAP2, COMP, CRIP1, CXADR, FGFR3, FMO1, GABRB1, GAP43, GDF10, GSC, HOXA5, HSD11B2, HSD17B2, HSPA6, HSPB3, ID4, IFI27, IGF2, KCNMB1, KRT14, KRT17, KRT34, MFAP5, MASP1, MEOX1, MEOX2, MGP, MMP1, MX1, MYBPH, MYH3, MYH11, NPAS1, NPPB, OLR1, PAX2, PAX9, PDE1A, PRELP, PRG4, PROM1, PRRX2, PTN, PTPRN, RELN, RGS1, SMOC1, STMN2, TAC1, THY1, TNFSF7, TNNT2, TRH, TUBB4, ZIC1 and ZIC2.
The cell line W9 is positive for the markers: AKR1C1, C7, CDH6, COL21A1, METTL7A, DLK1, EGR2, FOXF1, GDF5, GJB2, HOXA5, IGFBP5, KIAA0644, KRT19, MGP, OGN, PITX2, SERPINA3, SOX11, TFPI2 and ZIC2 and is negative for the markers: AGC1, ALDH1A1, AQP1, CFB, C3, C20orf103, CD24, CDH3, CLDN11, CNTNAP2, COL15A1, COMP, CRIP1, CRLF1, CRYAB, DKK2, FGFR3, FMO1, FMO3, FOXF2, GDF10, GSC, HSD11B2, HSD17B2, HSPA6, HSPB3, ICAM5, ID4, 1FI27, IGF2, KCNMB1, KRT14, KRTI7, KRT34, MFAP5, MASP1, MEOX1, MEOX2, MSX1, MX1, MYBPH, MYH3, MYH11, NPAS1, NPPB, OLR1, PAX2, PAX9, PDE1A, PENK, PRG4, PROM1, PRRX2, PTN, PTPRN, RARRES1, RASD1, RGS1, SFRP2, SNAP25, STMN2, TAC1, THY1, TNFSF7, TNNT2, TRH, TUBB4 and ZIC1.
The cell line MW4 is positive for the markers: AKR1C1, AREG, BEX1, C7, COL15A1, COL21A1, DIO2, METTL7A, DKK2, EGR2, FMO3, FOXF1, FOXF2, PITX2, PRELP, SERPINA3, SFRP2 and TFPI2 and is negative for the markers: ALDH1A1, AQP1, ATP8B4, CFB, C3, C20orf103, CD24, CDH3, CLDN11, CNTNAP2, CRIP1, CXADR, DLK1, GABRB1, GDF5, GDF10, GJB2, GSC, HOXA5, HSDI 1B2, HSD17B2, HSPA6, HSPB3, ICAM5, 1D4, IFI27, IGF2, KCNMB1, KRT14, KRT17, KRT19, KRT34, MFAP5, MASP1, MEOX1, MEOX2, MGP, MMP1, MSX1, MX1, MYBPH, MYH3, MYH11, NPASI, NPPB, OLR1, PAX2, PAX9, PDE1A, PENK, PRG4, PROM1, PRRX1, PTN, PTPRN, RARRES1, RELN, RGS1, SMOC1, STMN2, TAC1, TNNT2, TUBB4, ZIC1 and ZIC2,.
The cell line SK58 is positive for the markers: AKR1C1, AREG, BEX1, C7, COL15A1, COL21A1, METTL7A, EGR2, FMO1, FOXF1, PTGS2, SERPINA3, SFRP2, TAC1 and TFPI2 and is negative for the markers: ACTC, AGC1, ALDH1A1, AQP1, ATP8B4, CFB, C3, C20orf103, CD24, CDH3, CDH6, CLDN11, CNTNAP2, COP1, CRIP1, DIO2, DLK1, DPT, GABRB1, GDF5, GDF10, GSC, HOXA5, HSD11B2, HSD17B2, HSPB3, ID4, IFI27, IGF2, KCNMB1, KRT14, KRT17, KRT19, KRT34, MFAP5, MASP1, MEOX1, MEOX2, MGP, MMP1, MSX2, MX1, MYBPH, MYH3, MYH11, NPAS1, NPPB, OLR1, PAX2, PAX9, PDE1A, PRG4, PROM1, PRRX2, PTN, PTPRN, RARRES1, RELN, RGS1, SMOC1, STMN2, TNNT2, TRH, TUBB4, ZIC1 and ZIC2,.
The cell line SK25 is positive for the markers: BEX1, COL21A1, METTL7A, FMO1, FOXF1, LAMC2, SERPINA3, SFRP2 and WISP2 and is negative for the markers: ACTC, ALDH1A1, ANXA8, AQP1, ATP8B4, CFB, C3, C20orf103, CD24, CDH3, CLDN11, CNTNAP2, COMP, CRIP1, CRLF1, CXADR, DIO2, DKK2, DPT, EGR2, FGFR3, GABRB1, GAP43, GDF10, GJB2, GSC, HOXA5, HSD11B2, HSD17B2, HSPA6, HSPB3, ICAM5, ID4, IFI27, IGF2, KCNMB1, KIAA0644, KRT14, KRT17, KRT34, MFAP5, MASP1, MEOX1, MEOX2, MGP, MMP1, MSX2, MYBPH, MYH3, MYH11, NPAS1, NPPB, OGN, OLR1, PAX2, PAX9, PDE1A, PITX2, PRELP, PRG4, PROM1, PTN, RARRES1, RASD1, RGS1, SMOC1, STMN2, TAC1, TFPI2, TNFSF7, TNNT2, TRH, ZIC1 and ZIC2.
The cell line SK16 is positive for the markers: AREG, BEX1, COL15A1, COL21A1, METTL7A, EGR2, FMO1, FOXF1, LAMC2, MSX1, PITX2, SERPINA3, ZIC1 and ZIC2 and is negative for the markers: AGC1, ALDH1A1, AQP1, ATP8B4, CFB, C3, C20orf103, CD24, CDH3, CLDN11, CNTNAP2, COMP, CRIP1, CXADR, DIO2, DKK2, DPT, FGFR3, GABRB1, GDF10, GSC, HSD11B2, HSD17B2, HSPA6, HSPB3, ID4, IFI27, IGF2, KIAA0644, KRT14, KRT17, KRT19, KRT34, MFAP5, MASP1, MEOX1, MEOX2, MGP, MMP1, MSX2, MX1, MYBPH, MYH3, MYH11, TAGLN3, NPAS1, NPPB, OLR1, PAX2, PAX9, PENK, PRELP, PRG4, PROM1, PRRX2, PTN, RARRES1, RELN, RGS1, STMN2, TAC1, TFPI2, THY1, TNFSF7, TNNT2, TRH and TUBB4,.
The cell line EN20 is positive for the markers: BEX1, COL21A1, METTL7A, DLK1, FMO1, FOXF1, FST, GDF5, LAMC2, MGP, PRRX1, S100A4, SERPINA3, SOX11, TFPI2 and WISP2 and is negative for the markers: ALDH1A1, AQP1, ATP8B4, C3, C7, C20orf103, CD24, CDH3, CNTNAP2, COL15A1, COMP, CRIP1, CXADR, DIO2, DKK2, FGFR3, GABRB1, GAP43, GDF10, GSC, HOXA5, HSD11B2, HSD17B2, HSPA6, HSPB3, ICAM5, ID4, IFI27, KCNMB1, KRT14, KRT17, KRT34, MFAP5, MASP1, MEOX1, MEOX2, MMP1, MX1, MYBPH, MYH3, MYH11, NPAS1, NPPB, OLR1, PAX2, PDE1A, PITX2, PRELP, PRG4, PROM1, PTN, PTPRN, RASD1, RGS1, SFRP2, SMOC1, SNAP25, STMN2, TAC1, TNFSF7, TNNT2, TRH, TUBB4, ZIC1 and ZIC2,.
The cell line EN43 is positive for the markers: AKR1C1, BEX1, C7, CDH6, COL21A1, DIO2, METTL7A, DLK1, FMO1, FMO3, FOXF1, FOXF2, FST, GDF5, MMP1, MSX1, OGN, PRRX1, S100A4, SERPINA3 and SOX11 and is negative for the markers: ALDH1A1, ANXA8, AQP1, ATP8B4, C3, C20orf103, CD24, CDH3, CLDN11, CNTNAP2, COMP, CRIP1, CRLF1, DKK2, DPT, GABRB1, GAP43, GDF10, GJB2, GSC, HOXA5, HSD11B2, HSD17B2, HSPA6, ID4, IFI27, IGF2, KCNMB1, KRT14, KRT17, KRT19, KRT34, MFAP5, MASP1, MEOX1, MEOX2, MGP, MYBPH, MYH3, MYH11, NPAS1, NPPB, OLR1, PAX2, PAX9, PDE1A, PITX2, PRG4, PROM1, PTN, PTPRN, RASD1, RGS1, SFRP2, SMOC1, STMN2, THY1, TNNT2, TRH, TUBB4, ZIC1 and ZIC2.

TABLE II

Culture Conditions

1. Subconfluent Monolayer Culture: Cells are plated and exposed to any combination of culture media and/or supplemented factors, or cultured as described in the exemplary protocols listed in Table V, while said cells are in a subconcfluent state.
2. Confluent Monolayer Culture: Cells are plated and exposed to any combination of culture media and/or supplemented factors, or cultured as described in the exemplary protocols listed in Table V, while said cells are in a confluent monolayer state.
3. Micromass Culture: Cells are plated and exposed to any combination of culture media and/or supplemented factors, or cultured as described in the exemplary protocols listed in Table V, while said cells are in a highly dense micromass state as described herein.

TABLE II-continued

Culture Conditions

4. Subconfluent Mixed Culture: Cells are plated and exposed to any combination of culture media and/or supplemented factors, or cultured as described in the exemplary protocols listed in Table V, while said cells are in a subconfluent state and juxtaposed (co-cultured) potentially in physical contact with cells of another differentiated state or another distinguishable cell line of the present invention.
5. Subconfluent Transwell Culture: Cells are plated and exposed to any combination of culture media and/or supplemented factors, or cultured as described in the exemplary protocols listed in Table V, while said cells are in transwell vessels or tissue cultureware of similar design that allows the physical separation of diverse cell types but allowing a sharing of their media. Such subconfluent transwell culture is where the cell lines of the present invention are subconfluent and share culture media with a cell type of a different differentiated state wherein the cells of a different differentiated state may be themselves in a subconfluent or confluent state.
6. Confluent Mixed Culture: Cells are plated and exposed to any combination of culture media and/or supplemented factors, or cultured as described in the exemplary protocols listed in Table V, while said cells are in a confluent state and juxtaposed (co-cultured) potentially in physical contact with cells of another differentiated state or another distinguishable cell line of the present invention.
7. Confluent Transwell Culture: Cells are plated and exposed to any combination of culture media and/or supplemented factors, or cultured as described in the exemplary protocols listed in Table V, while said cells are in transwell vessels or tissue cultureware of similar design that allows the physical separation of diverse cell types but allowing a sharing of their media. Such subconfluent transwell culture is where the cell lines of the present invention are confluent and share culture media with a cell type of a different differentiated state wherein the cells of a different differentiated state may be themselves in a subconfluent or confluent state.
8. Micromass Mixed Culture: Cells are plated and exposed to any combination of culture media and/or supplemented factors, or cultured as described in the exemplary protocols listed in Table V, while said cells are in a highly dense micromass state as described herein and juxtaposed (co-cultured) potentially in physical contact with cells of another differentiated state or another distinguishable cell line of the present invention.
9. Micromass Transwell Culture: Cells are plated and exposed to any combination of culture media and/or supplemented factors, or cultured as described in the exemplary protocols listed in Table V, while said cells are in transwell vessels or tissue cultureware of similar design that allows the physical separation of diverse cell types but allowing a sharing of their media while said cells are in a highly dense micromass state as described herein. Such subconfluent transwell culture is where the cell lines of the present invention are confluent and share culture media with a cell type of a different differentiated state wherein the cells of a different differentiated state may be themselves in a subcontinent or confluent state.
10. Culture Exposed to Cell Extracts of Cells of a Different Differentiated State: Target cells are plated and exposed to any combination of culture media and/or supplemented factors, or cultured as described in the exemplary protocols listed in Table V, while said cells are in a subconfluent state and wherein the media for said cells contains extracts of cells of a differing differentiated state and wherein said target cells are exposed to conditions that facilitate the intracellular trafficking of molecules such as described in U.S. patent application Ser. No. 10/910,156 filed on Aug. 2, 2004 and titled "Methods for Altering Cell Fate", and U.S. patent application Ser. No. 10/015,824 filed on Dec. 10, 2001 and titled "Methods for Altering Cell Fate", both incorporated herein by reference in their entirety.

TABLE III

| Parental hES Cell Lines (WA09 or MA03) | ACTC No. | Cell Line | Cell Line Synonyms | Microarray Group | NMF Group Number | NMF Order |
|---|---|---|---|---|---|---|
| MA03 | 50 | B-26 | B26 | Illumina 1 | 4 | 71 |
| MA03 | 51 | B-2 | B2 | Illumina 1 | 9 | 69 |
| MA03 | 52 | B-29 | B-29 | Illumina 1 | 13 | 52 |
| MA03 | 53 | B-7 | B7 | Illumina 1 | 9 | 68 |
| MA03 | 54 | B-17 | B17 | Illumina 1 | 8 | 54 |
| MA03 | 55 | B-3 | B3 | Illumina 1 | 4 | 74 |
| MA03 | 56 | B-6 | B6 | Illumina 1 | 15 | 55 |
| MA03 | 57 | B-25 | B25 | Illumina 1 | 4 | 73 |
| MA03 | 58 | B-11 | B11 | Illumina 1 | 4 | 72 |
| MA03 | 59 | B-16 | B16 | Illumina 1 | 7 | 65 |
| MA03 | 60 | B-28 | B28 | Illumina 1 | 12 | 84 |
| MA03 | 61 | B-30 | B30 | Illumina 1 | 14 | 25 |
| MA03 | 62 | 2-2 | 2-2 (Rep1), 2-2 (Rep2), 2.2 | Illumina 1 | 1 | 89 (Rep1), 90 (Rep2) |
| MA03 | 63 | 2-1 | 2.1 | Illumina 1 | 1 | 88 |
| MA03 | 64 | 6-1 | 6.1 | Illumina 1 | 9 | 70 |
| MA03 | 65 | B-12 | B12 | Illumina 1 | 12 | 82 |
| MA03 | 66 | B-4 | B4 | Illumina 1 | 5 | 83 |
| MA03 | 67 | B-14 | B14 | Illumina 1 | NA | NA |
| MA03 | 68 | 5-4 | 5.4 | Illumina 1 | 122 | 32 |
| MA03 | 69 | 4-2 | 4.2 | Illumina 1 | 11 | 37 |
| MA03 | 70 | 2-3 | 2.3 | Illumina 1 | 23 | 94 |

TABLE III-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| MA03 | 71 | B-15 | B15 | Illumina 1 | 6 | 22 |
| MA03 | 72 | CM50-4 | CM50.4 | Illumina 1 | NA | NA |
| MA03 | 73 | CM0-3 | CM0.3 | Illumina 1 | 22 | 85 |
| MA03 | 74 | CM0-5 | CM0.5 | Illumina 1 | 22 | 86 |
| MA03 | 75 | CM50-5 | CM50.5 | Illumina 1 | 22 | 87 |
| MA03 | 76 | CM50-2 | CM50.2 | Illumina 1 | NA | NA |
| MA03 | 77 | CM0-2 | CM0.2 | Illumina 1 | 21 | 49 |
| MA03 | 78 | CM30-2 | CM30.2 | Illumina 1 | 10 | 42 |
| MA03 | 79 | CM20-4 | CM20.4 | Illumina 1 | 23 | 93 |
| MA03 | 80 | E26 | E26 | Illumina 1 | NA | NA |
| MA03 | 81 | E71 | E71 | Illumina 1 | NA | NA |
| WA09 | 82 | 4-D20-9 | 4-D20-9 | Illumina 1 | NA | NA |
| WA09 | 83 | 4-SKEL-19 | 4-SKEL-19 | Affymetrix | NA | NA |
| WA09 | 84 | 4-D20-8 | 4-D20-8 | Affymetrix | NA | NA |
| MA03 | 85 | E34 | E34 | Affymetrix | NA | NA |
| MA03 | 86 | E51 | E51 | Illumina 1 | 36 | 24 |
| WA09 | 87 | C4.4 | C4.4 | Affymetrix | NA | NA |
| MA03 | 88 | E3 | E3 | Illumina 1 | 30 | 75 |
| MA03 | 89 | E73 | E73 | Illumina 1 | 30 | 80 |
| MA03 | 90 | E93 | E93 | Illumina 1 | NA | NA |
| MA03 | 91 | E57 | E57 | Illumina 1 | 30 | 79 |
| WA09 | 92 | C4 ELSR #14 | C4 ELSR #14 | Illumina 1 | NA | NA |
| MA03 | 93 | E76 | E76 | Affymetrix | NA | NA |
| MA03 | 94 | E17 | E17 | Illumina 1 | NA | NA |
| MA03 | 95 | E40 | E40 | Illumina 1 | 32 | 28 |
| MA03 | 96 | E8 | E8 | Affymetrix | NA | NA |
| MA03 | 97 | E67 | E67 | Illumina 1 | 30 | 76 |
| MA03 | 98 | E15 | E15 | Illumina 1 | 26 | 26 |
| MA03 | 99 | E45 | E45 | Illumina 1 | 34 | 47 |
| MA03 | 100 | E72 | E72 | Illumina 1 | 7 | 66 |
| MA03 | 101 | E69 | E69 | Illumina 1 | 28 | 16 |
| MA03 | 102 | E75 | E75 | Illumina 1 | 7 | 67 |
| MA03 | 103 | M10 | M10 | Affymetrix | NA | NA |
| MA03 | 104 | M13 | M13 | Affymetrix | NA | NA |
| MA03 | 105 | E19 | E19 | Illumina 1 | 29 | 27 |
| WA09 | 106 | T44 | T44 | Illumina 1 | 114 | 18 |
| MA03 | 107 | E61 | E61 | Illumina 1 | NA | NA |
| WA09 | 108 | C4 ELSR #18 | C4 ELSR #18 | Illumina 1 | 41 | 97 |
| WA09 | 109 | RA-SKEL-8 | RA-SKEL-8 | Illumina 1 | 78 | 147 |
| WA09 | 110 | 4-SKEL-8 | 4-SKEL-8 | Affymetrix | NA | NA |
| WA09 | 111 | RA-PEND-15 | RA-PEND-15 | Illumina 1 | NA | NA |
| MA03 | 112 | E108 | E108 | Affymetrix | NA | NA |
| MA03 | 113 | E35 | E35 | Illumina 1 | NA | NA |
| MA03 | 114 | E33 | E33 | Illumina 1 | 31 | 46 |
| MA03 | 115 | E80 | E80 | Affymetrix | NA | NA |
| MA03 | 116 | E84 | E84 | Illumina 1 | 30 | 78 |
| MA03 | 117 | E109 | E109 | Affymetrix | NA | NA |
| WA09 | 118 | C4 ELS5 #6 | C4 ELS5 #6 | Illumina 1 | 38 | 9 |
| MA03 | 119 | J8 | J8 | Illumina 1 | 65 | 96 |
| WA09 | 120 | T43 | T43 | Illumina 1 | 114 | 17 |
| MA03 | 121 | E10 | E10 | Illumina 1 | NA | NA |
| WA09 | 122 | RA-PEND-6 | RA-PEND-6 | Illumina 1 | NA | NA |
| WA09 | 123 | RA-PEND-10 | RA-PEND-10 | Affymetrix | NA | NA |
| WA09 | 124 | RA-SKEL-3 | RA-SKEL-3 | Illumina 1 | NA | NA |
| WA09 | 125 | RA-SKEL-21 | RA-SKEL-21 | Affymetrix | NA | NA |
| WA09 | 126 | 4-SKEL-4 | 4-SKEL-4 | Affymetrix | NA | NA |
| WA09 | 127 | 4-SKEL-20 | 4-SKEL-20 | Affymetrix | NA | NA |
| WA09 | 128 | RA-PEND-4 | RA-PEND-4 | Illumina 1 | NA | NA |
| WA09 | 129 | RA-PEND-18 | RA-PEND-18 | Affymetrix | NA | NA |
| WA09 | 130 | C4 ELS5 #1 | C4 ELS5 #1 | Illumina 1 | 16 | 98 |
| WA09 | 131 | C4 ELSR #12 | C4 ELSR #12 | Illumina 1 | 18 | 99 |
| MA03 | 132 | E163 | E163 | Illumina 1 | NA | NA |
| WA09 | 133 | C4 Mesen. #3 | C4 Mesen. #3 | Illumina 1 | 20 | 45 |
| MA03 | 134 | G6 | G6 | Illumina 1 | NA | NA |
| WA09 | 135 | C4 ELS5 #5 | C4 ELS5 #5 | Illumina 1 | 17 | 100 |
| MA03 | 136 | J16 | J16 | Illumina 1 | 64 | 95 |
| WA09 | 137 | SK46 | SK46 | Illumina 1 | 92 | 186 |
| WA09 | 138 | SK47 | SK47 | Illumina 1 | 93 | 184 |
| WA09 | 139 | EN2 | EN2 | Illumina 1 | 47 | 167 |
| WA09 | 140 | EN26 | EN26 | Illumina 1 | 49 | 160 |
| WA09 | 141 | EN31 | EN31 | Illumina 1 | 52 | 172 |
| WA09 | 142 | SM2 | SM2 | Illumina 1 | 98 | 115 |
| WA09 | 143 | SM4 | SM4 | Illumina 1 | 105 | 109 |
| WA09 | 144 | EN4 | EN4 | Illumina 1 | 54 | 163 |
| WA09 | 145 | EN5 | EN5 | Illumina 1 | 57 | 162 |
| WA09 | 146 | SK52 | SK52 | Illumina 1 | 81 | 203 |

TABLE III-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 147 | SK43 | SK43 | Illumina 1 | 81 | 202 |
| WA09 | 148 | SK30 | SK30 | Illumina 1 | 88 | 176 |
| WA09 | 149 | SM42 | SM42 | Illumina 1 | 107 | 116 |
| WA09 | 150 | SM28 | SM28 | Illumina 1 | 101 | 112 |
| WA09 | 151 | SM49 | SM49 | Illumina 1 | 109 | 114 |
| WA09 | 152 | C4 ELSR #10 | C4 ELSR #10 | Affymetrix | NA | NA |
| WA09 | 153 | RA-SKEL-11 | RA-SKEL-11 | Illumina 1 | NA | NA |
| WA09 | 154 | RA-SMO-12 | RA-SMO-12 | Illumina 1 | NA | NA |
| WA09 | 155 | RA-D20-16 | RA-D20-16 | Illumina 1 | 72 | 58 |
| WA09 | 156 | SM22 | SM22 | Illumina 1 | 99 | 110 |
| WA09 | 157 | SK5 | SK5 | Illumina 1 | 94 | 148 |
| WA09 | 158 | SK18 | SK18 | Illumina 1 | 84 | 185 |
| WA09 | 169 | SK50 | SK50 | Illumina 1 | 81 | 199 |
| WA09 | 160 | SK54 | SK54 | Illumina 2 | 89 | 135 |
| MA03 | 161 | J4 | J4 | Illumina 1 | NA | NA |
| WA09 | 162 | SK17 | SK17 | Illumina 1 | 83 | 3 |
| WA09 | 163 | SK26 | SK26 | Illumina 1 | 85 | 198 |
| WA09 | 164 | SK31 | SK31 | Illumina 2 | 89 | 134 |
| WA09 | 165 | SK32 | SK32 | Illumina 1 | 90 | 189 |
| WA09 | 166 | SM25 | SM25 | Illumina 1 | 100 | 107 |
| WA09 | 167 | C4 ELSR #2 (Bio 1) | C4 ELSR #2 (Bio 1) | Illumina 1 | 19 | 102 |
| WA09 | 167 | C4 ELSR #2 (Bio 2) | C4 ELSR #2 (Bio 2) | Illumina 1 | 19 | 103 |
| WA09 | 167 | C4 ELSR #2 (Bio 3) | C4 ELSR #2 (Bio 3) | Illumina 1 | 19 | 101 |
| WA09 | 168 | SK3 | SK3 | Illumina 1 | NA | NA |
| WA09 | 169 | SK53 | SK53 | Illumina 1 | 82 | 193 |
| MA03 | 170 | E44 | E44 | Illumina 1 | 33 | 12 |
| MA03 | 171 | E65 | E65 | Affymetrix | NA | NA |
| MA03 | 172 | J13 | J13 | Illumina 1 | 63 | 5 |
| WA09 | 173 | EN1 | EN1 | Illumina 1 | 45 | 154 |
| WA09 | 174 | EN13 | EN13 | Illumina 1 | 43 | 149 |
| WA09 | 175 | EN42 | EN42 | Illumina 1 | 55 | 164 |
| WA09 | 176 | EN47 | EN47 | Illumina 1 | 56 | 152 |
| WA09 | 177 | SM27 | SM27 | Illumina 1 | NA | NA |
| MA03 | 178 | E50 | E50 | Illumina 1 | 35 | 56 |
| MA03 | 179 | E30 (Bio1) | E30 (Bio1) | Affymetrix | NA | NA |
| MA03 | 179 | E30 (Bio2) | E30 (Bio2) | Illumina 1 | 30 | 77 |
| MA03 | 180 | E122 | E122 | Affymetrix | NA | NA |
| WA09 | 181 | SK61 | SK61 | Illumina 1 | 82 | 190 |
| WA09 | 182 | SM17 | SM17 | Illumina 1 | 96 | 122 |
| WA09 | 183 | SM33 | SM33 | Illumina 1 | 104 | 125 |
| WA09 | 184 | EN7 | EN7 | Illumina 1 | 43 | 150 |
| WA09 | 185 | EN55 | EN55 | Illumina 1 | 61 | 161 |
| WA09 | 186 | T7 | T7 | Illumina 2 | 86 | 14 |
| WA09 | 187 | EN22 | EN22 | Illumina 1 | NA | NA |
| WA09 | 188 | SK58 | SK58 | Affymetrix | NA | NA |
| WA09 | 189 | MW2 | MW2 | Illumina 1 | 67 | 187 |
| WA09 | 190 | SK8 | SK8 | Illumina 1 | 95 | 195 |
| WA09 | 191 | SK20 | SK20 | Illumina 1 | NA | NA |
| WA09 | 192 | SK60 | SK60 | Illumina 1 | 82 | 191 |
| WA09 | 193 | MW6 | MW6 | Illumina 1 | 68 | 188 |
| WA09 | 194 | Z11 (Rep 1) | Z11 (Rep 1) | Illumina 1 | 139 | 104 |
| WA09 | 194 | Z11 (Rep 2) | Z11 (Rep 2) | Illumina 1 | 139 | 105 |
| WA09 | 195 | Z6 | Z6 | Illumina 1 | 138 | 120 |
| WA09 | 196 | W10 | W10 | Illumina 1 | 42 | 166 |
| WA09 | 197 | W11 | W11 | Illumina 1 | 117 | 157 |
| WA09 | 198 | T36 | T36 | Illumina 1 | 113 | 20 |
| WA09 | 199 | EN27 | EN27 | Illumina 1 | 50 | 159 |
| WA09 | 200 | Z7 | Z7 | Illumina 1 | 138 | 118 |
| WA09 | 201 | SM44 | SM44 | Illumina 1 | 108 | 113 |
| WA09 | 202 | EN38 | EN38 | Illumina 1 | 53 | 171 |
| WA09 | 203 | SK1 | SK1 | Illumina 1 | 79 | 182 |
| WA09 | 204 | SK44 | SK44 | Illumina 1 | 81 | 201 |
| WA09 | 205 | SK57 | SK57 | Illumina 1 | 87 | 197 |
| MA03 | 206 | J2 | J2 | Affymetrix | NA | NA |
| MA03 | 207 | E68 | E68 | Illumina 1 | 37 | 11 |
| MA03 | 208 | E169 | E169 | Illumina 1 | 28 | 15 |
| MA03 | 209 | E164 | E164 | Illumina 1 | 27 | 63 |
| WA09 | 210 | T42 | T42 | Illumina 1 | 113 | 21 |
| WA09 | 211 | T14 | T14 | Illumina 1 | 111 | 19 |
| WA09 | 212 | RA-D20-6 | RA-D20-6 | Affymetrix | NA | NA |
| WA09 | 213 | Z8 | Z8 | Illumina 1 | 100 | 108 |
| WA09 | 214 | SK40 | SK40 | Illumina 1 | 91 | 183 |
| WA09 | 215 | EN11 | EN11 | Illumina 1 | 42 | 165 |

TABLE III-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 216 | EN18 | EN18 | Illumina 1 | 45 | 153 |
| WA09 | 217 | EN23 | EN23 | Illumina 1 | NA | NA |
| WA09 | 218 | SK14 | SK14 | Illumina 1 | 82 | 192 |
| WA09 | 219 | SK10 | SK10 | Illumina 1 | 80 | 181 |
| WA09 | 220 | EN51 | EN51 | Illumina 1 | 59 | 173 |
| WA09 | 221 | EN16 | EN16 | Illumina 1 | 44 | 168 |
| MA03 | 222 | E53 | E53 | Illumina 1 | NA | NA |
| MA03 | 223 | E111 | E111 | Illumina 1 | 24 | 48 |
| WA09 | 224 | SK49 | SK49 | Illumina 1 | NA | NA |
| WA09 | 225 | SM8 | SM8 | Illumina 1 | 110 | 106 |
| WA09 | 226 | RA-D20-5 | RA-D20-5 | Illumina 1 | 74 | 57 |
| WA09 | 227 | RA-D20-24 | RA-D20-24 | Affymetrix | NA | NA |
| WA09 | 228 | W7 | W7 | Affymetrix | NA | NA |
| WA09 | 229 | 4-D20-14 | 4-D20-14 | Illumina 1 | NA | NA |
| WA09 | 230 | RA-D20-19 | RA-D20-19 | Illumina 1 | 73 | 59 |
| WA09 | 231 | T20 | T20 | Affymetrix | NA | NA |
| WA09 | 232 | RA-SMO-19 | RA-SMO-19 | Illumina 1 | NA | NA |
| MA03 | 233 | M11 | M11 | Affymetrix | NA | NA |
| WA09 | 234 | EN9 | EN9 | Illumina 1 | NA | NA |
| WA09 | 235 | Q7 | Q7 | Illumina 1 | 71 | 194 |
| WA09 | 236 | U31 | U31 | Illumina 1 | 116 | 64 |
| WA09 | 237 | EN19 | EN19 | Illumina 1 | 46 | 175 |
| WA09 | 238 | C4 ELS5 #8 | C4 ELS5 #8 | Illumina 1 | 39 | 8 |
| WA09 | 239 | Q8 | Q8 | Illumina 1 | NA | NA |
| WA09 | 240 | SK26 | SK25 | Affymetrix | NA | NA |
| WA09 | 241 | EN20 | EN20 | Affymetrix | NA | NA |
| WA09 | 242 | MW1 | MW1 | Illumina 2 | 66 | 4 |
| WA09 | 243 | C4 ELSR #13 | C4 ELSR #13 | Illumina 1 | 40 | 10 |
| WA09 | 244 | Z3 | Z3 | Affymetrix | NA | NA |
| WA09 | 245 | W8 (Rep 1) | W8 (Rep 1) | Illumina 1 | 120 | 151 |
| WA09 | 245 | W8 (Rep 2) | W8 (Rep 2) | Affymetrix | NA | NA |
| WA09 | 246 | SK28 | SK28 | Illumina 1 | 87 | 196 |
| MA03 | 247 | E120 | E120 | Illumina 1 | 25 | 44 |
| WA09 | 248 | SM51 | SM51 | Illumina 1 | NA | NA |
| WA09 | 249 | EN8 | EN8 | Illumina 1 | NA | NA |
| WA09 | 250 | SK11 | SK11 | Illumina 1 | 81 | 200 |
| WA09 | 251 | EN43 | EN43 | Affymetrix | | |
| WA09 | 252 | 4-D20-3 | 4-D20-3 | Affymetrix | NA | NA |
| WA09 | 253 | EN44 | EN44 | Illumina 1 | NA | NA |
| WA09 | 254 | EN50 | EN50 | Illumina 1 | 58 | 178 |
| WA09 | 255 | Z2 | Z2 | Illumina 1 | 140 | 117 |
| WA09 | 256 | SM30 | SM30 | Illumina 1 | 103 | 124 |
| WA09 | 257 | EN53 | EN53 | Illumina 1 | 60 | 179 |
| WA09 | 258 | SK27 | SK27 | Illumina 1 | 86 | 13 |
| WA09 | 259 | U18 | U18 | Illumina 1 | 115 | 62 |
| WA09 | 260 | SM35 | SM35 | Illumina 1 | NA | NA |
| WA09 | 261 | EN25 | EN25 | Illumina 1 | 48 | 174 |
| WA09 | 262 | C4 ELSR 6 | C4 ELSR 6 | Affymetrix | NA | NA |
| WA09 | 263 | Z1 | Z1 | Illumina 1 | 138 | 119 |
| MA03 | 264 | F15 | F15 | Affymetrix | NA | NA |
| WA09 | 265 | RA-SKEL-9 | RA-SKEL-9 | Illumina 1 | NA | NA |
| MA03 | 266 | E85 | E85 | Affymetrix | NA | NA |
| WA09 | 267 | W4 | W4 | Illumina 1 | 88 | 177 |
| WA09 | 268 | MEL-2 | MEL-2 | Affymetrix | NA | NA |
| WA09 | 269 | LS2 | LS2 | Illumina 1 | NA | NA |
| WA09 | 270 | 7-SKEL-4 | 7-SKEL-4 | Illumina 2 | 129 | 130 |
| WA09 | 271 | 7-SKEL-7 | 7-SKEL-7 | Illumina 2 | 129 | 132 |
| WA09 | 272 | 7-PEND-9 | 7-PEND-9 | Illumina 2 | 125 | 128 |
| WA09 | 273 | 7-PEND-16 | 7-PEND-16 | Illumina 2 | 125 | 127 |
| WA09 | 274 | 7-SKEL-6 | 7-SKEL-6 | Illumina 2 | 129 | 131 |
| WA09 | 275 | LS3 | LS3 | Illumina 1 | | |
| WA09 | 276 | 7-SMOO-19 | 7-SMOO-19 | Illumina 2 | 131 | 140 |
| WA09 | 277 | 7-SMOO-29 | 7-SMOO-29 | Illumina 2 | 134 | 141 |
| WA09 | 278 | 7-SMOO-32 | 7-SMOO-32 | Illumina 2 | 135 | 136 |
| WA09 | 279 | 7-SMOO-33 | 7-SMOO-33 | Illumina 1 | NA | NA |
| WA09 | 280 | 7-SMOO-4 | 7-SMOO-4 | Illumina 1 | NA | NA |
| WA09 | 281 | 7-SMOO-9 | 7-SMOO-9 | Illumina 2 | 134 | 142 |
| WA09 | 282 | 7-SMOO-17 | 7-SMOO-17 | Illumina 1 | NA | NA |
| WA09 | 283 | 7-PEND-24 | 7-PEND-24 | Illumina 2 | 124 | 156 |
| WA09 | 284 | 7-SKEL-32 | 7-SKEL-32 | Illumina 1 | NA | NA |
| WA09 | 285 | 7-SMOO-13 | 7-SMOO-13 | Illumina 1 | NA | NA |
| WA09 | 286 | 7-SMOO-25 | 7-SMOO-25 | Illumina 2 | 132 | 168 |
| WA09 | 287 | 7-SMOO-12 | 7-SMOO-12 | Illumina 2 | 130 | 138 |
| WA09 | 288 | 7-PEND-30 | 7-PEND-30 | Illumina 2 | 126 | 126 |
| WA09 | 289 | 7-SKEL-25 | 7-SKEL-25 | Illumina 1 | | |
| WA09 | 290 | 7-SMOO-6 | 7-SMOO-6 | Illumina 2 | 136 | 139 |

TABLE III-continued

| Parental hES Cell Lines (WA09 or MA03) | ACTC No. | Cell Line | Cell Line Synonyms | Microarray Group | NMF Group Number | NMF Order |
|---|---|---|---|---|---|---|
| WA09 | 291 | 7-SMOO-26 | 7-SMOO-26 | Illumina 2 | 133 | 137 |
| WA09 | 292 | 7-SMOO-22 | 7-SMOO-22 | Illumina 1 | NA | NA |
| WA09 | 293 | 7-SMOO-8 | 7-SMOO-8 | Illumina 1 | NA | NA |
| WA09 | 294 | 7-SKEL-14 | 7-SKEL-14 | Illumina 1 | NA | NA |
| WA09 | 295 | 7-SKEL-11 | 7-SKEL-11 | Illumina 1 | NA | NA |
| WA09 | 296 | 7-SKEL-2 | 7-SKEL-2 | Illumina 2 | 127 | 129 |
| WA09 | 297 | 7-SKEL-22 | 7-SKEL-22 | Illumina 2 | 128 | 133 |
| WA09 | 298 | 7-SMOO-7 | 7-SMOO-7 | Illumina 2 | 137 | 1 |
| WA09 | 299 | 7-PEND-12 | 7-PEND-12 | Illumina 2 | 124 | 155 |
| WA09 | 300 | 7-SMOO-27 | 7-SMOO-27 | NA | NA | NA |
| WA09 | 301 | 7-PEND-13 | 7-PEND-13 | NA | NA | NA |
| WA09 | 302 | 7-PEND-11 | 7-PEND-11 | NA | NA | NA |
| WA09 | 303 | 7-PEND-15 | 7-PEND-15 | NA | NA | NA |
| WA09 | 304 | 7-PEND-32 | 7-PEND-32 | NA | NA | NA |
| WA09 | 305 | 7-PEND-26 | 7-PEND-26 | NA | NA | NA |
| WA09 | 306 | 7-SKEL-24 | 7-SKEL-24 | NA | NA | NA |
| WA09 | 307 | 7-PEND-10 | 7-PEND-10 | NA | NA | NA |
| WA09 | 308 | 7-PEND-23 | 7-PEND-23 | NA | NA | NA |
|  | 309 | 10-RPE-9 | 10-RPE-9 | NA | NA | NA |
|  | 310 | 10-RPE-8 | 10-RPE-8 | NA | NA | NA |
| WA09 | 311 | RA-PEND-19 | RA-PEND-19 | NA | NA | NA |
| MA03 | NA | X4.1 | X4.1 | Illumina 1 | 3 | 29 |
| MA03 | NA | X4.3 | X4.3 | Illumina 1 | 3 | 31 |
| MA03 | NA | B-10 | B-10 | Illumina 1 | 3 | 30 |
| MA03 | NA | B-1 | B-1 | Illumina 1 | 2 | 39 |
| MA03 | NA | X4 | X4 | Illumina 1 | 121 | 40 |
| MA03 | NA | X5 | X5 | Illumina 1 | 123 | 81 |
| MA03 | NA | B-20 | B-20 | Illumina 1 | 6 | 23 |
| MA03 | NA | B-22 | B-22 | Illumina 1 | 10 | 41 |
| MA03 | NA | X6 | X6 | Illumina 1 | 10 | 43 |
| MA03 | NA | CM10.1 | CM10.1 | Illumina 1 | 11 | 33 |
| MA03 | NA | X2 | X2 | Illumina 1 | 11 | 34 |
| MA03 | NA | B-27 | B-27 | Illumina 1 | 11 | 35 |
| MA03 | NA | B-9 | B-9 | Illumina 1 | 11 | 36 |
| MA03 | NA | X4.4 | X4.4 | Illumina 1 | 11 | 38 |
| MA03 | NA | E31 | E31 | Illumina 1 | 21 | 51 |
| MA03 | NA | CM10-4 | CM10-4 | Illumina 1 | 23 | 91 |
| MA03 | NA | CM30-5 | CM30-5 | Illumina 1 | 23 | 92 |
| MA03 | NA | EN28 | EN28 | Illumina 1 | 51 | 170 |
| WA09 | NA | Q4 | Q4 | Illumina 1 | 69 | 143 |
| WA09 | NA | Q6 | Q6 | Illumina 1 | 70 | 180 |
| WA09 | NA | RA-PEND-17 (Bio 1) | RA-PEND-17 (Bio 1) | Illumina 1 | 75 | 146 |
| WA09 | NA | RA-PEND-17 (Bio 2) | RA-PEND-17 (Bio 2) | Affymetrix |  |  |
| WA09 | NA | RA-SKEL-18 (Rep 1) | RA-SKEL-18 (Rep 1) | Illumina 1 | 76 | 144 |
| WA09 | NA | RA-SKEL-18 (Rep 2) | RA-SKEL-18 (Rep 2) | Affymetrix | NA | NA |
| WA09 | NA | RA-SKEL-6 | RA-SKEL-6 | Illumina 1 | 77 | 145 |
| WA09 | NA | SM19 | SM-19 | Illumina 1 | 97 | 121 |
| WA09 | NA | SM29 | SM-29 | Illumina 1 | 102 | 111 |
| WA09 | NA | SM40 | SM-40 | Illumina 1 | 106 | 123 |
| WA09 | NA | T23 | T-23 | Illumina 1 | 112 | 60 |
| WA09 | NA | T4 | T-4 | Illumina 1 | 112 | 61 |
| WA09 | NA | U30 | U-30 | Affymetrix | 116 | 63 |
| WA09 | NA | W2 | W-2 | Illumina 1 | 118 | 169 |
| WA09 | NA | W3 | W-3 | Illumina 1 | 119 | 2 |
| MA03 | NA | E11 | E-11 | Illumina 1 | 21 | 50 |
| WA09 | NA | SK15 | SK15 | Affymetrix | NA | NA |
| MA03 | NA | E55 | E55 | Affymetrix | NA | NA |
| MA03 | NA | E132 | E132 | Affymetrix | NA | NA |
| WA09 | NA | RA-SMO-10 | RASMO10 | Affymetrix | NA | NA |
| WA09 | NA | RA-SMO-14 | RASMO14 | Affymetrix | NA | NA |
| WA09 | NA | W9 | W9 | Affymetrix | NA | NA |
| WA09 | NA | MW4 | MW4 | Affymetrix | NA | NA |
| WA09 | NA | SK16 | SK16 | Affymetrix | NA | NA |

TABLE IV

A comparison of gene expression markers in human adipocyte stem cells (ACSs), human bone marrow mesenchymal stem cells (MSCs), human adult dental pulp stem cells (DPSCs), cultured human foreskin fibroblasts (Fibro), a clonal hEP line not capable of COL2A1 induction 7SMOO7, and the human embryonic progenitors SM30, E15, 4D20.8, 7SMOO32, MEL2 and SK11 each capable of induced COL2A1 Expression.

| Gene | ASCs | MSCs | DPSCs | SM30 | E15 | 4D20.8 | 7SMOO32 | MEL2 | SK11 | 7PEND24 | Fibro | 7SMOO7 |
|---|---|---|---|---|---|---|---|---|---|---|---|---|
| SOX9 | + (717) | +(1128) | + (639) | +/− (214) | +(452) | + (250) | + (1397) | + (269) | + (386) | + (559) | + (322) | + (731) |
| LHX8 | − (81) | − (76) | + (987) | − (84) | ND | + (1194) | − (81) | − (73) | − (79) | − (156) | − (80) | − (93) |
| AQP1 | − (108) | − (102) | − (105) | − (105) | − (139) | − (97) | − (106) | − (104) | − (109) | − (97) | − (96) | − (99) |
| CD166 | + (1410) | + (2901) | + (4031) | − (125) | + (341) | + (2921) | + (3265) | + (2633) | + (1852) | + (2261) | + (1733) | + (2315) |
| ENG | + (3497) | + (5521) | + (1296) | + (2369) | + (453) | + (2798) | + (2302) | + (1856) | + (820) | + (726) | + (1729) | + (1026) |
| CD90 | + (4739) | + (6659) | + 16270 | +/− (282) | + (742) | + (3589) | + (902) | + (788) | + (617) | − (100) | + 13439 | + (2801) |
| ITGA2 | + (563) | + (970) | +/− (216) | − (131) | − (176) | − (140) | + (426) | − (52) | − (184) | + (505) | +/− (280) | +/− (276) |
| CD74 | + (990) | + (5093) | +/− (220) | − (131) | − (135) | − (88) | − (97) | − (36) | − (108) | − (125) | − (117) | − (150) |
| KCNK2 | + (1707) | + (2025) | + (470) | − (107) | − (139) | − (193) | + (382) | − (39) | − (106) | − (108) | + (833) | + (280) |
| NNAT | − (133) | − (93) | − (166) | − (105) | + (1090) | − (94) | − (117) | − (100) | − (99) | − (134) | − (101) | − (93) |

Numbers in parenthesis are RFU values.

Negative expression indicated by shaded boxes.

(ND means No Data)

TABLE V

Exemplary Differentiation Protocols

Adipogenesis Protocol 1

| | | |
|---|---|---|
| Reagents | 1. | DMEM (GibcoBRL-Cat# 11965-084) |
| | 2. | Calf Serum (GibcoBRL-Cat#16170-078) |
| | 3. | Fetal Bovine Serum (GibcoBRL-Cat# 10437-028) |
| | 4. | Isobutylmethylxanthine (IBMX; Sigma I-7018) |
| | 5. | Dexamethasone (Sigma D-4902) |
| | 6. | Insulin (Bovine; Sigma I-5500) |
| | 7. | MEM Sodium Pyruvate (100 mM; GibcoBRL Cat#11360-070) |
| | 8. | Pen/Strep/Glutamine (100x P/S/G; GibcoBRL Cat#10378-016) |
| Preparation of solutions | 1. | 10% Calf Serum/DMEM: 60 mL Calf Serum; 6 mL 100 mM MEM Sodium Pyruvate; 6 mL 100x P/S/G; 500 mL DMEM. |
| | 2. | 10% FBS/DMEM: 60 mL Fetal Bovine Serum (Filter Sterilized); 6 mL 100 mM MEM Sodium Pyruvate; 6 mL 100x P/S/G; 500 mL DMEM. |
| | 3. | IBMX Solution (make fresh): Dissolve IBMX in a solution made of 0.5N KOH to a final concentration of 0.0115 g/mL; filter sterilize through a 0.22 mm syringe filter. |
| | 4. | Insulin Stock Solution: 167 µM (1 mg/mL) in 0.02M HCl; Filter sterilized through 0.22 mm filter; Can store at −20° C. for long term, 4° C. short term. |
| | 5. | Dexamethasone Stock Solutions: Freezer Stock 10 mM of Dex in 100% ethanol (store at −20° C.); Working Stock: Dilute Freezer stock to 1 mM in PBS; Filter sterilize and store at 4° C. |
| | 6. | MDI Induction Media (10 mL/10 cm plate; 5 mL/6 cm plate): To required volume of 10% FBS/DMEM add: 1:100 IBMX; 1:1000 Insulin; 1:1000 Dexamethasone working stock. |
| | 7. | Insulin Media (10 mL/10 cm plate; 5 mL/6 cm plate): To required volume of 10% FBS/DMEM add: 1:100 Insulin (final concentration 10.0 ug/mL). |
| | 8. | Oil red O stock solution (0.5 g/100 ml isopropanol); Just before staining: mix 60 ml of stock with 40 ml of H$_2$0, let it sit for 1 hr at RT; filter through whatman paper 3MM. |
| | | Procedures |
| Clonal embryonic preadipocyte maintenance and passage | | Cells are plated in their standard growth media (West et al., 2008, Regenerative Medicine vol. 3(3) pp. 287-308; see Supplementary Table I) and incubated 37° C. in 10% CO$_2$ and preferable in 5% ambient oxygen. Cells are frequently observed to prevent them from becoming too confluent (>70%), until differentiation is induced. |
| Adipocyte Differentiation Protocol | 1 | Grow embryonic preadipocytes to confluency in their standard growth media (West et al., 2008, Regenerative Medicine vol. 3(3) pp. 287-308). |
| | 2. | After two days of post confluency (which is counted as day 0), stimulate the cells with MDI induction media. |
| | 3. | After two days of MDI an induction medium (which is called as day 2) replace the MDI induction media with Insulin Media and feed every two days. |

TABLE V-continued

| Exemplary Differentiation Protocols | | |
|---|---|---|
| Staining procedure | 1. | Aspirate media, add formaldehyde slowly and let sit for 30 min. |
| | 2. | Aspirate formaldehyde and add oil red O solution to cover the well, leave 1 hr at RT. |
| | 3. | Remove the stain and wash with distilled water twice. Photograph. |

Adipogenesis Protocol 2

Cells are grown to confluence in their standard growth medium (West et al., 2008, Regenerative Medicine vol. 3(3) pp. 287-308), medium is removed and replaced by serum-free differentiation medium (DMEM/F12 containing 1 μM bovine insulin, 100 nM hydrocortisone, 10 μg of transferrin/mL, 1 nM thyronine, 1 μM rosiglitazone, 33 μM biotin, and 17 μM pantothenic acid) to induce adipocyte differentiation for 3 d. After 3 d of culture, the medium is changed to differentiation medium without rosiglitazone for another 5 d. The mRNA from cultured cells was extracted at 0, 2, 5, 7 and 14 d of incubation for transcript analysis as described herein.

Differentiation Factor Protocol 1

Cells are seeded in a 12 well plate precoated with fibronectin (Gibco) at a high density (1.5 × 10⁶ cells/well). Cells are fed three times per week for 14 days with a basal media of knock out DMEM with penicillin/streptomycin and 16% knock out serum replacement. Individual differentiation factors added to this basal medium chosen from Table III.
Control five day quiescent cells are plated at 3.0 × 10⁵ cells/well and at confluence fed media with serum or other growth supplements reduced to 10% of normal values. The cells are refed two days prior to harvest.

Angiogenesis Protocols

| | |
|---|---|
| Endothelial Formation Protocol (Tube Formation) | The tube formation assay is carried out on 24-well plates previously coated with 250 μl of matrigel per well (BD Biosciences, cat. # 356237). The plates are pre-incubated for 30 minutes at 37° C. before seeding the cells. Subsequently, the cells to be differentiated are seeded at a density of 5 × 10⁴ cells/well in 1 ml of EGM2 media (LONZA cat. # CC-3162). The tube formation assays were analyzed at 24 and 96 hours. Cells are photographed for scoring of the quantity and quality of tube formation as is well-known in the art. RNA is harvested for Q-PCR and microarray analysis of gene expression and markers of endothelial cell differentiation such as the up-regulation of VWF, CDH5 (VE-Cadherin), CD31, KDR, is assayed. |
| Mural Cell Integration into Endothelial Tube Protocol | Endothelial tubes are generated as described in Endothelial Formation Protocol (Tube Formation)Above. To measure tube stability and cell integration, 5 × 10⁴ HUVEC or cells of the present invention including but not limited to the cell line W10 or cells with markers thereof, are mixed with 1 × 10⁴ cells that are to be assayed. HUVEC or similar cells capable of tube formation are labeled with the red dye PKH26 (Sigma, cat. # MINI26); all other cell lines to be tested for mural cell capacity in this assay are labeled with the green dye PKH2 (Sigma, cat. # PKH2GL-1KT). The cell labeling was performed according to the manufacture's protocol.). The tube formation and mural integration assays are analyzed at 24 and 96 hours. Fluorescence and transmitted light images were taken at a magnification of 4x using a Nikon Eclipse TE 2000-U microscope equipped with an EXFO X-Cite 120 illumination system. |

Osteogenic Protocol 1

Tissue culture plates are exposed to 12 ug/mL of Type I collagen (gelatin) and 12 ug/mL of vitronectin for 24 hours. This gelatin/vitronectin solution is then aspirated and the cell lines of the present invention are added at confluent density. Osteogenic media comprising: DMEM (low glucose) with L-Glutamine, 10% fetal bovine serum, 0.1 uM dexamethasone, 0.2 mM ascorbic acid 2-phosphate, 10 mM glycerol 2-phosphate, and 100 nM BMP7 is added for 15-21 days. The degree of steogenesis is scored by relative staining with Alizarin red S performed as follows: Alizarin red S (Sigma) (40 mM) is prepared in dH₂O and the pH is adjusted to 4.1 using 10% (v/v) ammonium hydroxide. Monolayers in 6-well plates (10 cm2/well) are washed with PBS and fixed in 10% (v/v) formaldehyde (Sigma-Aldrich) at room temperature for 15 min. The monolayers are then washed twice with excess dH₂O prior to addition of 1 mL of 40 mM Alizarin red S (pH 4.1) per well. The plates are incubated at room temperature for 20 min with gentle shaking. After aspiration of the unincorporated dye, the wells are washed four times with 4 mL dH₂O while shaking for 5 min. The plates are then left at an angle for 2 min to facilitate removal of excess water, reaspirated, and then stored at −20° C. prior to dye extraction. Stained monolayers are visualized by phase microscopy using an inverted microscope (Nikon).
For quantification of staining, 800 uL 10% (v/v) acetic acid is added to each well, and the plate is incubated at room temperature for 30 min with shaking. The monolayer (loosely attached to the plate) is scraped from the plate with a cell scraper (Fisher Lifesciences) and transferred with 10% (v/v) acetic acid to a 1.5-mL microcentrifuge tube with a wide-mouth pipette. After vortexing for 30 s, the slurry is overlaid with 500 uL mineral oil (Sigma-Aldrich), heated to exactly 85° C. for 10 min, and transferred to ice for 5 min. Care should be taken at this point to avoid opening of the tubes until fully cooled. The slurry is then centrifuged at 20,000 g for 15 min and 500 uL of the supernatant is removed to a new 1.5-mL microcentrifuge tube. 200 uL of 10% (v/v) ammonium hydroxide is added to neutralize the acid. The pH can be measured at this point to ensure that it is between 4.1 and 4.5. Aliquots (150 uL) of the TABLE V-continued Exemplary Differentiation Protocols supernatant are read in triplicate at 405 nm in 96-well format using opaque-walled, transparent-bottomed
plates (Fisher Lifesciences) as described (Gregory, C A et al, An Alizarin red-based assay of
mineralization by adherent cells in culture: comparison with cetylpyridinium chloride extraction,
Analytical Biochemistry 329 (2004) 77-84).

In vitro conditions to induce chondrogenenesis - Pellet Culture.

Functional differentiation assays utilizing the cells of the present invention can employ micromass and
pellet protocols that are well known in the art as capable of causing bone marrow, adipose, and tooth-
derived mesenchymal stem cells to differentiate into chondrogenic lineages. To demonstrate that
individual cell lines are capable of differentiating into chondrogenic lineages we assayed by qPCR
transcript levels for COL2A1, ACAN, CRTL1, CILP, BGN, and CRTAC1 (CEP-68).
In the case of the Chondrogenic Pellet Protocol:

1. Cells are cultured in gelatin (0.1%) coated Corning tissue culture treated cultureware and detached with 0.25% trypsin/EDTA (Invitrogen, Carlsbad, CA, Gibco) diluted 1:3 with PBS (Ca, Mg free). After detachment and addition of growth medium cells are counted using a Coulter counter and appropriate number of cells needed for experiment (e.g. 10 × 106 or more) are transferred into a sterile polyproylene tube and spun at 150 g for 5 min at room temperature.
2. The supernatant is aspirated and discarded. The cells are washed with the addition of Incomplete Chondrogenic Medium consisting of hMSC Chondro BulletKit (PT-3925) to which is added supplements (Lonza, Basel, Switzerland, Poietics Single-Quots, Cat. # PT-4121). Supplements added to prepare Incomplete Chondrogenic Medium are: Dexamethasone (PT-4130G), Ascorbate (PT-4131G), ITS + supplements (4113G), Pyruvate (4114G), Proline (4115G), Gentamicin (4505G), Glutatnine (PT-4140G).
3. Cells are spun at 150 g at room temperature, the supernatant is aspirated and cell the pellet is resuspended (once more) with 1.0 ml Incomplete Chondrogenic Medium per 7.5 × 10e5 cells, and spun at 150 x g for 5 minutes. The supernatant is aspirated and discarded. The Chondrogenesis culture protocol as described by Lonza is followed with some modifications (as written below).
4. Cell pellets are resuspended in Complete Chondrogenic medium to a concentration of 5.0 × 10e5 cells per ml. Complete Chondrogenic Medium consists of Lonza Incomplete Medium plus TGFβ3 (Lonza, PT-4124). Sterile lyophilized TGFβ3 is reconstituted with the addition of sterile 4 mM HCl containing 1 mg/ml BSA to a concentration of 20 ug/ml and is stored after aliquoting at −80° C. Complete Chondrogenic medium is prepared just before use by the addition of 1 ul of TGFβ3 for each 2 ml of Incomplete Chondrogenic medium (final TGFβ3 concentration is 10 ng/ml).
5. An aliquot of 0.5 ml (2.5 × $10^5$ cells) of the cell suspension is placed into sterile 15 ml polypropylene culture tubes. Cells are spun at 150 x g for 5 minutes at room temperature.
6. Following centrifugation the caps of the tubes are loosened one half turn to allow gas exchange. The tubes are placed in an incubator at 37° C., in a humidified atmosphere of 10% $CO_2$ and 5% $O_2$. Pellets are not disturbed for 24 hours.
7. Cell pellets are fed every 2-3 days by completely replacing the medium in each tube by aspirating the old medium with sterile 1-200 ul pipette tip and adding 0.5 ml of freshly prepared Complete Chondrogenic Medium to each tube.
8. After replacing the medium and ensuring that the pellet is free-floating, caps are loosened and tubes returned to the incubator.
9. Pellets are harvested after varying time points in Chondrogenic medium and prepared for histology by fixation with Neutral Buffered Formalin and/or the pellets are combined and prepared for RNA extraction using Rneasy mini Kits (Qiagen, Germantown, MD, Cat. No. 74104). The protocol for RNA extraction is followed as described by the Qiagen Handbook. RNA yield is maximized by using Qiagen's QiaShredder (Cat. # 79654) to homogenize samples following lysis of cell pellets with RLT buffer (provided in Rneasy mini kits) prior to RNA extraction.

In vitro conditions to induce chondrogenenesis - Micromass Culture.

1. Cells are cultured in gelatin (0.1%) coated Corning tissue culture treated cultureware and detached with 0.25% trypsin/EDTA (Gibco) diluted 1:3 with PBS (Gibco Ca, Mg free). After detachment and addition of growth medium cells are counted using a Coulter counter and appropriate number of cells needed for experiment (e.g. 10 × $10^6$ cells or more) are resuspended at a cell density of 20 × $10^6$ cells/ml in growth medium.
2. 10 ul aliquots are seeded onto Corning Tissue Culture Treated Polystyrene plates or dishes. Twenty five or more micromass aliqouts (200,000 cells/10 ul aliquot) are seeded.
3. The seeded micromasses are placed in a humidified incubator at 37° C. with 5% $O_2$ and 10% $CO_2$ for 90 minutes to 2 hours for attachment.
4. Growth medium is added and the following morning is replaced, after aspiration and washing with PBS (Ca, Mg free), with Complete Chondrogenic Medium (prepared as described above for the pellet micromasses). For example 6 ml Complete Chondrogenic medium/10 cm dish is added. Cells are maintainied in a humidified incubator at 37° C. with 5% $O_2$, 10% $CO_2$ and chondrogenic medium replaced with freshly prepared medium every 2-3 days.
5. After varying periods of time in Chondrogenic medium RNA is extracted using Qiagen Rneasy kits (Qiagen Cat. No. 74104) as described in the Qiagen Handbook. RNA yield is maximized by using Qiagen's QiaShredder (Cat. # 79654 to homogenize samples following lysis of micromasses with RLT buffer, (which is provided with the Rneasy mini kits) prior to RNA extraction. An alternative to Lonza Chondrogenic medium is CellGro (Cat. No. 15-013-CV) from Media Tech. To each 500 ml, the following supplements are added: 5.0 ml Pen/Strep (Gibco Cat. No. 15140), 5.0 ml Glutamax (Gibco Cat. No. 35050), Dexamethasone (Sigma, St. Louis, MO, Cat. No. D1756-100) -500 ul of 0.1 mM for a final concentration of 0.1 uM; L-Proline (Sigma Cat. No. D49752) -500 ul 0.35M for a final concentration of 0.35 mM; Ascorbic Acid-2-phosphate (Sigma, Cat. No. 49792, Fluka) -500 ul 0.17M for a final concentration 0.17 mM; ITS Premix (BD, Franklin Lakes, NJ, sterile Cat. No. 47743-628) -500 ul of 1000x concentrate for a final concentration of 6.25 ug/ml insulin, 6.25 ug/ml transferrin, 6.25 ng/ml selenious acid, serum albumin 1.25 mg/ml, 5.35 ug/ml linoleic acid.

TABLE V-continued

Exemplary Differentiation Protocols

Following addition of constituents above the media is filtered through a 500 ml Corning 0.2 micron filter unit.
As an alternative to Lonza TGFβ3 descibed above we use TGFβ3 (R&D Systems, Minneapolis MN, Cat. No. 243-B3-010). It is prepared, aliquoted and stored and used similarly to that purchased from Lonza.

Differentiation in gels containing crosslinked hyaluronic acid and gelatin

The cell lines of the present invention may also be differentiated within hydrogels, including crosslinked gels containing hyaluronic acid and gelatin with or without added factors listed in Table III. Cells are trypsinized and suspended at 1-30 × 10e6 cells/ml HyStem-CSS (Glycosan Hydrogel Kit GS319) according to manufacturers directions.

1. Preparation of HyStem-CSS:
   HyStem (thiol-modified hyaluranan) is dissolved in 1 ml degassed deionized water (taking about 20 minutes). Gelin-S (thiol modified gelatin) is dissolved in 1 ml degassed deionized water and PEGSSDA (disulfide-containing PEG diacrylate) is dissolved in 0.5 ml degassed deionized water (designated herein as "PEGSSDA solution"). Then HyStem (1 ml) is mixed with Gelin-S (1 ml) without creating air bubbles, immediately before use (designated herein as "HyStem: Gelin-S mix").

2. Retinoic acid and EGF-Containing HyStem-CSS:
   In the case of differentiation in HyStem hydrogel containing RA and EGF, 17 million cells are pelleted and resuspended in 1.4 ml Hystem: Gelin-S mix. Then 0.35 ml of PEGSSDA solution is added, pipetted up and down, without creating air bubbles, and 100 ul aliquots are quickly placed onto multiple 24 well inserts (Corning Cat #3413). After gelation, in 20 minutes, encapsulated cells are fed 2 ml growth media with trans-RA (1 uM) (Sigma, Cat # 2625) or 2 ml growth media with EGF 100 ng/ml (R&D systems Cat# 236-EG). Cells are fed three times weekly. After 28 days, cells are lysed and RNA harvested using RNeasy micro kits (Qiagen Cat # 74004) for qPCR or microarray analysis as described herein.

3. Differentiation in Hydrogels Containing Crosslinked Hyaluronic Acid and Gelatin to Induce Chondrogenesis:
   Cells are suspended at a density of 20 × 10e6 cells/ml in 1.4 ml Hystem: Gelin-S mix. Then 0.35 ml of PEGSSDA solution is added, pipetted up and down, without creating air bubbles, and 100 ul aliquots are quickly placed onto multiple 24 well inserts (Corning Cat #3413). After gelation, in 20 minutes, encapsulated cells are fed 2 ml Complete Chondrogenic Medium which consists of Lonza Incomplete Medium plus TGFβ3 (Lonza, PT-4124). Incomplete Chondrogenic Medium consisting of hMSC Chondro BulletKit (PT-3925) to which is added supplements (Lonza, Basel, Switzerland, Poietics Single-Quots, Cat. # PT-4121). Supplements added to prepare Incomplete Chondrogenic Medium are: Dexamethasone (PT-4130G), Ascorbate (PT-4131G), ITS + supplements (4113G), Pyruvate (4114G), Proline (4115G), Gentamicin (4505G), Glutamine (PT-4140G). Sterile lyophilized TGFβ3 is reconstituted with the addition of sterile 4 mM HCl containing 1 mg/ml BSA to a concentration of 20 ug/ml and is stored after aliquoting at −80° C. Complete Chondrogenic medium is prepared just before use by the addition of 1 ul of TGFβ3 for each 2 ml of Incomplete Chondrogenic medium (final TGFβ3 concentration is 10 ng/ml). Cells are refed three times a week and cultured for a total of 14 days. Cells are then lysed and RNA harvested using RNeasy micro kits (Qiagen Cat # 74004).

Differentiation of confluent cultures in the presence of EGF

Cell of the present invention are grown to confluence in a 10 cm cell culture dish which may take 0.5-2 weeks depending upon the initial seeding density and the rate of growth of the cell line. Cells are fed growth media plus 100 ng/ml EGF when they reach confluence and are fed three times a week. After 28 days, cells are lysed and RNA prepared using RNeasy mini kits (Qiagen Cat #71404).

Table 6 is a summary of genes expressed on an mRNA level as determined by Illumina microarrays (P=positive) or not expressed (N-negative) or indeterminate (p/n) or (n/p) in human ES-derived clonal embryonic progenitor cell lines observed to be chondrogenic in the presence of TGF beta family members. Data shown is for the cells when cultured in the undifferentiated state and held for five days of quiescence as described herein. Also shown for comparison is parallel data obtained from bone marrow mesenchymal stem cells (MSCs).

| CD74 Illumina | MSCs | SK11 | E15 | 7PEND24 | 4D20.8 | SM30 | 7SMOO32 | MEL2 | EN7 |
| --- | --- | --- | --- | --- | --- | --- | --- | --- | --- |
| Probe ID (1240070) | P | N | N | N | N | N | N | N | N |
| TBX15 | P | P | P | P | N | N | N | N | N |
| LHX8 | N | N | N | P | P | N | N | N | N |
| BARX1 | N | N | N | P | P | N | N | N | N |
| PITX1 | P | P | N | N | N | P | N | p/n | N |
| BMP5 | N | N | N | n/p | N | N | P | N | p/n |
| HAND2 | N | N | N | p/n | N | N | N | P | N |
| ZIC2 | N | P | p/n | N | N | P | N | N | P |
| AJAP1 | N | N | P | N | N | N | N | N | N |
| ALDH1A2 | N | N | N | N | N | N | N | P | N |
| LHX1 | N | N | N | N | N | N | P | N | N |
| HOXB2 | n/p | N | P | N | N | N | N | N | P |
| RGS1 | N | N | N | N | N | N | N | N | P |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method of increasing expression of COL2A1 and minimizing expression of COL10A1 in a clonal embryonic progenitor cell line that does not display SSEA4, TRA1-60 or TRA1-81 sero-positivity and is capable of further differentiating into more than one cell type, wherein the method comprises differentiating said clonal embryonic progenitor cell line in the presence of GDF5 or BMP6, and in the presence of TGFβ, thereby increasing the expression of COL2A1 and minimizing the expression of COL10A1 by the embryonic progenitor cell line.

2. The method of claim 1, wherein the TGFβ is TGFβ3.

3. The method of claim 1, wherein the GDF5 is present at a concentration between about 10-1,000 ng/mL.

4. The method of claim 2, wherein the TGFβ3 is present at a concentration between about 1-100 ng/mL.

5. A method of conditioning a clonal embryonic progenitor cell line that does not display SSEA4, TRA1-60 or TRA1-81 sero-positivity and is capable of further differentiating into more than one cell type, the method comprising culturing said clonal embryonic progenitor cell line in the presence of one or more BMP factors selected from TGF 3, GDF5, BMP2, BMP4, BMP6 and BMP7 to induce or increase expression of COL2A1, COL10A1, CRTAC1, tenomodulin, sialoprotein II, COL9A2, or CHAD by said clonal embryonic progenitor cell line.

6. The method of claim 5, wherein said GDF5 is present at a concentration between about 10-1,000 ng/mL.

7. The method of claim 5, wherein said TGFβ3 is present at a concentration between about 1-100 ng/mL.

8. The method of claim 5, wherein said clonal embryonic progenitor cell line is EN7, 7PEND24, SM30, E15, 4D20.8, 7SMOO32, MEL2 or SK11.

9. The method of claim 6, wherein said TGFβ3 is present at a concentration between about 1-100 ng/mL.

10. The method of claim 5, wherein said clonal embryonic progenitor cell line is cultured in the presence of one or more BMP factors comprising: (a) TGFβ3, (b) GDF5, (c) BMP4, (d) BMP6, (e) BMP7, (f) TGFβ3 and BMP4, (g) TGFβ3 and BMP6, (h) TGFβ3 and BMP7, (i) TGFβ3 and GDF5, (j) BMP2, BMP4 and TGFβ3, (k) BMP2 and BMP7, (l) BMP2, BMP7 and TGFβ3, or (m) BMP4, BMP7 and TGFβ3.

11. The method of claim 5, wherein said clonal embryonic progenitor cell line is cultured in the presence of one or more BMP factors comprising BMP2 and TGFβ3, or BMP4 and TGFβ3.

12. The method of claim 5, wherein expression of COL2A1 is induced or increased when said clonal embryonic progenitor cell line is cultured in the presence of one or more BMP factors comprising: (a) TGFβ3, (b) GDF5, (c) BMP4, (d) BMP6, (e) BMP7, (f) TGFβ3 and BMP4, (g) TGFβ3 and BMP6, (h) TGFβ3 and BMP7, (i) TGFβ3 and GDF5, (j) BMP2, BMP4 and TGFβ3, (k) BMP2 and BMP7, (l) BMP2, BMP7 and TGFβ3, (m) BMP4, BMP7 and TGFβ3, or (n) TGFβ3 and BMP2.

13. The method of claim 5, wherein expression of CRTAC1 is induced or increased when said clonal embryonic progenitor cell line is cultured in the presence of one or more BMP factors comprising: (a) TGFβ3, (b) GDF5, (c) BMP4, (d) BMP6, (e) BMP7, (f) TGFβ3 and BMP4, (g) TGFβ3 and BMP6, (h) TGFβ3 and BMP7, (i) TGFβ3 and GDF5, (j) BMP2 and BMP4, (k) BMP2, BMP4 and TGFβ3, (l) BMP2 and BMP7, (m) BMP2, BMP7 and TGFβ3, (n) BMP4 and BMP7, or (o) BMP4, BMP7 and TGFβ3.

14. The method of claim 5, wherein expression of tenomodulin is induced or increased when said clonal embryonic progenitor cell line is cultured in the presence of one or more BMP factors comprising BMP4 or BMP7.

15. The method of claim 5, wherein expression of sialoprotein II is induced or increased when said clonal embryonic progenitor cell line is cultured in the presence of one or more BMP factors comprising: (a) BMP2 and TGFβ3, (b) BMP4 and TGFβ3, or (c) TGFβ3.

16. The method of claim 5, wherein expression of COL10A1 is induced or increased when said clonal embryonic progenitor cell line is cultured in the presence of one or more BMP factors comprising: (a) TGFβ3 and BMP4, (b) TGFβ3 and BMP6, (c) TGFβ3 and BMP7, (d) BMP2, BMP4 and TGFβ3, (e) BMP2 and BMP7, (f) BMP2, BMP7 and TGFβ3, or (g) BMP4, BMP7 and TGFβ3.

17. The method of claim 5, wherein said clonal embryonic progenitor cell line is cultured in the presence of one or more BMP factors comprising: (a) TGFβ3, (b) BMP4 and TGFβ3, (c) GDF5 and TGFβ3, or (d) BMP7 and TGFβ3.

18. The method of claim 1, wherein the BMP6 is present at a concentration of about 30 ng/mL.

19. The method of claim 1, wherein expression of CRTAC1 is also increased.

20. The method of claim 1, wherein the clonal embryonic progenitor cell line is 4D20.8.

* * * * *